United States Patent
Hoflack et al.

(10) Patent No.: US 10,377,772 B2
(45) Date of Patent: Aug. 13, 2019

(54) MACROCYCLIC LRRK2 KINASE INHIBITORS

(71) Applicant: Oncodesign S.A., Dijon (FR)

(72) Inventors: Jan Hoflack, Malle (BE); Petra Blom, Destelbergen (BE); Olivier Lavergne, Palaiseau (FR); Sylvie Gomez, Totana (ES)

(73) Assignee: Oncodesign S.A., Dijon (FR)

( * ) Notice: Subject to any disclaimer, the term of this patent is extended or adjusted under 35 U.S.C. 154(b) by 0 days.

(21) Appl. No.: 15/511,879

(22) PCT Filed: Sep. 17, 2015

(86) PCT No.: PCT/EP2015/071349
§ 371 (c)(1),
(2) Date: Mar. 16, 2017

(87) PCT Pub. No.: WO2016/042089
PCT Pub. Date: Mar. 24, 2016

(65) Prior Publication Data
US 2017/0240565 A1    Aug. 24, 2017

(30) Foreign Application Priority Data
Sep. 17, 2014 (EP) .................... 14290279

(51) Int. Cl.
*C07D 487/22* (2006.01)
*C07D 498/22* (2006.01)

(52) U.S. Cl.
CPC ......... *C07D 498/22* (2013.01); *C07D 487/22* (2013.01)

(58) Field of Classification Search
CPC ............. C07D 487/22; C07D 498/22
See application file for complete search history.

(56) References Cited

U.S. PATENT DOCUMENTS

| | | | |
|---|---|---|---|
| 6,194,410 B1 | 2/2001 | Bos et al. | |
| 6,369,086 B1 | 4/2002 | Davis et al. | |
| 6,369,087 B1 | 4/2002 | Whittle et al. | |
| 6,372,733 B1 | 4/2002 | Caldwell et al. | |
| 6,372,778 B1 | 4/2002 | Tung et al. | |
| 7,067,507 B2 * | 6/2006 | Pulley | C07D 273/02 514/183 |

FOREIGN PATENT DOCUMENTS

| | | | |
|---|---|---|---|
| EP | 0729758 A3 | 10/1997 | |
| EP | 0721331 B1 | 5/2001 | |
| EP | 1354884 B1 | 10/2007 | |
| EP | 1908764 A1 | 9/2008 | |
| WO | WO2006045392 A2 | 5/2006 | |
| WO | WO2006068492 A1 | 6/2006 | |
| WO | WO2007014979 A1 | 2/2007 | |
| WO | WO2007058627 A1 | 5/2007 | |
| WO | WO2009127642 A2 | 10/2009 | |
| WO | WO2011038572 A1 | 4/2011 | |
| WO | WO2013001310 A1 | 1/2013 | |
| WO | WO2013046029 A1 | 4/2013 | |

OTHER PUBLICATIONS

Kethiri. Expert Opinion on Therapeutic Patents, 2014, 24(7), 745-57 (Year: 2014).*
Anders (European Journal of Organic Chemistry, 2004, 5020-26 (Year: 2004).*
"Metabolite", http://www.encyclopedia.com/doc/1E1-nnetabolit.html, accessed Jan. 25, 2008 (Year: 2008).*
Zawilska. Pharmacological Reports, 2013, 65, 1-14 (Year: 2013).*
European Search Report dated Jan. 28, 2015 for EP Application No. 14290279.0 Sep. 17, 2014. pp. 1-9.
International Search Report and Written Opinion dated Apr. 11, 2015 for PCT/EP2015/0713490 Filed Sep. 17, 2015. pp. 1-12.
International Preliminary Report on Patentability dated Mar. 21, 2017 for PCT/EP2015/0713490 Filed Sep. 17, 2015. pp. 1-8.
"Mutant LRRK2 BAC transgenic mice recapitulate cardinal features of Parkinson's disease", Yanping Li et al., NIH Public Access, Jul. 2009.
"Leucine-rich repeat kinase 2 inhibitors: a review of recent patents", Raghava R. Kethiri et al., Expert Opinion on Therapeutic Patent, Jul. 1, 2017.

* cited by examiner

*Primary Examiner* — Noble E Jarrell
(74) *Attorney, Agent, or Firm* — Dinsmore & Shohl LLP

(57) ABSTRACT

The present invention relates to novel macrocyclic compounds of formula (I) and compositions containing said compounds acting as kinase inhibitors, in particular as inhibitors of LRRK2 (Leucine-Rich Repeat Kinase 2). Moreover, the present invention provides processes for the preparation of the disclosed compounds, as well as methods of using them, for instance as a medicine or diagnostic agent, in particular for the treatment and/or diagnosis of diseases characterized by LRRK2 kinase activity such as neurological disorders including Parkinson's disease and Alzheimer's disease.

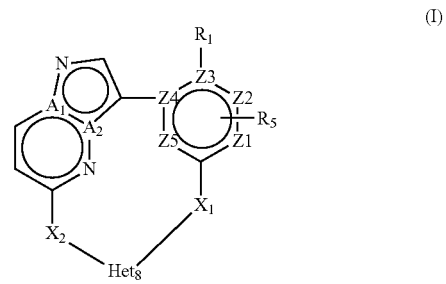

(I)

22 Claims, No Drawings

MACROCYCLIC LRRK2 KINASE INHIBITORS

FIELD OF THE INVENTION

The present invention relates to novel macrocyclic compounds and compositions containing said compounds acting as kinase inhibitors, in particular as inhibitors of LRRK2 (Leucine-Rich Repeat Kinase 2). Moreover, the present invention provides processes for the preparation of the disclosed compounds, as well as methods of using them, for instance as a medicine or diagnostic agent, in particular for the treatment and/or diagnosis of diseases characterized by LRRK2 kinase activity such as neurological disorders including Parkinson's disease and Alzheimer's disease.

BACKGROUND OF THE INVENTION

Parkinson's disease is a degenerative disorder of the central nervous system. It results from the death of dopaminergic neurones in the midbrain. In the early stages of the disease the most obvious symptoms are movement-related such as shaking, slowness of movement and difficulty with walking. Later on also cognitive and behavioural problems arise, with dementia commonly occurring in the advanced stages of the disease. Although Parkinson's disease is generally considered to be sporadic, within the last decade, a few mutations in the LRRK2 (leucine rich repeat kinase 2) gene have been linked to Parkinson's disease (WO2006068492 and WO2006045392). LRRK2, also known as dardarin, is a member of the leucine-rich repeat kinase family having mixed-lineage kinase activity, in particular in the brain, but also in other tissues throughout the body. Researchers have identified over 20 LRRK2 mutations in families with late-onset Parkinson Disease. For example the G2019S mutation co-segregates with autosomal dominant Parkinsonism and accounts for about 6% of familial Parkinson's disease cases and 3% sporadic Parkinson's disease cases in Europe. The G2019S mutation occurs in the highly conserved kinase domain and it has therefore been postulated that the G2019S mutation may have an effect on kinase activity (WO2006068492). Furthermore, amino acid substitutions at a second residue R1441 are also associated with Parkinson's disease and have also been shown to elevate LRRK2 kinase activity. Over-expression of the mutant LRRK2 protein R1441G in transgenic mouse models (Li, Y et al. 2009, Nature Neuroscience 12:826-828) is associated with symptoms of Parkinson's disease as well as reduced dopamine release, suggesting that inhibitors of LRRK2 could also positively regulate dopamine release and have potential utility in treatment of conditions characterized by reduced dopamine levels, such as withdrawal symptoms/relapse associated with drug addiction; Tauopathy diseases such as Alzheimer's disease, argyrophilic grain disease, Pick's disease, corticobasal degeneration; inherited frontotemporal dementia; and Parkinson's disease. Two further mutations in LRRK2 have been clinically associated with the transition from mild cognitive impairment to Alzheimer's disease (WO200714979). These data further provide evidence that inhibitors of LRRK2 kinase activity could be useful for the treatment of dementias and related neurodegenerative disorders.

Thus, pharmacological inhibition of LRRK2 kinase is an attractive strategy towards mechanism-based therapies in neurodegenerative disorders, such as Parkinson's disease and Alzheimer's disease. It was therefore an object of the present invention to provide compounds and compositions comprising said compounds, acting as inhibitors of LRRK2 kinases.

Until today several (non-macrocyclic) pyrazolopyrimidines have been suggested for the treatment of neuronal disorders, in particular Alzheimer's disease and/or Parkinson's disease (see for example EP1908764, U.S. Pat. No. 6,194,410, EP1354884, EP0729758 and U.S. Pat. No. 6,194,410). However, none of the compounds disclosed in said references have been shown to have LRRK2 inhibitory activity.

Furthermore, the currently developed LRRK2 kinase inhibitors, in particular those for the treatment of neuronal disorders, do not comprise macrocyclic pyrazolopyrimidine moieties (see for example WO2009127652, WO2011038572).

Nonetheless, there is a continuing need to design and develop LRRK2 kinase inhibitors for the treatment of neuronal disorders. We have now found that the macrocyclic pyrazolopyrimidines and pharmaceutically acceptable compositions according to this invention are useful for the treatment of several neuronal disorders associated with LRRK2 kinase activity.

SUMMARY OF THE INVENTION

We have surprisingly found that the macrocyclic compounds described herein act as kinase inhibitors, in particular LRRK2 kinase inhibitors.

In a first objective the present invention provides a compound of Formula I or a stereoisomer, tautomer, racemic, metabolite, pro- or predrug, salt, hydrate, N-oxide form, or solvate thereof,

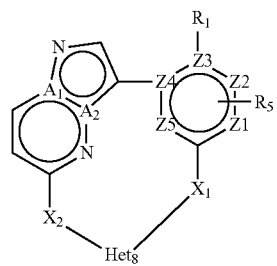

Wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;
$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;
$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$ are each independently selected from —H, —$C_{1-6}$alkyl, —$C_{3-6}$cycloalkyl and -$Het_2$:

$R_{37}$ and $R_{38}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S; wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is option- ally and independently substituted with from 1 to 3 -halo; wherein when $R_1$—H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

In particular, the present invention provides a compound of Formula I or a stereoisomer, tautomer, racemic, metabolite, pro- or predrug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$— and —O—;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—

$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S; wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo; wherein when $R_1$ is —H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

More in particular the present invention provides a compound of Formula I or a stereoisomer, tautomer, racemic, metabolite, pro- or predrug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —O—$C_{3-6}$cycloalkyl, —$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$ $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a bivalent 3- to 10-membered heterocycle having from 1 to 3 heteroatoms selected from O, N and S;

wherein at least one of said heteroatoms is attached to $X_1$ or $X_2$;

wherein when $R_1$ is —H, then at least one heteroatom of $Het_8$ is attached to $X_2$; and wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and $A_1$ and $A_2$ are each independently selected from C and N.

More in particular the present invention provides a compound of Formula Ia or a stereoisomer, tautomer, racemic, metabolite, pro- or predrug, salt, hydrate, N-oxide form, or solvate thereof,

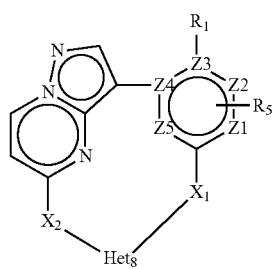

Ia

Wherein

R₁ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$ R$_{34}$, R$_{35}$ and R$_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;
  wherein when R$_1$ is —H, then at least one heteroatom of Het$_8$ is attached to X$_2$ Z$_1$, Z$_2$, Z$_3$, Z$_4$ and Z$_5$ are each independently selected from C and N.

More in particular the present invention provides a compound of Formula Ia or a stereoisomer, tautomer, racemic, metabolite, pro- or predrug, salt, hydrate, N-oxide form, or solvate thereof, wherein R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$, R$_{34}$, R$_{35}$ and R$_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$— and —O—;

X$_2$ is selected from —C$_{1-6}$alkyl-, —O—C$_{1-6}$alkyl-, —S—C$_{1-6}$alkyl-, —C$_{1-6}$alkyl-NR$_2$—C$_{1-6}$alkyl-, —NR$_2$—C$_{1-6}$alkyl-, —NR$_2$—, and —O—;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;
  wherein when R$_1$ is —H, then at least one heteroatom of Het$_8$ is attached to X$_2$ Z$_1$, Z$_2$, Z$_3$, Z$_4$ and Z$_5$ are each independently selected from C and N.

In a further embodiment, the present invention provides a compound of Formula Ia or a stereoisomer, tautomer, racemic, metabolite, pro- or predrug, salt, hydrate, N-oxide form, or solvate thereof, wherein R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_6$, R$_7$, R$_9$, R$_{10}$, R$_{11}$, R$_{12}$, R$_{13}$, R$_{14}$, R$_{15}$, R$_{16}$, R$_{19}$, R$_{20}$, R$_{21}$, R$_{22}$, R$_{31}$, R$_{32}$, R$_{33}$ and R$_{34}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$;

X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
  wherein at least one of said heteroatoms is attached to X$_1$ or X$_2$;
  wherein when R$_1$ is —H, then at least one heteroatom of Het$_8$ is attached to X$_2$; and
  wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N.

In a further embodiment, the present invention provides a compound of Formula Ia or of Formula I or a stereoisomer, tautomer, racemic, metabolite, pro- or predrug, salt, hydrate, N-oxide form, or solvate thereof, wherein each of said Z$_1$, Z$_2$, Z$_3$, Z$_4$ and Z$_5$ is C; and wherein the further definitions and provisions as defined herein above apply.

In a further embodiment, the present invention provides a compound of Formula Ia or a stereoisomer, tautomer, racemic, metabolite, pro- or predrug, salt, hydrate, N-oxide form, or solvate thereof, wherein said Het$_8$ is a saturated 3- to 10-membered heterocycle having from 1 to 3 heteroatoms selected from O, N and S; and wherein the further definitions and provisions as defined herein above apply.

In a further embodiment, the present invention provides a compound of Formula I or a stereoisomer, tautomer, racemic, metabolite, pro- or predrug, salt, hydrate, N-oxide form, or solvate thereof,
wherein
A$_1$ and A$_2$ are each independently selected from C and N;
R$_1$ is selected from —H and -halo;
R$_5$ is selected from —H, -halo and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —C$_{1-6}$alkyl-, —O—C$_{1-6}$alkyl-, —NR$_2$—C$_{1-6}$alkyl-, —NR$_2$—, —O—;
Het$_8$ is a 3- to 10-membered heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, —C$_{1-6}$alkyl-C$_{3-6}$cycloalkyl, —(C=O)—C$_{1-6}$alkyl, and —(C=O)—C$_{3-6}$cycloalkyl; and
Z$_1$, Z$_2$, Z$_3$, Z$_4$ and Z$_5$ are each C.

In a further embodiment, the present invention provides a compound of Formula I or a stereoisomer, tautomer, racemic, metabolite, pro- or predrug, salt, hydrate, N-oxide form, or solvate thereof,
wherein
A$_1$ and A$_2$ are each independently selected from C and N;
R$_1$ is selected from —H and -halo;
R$_5$ is selected from —H, -halo and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —O—C$_{1-6}$alkyl-, —NR$_2$—C$_{1-6}$alkyl-, —NR$_2$—, —O—;
Het$_8$ is a 3- to 10-membered heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, and —C$_{1-6}$alkyl-C$_{3-6}$cycloalkyl; and
Z$_1$, Z$_2$, Z$_3$, Z$_4$ and Z$_5$ are each C.

In a further embodiment, the present invention provides a compound of Formula I or a stereoisomer, tautomer, racemic, metabolite, pro- or predrug, salt, hydrate, N-oxide form, or solvate thereof, wherein A$_1$ is N and A$_2$ is C.

In a further embodiment, the present invention provides a compound of Formula Ia or a stereoisomer, tautomer, racemic, metabolite, pro- or predrug, salt, hydrate, N-oxide form, or solvate thereof

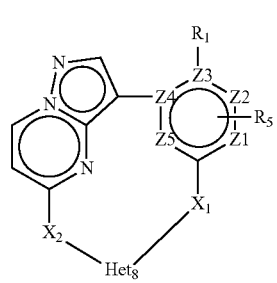

Ia

Wherein
R$_1$ is selected from —H and -halo;
R$_5$ is attached to Z$_1$ and is selected from —H and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —O—C$_{1-6}$alkyl-, —NR$_2$—C$_{1-6}$alkyl-, —NR$_2$—, —O—;
Het$_8$ is a 3- to 10-membered N-containing heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; and
Z$_1$, Z$_2$, Z$_3$, Z$_4$ and Z$_5$ are each C.

More in particular the present invention provides a compound selected from the list comprising:

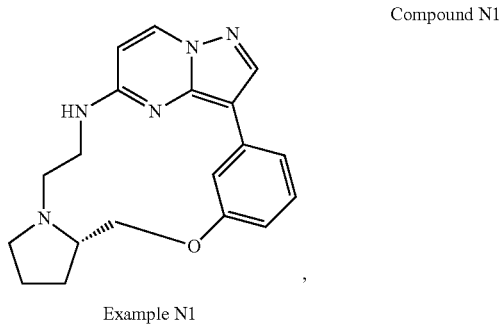

Compound N1

Example N1

Compound N2
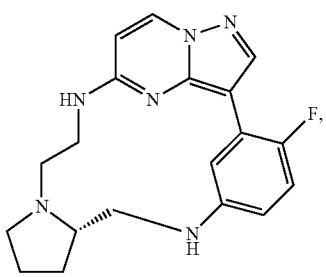
Example N2
Compound N3
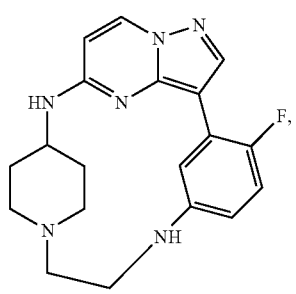
Example N3
Compound N4
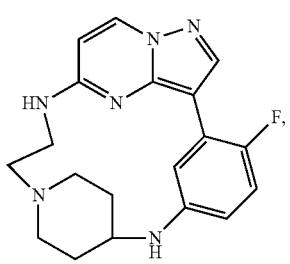
Example N4
Compound N5
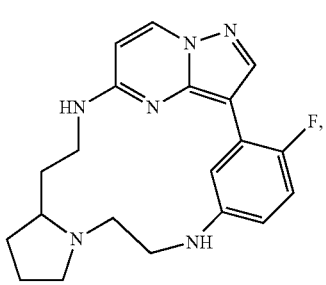
Example N5
Compound N6
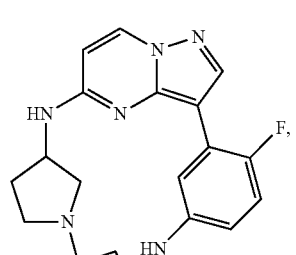
Example N6
Compound N7
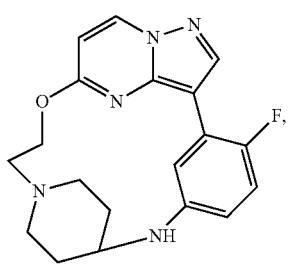
Example N7
Compound N8
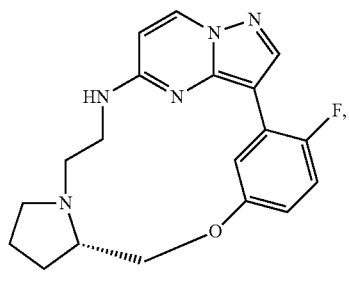
Example N8
Compound N9
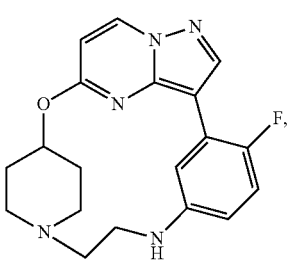
Example N9
Compound N10
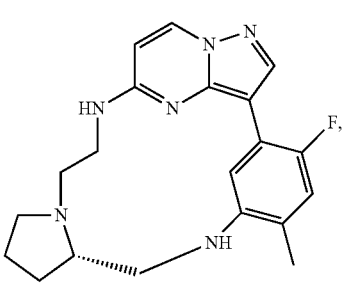
Example N10
Compound N11
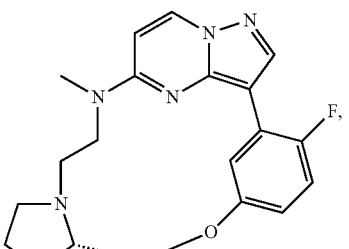
Example N11

Compound N12
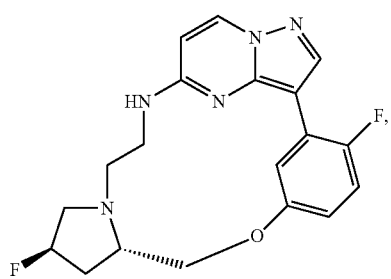
Example N12
Compound N13
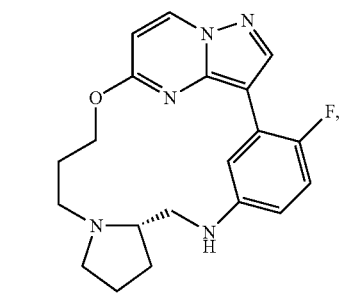
Example N13
Compound N14
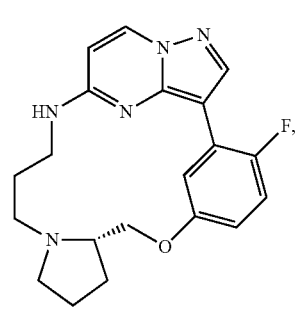
Example N14
Compound N15
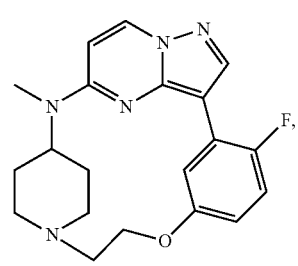
Example N15
Compound N16
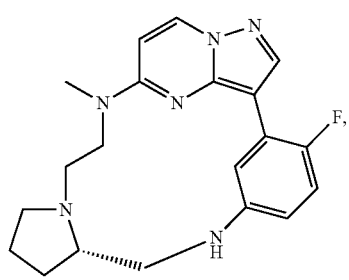
Example N16
Compound N17
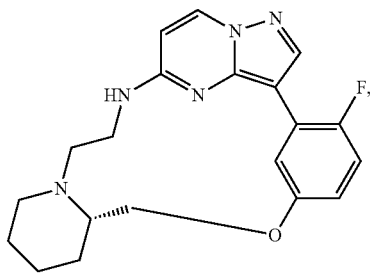
Example N17
Compound N18
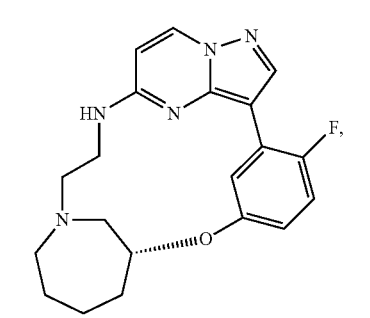
Example N18
Compound N19
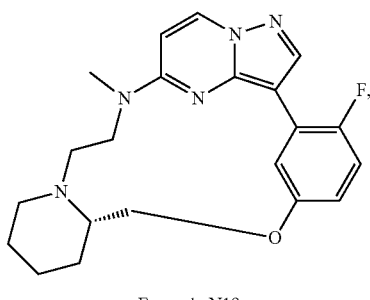
Example N19
Compound N20
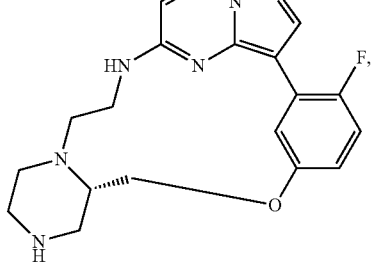
Example N20
Compound N21
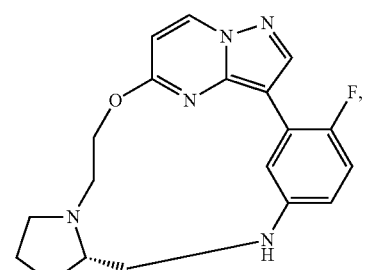
Example N21

Compound N22
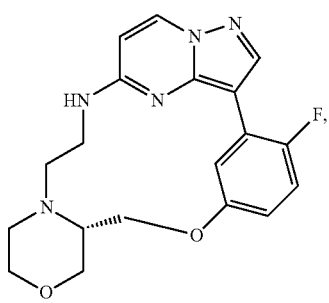
Example N22
Compound N23
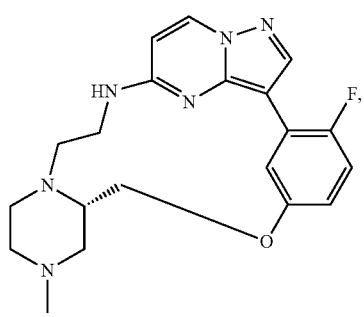
Example N23
Compound N24
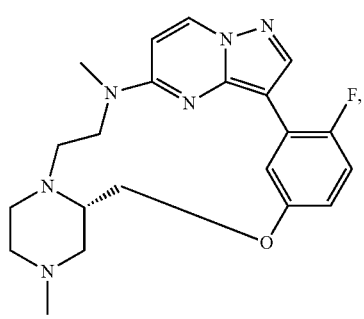
Example N24
Compound N25
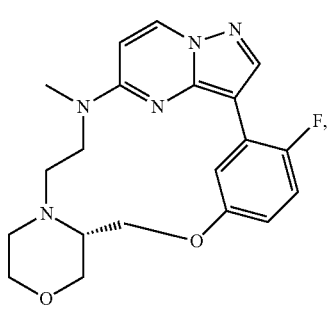
Example N25
Compound N26
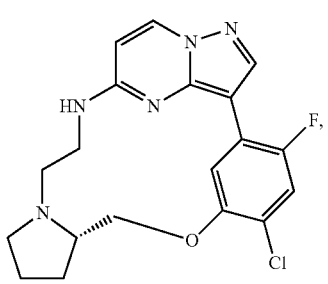
Example N26
Compound N27
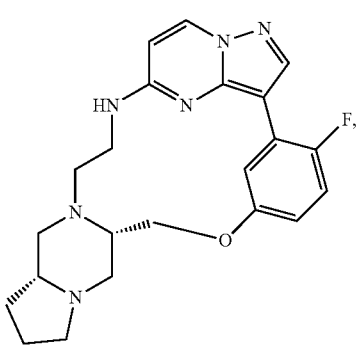
Example N27
Compound N28
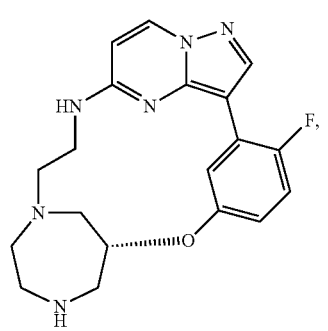
Example N28
Compound N29
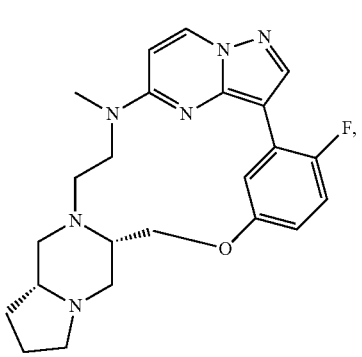
Example N29

-continued
Compound N30
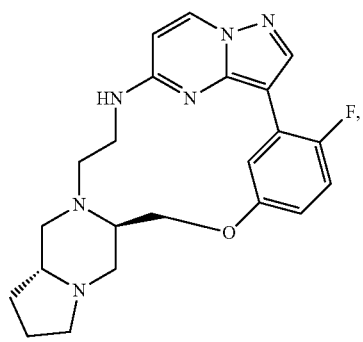
Example N30
Compound N31
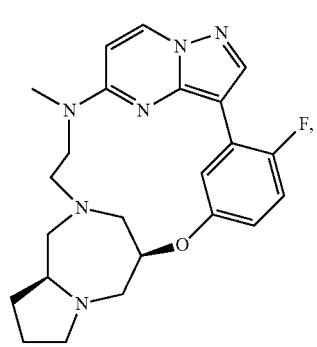
Example N31
Compound N32
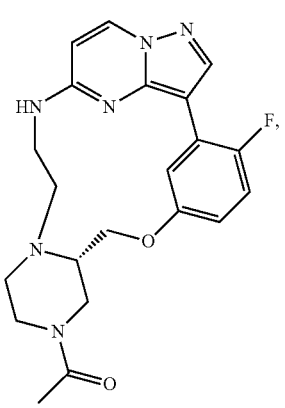
Example N32
Compound N33
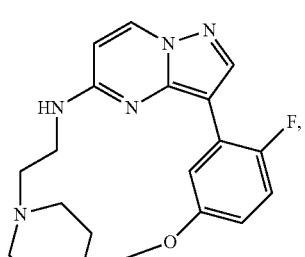
Example N33
-continued
Compound N34
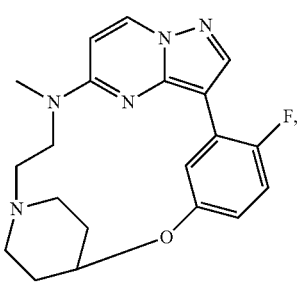
Example N34
Compound N35
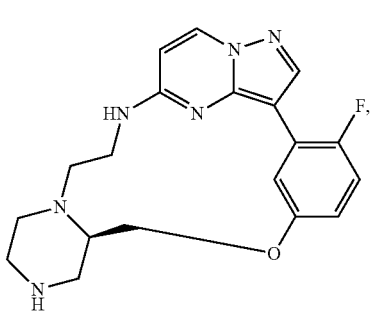
Example N35
Compound N36
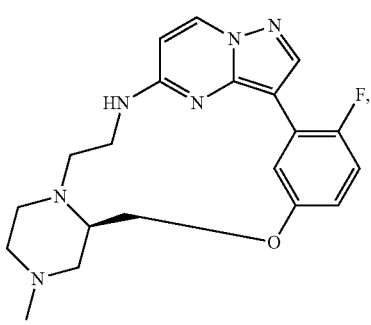
Example N36
Compound N37
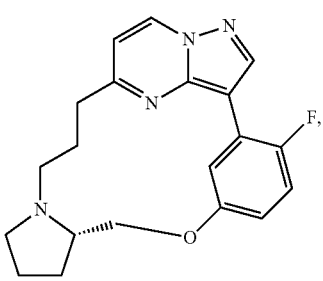
Example N37

Compound N38
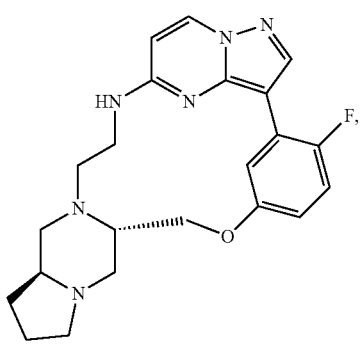
Example N38
Compound N39
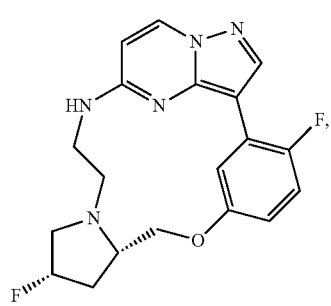
Example N39
Compound N40
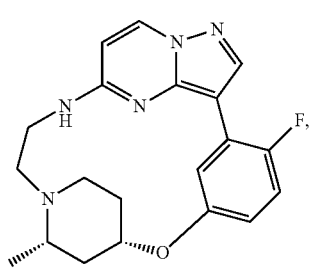
Example N40
Compound N41
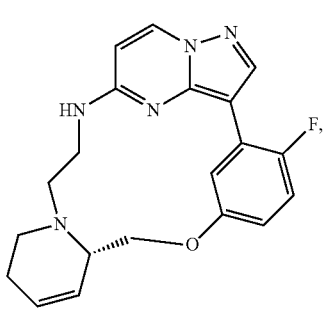
Example N41
Compound N42
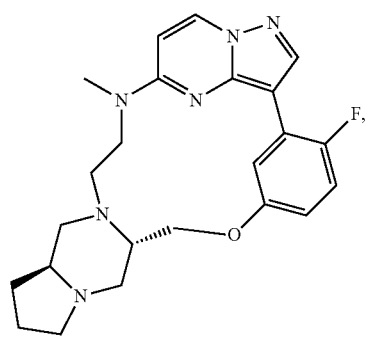
Example N42
Compound N43
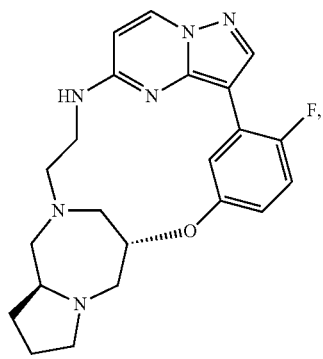
Example N43
Compound N44
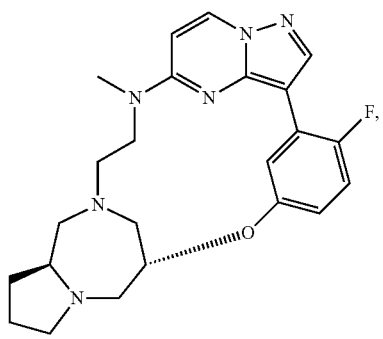
Example N44
Compound N45
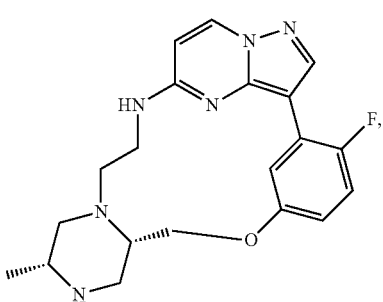
Example N45

Compound N46
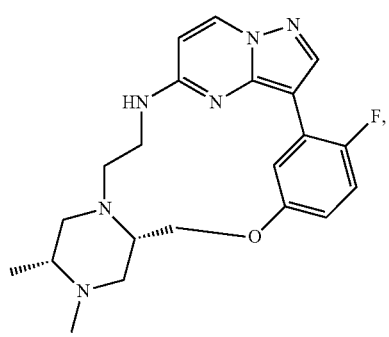
Example N46
Compound N47
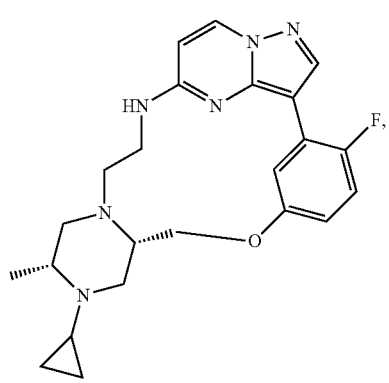
Example N47
Compound N48
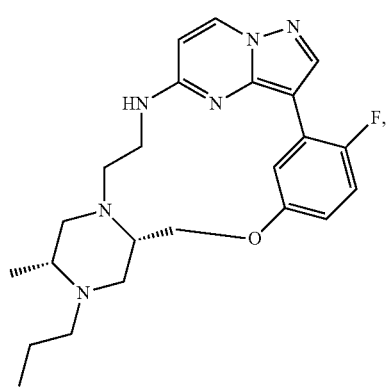
Example N48
Compound N49
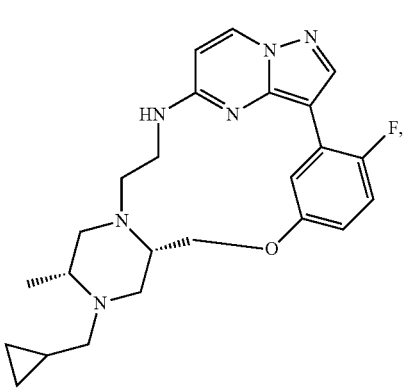
Example N49
Compound N50
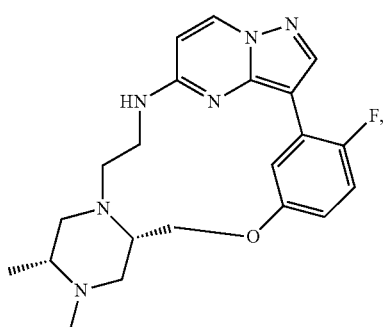
Example N50
Compound N51
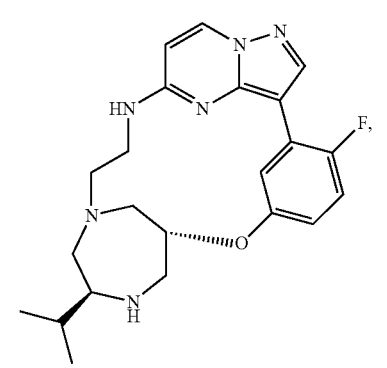
Example N51
Compound N52
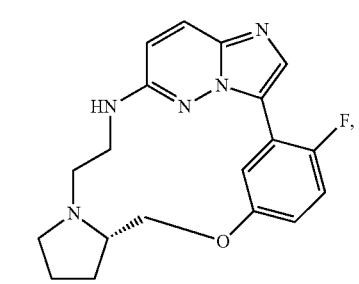
Example N52
Compound N53
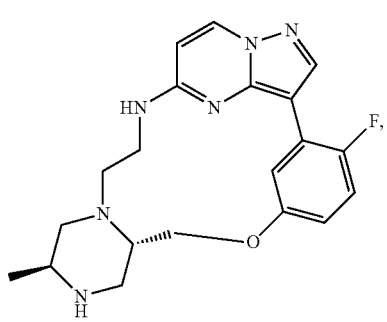
Example N53

Compound N54
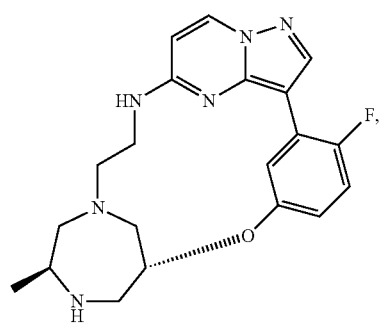
Example N54
Compound N55
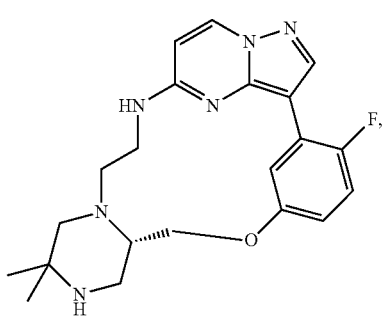
Example N55
Compound N56
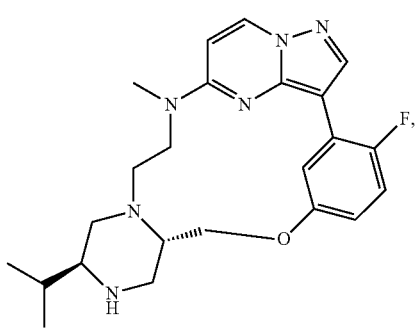
Example N56
Compound N57
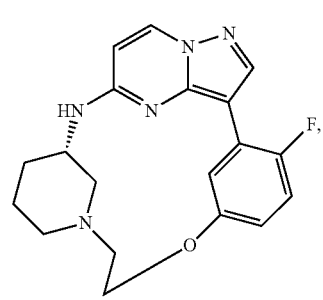
Example N57
Compound N58
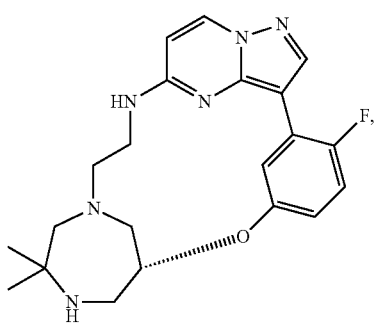
Example N58
Compound N59
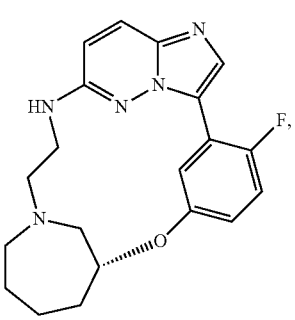
Example N59
Compound N60
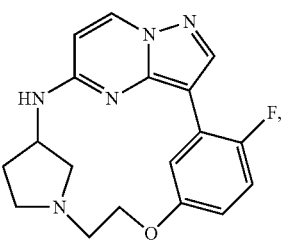
Example N60
Compound N61
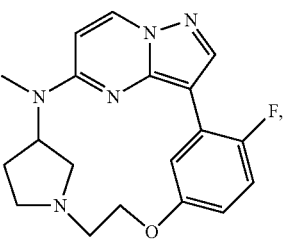
Example N61

Compound N62
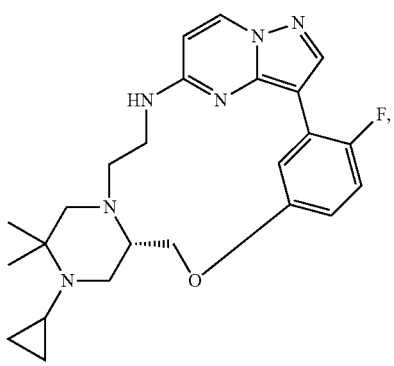
Example N62
Compound N63
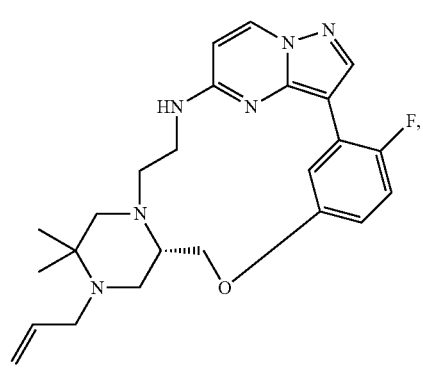
Example N63
More in particular the present invention provides a compound selected from the list comprising:
Compound N46
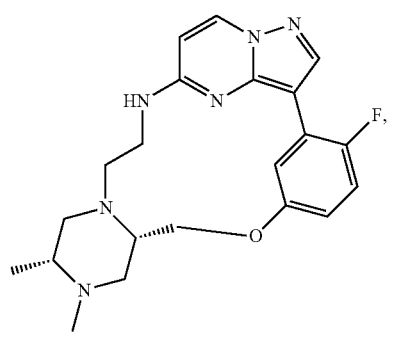
Example N46
Compound N47
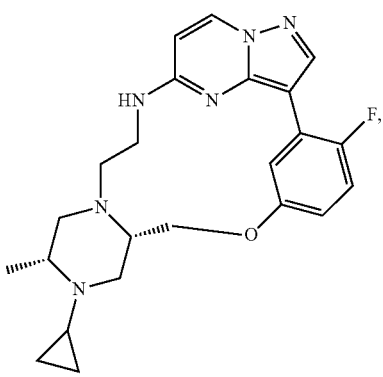
Example N47
Compound N48
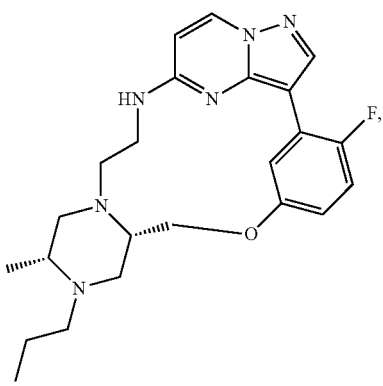
Example N48
Compound N49
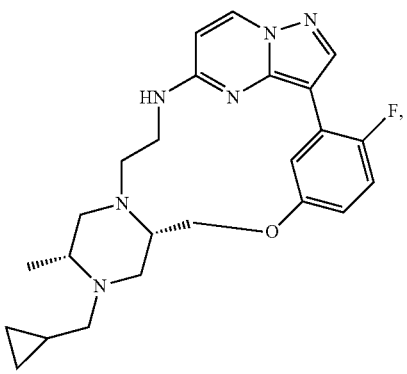
Example N49

Compound N43
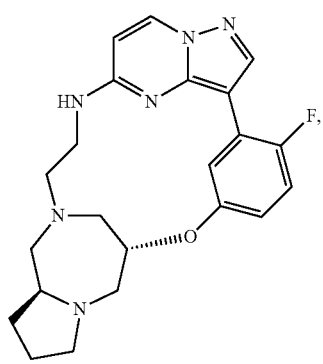
Example N43
Compound N45
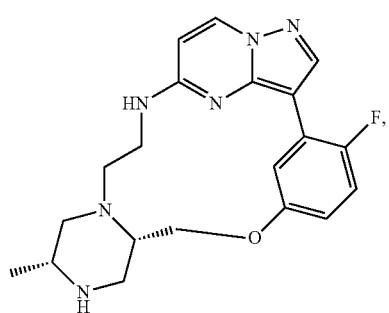
Compound N50
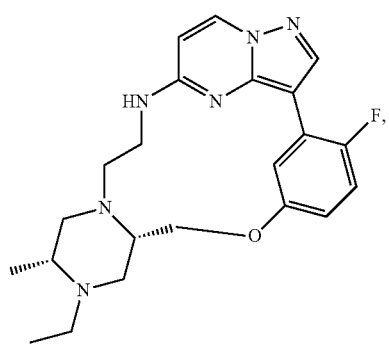
Compound N27
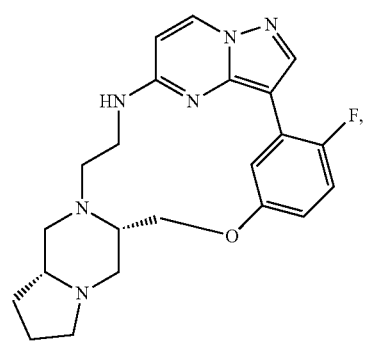
Example N27
Compound N44
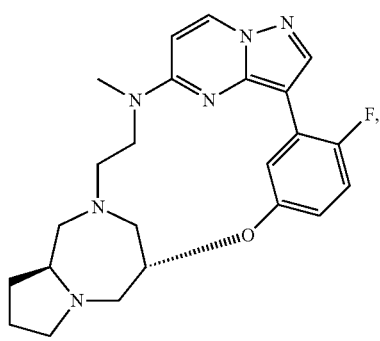
Example N44
Compound N59
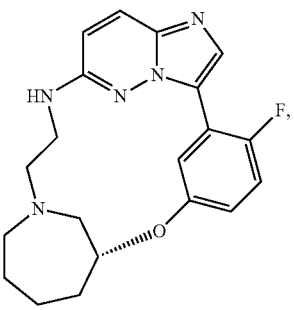
Example N59
Compound N60
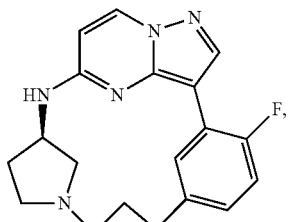
Example N60
Compound N62
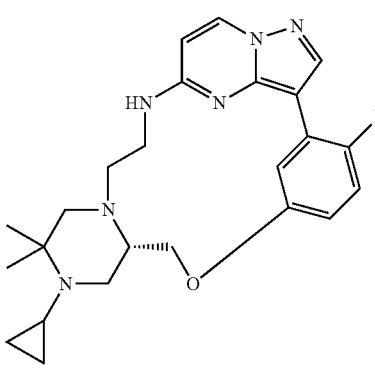, and
Example N62

-continued
Compound N63
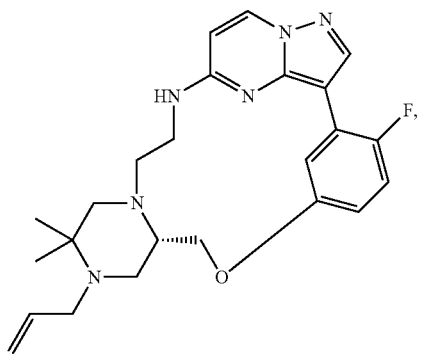
Example N63
More in particular the present invention provides a compound selected from the list comprising:
Compound N27
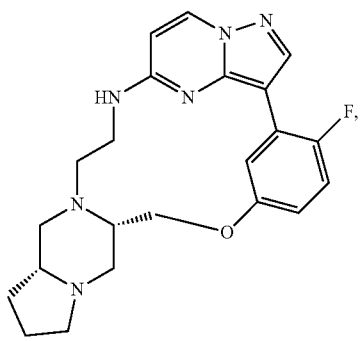
Example N27
Compound N43
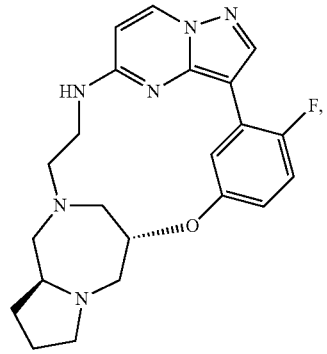
Example N43
Compound N44
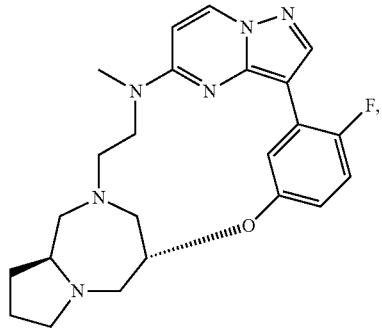
Example N44
-continued
Compound N45
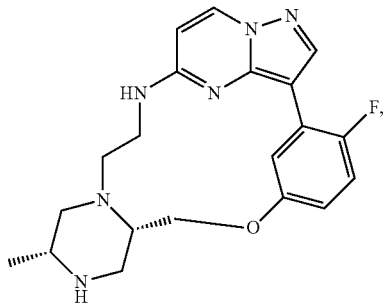
Example N45
Compound N59
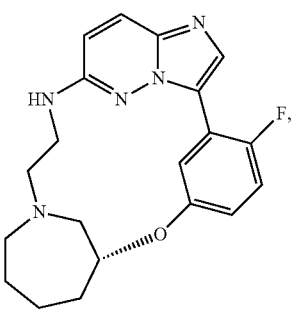
Example N59
Compound N60
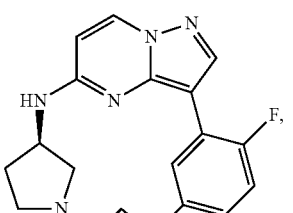
Example N60
Compound N62
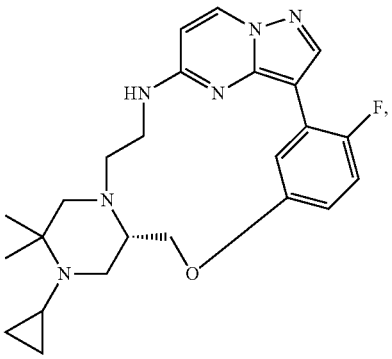
Example N62

Compound N63

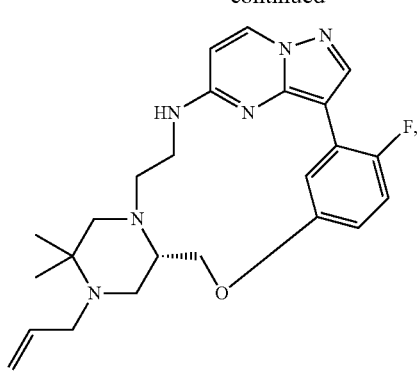

Example N63

More in particular the present invention provides a compound selected from the list comprising:

Compound N60

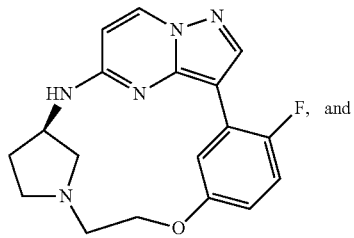

Example N60

Compound N45

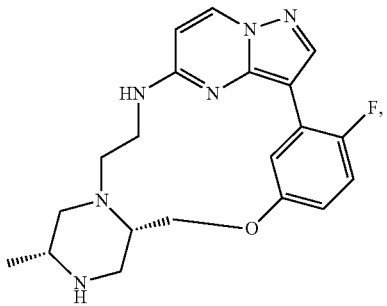

Example N45

In a further particular embodiment, the present invention provides a compound according to this invention, wherein $R_5$ is linked to the aryl or heteroaryl moiety at position $Z_1$ in accordance with the numbering as provided in Formula I or Ia.

In yet a further particular embodiment, the present invention provides a compound according to this invention, wherein said compound is the S-enantiomer.

In yet a further particular embodiment, the present invention provides a compound according to this invention, wherein said compound is the R-enantiomer.

It is a further object of the present invention to provide (pharmaceutical) compositions comprising a compound according to this invention. In particular, the compounds and compositions according to this invention are suitable for use as a human or veterinary medicine. The compounds and compositions according to this invention are suitable for inhibiting the activity of a kinase, in particular LRRK2 kinase, and may be used for the treatment and/or prevention of neurological disorders such as Alzheimer's disease or Parkinson's disease.

In a final objective, the present invention provides a method for the prevention and/or treatment of a neurological disorder, such as Alzheimer's disease or Parkinson's disease; said method comprising administering to a subject in need thereof a compound or a composition according to this invention.

Alternatively, the present invention provides a compound of Formula I or a stereoisomer, tautomer, racemic, metabolite, pro- or predrug, salt, hydrate, N-oxide form, or solvate thereof,

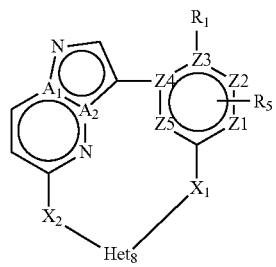

I

Wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$ are each independently selected from —H, —$C_{1-6}$alkyl, —$C_{3-6}$cycloalkyl and -Het$_2$:

$R_{37}$ and $R_{38}$ are each independently selected from —H, -halo, —OH, —$C_{1-6}$alkyl, —O—$C_{1-6}$alkyl, —S—$C_{1-6}$alkyl, —$C_{3-6}$cycloalkyl, —Ar$_7$ and -Het$_7$;

$X_1$ is selected from —$C_{1-6}$alkyl-, —O—$C_{1-6}$alkyl-, —S—$C_{1-6}$alkyl-, —$C_{1-6}$alkyl-NR$_3$—$C_{1-6}$alkyl-, —NR$_3$—$C_{1-6}$alkyl-, —NR$_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —NR$_{33}$R$_{34}$;

$X_2$ is selected from —$C_{1-6}$alkyl-, —O—$C_{1-6}$alkyl-, —S—$C_{1-6}$alkyl-, —$C_{1-6}$alkyl-NR$_2$—$C_{1-6}$alkyl-, —NR$_2$—$C_{1-6}$alkyl-, —NR$_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3-halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Het$_8$ is a 3- to 10-membered heterocycle having from 1 to 3 heteroatoms selected from O, N and S;
    wherein said Het$_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —NR$_{21}$R$_{22}$; wherein each of said —$C_{1-6}$alkyl is optionally and independently substituted with from 1 to 3 -halo;
    wherein when $R_1$—H, then at least one heteroatom of Het$_8$ is attached to $X_2$ $Z_1$, $Z_2$, $Z_3$, $Z_4$ and $Z_5$ are each independently selected from C and N; and $A_1$ and $A_2$ are each independently selected from C and N.

In particular, the present invention provides a compound of Formula I or a stereoisomer, tautomer, racemic, metabolite, pro- or predrug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —$C_{3-6}$cycloalkyl, —O—$C_{3-6}$cycloalkyl, —Ar$_1$ and -Het$_1$; wherein each of said —$C_{1-6}$alkyl is optionally and independently substituted with from 1 to 3 substituents selected from -halo, —OR$_{35}$, —NR$_{11}$R$_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —OH, —$C_{1-6}$alkyl, —O—$C_{1-6}$alkyl, —S—$C_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —$C_{3-6}$cycloalkyl, —O—$C_{3-6}$cycloalkyl, —Ar$_5$ and -Het$_5$; wherein each of said —$C_{1-6}$alkyl is optionally and independently substituted with from 1 to 3 substituents selected from -halo, —OR$_{36}$, —NR$_{23}$R$_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —OR$_{27}$, and —NR$_{13}$R$_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —OR$_{28}$, and —NR$_{15}$R$_{16}$;

$R_4$ and $R_8$ are each independently selected from -halo, —OH, —$C_{1-6}$alkyl, —O—$C_{1-6}$alkyl, —S—$C_{1-6}$alkyl, —NR$_{17}$R$_{18}$, —$C_{3-6}$cycloalkyl, —O—$C_{3-6}$cycloalkyl, —Ar$_4$ and -Het$_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —Ar$_6$ and -Het$_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -Het$_6$, —Ar$_6$ and —NR$_{37}$R$_{38}$;

$R_{27}$ and $R_{28}$, are each independently selected from —H, —$C_{1-6}$alkyl, —$C_{3-6}$cycloalkyl and -Het$_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —Ar$_7$ and -Het$_7$;

$X_1$ is selected from —$C_{1-6}$alkyl-, —O—$C_{1-6}$alkyl-, —S—$C_{1-6}$alkyl-, —$C_{1-6}$alkyl-NR$_3$—$C_{1-6}$alkyl-, —NR$_3$—$C_{1-6}$alkyl-, and —NR$_3$—;

$X_2$ is selected from —O—$C_{2-3}$alkyl-, —S—$C_{2-3}$alkyl-, —NR$_2$—$C_{2-3}$alkyl-, —NR$_2$—, and —O—;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Het$_8$ is a 3- to 10-membered heterocycle having from 1 to 3 heteroatoms selected from O, N and S;
    wherein said Het$_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —NR$_{21}$R$_{22}$; wherein each of said —$C_{1-6}$alkyl is optionally and independently substituted with from 1 to 3 -halo;
    wherein when $R_1$ is —H, then at least one heteroatom of Het$_8$ is attached to $X_2$ $Z_1$, $Z_2$, $Z_3$, $Z_4$ and $Z_5$ are each independently selected from C and N; and $A_1$ and $A_2$ are each independently selected from C and N.

More in particular the present invention provides a compound of Formula I or a stereoisomer, tautomer, racemic, metabolite, pro- or predrug, salt, hydrate, N-oxide form, or solvate thereof, wherein, $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$;
    wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —O—$C_{3-6}$cycloalkyl, —$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$ $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a bivalent 3- to 10-membered heterocycle having from 1 to 3 heteroatoms selected from O, N and S;
    wherein at least one of said heteroatoms is attached to $X_1$ or $X_2$;
    wherein when $R_1$ is —H, then at least one heteroatom of $Het_8$ is attached to $X_2$; and
    wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and $A_1$ and $A_2$ are each independently selected from C and N.

More in particular the present invention provides a compound of Formula Ia or a stereoisomer, tautomer, racemic, metabolite, pro- or predrug, salt, hydrate, N-oxide form, or solvate thereof,

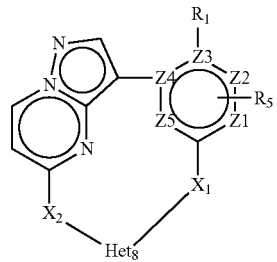

Ia

Wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_2$ $Z_1$, $Z_2$, $Z_3$, $Z_4$ and $Z_5$ are each independently selected from C and N.

More in particular the present invention provides a compound of Formula Ia or a stereoisomer, tautomer, racemic, metabolite, pro- or predrug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, and —$NR_3$—;

$X_2$ is selected from —O—$C_{2-3}$alkyl-, —S—$C_{2-3}$alkyl-, —$NR_2$—$C_{2-3}$alkyl-, —$NR_2$—, and —O—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —C$_{1-6}$alkyl, —O—C$_{1-6}$alkyl, —S—C$_{1-6}$alkyl, —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;
wherein when R$_1$ is —H, then at least one heteroatom of Het$_8$ is attached to X$_2$ Z$_1$, Z$_2$, Z$_3$, Z$_4$ and Z$_5$ are each independently selected from C and N.

In a further embodiment, the present invention provides a compound of Formula Ia or a stereoisomer, tautomer, racemic, metabolite, pro- or predrug, salt, hydrate, N-oxide form, or solvate thereof, wherein R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$;
wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_6$, R$_7$, R$_9$, R$_{10}$, R$_{11}$, R$_{12}$, R$_{13}$, R$_{14}$, R$_{15}$, R$_{16}$, R$_{19}$, R$_{20}$, R$_{21}$, R$_{22}$, R$_{31}$, R$_{32}$, R$_{33}$ and R$_{34}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
wherein at least one of said heteroatoms is attached to X$_1$ or X$_2$;
wherein when R$_1$ is —H, then at least one heteroatom of Het$_8$ is attached to X$_2$; and
wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N.

In a further embodiment, the present invention provides a compound of Formula Ia or a stereoisomer, tautomer, racemic, metabolite, pro- or predrug, salt, hydrate, N-oxide form, or solvate thereof, wherein each of said Z$_1$, Z$_2$, Z$_3$, Z$_4$ and Z$_5$ is C; and wherein the further definitions and provisions as defined herein above apply.

In a further embodiment, the present invention provides a compound of Formula Ia or a stereoisomer, tautomer, racemic, metabolite, pro- or predrug, salt, hydrate, N-oxide form, or solvate thereof, wherein said Het$_8$ is a saturated 3- to 10-membered heterocycle having from 1 to 3 heteroatoms selected from O, N and S; and wherein the further definitions and provisions as defined herein above apply.

In a further embodiment, the present invention provides a compound of Formula Ia or a stereoisomer, tautomer, racemic, metabolite, pro- or predrug, salt, hydrate, N-oxide form, or solvate thereof

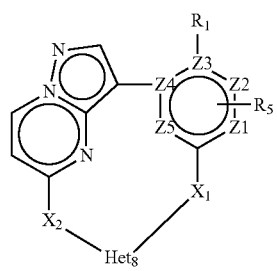

Ia

Wherein $R_1$ is -halo;
$R_5$ is attached to $Z_1$ and is selected from —H and —$C_{1-6}$alkyl;
$R_2$ is selected from —H and —$C_{1-6}$alkyl;
$R_3$ is selected from —H and —$C_{1-6}$alkyl;
$X_1$ is selected from —O—$C_{1-6}$alkyl-, —$NR_3$—$C_{1-6}$alkyl-, —$NR_3$—, —O—;
$X_2$ is selected from —O—$C_{1-6}$alkyl-, —$NR_2$—$C_{1-6}$alkyl-, —$NR_2$—, —O—;
$Het_8$ is a 3- to 10-membered N-containing heterocycle; wherein said $Het_8$ is optionally substituted with 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; and
$Z_1$, $Z_2$, $Z_3$, $Z_4$ and $Z_5$ are each C.

More in particular the present invention provides a compound selected from the list comprising:

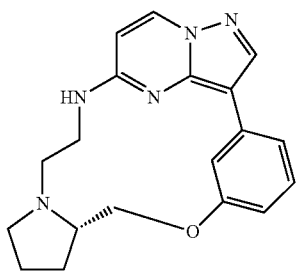

Example N1

Compound N1

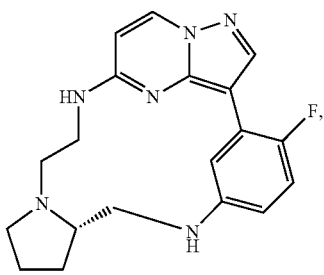

Example N2

Compound N2

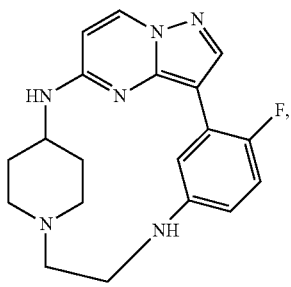

Example N3

Compound N3

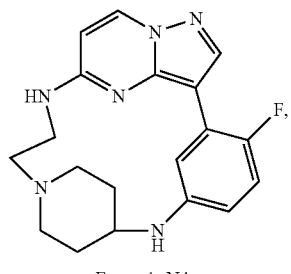

Example N4

Compound N4

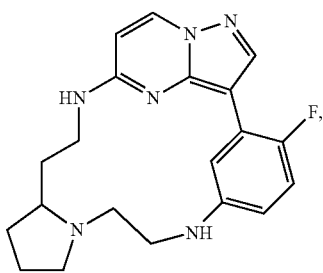

Example N5

Compound N5

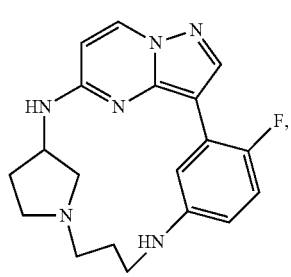

Example N6

Compound N6

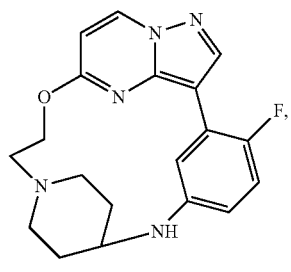

Example N7

Compound N7

-continued

Compound N8

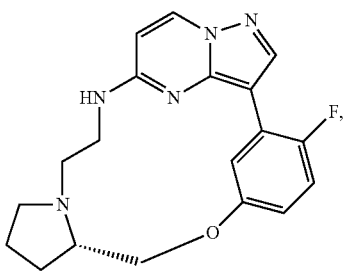

Example N8

Compound N9

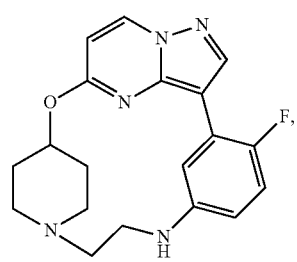

Example N9

Compound N10

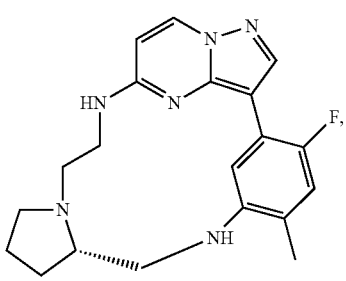

Example N10

Compound N11

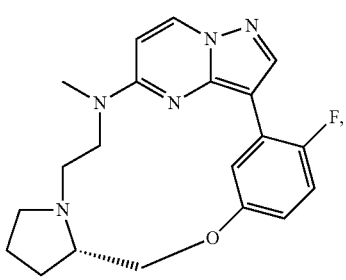

Example N11

Compound N12

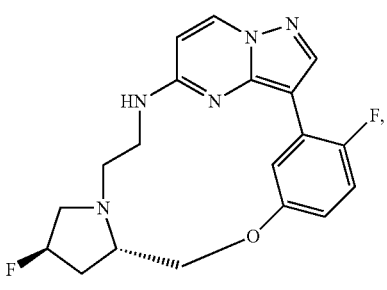

Example N12

-continued

Compound N13

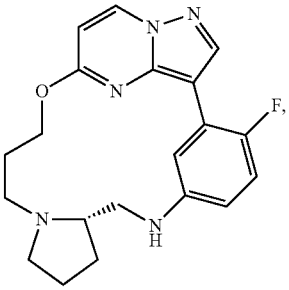

Example N13

Compound N14

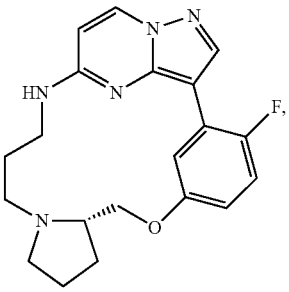

Example N14

Compound N15

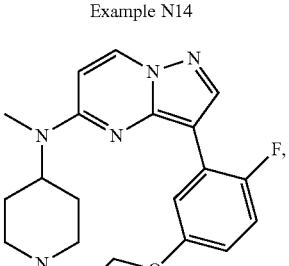

Example N15

In a further particular embodiment, the present invention provides a compound according to this invention, wherein $R_5$ is linked to the aryl or heteroaryl moiety at position $Z_1$ in accordance with the numbering as provided in Formula I or Ia.

In yet a further particular embodiment, the present invention provides a compound according to this invention, wherein said compound is the S-enantiomer.

In yet a further particular embodiment, the present invention provides a compound according to this invention, wherein said compound is the R-enantiomer.

It is a further object of the present invention to provide (pharmaceutical) compositions comprising a compound according to this invention. In particular, the compounds and compositions according to this invention are suitable for use as a human or veterinary medicine.

The compounds and compositions according to this invention are suitable for inhibiting the activity of a kinase, in particular LRRK2 kinase, and may be used for the treatment and/or prevention of neurological disorders such as Alzheimer's disease or Parkinson's disease.

In a final objective, the present invention provides a method for the prevention and/or treatment of a neurological disorder, such as Alzheimer's disease or Parkinson's disease; said method comprising administering to a subject in need thereof a compound or a composition according to this invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula I or a stereoisomer, tautomer, racemic, metabolite, pro- or pre-drug, salt, hydrate, N-oxide form, or solvate thereof

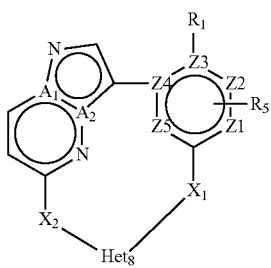

I

Wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$ are each independently selected from —H, —$C_{1-6}$alkyl, —$C_{3-6}$cycloalkyl and -$Het_2$:

$R_{37}$ and $R_{38}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;
wherein when $R_1$—H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

Unless indicated otherwise, all of the above radicals can be read both ways. For example, when $X_1$ is —$NR_3$—$C_{1-6}$alkyl-, the —$C_{1-6}$alkyl- may be attached to $Het_8$ and —$NR_3$— attached to the $Z_1$-$Z_5$ aryl or heteroaryl moiety. Alternatively, the —$C_{1-6}$alkyl- may be attached to the $Z_1$-$Z_5$ aryl or heteroaryl moiety and —NR₃— attached to Het₈. What is called "left part" of a radical is for example when X₁ is —NR₃—C₁₋₆alkyl-, —NR₃—, and the "right part" is —C₁₋₆alkyl-.

Preferably, X₁ is such as the left part of the possible values of X₁ (i.e. in particular —O from —O—C₁₋₆alkyl, —S from —S—C₁₋₆alkyl, —NR₃ from —NR₃—C₁₋₆alkyl, etc) is attached to the Z₁-Z₅ aryl or heteroaryl moiety. Alternatively, X₁ is such as the right part of the possible values of X₁ (i.e. in particular (C₁₋₆alkyl)- from —O—C₁₋₆alkyl, —S—C₁₋₆alkyl and —NR₃—C₁₋₆alkyl, etc) is attached to the Z₁-Z₅ aryl or heteroaryl moiety.

Preferably, X₂ is such as the left part of the possible values of X₂ (i.e. in particular —O from —O—C₁₋₆alkyl, —S from —S—C₁₋₆alkyl, —NR₂ from —NR₂—C₁₋₆alkyl, etc) is attached to the pyrazolopyrimidine moiety. Alternatively, X₂ is such as the right part of the possible values of X₂ (i.e. in particular (C₁₋₆alkyl)- from —O—C₁₋₆alkyl, —S—C₁₋₆alkyl and —NR₂—C₁₋₆alkyl, etc) is attached to the pyrazolopyrimidine moiety.

The same principle applies to all the radicals of the invention unless specified otherwise.

When describing the compounds of the invention, the terms used are to be construed in accordance with the following definitions, unless a context dictates otherwise:

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, C₁₋₆alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. C₁—C₆ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopropyl, cyclobutyl, cyclopentyl, and cyclohexyl.

The term "optionally substituted alkyl" refers to an alkyl group optionally substituted with one or more substituents (for example 1 to 3 substituents, for example 1, 2 or 3 substituents or 1 to 2 substituents) at any available point of attachment. Non-limiting examples of such substituents include -halo, —OH, primary and secondary amides, —O—C₁₋₆alkyl, —S—C₁₋₆alkyl, heteroaryl, aryl, and the like.

The term "cycloalkyl" by itself or as part of another substituent is a cyclic alkyl group, that is to say, a monovalent, saturated, or unsaturated hydrocarbyl group having a cyclic structure. Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms. Examples of cycloalkyl groups include but are not limited to cyclopropyl, cyclobutyl, cyclopentyl, cyclohexyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom. To illustrate this applying the asterisk nomenclature of this invention, a C₃ alkylene group may be for example *—CH₂CH₂CH₂—*, *—CH(—CH₂CH₃)—*, or *—CH₂CH(—CH₃)—*. Likewise a C₃ cycloalkylene group may be

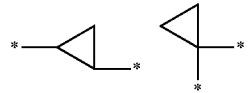

The terms "heterocycle" as used herein by itself or as part of another group refer to non-aromatic, fully saturated or partially unsaturated cyclic groups (for example, 3 to 6 membered monocyclic ring systems) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro- 2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, pyrrolopiperazinyl, 3-azabicyclo[3.1.0]hexanyl, 2-azabicyclo[3.1.0]hexanyl, 2-azabicyclo[2.2.1]heptanyl, octahydropyrrolo[1,2-a]pyrazinyl, octahydro-1H-pyrrolo[1,2-a]pyrazinyl, 3,4-dihydro-2H-benzo[6][1,4]oxazinyl, 2-oxa-5-azabicyclo[4.1.0]heptanyl, 1,4-oxazepanyl, and tetrahydrofuranyl.

The term "aryl" as used herein refers to a polyunsaturated, aromatic hydrocarbyl group having a single ring (i.e. phenyl). Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4- dihydronaphthyl, dibenzo[a,d]cycloheptenyl, and 1-, 2-, 3-, 4-, or 5-pyrenyl; in particular phenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment, selected from those defined above for substituted alkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 6 carbon-atom aromatic rings in which one or more carbon atoms can be replaced by oxygen, nitrogen or sulfur atoms. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted alkyl.

The term "halo" or "halogen" as a group or part of a group is generic for fluoro, chloro, bromo, or iodo, as well as any suitable isotope thereof.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent.

Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

In addition, the invention includes isotopically-labelled compounds and salts, which are identical to compounds of formula (I), but for the fact that one or more atoms are replaced by an atom having an atomic mass or mass number different from the atomic mass or mass number most commonly found in nature. Examples of isotopes that can be incorporated into compounds of formula (I) are isotopes of hydrogen, carbon, nitrogen, fluorine, such as $^3$H, $^{11}$C, $^{13}$N, $^{14}$C, $^{15}$O and $^{18}$F. Such isotopically-labelled compounds of formula (I) are useful in drug and/or substrate tissue distribution assays. For example $^{11}$C and $^{18}$F isotopes are particularly useful in PET (Positron Emission Tomography). PET is useful in brain imaging. Isotopically labeled compounds of formula (I) can generally be prepared by carrying out the procedures disclosed below, by substituting a readily available non-isotopically labeled reagent with an isotopically labeled reagent.

Whenever used in the present invention the term "compounds of the invention" or a similar term is meant to include the compounds of general Formula I and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

Preferably, compounds of Formula I are defined as such that $A_1$ and $A_2$ are selected from C and N; wherein when $A_1$ is C, then $A_2$ is N; and wherein when $A_2$ is C, then $A_1$ is N; More preferably, $A_1$ is N and $A_2$ is C. Alternatively, $A_2$ is N and $A_1$ is C;

Preferably, $R_1$ is selected from —H, -halo, —OH, —$C_{1-6}$alkyl, —O—$C_{1-6}$alkyl, —S—$C_{1-6}$alkyl, —$NR_9R_{10}$, —(C═O)—$R_4$, —(C═S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and —$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl.

More preferably, $R_1$ is selected from —H, -halo, and —$C_{1-6}$alkyl; wherein each of said $C_{1-6}$alkyl is optionally and independently substituted with from 1 to 3 -halo or —$C_{1-6}$alkyl. More preferably $R_1$ is -halo, even more preferably $R_1$ is —F.

Preferably, $R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C═O)—$R_8$, —(C═S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl.

More preferably, R$_5$ is selected from —H, -halo, and —C$_{1-6}$alkyl; wherein each of said C$_{1-6}$alkyl is optionally and independently substituted with from 1 to 3 -halo, or —C$_{1-6}$alkyl. More preferably R$_5$ is selected from —H, —F, and a methyl group. Even more preferably, R$_5$ is —H.

Preferably R$_5$ is attached to Z$_1$.

Preferably, R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$.

More preferably, R$_2$ is selected from —H and —C$_{1-6}$alkyl; more preferably R$_2$ is selected from —H and a methyl group. Preferably, R$_2$ is —H. Alternatively, R$_2$ is a methyl group.

Preferably, R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$.

More preferably, R$_3$ is selected from —H and —C$_{1-6}$alkyl; more preferably R$_3$ is selected from —H and a methyl group. Preferably, R$_3$ is —H. Alternatively, R$_3$ is a methyl group.

Preferably, R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$.

More preferably, R$_4$ is selected from -halo, —OH, or —C$_{1-6}$alkyl; and R$_8$ is selected from -halo, —OH, or —C$_{1-6}$alkyl.

Preferably, R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$, R$_{34}$, R$_{35}$ and R$_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$.

More preferably R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$, R$_{34}$, R$_{35}$ and R$_{36}$ are each independently selected from —H, and —C$_{1-6}$alkyl, Preferably, R$_{27}$ and R$_{28}$, are each independently selected from —H, —C$_{1-6}$alkyl, —C$_{3-6}$cycloalkyl and Het$_2$.

More preferably, R$_{27}$ and R$_{28}$ are each independently selected from —H and —C$_{1-6}$alkyl, more preferably R$_{27}$ and R$_{28}$ are both —H.

Preferably, R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$.

More preferably, R$_{37}$ and R$_{38}$ are each independently selected from —H and —C$_{1-6}$alkyl.

Preferably, X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$.

More preferably, X$_1$ is selected from —O—C$_{1-6}$alkyl-, NR$_3$—C$_{1-6}$alkyl-, —NR$_3$—, —O—; wherein each of said C$_{1-6}$alkyl is optionally and independently substituted with from 1 to 3 -halo, —OH, and —C$_{1-6}$alkyl.

Preferably, X$_2$ is selected from —C$_{1-6}$alkyl-, —O—C$_{1-6}$alkyl-, —S—C$_{1-6}$alkyl-, —C$_{1-6}$alkyl-NR$_2$—C$_{1-6}$alkyl-, —NR$_2$—C$_{1-6}$alkyl-, —NR$_2$—, —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$.

More preferably, X$_2$ is selected from —O—C$_{1-6}$alkyl-, NR$_2$—C$_{1-6}$alkyl-, —NR$_2$—, —O—; wherein each of said C$_{1-6}$alkyl is optionally and independently substituted with from 1 to 3 -halo, —OH, and —C$_{1-6}$alkyl.

Preferably, Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, —NR$_{19}$R$_{20}$; wherein each of said —C$_{1-6}$alkyl is optionally and independently substituted with from 1 to 3 -halo.

More preferably, Ar$_1$, Ar$_4$, Ar$_5$, Ar$_6$, and Ar$_7$ are each independently selected from a 5- to 6-membered aromatic cycle optionally comprising 1 or 2 N atoms.

Preferably, Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo.

More preferably, Het$_1$, Het$_2$, Het$_4$, Het$_5$, Het$_6$, and Het$_7$ are each independently selected from a 3- to 6-membered heterocycle having from 1 to 3 N atoms.

Preferably, Het$_8$ is a 3- to 10-membered heterocycle having from 1 to 3 heteroatoms selected from O, N and S; wherein said Het$_8$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;

wherein when R$_1$ is —H, then at least one heteroatom of Het$_8$ is attached to X$_2$ More preferably, Het$_8$ is a 3- to 10-membered heterocycle having from 1 to 3 heteroatoms selected from O, N and S; wherein said Het$_8$ is optionally and independently substituted with from 1 to 3 substituents selected from -halo, —C$_{1-6}$alkyl, —O—C$_{1-6}$alkyl, =O; wherein each of said —C$_{1-6}$alkyl is optionally and independently substituted with from 1 to 3 -halo;

wherein when R$_1$ is —H, then at least one heteroatom of Het$_8$ is attached to X$_2$ More preferably, Het$_8$ is selected from piperazinyl, piperidinyl, pyrrolidinyl, pyrrolopiperazinyl, 3-azabicyclo[3.1.0]hexanyl, 2-azabicyclo[3.1.0]hexanyl, 2-azabicyclo[2.2.1]heptanyl, octahydropyrrolo[1,2-a]pyrazinyl, octahydro-1H-pyrrolo[1,2-a]pyrazinyl, tetrahydroquinolinyl, tetrahydroisoquinolinyl, morpholinyl, 3,4-dihydro-2H-benzo[6][1,4]oxazinyl, 2-oxa-5-azabicyclo[4.1.0]

heptanyl, 1,4-oxazepanyl, homopiperazinyl. Even more preferably, Het$_8$ is selected from pyrrolidinyl, piperazinyl, and piperidinyl.
Very preferably, Het8 is selected from

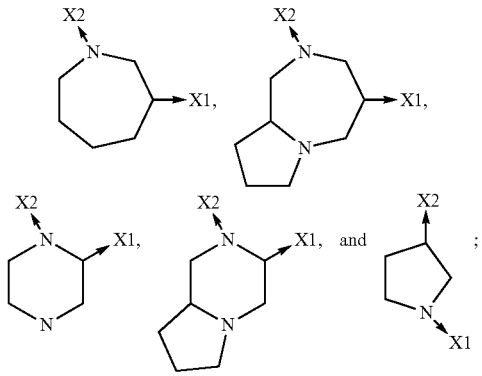

wherein when $R_1$ is —H, then at least one heteroatom of Het$_8$ is attached to $X_2$ More preferably, Het8 is selected from or

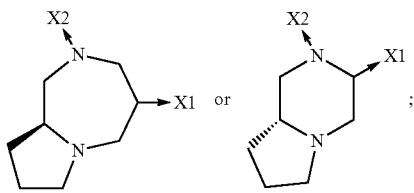

wherein when $R_1$ is —H, then at least one heteroatom of Het$_8$ is attached to $X_2$
Even more preferably Het8 is selected from

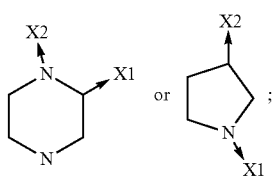

wherein when $R_1$ is —H, then at least one heteroatom of Het$_8$ is attached to $X_2$
Even more preferably Het8 is

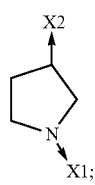

wherein when $R_1$ is —H, then at least one heteroatom of Het$_8$ is attached to $X_2$
In all the exemplified Het8 groups above and below, the arrows indicates the attachment point.

For example,

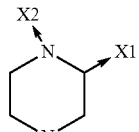

means that the nitrogen atom is directly attached to the $X_2$ group and the Carbon atom next to it is directly attached to the X1 group.
Preferably, $Z_1$, $Z_2$, $Z_3$, $Z_4$ and $Z_5$ are each independently selected from C and N.
More preferably, $Z_1$, $Z_2$, $Z_3$, $Z_4$ and $Z_5$ are each C.
In a particular embodiment, the present invention provides compounds of Formula I or a stereoisomer, tautomer, racemic, metabolite, pro- or predrug, salt, hydrate, N-oxide form, or solvate thereof

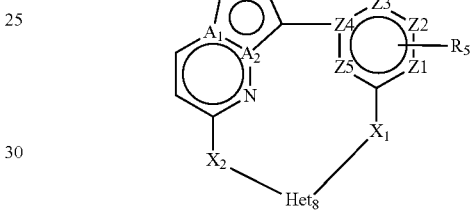

I

Wherein one or more of the following applies:
$R_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

$R_5$ is attached to $Z_1$ or $Z_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

$R_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

$R_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

$R_4$ and $R_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —C$_{1-6}$alkyl, —O—C$_{1-6}$alkyl, —S—C$_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$ are each independently selected from —H, —$C_{1-6}$alkyl, —$C_{3-6}$cycloalkyl and -$Het_2$:

$R_{37}$ and $R_{38}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;
wherein when $R_1$—H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

In particular, $X_1$, and $X_2$ as used herein, represent biradicals, which taken together with the radicals to which they are attached form a macrocyclic pyrazolopyrimidine compound. Said biradicals may be present in either of both directions in the macrocyclic pyrazolopyrimidine, but are preferably present in the direction as described below:

Referring to formula I:

$X_1$ is selected from the list comprising *—$C_{1-6}$alkyl-, *—O—$C_{1-6}$alkyl-, *—S—$C_{1-6}$alkyl-, *—$C_{1-6}$alkyl-$NR_3$—$C_{1-6}$alkyl-, *—$NR_3$—$C_{1-6}$alkyl-, *—$NR_3$—, *—O—; * wherein said biradical is preferably attached to the aryl or heteroaryl moiety via *;

$X_2$ is selected from the list comprising *—$C_{1-6}$alkyl-, *—O—$C_{1-6}$alkyl-, *—S—$C_{1-6}$alkyl-, *—$C_{1-6}$alkyl-$NR_2$—$C_{1-6}$alkyl-, *—$NR_2$—$C_{1-6}$alkyl-, *—$NR_2$—, *—O—; * wherein said biradical is preferably attached to the pyrazolopyrimidine moiety via *;

In a preferred embodiment, the present invention provides compounds of formula I or a stereoisomer, tautomer, racemic, metabolite, pro- or predrug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$— and —O—;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
  wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;
  wherein when $R_1$ is —H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

In a particular embodiment the present invention provides compounds of formula I or a stereoisomer, tautomer, racemic, metabolite, pro- or predrug, salt, hydrate, N-oxide form, or solvate thereof, wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —O—$C_{3-6}$cycloalkyl, —$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$ $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a bivalent 3- to 10-membered heterocycle having from 1 to 3 heteroatoms selected from O, N and S;
  wherein at least one of said heteroatoms is attached to $X_1$ or $X_2$;
  wherein when $R_1$ is —H, then at least one heteroatom of $Het_8$ is attached to $X_2$; and
  wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and $A_1$ and $A_2$ are each independently selected from C and N.

In a further particular embodiment the present invention provides compounds of formula Ia or a stereoisomer, tautomer, racemic, metabolite, pro- or predrug, salt, hydrate, N-oxide form, or solvate thereof,

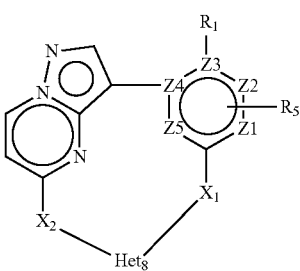

Ia

Wherein
R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$ R$_{34}$, R$_{35}$ and R$_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;
wherein when R$_1$ is —H, then at least one heteroatom of Het$_8$ is attached to X$_2$ Z$_1$, Z$_2$, Z$_3$, Z$_4$ and Z$_5$ are each independently selected from C and N.

Preferably, compounds of Formula Ia are defined as such that
A$_1$ and A$_2$ are selected from C and N; wherein when A$_1$ is C, then A$_2$ is N; and wherein when A$_2$ is C, then A$_1$ is N;
More preferably, A$_1$ is N and A$_2$ is C. Alternatively, A$_2$ is N and A$_1$ is C;
Preferably, R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and —Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl.
More preferably, R$_1$ is selected from —H, -halo, and —C$_{1-6}$alkyl; wherein each of said C$_{1-6}$alkyl is optionally and independently substituted with from 1 to 3 -halo or —C$_{1-6}$alkyl. More preferably R$_1$ is -halo, even more preferably R$_1$ is —F.

Preferably, R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl.

More preferably, $R_5$ is selected from —H, -halo, and —$C_{1-6}$alkyl; wherein each of said $C_{1-6}$alkyl is optionally and independently substituted with from 1 to 3 -halo, or —$C_{1-6}$alkyl. More preferably $R_5$ is selected from —H, —F, and a methyl group. Even more preferably, $R_5$ is —H.

Preferably $R_5$ is attached to $Z_1$.

Preferably, $R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$.

More preferably, $R_2$ is selected from —H and —$C_{1-6}$alkyl; more preferably $R_2$ is selected from —H and a methyl group. Preferably, $R_2$ is —H. Alternatively, $R_2$ is a methyl group.

Preferably, $R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$.

More preferably, $R_3$ is selected from —H and —$C_{1-6}$alkyl; more preferably $R_3$ is selected from —H and a methyl group. Preferably, $R_3$ is —H. Alternatively, $R_3$ is a methyl group.

Preferably, $R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$.

More preferably, $R_4$ is selected from -halo, —OH, or —$C_{1-6}$alkyl; and $R_8$ is selected from -halo, —OH, or —$C_{1-6}$alkyl.

Preferably, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$.

More preferably $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, and —$C_{1-6}$alkyl, Preferably, $R_{27}$ and $R_{28}$, are each independently selected from —H, —$C_{1-6}$alkyl, —$C_{3-6}$cycloalkyl and $Het_2$.

More preferably, $R_{27}$ and $R_{28}$ are each independently selected from —H and —$C_{1-6}$alkyl, more preferably $R_{27}$ and $R_{28}$ are both —H.

Preferably, $R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$.

More preferably, $R_{37}$ and $R_{38}$ are each independently selected from —H and —$C_{1-6}$alkyl.

Preferably, $X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$.

More preferably, $X_1$ is selected from —O—$C_{1-6}$alkyl-, $NR_3$—$C_{1-6}$alkyl-, —$NR_3$—, —O—; wherein each of said $C_{1-6}$alkyl is optionally and independently substituted with from 1 to 3 -halo, —OH, and —$C_{1-6}$alkyl.

Preferably, $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$.

More preferably, $X_2$ is selected from —O—$C_{1-6}$alkyl-, $NR_2$—$C_{1-6}$alkyl-, —$NR_2$—, —O—; wherein each of said $C_{1-6}$alkyl is optionally and independently substituted with from 1 to 3 -halo, —OH, and —$C_{1-6}$alkyl.

Preferably, $Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, —$NR_{19}R_{20}$; wherein each of said —$C_{1-6}$alkyl is optionally and independently substituted with from 1 to 3 -halo.

More preferably, $Ar_1$, $Ar_4$, $Ar_5$, $Ar_6$, and $Ar_7$ are each independently selected from a 5- to 6-membered aromatic cycle optionally comprising 1 or 2 N atoms.

Preferably, $Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo.

More preferably, $Het_1$, $Het_2$, $Het_4$, $Het_5$, $Het_6$, and $Het_7$ are each independently selected from a 3- to 6-membered heterocycle having from 1 to 3 N atoms.

Preferably, $Het_8$ is a 3- to 10-membered heterocycle having from 1 to 3 heteroatoms selected from O, N and S; wherein said $Het_8$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_2$ More preferably, $Het_8$ is selected from piperazinyl, piperidinyl, pyrrolidinyl, pyrrolopiperazinyl, 3-azabicyclo[3.1.0]hexanyl, 2-azabicyclo[3.1.0]hexanyl, 2-azabicyclo[2.2.1]heptanyl, octahydropyrrolo[1,2-a]pyrazinyl, octahydro-1H-pyrrolo[1,2-a]pyrazinyl, tetrahydroquinolinyl, tetrahydroisoquinolinyl, morpholinyl, 3,4-dihydro-2H-benzo[6][1,4]oxazinyl, 2-oxa-5-azabicyclo[4.1.0]heptanyl, 1,4-oxazepanyl, homopiperazinyl. Even more preferably, $Het_8$ is selected from pyrrolidinyl, piperazinyl, and piperidinyl;

wherein when $R_1$ is —H, then at least one heteroatom of $Het_8$ is attached to $X_2$ Very preferably, Het8 is selected from

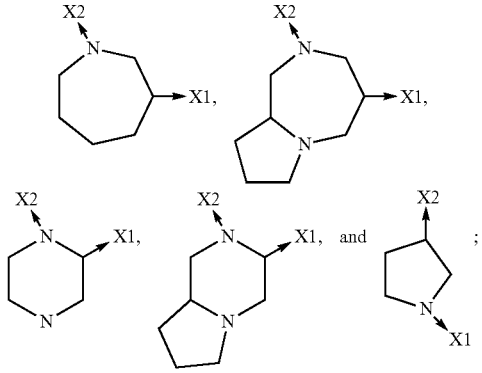

wherein when $R_1$ is —H, then at least one heteroatom of $Het_8$ is attached to $X_2$
More preferably, Het8 is selected from

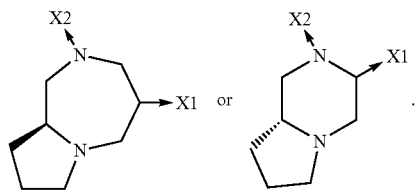

wherein when $R_1$ is —H, then at least one heteroatom of $Het_8$ is attached to $X_2$
Even more preferably Het8 is selected from

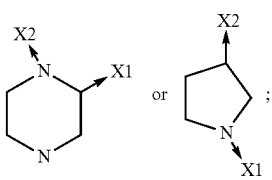

wherein when $R_1$ is —H, then at least one heteroatom of $Het_8$ is attached to $X_2$
Even more preferably Het8 is

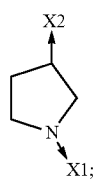

wherein when $R_1$ is —H, then at least one heteroatom of $Het_8$ is attached to $X_2$
Preferably, $Z_1$, $Z_2$, $Z_3$, $Z_4$ and $Z_5$ are each independently selected from C and N.
More preferably, $Z_1$, $Z_2$, $Z_3$, $Z_4$ and $Z_5$ are each C.
In a further particular embodiment the present invention provides compounds of formula Ia or a stereoisomer, tautomer, racemic, metabolite, pro- or predrug, salt, hydrate, N-oxide form, or solvate thereof,

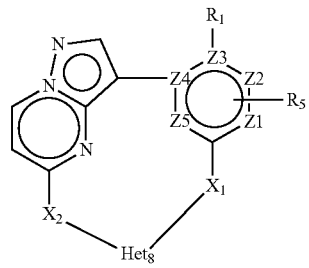

Wherein one or more of the following applies:
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-NR$_3$—$C_{1-6}$alkyl-, —NR$_2$—$C_{1-6}$alkyl-, —NR$_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3-halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —NR$_{21}$R$_{22}$; wherein each of said —$C_{1-6}$alkyl is optionally and independently substituted with from 1 to 3 -halo; wherein when R$_1$ is —H, then at least one heteroatom of Het$_8$ is attached to X$_2$ $Z_1$, $Z_2$, $Z_3$, $Z_4$ and $Z_5$ are each independently selected from C and N.

In another particular embodiment the present invention provides compounds of formula Ia or a stereoisomer, tautomer, racemic, metabolite, pro- or predrug, salt, hydrate, N-oxide form, or solvate thereof, wherein R$_1$ is selected from —H, -halo, —OH, —$C_{1-6}$alkyl, —O—$C_{1-6}$alkyl, —S—$C_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —$C_{3-6}$cycloalkyl, —O—$C_{3-6}$cycloalkyl, —Ar$_1$ and -Het$_1$; wherein each of said —$C_{1-6}$alkyl is optionally and independently substituted with from 1 to 3 substituents selected from -halo, —OR$_{35}$, —NR$_{11}$R$_{12}$, —O—$C_{1-6}$alkyl, and —S—$C_{1-6}$alkyl;

R$_5$ is attached to $Z_1$ or $Z_5$ and is selected from —H, -halo, —OH, —$C_{1-6}$alkyl, —O—$C_{1-6}$alkyl, —S—$C_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —$C_{3-6}$cycloalkyl, —O—$C_{3-6}$cycloalkyl, —Ar$_5$ and -Het$_5$; wherein each of said —$C_{1-6}$alkyl is optionally and independently substituted with from 1 to 3 substituents selected from -halo, —OR$_{36}$, —NR$_{23}$R$_{24}$, —O—$C_{1-6}$alkyl, and —S—$C_{1-6}$alkyl;

R$_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —$C_{1-6}$alkyl, —O—$C_{1-6}$alkyl, —S—$C_{1-6}$alkyl, —NR$_{17}$R$_{18}$, —$C_{3-6}$cycloalkyl, —O—$C_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$, R$_{34}$, R$_{35}$ and R$_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —Ar$_6$ and -Het$_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -Het$_6$, —Ar$_6$ and —NR$_{37}$R$_{38}$;

R$_{27}$ and R$_{28}$, are each independently selected from —H, —$C_{1-6}$alkyl, —$C_{3-6}$cycloalkyl and -Het$_2$:

R$_{37}$ and R$_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —Ar$_7$ and -Het$_7$;

$X_1$ is selected from —$C_{1-6}$alkyl-, —O—$C_{1-6}$alkyl-, —S—$C_{1-6}$alkyl-, —$C_{1-6}$alkyl-NR$_3$—$C_{1-6}$alkyl-, —NR$_3$—$C_{1-6}$alkyl-, —NR$_3$— and —O—;

$X_2$ is selected from —$C_{1-6}$alkyl-, —O—$C_{1-6}$alkyl-, —S—$C_{1-6}$alkyl-, —$C_{1-6}$alkyl-NR$_2$—$C_{1-6}$alkyl-, —NR$_2$—$C_{1-6}$alkyl-, —NR$_2$—, and —O—;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —$C_{1-6}$alkyl, —O—$C_{1-6}$alkyl, —S—$C_{1-6}$alkyl, —NR$_{19}$R$_{20}$; wherein each of said —$C_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —NR$_{21}$R$_{22}$; wherein each of said —$C_{1-6}$alkyl is optionally and independently substituted with from 1 to 3 -halo;
  wherein when R$_1$ is —H, then at least one heteroatom of Het$_8$ is attached to X$_2$ $Z_1$, $Z_2$, $Z_3$, $Z_4$ and $Z_5$ are each independently selected from C and N.

In another particular embodiment the present invention provides compounds of formula Ia or a stereoisomer, tautomer, racemic, metabolite, pro- or predrug, salt, hydrate, N-oxide form, or solvate thereof, wherein R$_1$ is selected from —H, -halo, —OH, —$C_{1-6}$alkyl, —O—$C_{1-6}$alkyl, —S—$C_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —$C_{3-6}$cycloalkyl, —O—$C_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

R$_6$, R$_7$, R$_9$, R$_{10}$, R$_{11}$, R$_{12}$, R$_{13}$, R$_{14}$, R$_{15}$, R$_{16}$, R$_{19}$, R$_{20}$, R$_{21}$, R$_{22}$, R$_{31}$, R$_{32}$, R$_{33}$ and R$_{34}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
wherein at least one of said heteroatoms is attached to X$_1$ or X$_2$;
wherein when R$_1$ is —H, then at least one heteroatom of Het$_8$ is attached to X$_2$; and
wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N.

In a specific embodiment the present invention provides a compound of formula Ia or a stereoisomer, tautomer, racemic, metabolite, pro- or predrug, salt, hydrate, N-oxide form, or solvate thereof as defined in anyone of claims 1 to 6, wherein each of said Z$_1$, Z$_2$, Z$_3$, Z$_4$ and Z$_5$ is C; and wherein the further definitions and provisions as defined herein above apply.

In a specific embodiment the present invention provides a compound of formula Ia or a stereoisomer, tautomer, racemic, metabolite, pro- or predrug, salt, hydrate, N-oxide form, or solvate thereof as defined in anyone of claims 1 to 7, wherein said Het$_8$ is a saturated 3- to 10-membered heterocycle having from 1 to 3 heteroatoms selected from O, N and S; and wherein the further definitions and provisions as defined herein above apply.

In a specific embodiment the present invention provides a compound of formula I or a stereoisomer, tautomer, racemic, metabolite, pro- or predrug, salt, hydrate, N-oxide form, or solvate thereof, wherein
A$_1$ and A$_2$ are each independently selected from C and N;
R$_1$ is selected from —H and -halo;
R$_5$ is selected from —H, -halo and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —C$_{1-6}$alkyl-, —O—C$_{1-6}$alkyl-, —NR$_2$—C$_{1-6}$alkyl-, —NR$_2$—, —O—;
Het$_8$ is a 3- to 10-membered heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, —C$_{1-6}$alkylC$_{3-6}$cycloalkyl, —(C=O)—C$_{1-6}$alkyl, and —(C=O)—C$_{3-6}$cycloalkyl; and
Z$_1$, Z$_2$, Z$_3$, Z$_4$ and Z$_5$ are each C.

More preferably,
A$_1$ and A$_2$ are each independently selected from C and N;
R$_1$ is selected from —H and -halo;
R$_5$ is selected from —H, -halo and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —O—C$_{1-6}$alkyl-, —NR$_2$—C$_{1-6}$alkyl-, —NR$_2$—, —O—;
Het$_8$ is a 3- to 10-membered heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, and —C$_{1-6}$alkylC$_{3-6}$cycloalkyl; and
Z$_1$, Z$_2$, Z$_3$, Z$_4$ and Z$_5$ are each C.

Even more preferably, A$_1$ is N and A$_2$ is C.

In a specific embodiment the present invention provides a compound of formula Ia or a stereoisomer, tautomer, racemic, metabolite, pro- or predrug, salt, hydrate, N-oxide form, or solvate thereof, wherein $R_1$ is selected from —H and -halo;
$R_5$ is attached to $Z_1$ and is selected from —H and —$C_{1-6}$alkyl;
$R_2$ is selected from —H and —$C_{1-6}$alkyl;
$R_3$ is selected from —H and —$C_{1-6}$alkyl;
$X_1$ is selected from —O—$C_{1-6}$alkyl-, —$NR_3$—$C_{1-6}$alkyl-, —$NR_3$—, —O—;
$X_2$ is selected from —O—$C_{1-6}$alkyl-, —$NR_2$—$C_{1-6}$alkyl-, —$NR_2$—, —O—;
$Het_8$ is a 3- to 10-membered N-containing heterocycle; wherein said $Het_8$ is optionally substituted with 1 to 3 substituents selected from -halo, —OH, —$C_{1-6}$alkyl, —$C_{1-6}$alkylene, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; and
$Z_1$, $Z_2$, $Z_3$, $Z_4$ and $Z_5$ are each C.

In yet another particular embodiment, the present invention provides a compound or a stereoisomer, tautomer, racemic, metabolite, pro- or predrug, salt, hydrate, N-oxide form, or solvate thereof, selected from the list comprising:

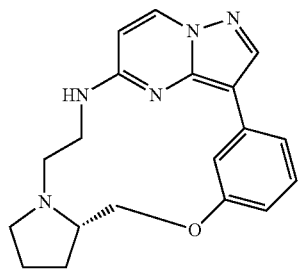

Example N1

Compound N1

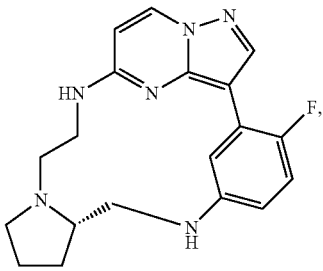

Example N2

Compound N2

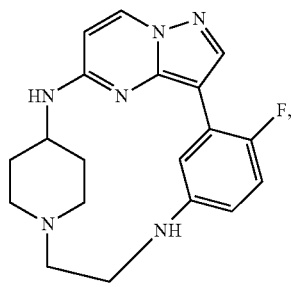

Example N3

Compound N3

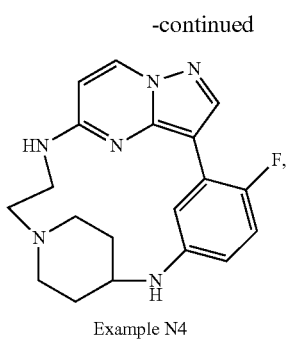

Example N4

Compound N4

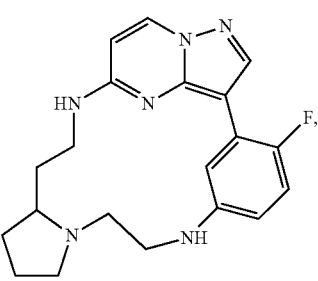

Example N5

Compound N5

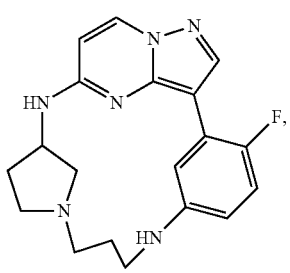

Example N6

Compound N6

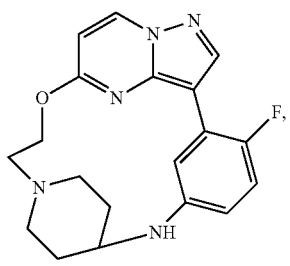

Example N7

Compound N7

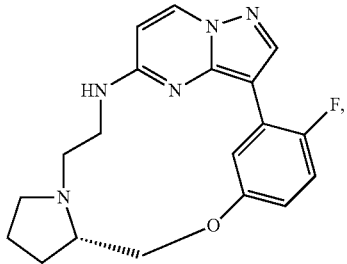

Example N8

Compound N8

-continued
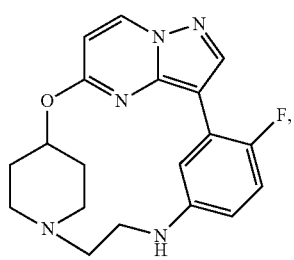
Compound N9
Example N9
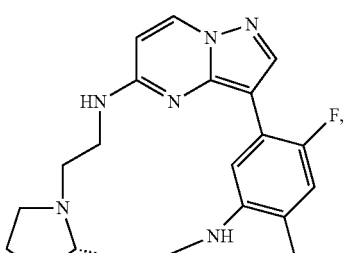
Compound N10
Example N10
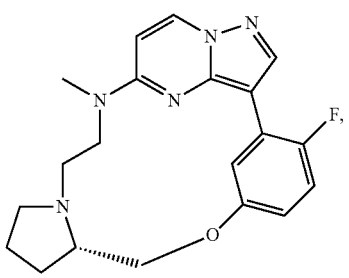
Compound N11
Example N11
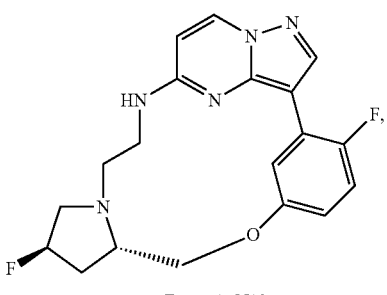
Compound N12
Example N12
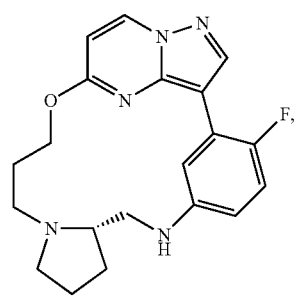
Compound N13
Example N13
-continued
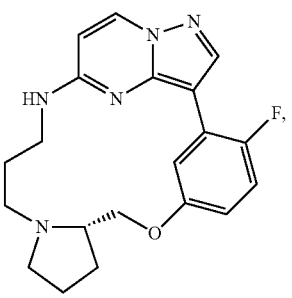
Compound N14
Example N14
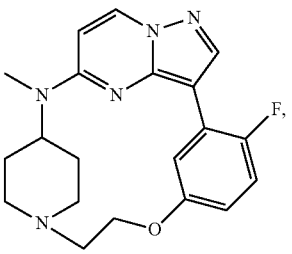
Compound N15
Example N15
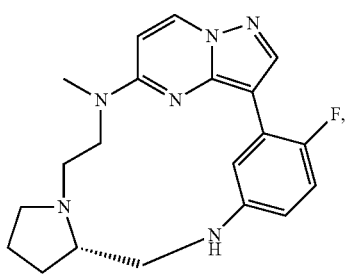
Compound N16
Example N16
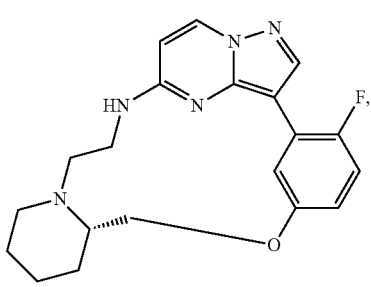
Compound N17
Example N17
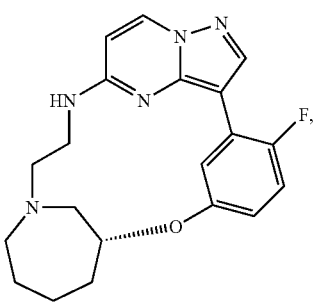
Compound N18
Example N18

Compound N19
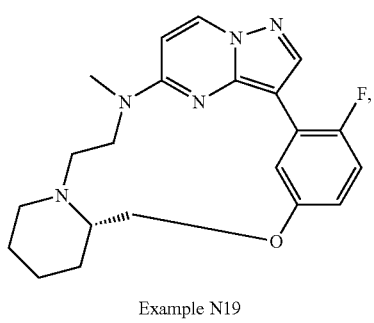
Example N19
Compound N20
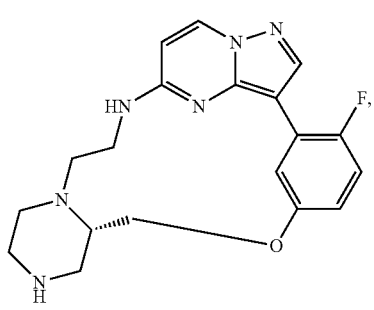
Example N20
Compound N21
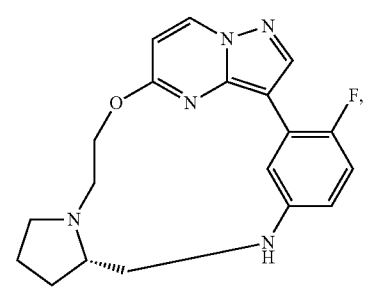
Example N21
Compound N22
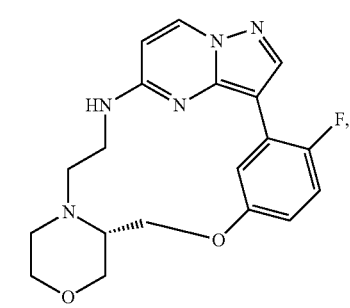
Example N22
Compound N23
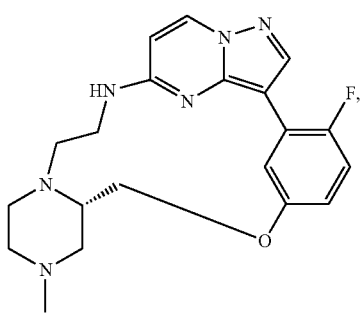
Example N23
Compound N24
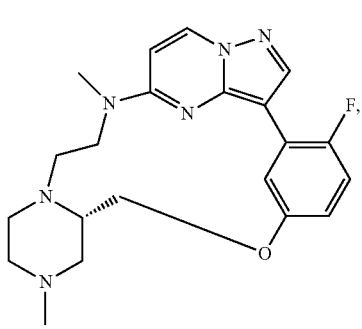
Example N24
Compound N25
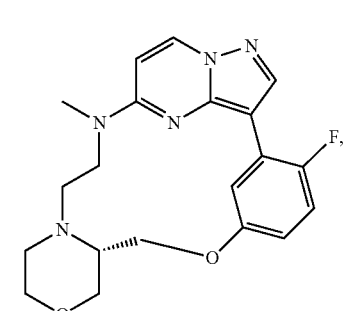
Example N25
Compound N26
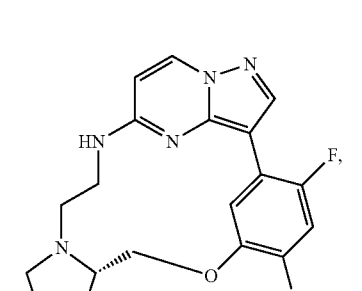
Example N26

Compound N27
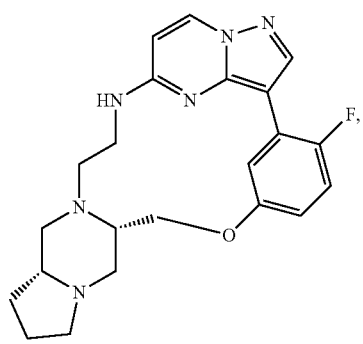
Example N27
Compound N28
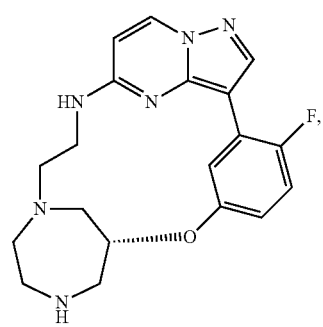
Example N28
Compound N29
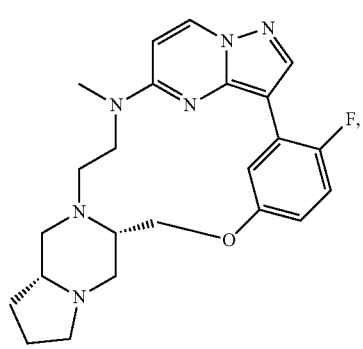
Example N29
Compound N30
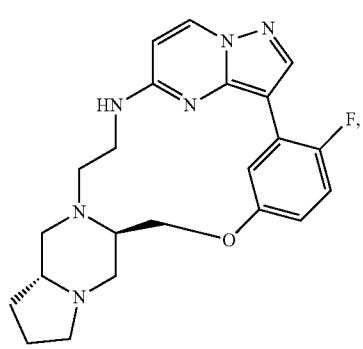
Example N30
Compound N31
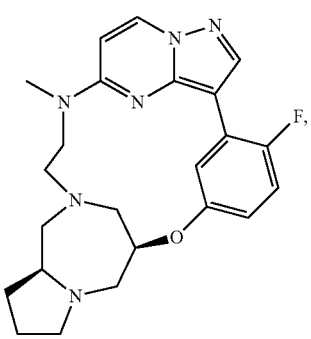
Example N31
Compound N32
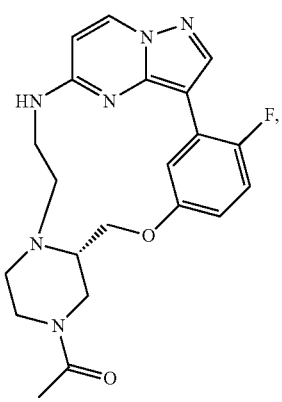
Example N32
Compound N33
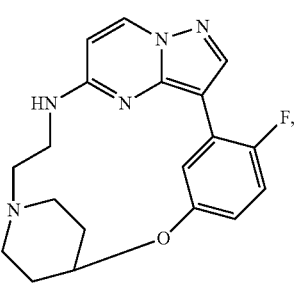
Example N33
Compound N34
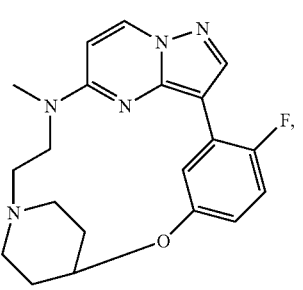
Example N34

Compound N35

Example N35

Compound N36

Example N36

Compound N37

Example N37

Compound N38

Example N38

Compound N39

Example N39

Compound N40

Example N40

Compound N41

Example N41

Compound N42

Example N42

Compound N43
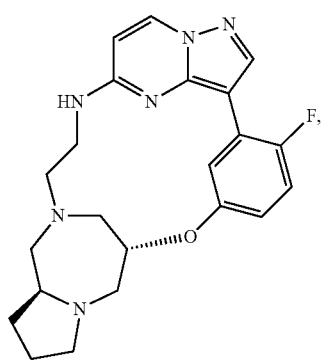
Example N43
Compound N44
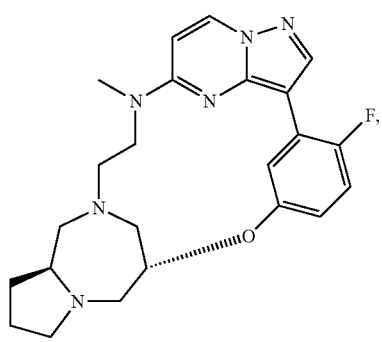
Example N44
Compound N45
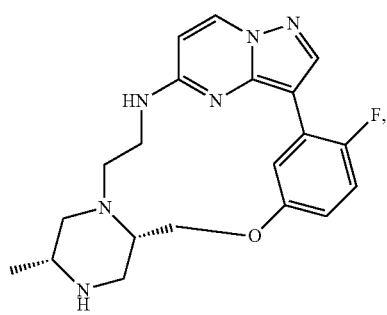
Example N45
Compound N46
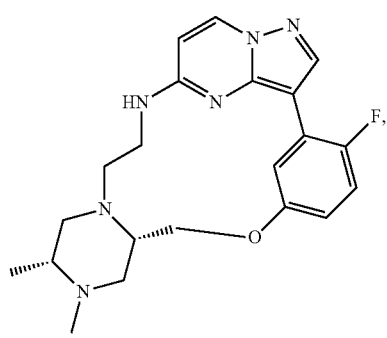
Example N46
Compound N47
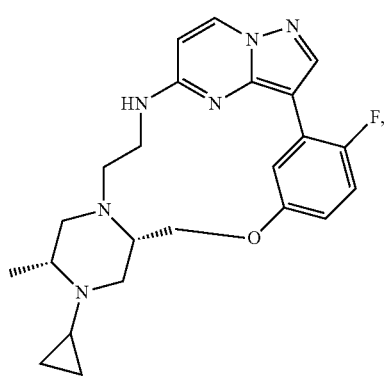
Example N47
Compound N48
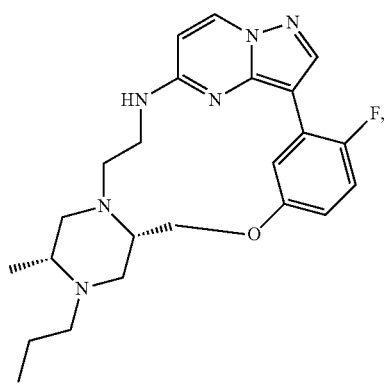
Example N48
Compound N49
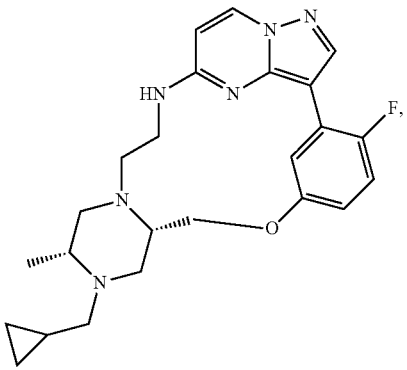
Example N49
Compound N50
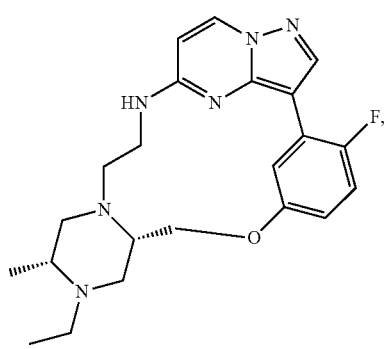
Example N50

Compound N51
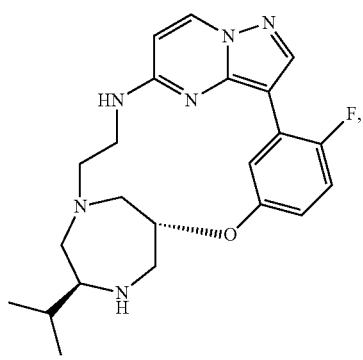
Example N51
Compound N52
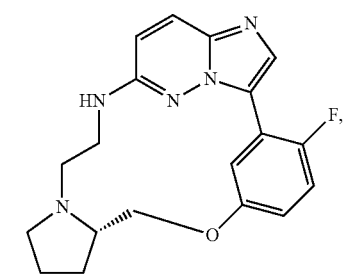
Example N52
Compound N53
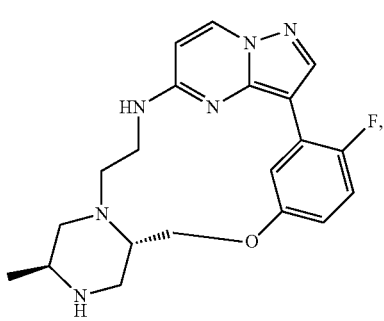
Example N53
Compound N54
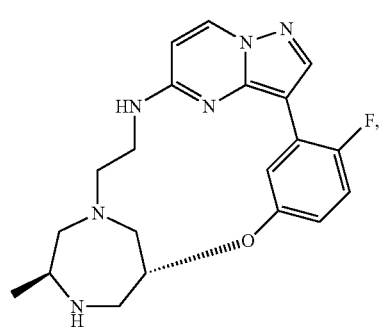
Example N54
Compound N55
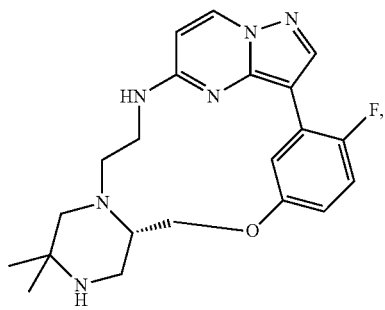
Example N55
Compound N56
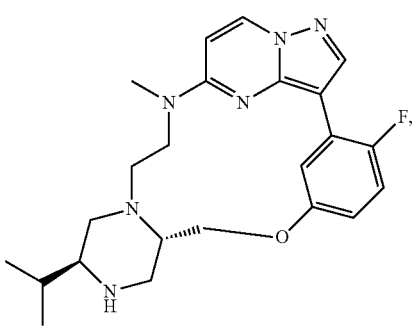
Example N56
Compound N57
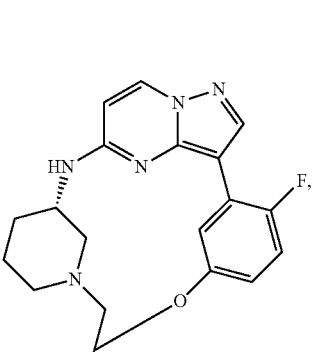
Example N57
Compound N58
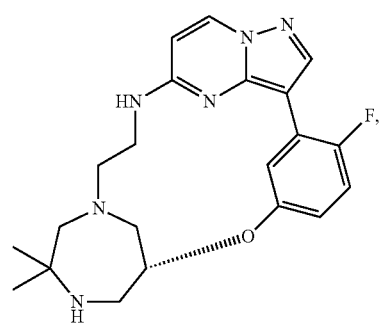
Example N58

-continued
Compound N59
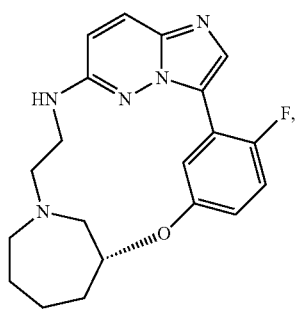
Example N59
Compound N60
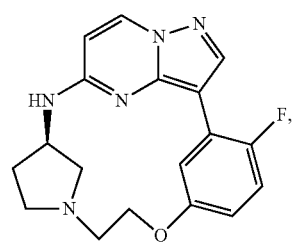
Example N60
Compound N61
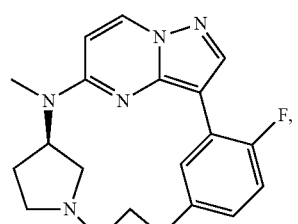
Example N61
Compound N62
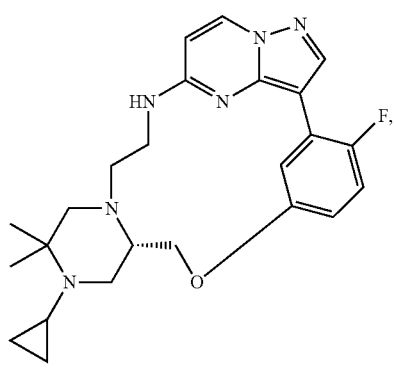
Example N62
-continued
Compound N63
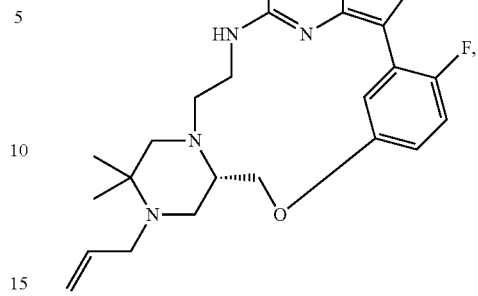
Example N63
In a preferred embodiment, the present invention provides a compound selected from the list comprising:
Compound N27
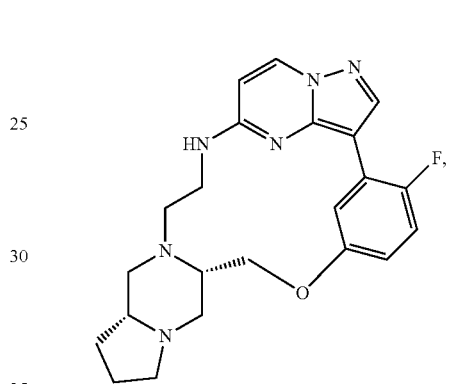
Example N27
Compound N59
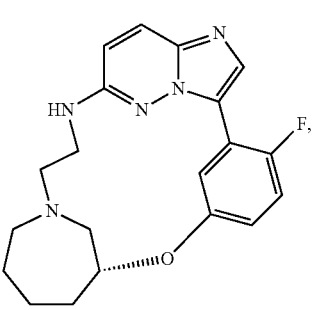
Example N59
Compound N43
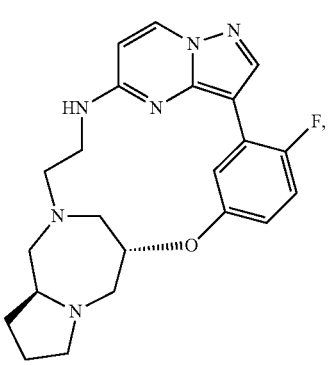
Example N43

Compound N60

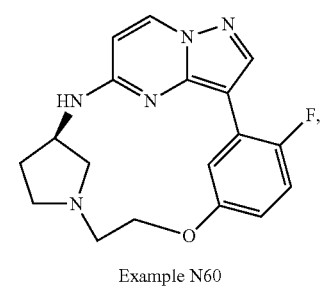

Example N60

Compound N44

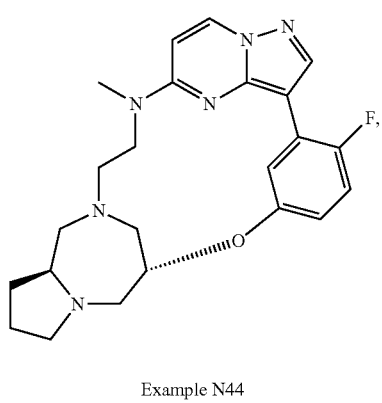

Example N44

Compound N62

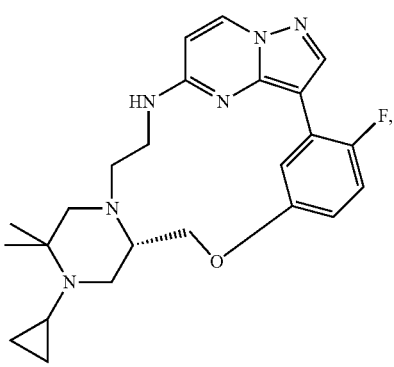

Example N62

Compound N45

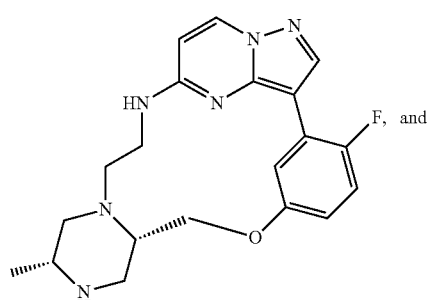

Example N45

Compound N63

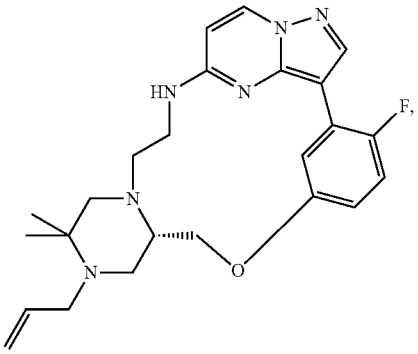

Example N63

Preferably the present invention provides a compound which is

Compound N60

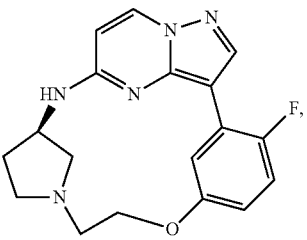

Example N60

Compound N45

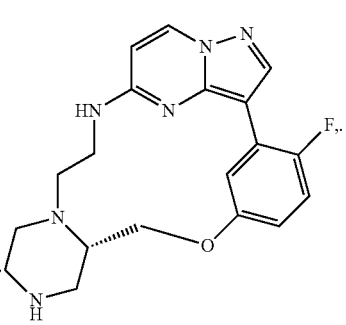

Example N45 and

In particular in the compounds according to this invention, the $R_5$ is linked to the aryl or heteroaryl moiety at position $Z_1$ in accordance with the numbering as provided in Formula I or Ia.

Furthermore, the present invention provides a compound according to this invention, wherein said compound is the S-enantiomer.

Furthermore, the present invention provides a compound according to this invention, wherein said compound is the R-enantiomer.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful in human or veterinary medicine, in particular for use as kinase inhibitors, more in particular for the inhibition of LRRK2 kinase.

The present invention further provides the use of a compound as defined hereinbefore or the use of a composition comprising said compound, as a human or veterinary medicine, in particular for the prevention and/or treatment of neurological disorders such as but not limited to Parkinson's disease and Alzheimer's disease.

In a preferred embodiment, the invention provides the use of a compound as defined hereinbefore or the use of a composition comprising said compound in the prevention and/or treatment of neurological disorders such as but not limited to Parkinson's disease and Alzheimer's disease.

The present invention further provides a compound as defined hereinbefore or a composition comprising said compound for use in the prevention and/or treatment of neurological disorders such as but not limited to Parkinson's disease and Alzheimer's disease.

Further embodiments of the present invention are detailed herein below in the form of numbered statements:

1. A compound of Formula I or a stereoisomer, tautomer, racemic, metabolite, pro- or predrug, salt, hydrate, N-oxide form, or solvate thereof,

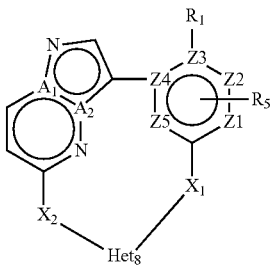

I

Wherein $R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$ are each independently selected from —H, —$C_{1-6}$alkyl, —$C_{3-6}$cycloalkyl and -$Het_2$:

$R_{37}$ and $R_{38}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$CO_{16}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$CO_{16}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S; wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;
wherein when $R_1$=H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

2. A compound as defined in statement 1, wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$— and —O—;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;
wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_2$ $Z_1$, $Z_2$, $Z_3$, $Z_4$ and $Z_5$ are each independently selected from C and N; and $A_1$ and $A_2$ are each independently selected from C and N.

3. A compound as defined in statement 1, wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —O—$C_{3-6}$cycloalkyl, —$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$ $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a bivalent 3- to 10-membered heterocycle having from 1 to 3 heteroatoms selected from O, N and S;
wherein at least one of said heteroatoms is attached to $X_1$ or $X_2$;
wherein when $R_1$ is —H, then at least one heteroatom of $Het_8$ is attached to $X_2$; and
wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and $A_1$ and $A_2$ are each independently selected from C and N.

4. A compound of Formula Ia or a stereoisomer, tautomer, racemic, metabolite, pro- or predrug, salt, hydrate, N-oxide form, or solvate thereof,

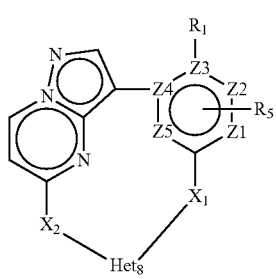

Ia

Wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$;

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$ $X_2$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3-halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_2$ $Z_1$, $Z_2$, $Z_3$, $Z_4$ and $Z_5$ are each independently selected from C and N.

5. A compound as defined in statement 4, wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$;

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$— and —O—;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, —$NR_{19}R_{20}$; wherein each of said —$C_{1-6}$alkyl is optionally and independently substituted with from 1 to 3-halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S;

wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

wherein when $R_1$ is —H, then at least one heteroatom of $Het_8$ is attached to $X_2$ $Z_1$, $Z_2$, $Z_3$, $Z_4$ and $Z_5$ are each independently selected from C and N.

6. A compound as defined in statement 4 wherein
$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_6$, $R_7$, $R_9$, $R_{10}$, $R_{11}$, $R_{12}$, $R_{13}$, $R_{14}$, $R_{15}$, $R_{16}$, $R_{19}$, $R_{20}$, $R_{21}$, $R_{22}$, $R_{31}$, $R_{32}$, $R_{33}$ and $R_{34}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

R$_{27}$ and R$_{28}$, are each independently selected from —H, —C$_{1-6}$alkyl, —C$_{3-6}$cycloalkyl and -Het$_2$:

R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$ X$_2$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
wherein at least one of said heteroatoms is attached to X$_1$ or X$_2$;
wherein when R$_1$ is —H, then at least one heteroatom of Het$_8$ is attached to X$_2$; and
wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N.

7. A compound of Formula Ia or Formula I or a stereoisomer, tautomer, racemic, metabolite, pro- or predrug, salt, hydrate, N-oxide form, or solvate thereof as defined in anyone of statements 1 to 6, wherein each of said Z$_1$, Z$_2$, Z$_3$, Z$_4$ and Z$_5$ is C; and wherein the further definitions and provisions as defined in statements 1 to 6 apply.

8. A compound as defined in one of statements 1 to 3 wherein
A$_1$ and A$_2$ are each independently selected from C and N;
R$_1$ is selected from —H and -halo;
R$_5$ is selected from —H, -halo and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —C$_{1-6}$alkyl-, —O—C$_{1-6}$alkyl-, —NR$_2$—C$_{1-6}$alkyl-, —NR$_2$—, —O—;
Het$_8$ is a 3- to 10-membered heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, —C$_{1-6}$alkyl-C$_{3-6}$cycloalkyl, —(C=O)—C$_{1-6}$alkyl, and —(C=O)—C$_{3-6}$cycloalkyl; and
Z$_1$, Z$_2$, Z$_3$, Z$_4$ and Z$_5$ are each C.

9. A compound as defined in statement 8 wherein
A$_1$ and A$_2$ are each independently selected from C and N;
R$_1$ is selected from —H and -halo;
R$_5$ is selected from —H, -halo and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —O—C$_{1-6}$alkyl-, —NR$_2$—C$_{1-6}$alkyl-, —NR$_2$—, —O—;
Het$_8$ is a 3- to 10-membered heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, and —C$_{1-6}$alkyl-C$_{3-6}$cycloalkyl; and
Z$_1$, Z$_2$, Z$_3$, Z$_4$ and Z$_5$ are each C.

10. A compound as defined in statement 8 or 9 wherein A$_1$ is N and A$_2$ is C.

11. A compound of Formula Ia or a stereoisomer, tautomer, racemic, metabolite, pro- or predrug, salt, hydrate, N-oxide form, or solvate thereof,

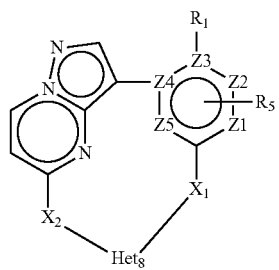

Ia

Wherein
R$_1$ is selected from —H and -halo;
R$_5$ is attached to Z$_1$ and is selected from —H and —C$_{1-6}$alkyl;
R$_2$ is selected from —H and —C$_{1-6}$alkyl;
R$_3$ is selected from —H and —C$_{1-6}$alkyl;
X$_1$ is selected from —O—C$_{1-6}$alkyl-, —NR$_3$—C$_{1-6}$alkyl-, —NR$_3$—, —O—;
X$_2$ is selected from —O—C$_{1-6}$alkyl-, —NR$_2$—C$_{1-6}$alkyl-, —NR$_2$—, —O—;
Het$_8$ is a 3- to 10-membered N-containing heterocycle; wherein said Het$_8$ is optionally substituted with 1 to 3 substituents selected from -halo, —OH, —C$_{1-6}$alkyl, —C$_{1-6}$alkylene, —C$_{3-6}$cycloalkyl, —O—C$_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; and
$Z_1$, $Z_2$, $Z_3$, $Z_4$ and $Z_5$ are each C.
12. A compound selected from the list comprising:
Compound N1
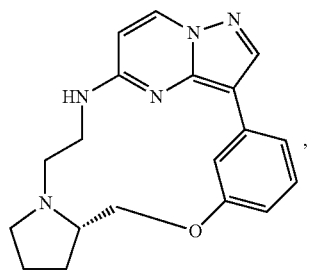
Example N1
Compound N2
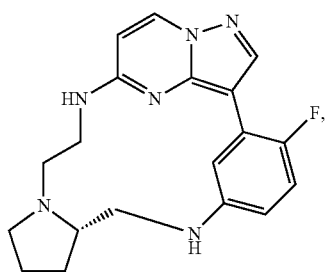
Example N2
Compound N3
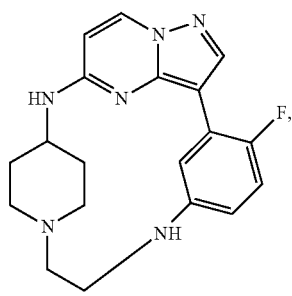
Example N3
Compound N4
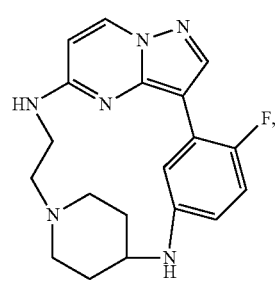
Example N4
-continued
Compound N5
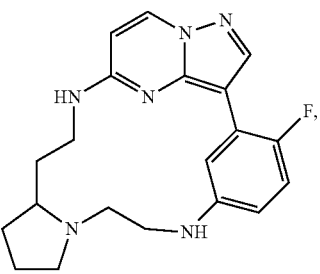
Example N5
Compound N6
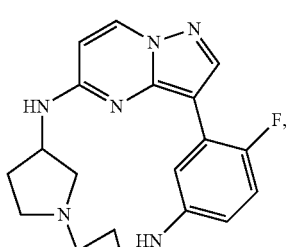
Example N6
Compound N7
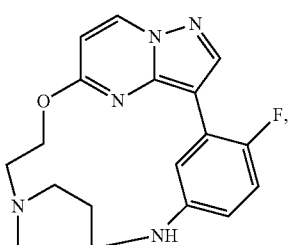
Example N7
Compound N8
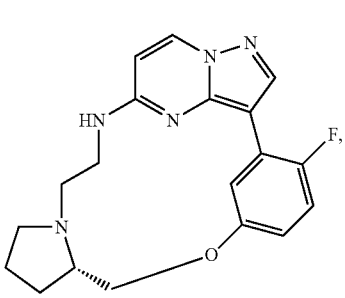
Example N8
Compound N9
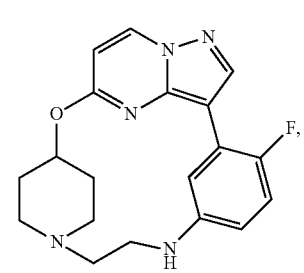
Example N9

Compound N10
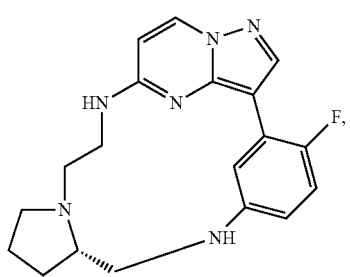
Example N10
Compound N11
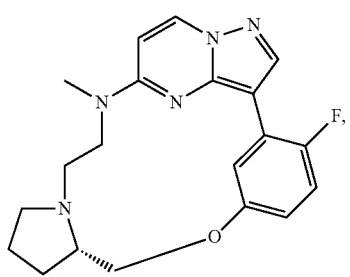
Example N11
Compound N12
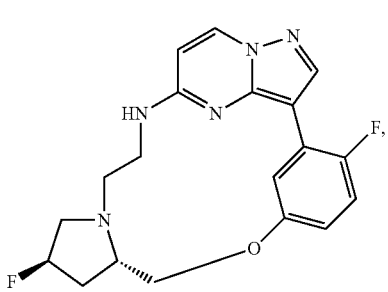
Example N12
Compound N13
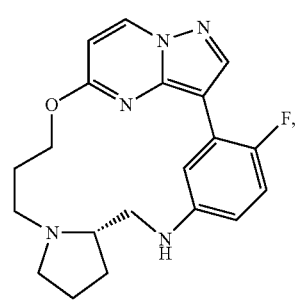
Example N13
Compound N14
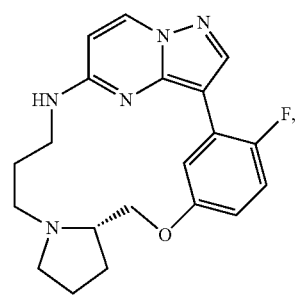
Example N14
Compound N15
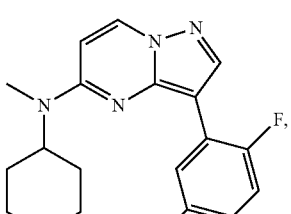
Example N15
Compound N16
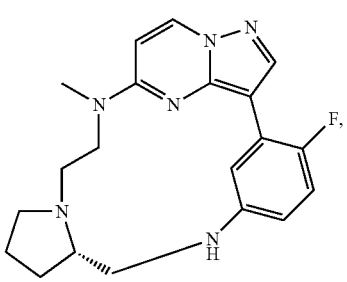
Example N16
Compound N17
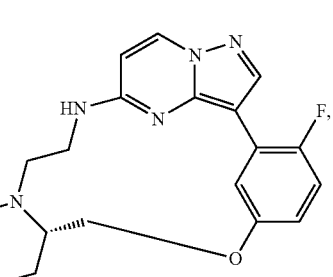
Example N17
Compound N18
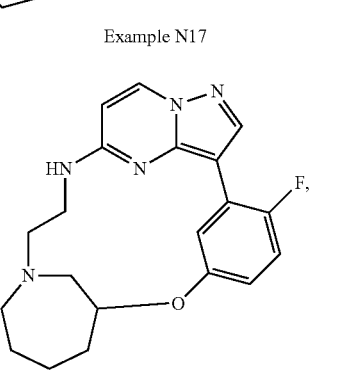
Example N18
Compound N19
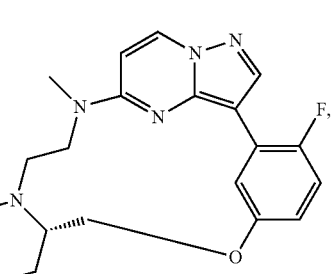
Example N19

Compound N20

Example N20

Compound N21

Example N21

Compound N22

Example N22

Compound N23

Example N23

Compound N24

Example N24

Compound N25

Example N25

Compound N26

Example N26

Compound N27

Example N27

Compound N28
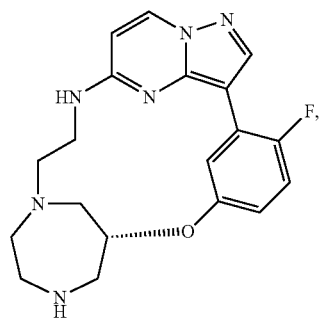
Example N28
Compound N29
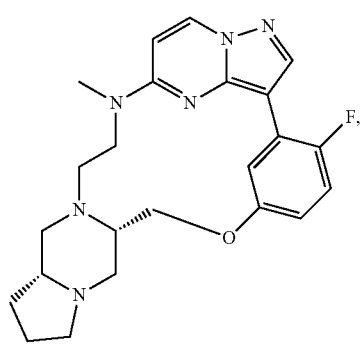
Example N29
Compound N30
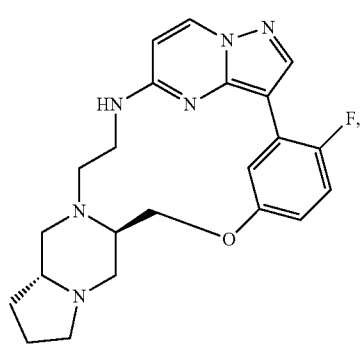
Example N30
Compound N31
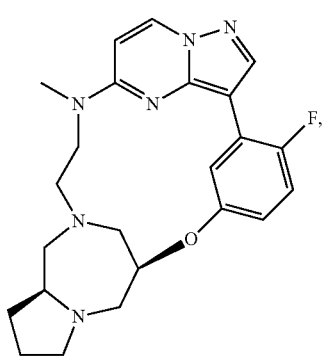
Example N31
Compound N32
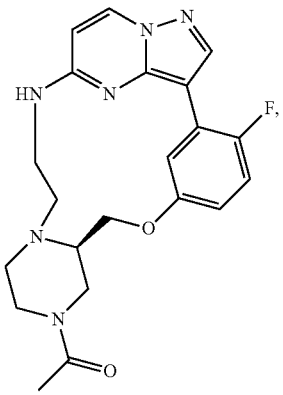
Example N32
Compound N33
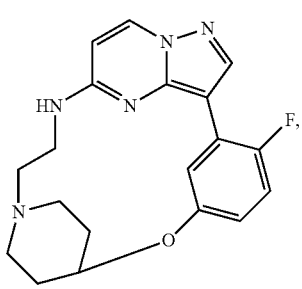
Example N33
Compound N34
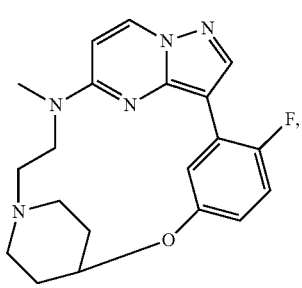
Example N34
Compound N35
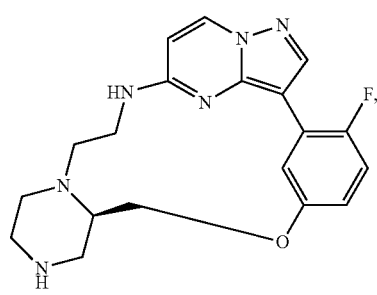
Example N35

Compound N36
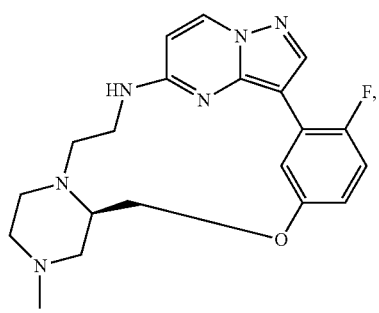
Example N36
Compound N37
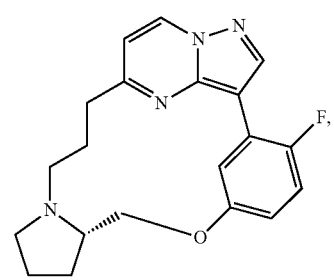
Example N37
Compound N38
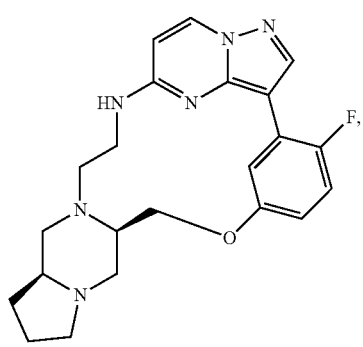
Example N38
Compound N39
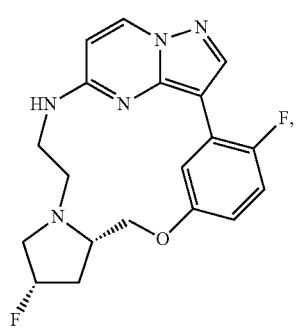
Example N39
Compound N40
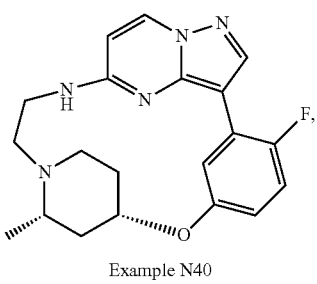
Example N40
Compound N41
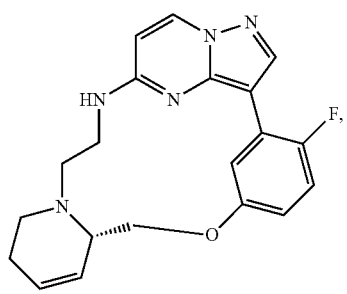
Example N41
Compound N42
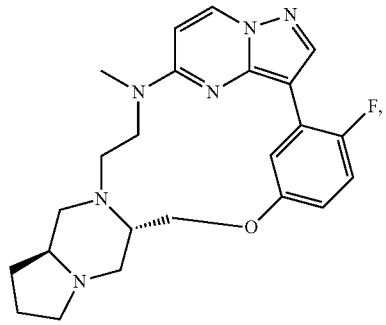
Example N42
Compound N43
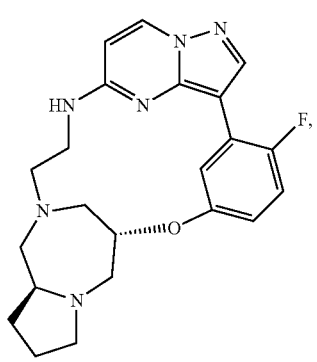
Example N43

Compound N44
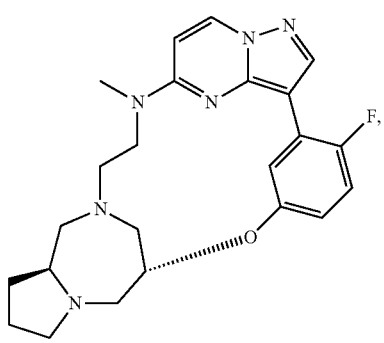
Example N44
Compound N45
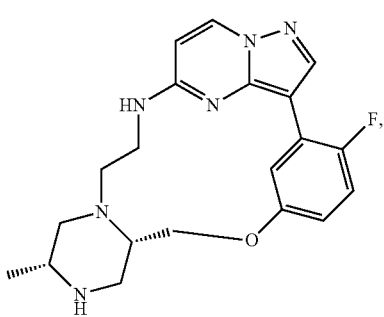
Example N45
Compound N46
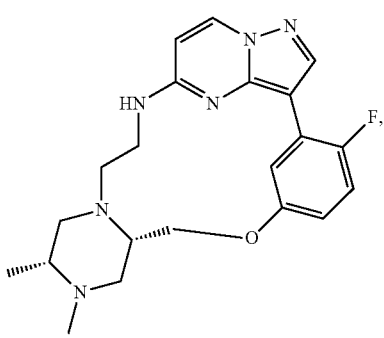
Example N46
Compound N47
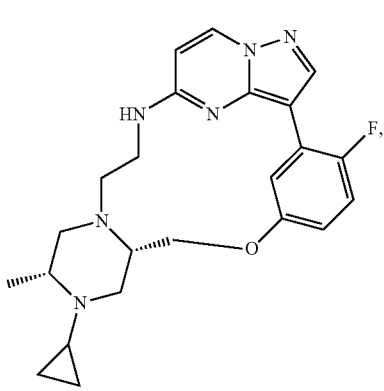
Example N47
Compound N48
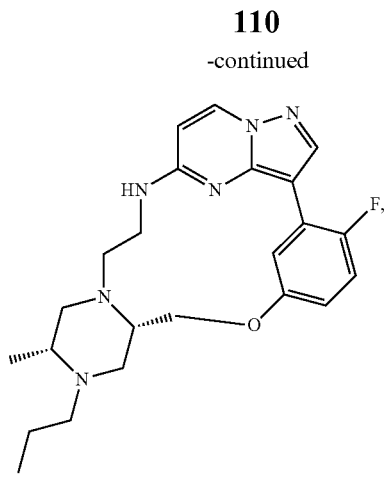
Example N48
Compound N49
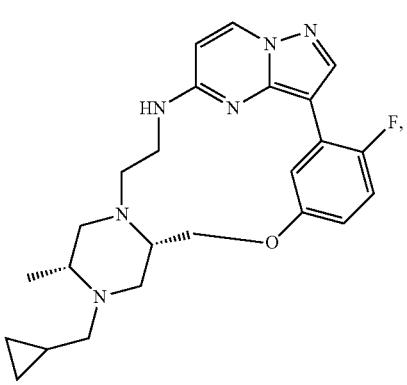
Example N49
Compound N50
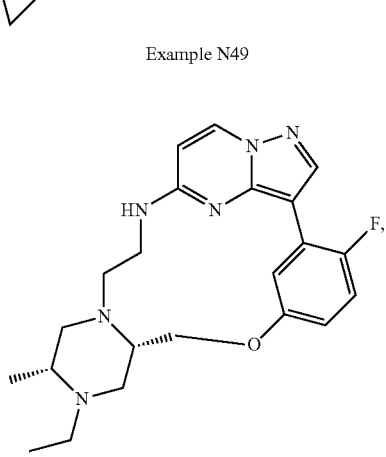
Example N50
Compound N51
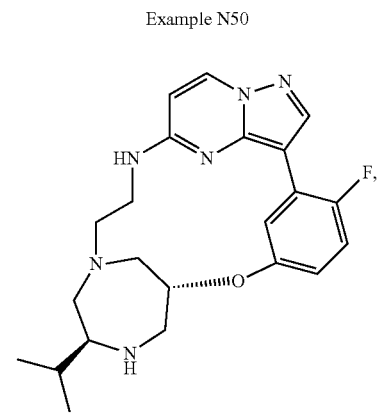
Example N51

Compound N52
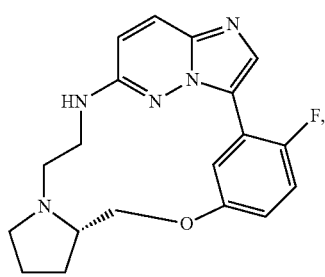
Example N52
Compound N53
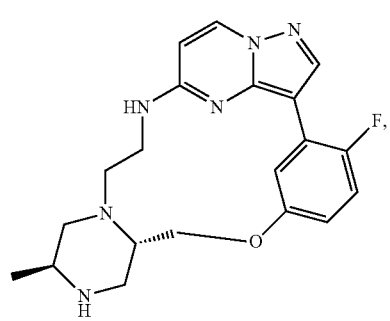
Example N53
Compound N54
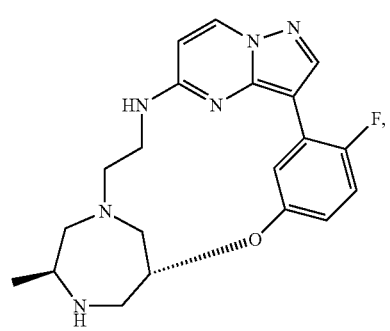
Example N54
Compound N55
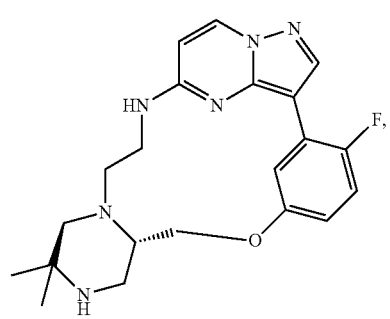
Example N55
Compound N56
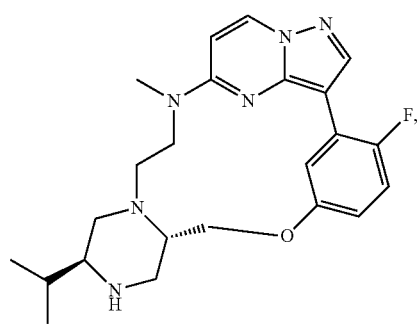
Example N56
Compound N57
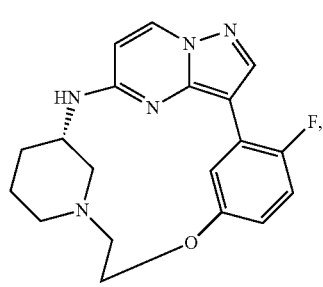
Example N57
Compound N58
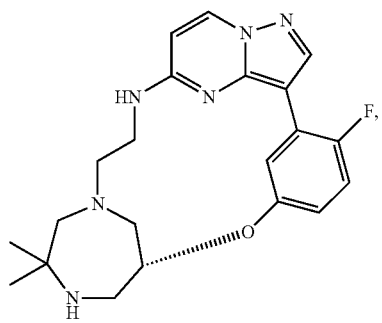
Example N58
Compound N59
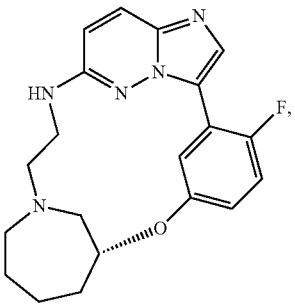
Example N59

-continued
Compound N60
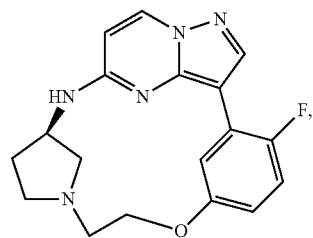
Example N60
Compound N61
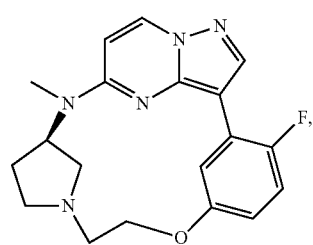
Example N61
Compound N62
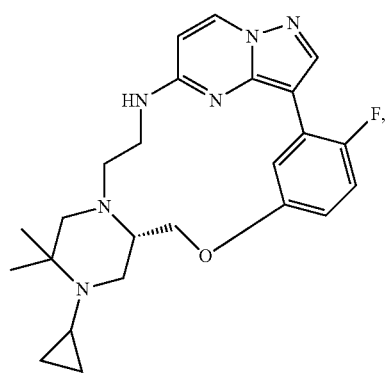
Example N62
Compound N63
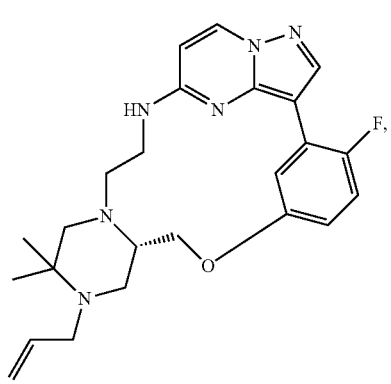
Example N63
13. A compound as defined in statement 11 which is selected from
Compound N46
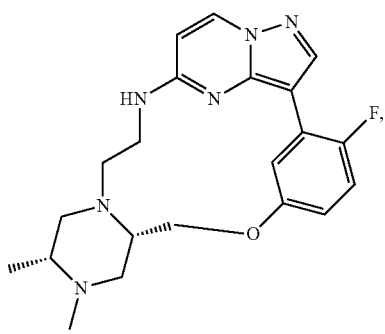
Example N46
Compound N27
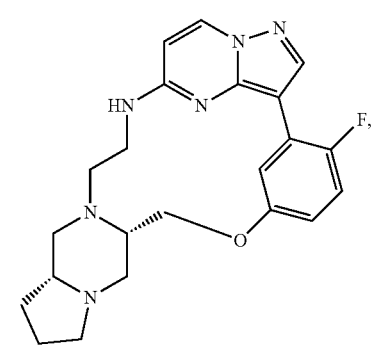
Example N27
Compound N47
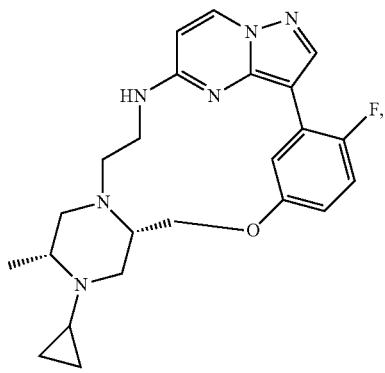
Example N47
Compound N43
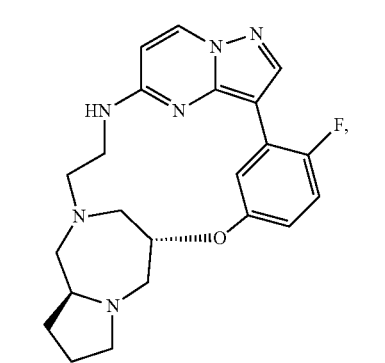
Example N43

-continued
Compound N48
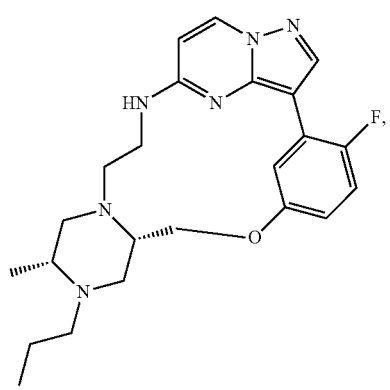
Example N48
Compound N44
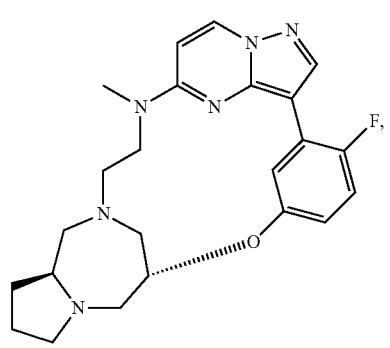
Example N44
Compound N50
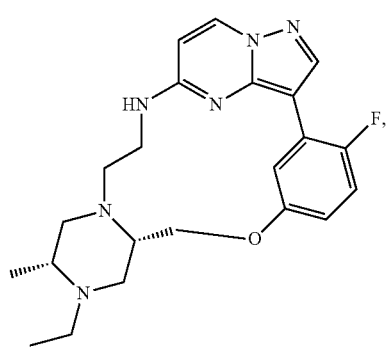
Example N50
Compound N45
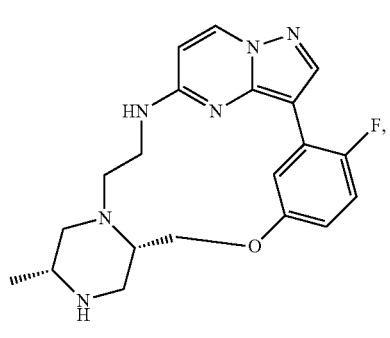
Example N45
-continued
Compound N49
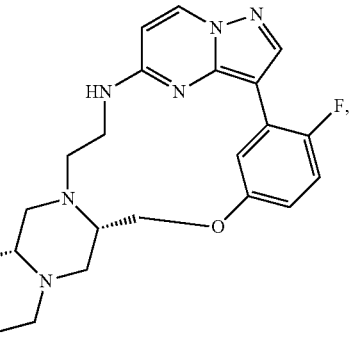
Example N49
Compound N59
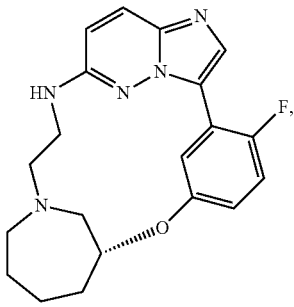
Example N59
Compound N63
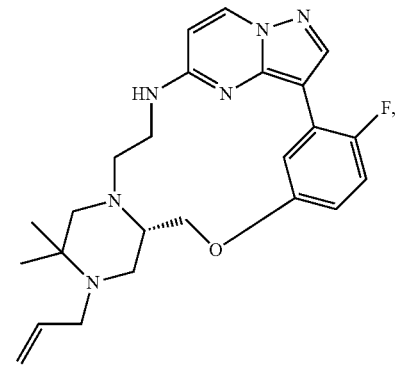
Example N63
Compound N62
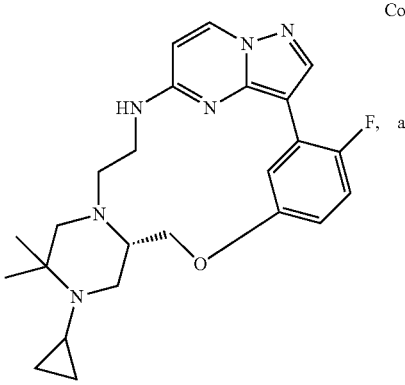
Example N62

-continued
Compound N60
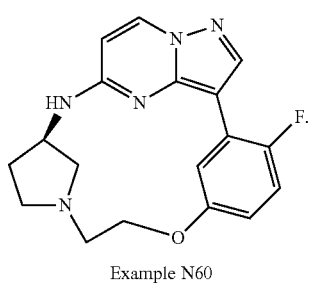
Example N60
14. A compound as defined in statement 13 which is selected from
Compound N27
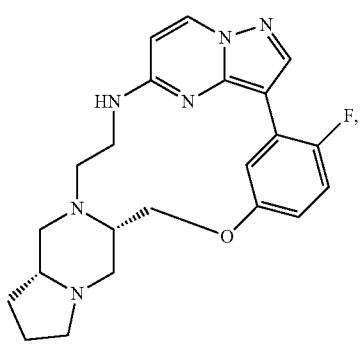
Example N27
Compound N44
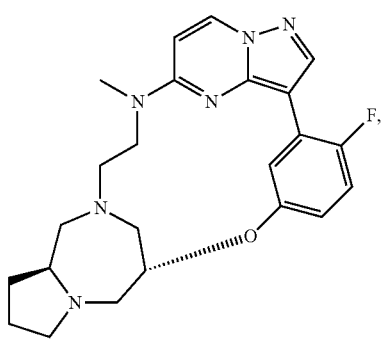
Example N44
Compound N43
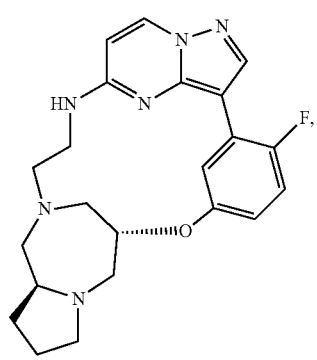
Example N43
-continued
Compound N45
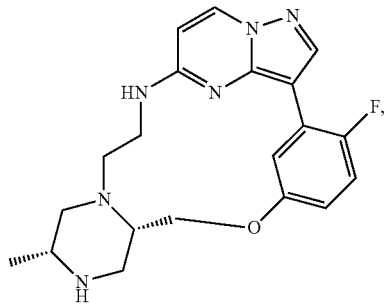
Example N45
Compound N59
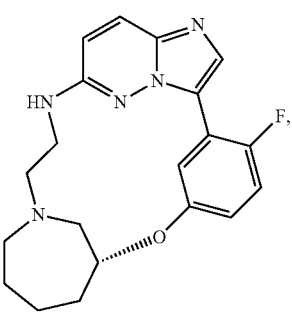
Example N59
Compound N62
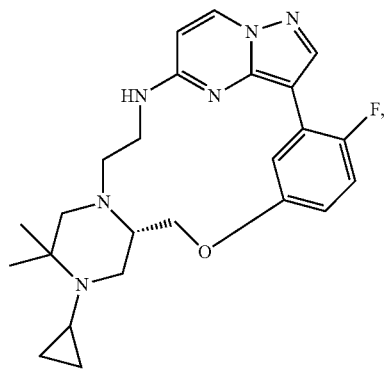
Example N62
Compound N60
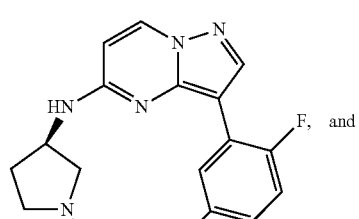
F, and
Example N60

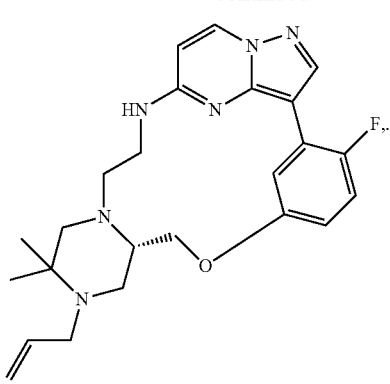

Compound N63

Example N63

15. A compound as defined in statement 12 which is selected from

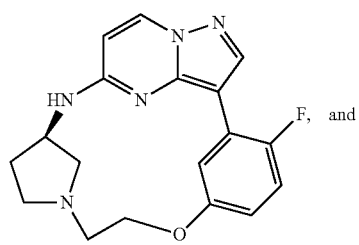

Compound N60

Example N60

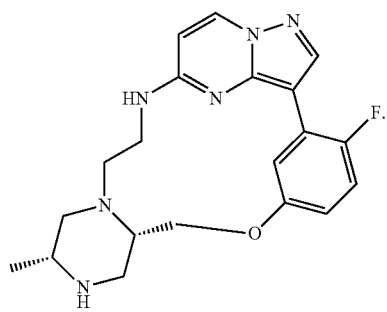

Compound N45

Example N45

16. A compound according to any one of statements 1 to 11; wherein $R_5$ is linked to the aryl or heteroaryl moiety at position $Z_1$ in accordance with the numbering as provided in Formula I or Ia.
17. A compound according to any one of statements 1 to 12; wherein said compound is the S-enantiomer.
18. A compound according to any one of statements 1 to 12; wherein said compound is the R-enantiomer.
19. A pharmaceutical composition comprising a compound according to anyone of statements 1 to 18.
20. A compound according to anyone of statements 1 to 18 or a composition according to statement 19 for use as a medicine.
21. A compound according to anyone of statements 1 to 18 or a composition according to statement 19 for use in the diagnosis, prevention and/or treatment of a LRRK2-kinase associated disease.
22. A compound according to anyone of statements 1 to 18 or a composition according to statement 19 for use in the diagnosis, prevention and/or treatment of a LRRK2-kinase associated disease; wherein the LRRK2-kinase associated disease is a neurological disorders, such as Parkinson's disease or Alzheimer's disease.
23. Use of a compound as defined in any one of statements 1 to 18, or a composition as defined in statement 19, suitable for inhibiting the activity of a kinase; in particular a LRRK2 kinase.
24. Use of a compound according to anyone of statement 1 to 18 or a composition according to statement 19, for the diagnosis, prevention and/or treatment of a LRRK2-kinase associated disease.
25. A method for the prevention and/or treatment of a LRRK2-kinase associated disease; said method comprising administering to a subject in need thereof a compound according to any one of statements 1 to 19 or a composition according to statement 12.

Method of Treatment

Compounds of formula (I) and (Ia) a stereoisomer, tautomer, racemic, metabolite, pro- or predrug, salt, hydrate, N-oxide form, or solvate thereof, are inhibitors of LRRK2 kinase activity and are thus believed to be of potential use in the treatment of neurological disorders including Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, and renal, breast, lung, prostate cancers as well as acute myelogenous leukemia (AML).

In the context of the present invention, treatment of Parkinson's disease refers to the treatment of idiopathic Parkinson's disease and familial Parkinson's disease. In one embodiment, familial Parkinson's disease includes patients expressing LRRK2 kinase bearing the G2019S mutation or the R1441G mutation. Treatment of Parkinson's disease may be symptomatic or may be disease modifying. In one embodiment, treatment of Parkinson's disease refers to symptomatic treatment. Compounds of the present invention may also be useful in treating patients identified as susceptible to progression to severe Parkinsonism by means of one or more subtle features associated with disease progression such as family history, olfaction deficits, constipation, cognitive defects, gait or biological indicators of disease progression gained from molecular, biochemical, immunological or Imaging technologies. In this context, treatment may be symptomatic or disease modifying.

In the context of the present invention, treatment of Alzheimer's disease refers to the treatment of idiopathic Alzheimer's disease and familial Alzheimer's disease. Treatment of Alzheimer's disease may be symptomatic or may be disease modifying. In one embodiment, treatment of Alzheimer's disease refers to symptomatic treatment.

Similarly, treatment of dementia (including Lewy body dementia and vascular dementia), age related memory dysfunction, mild cognitive impairment argyrophilic grain disease, Pick's disease, corticobasal degeneration, progressive supranuclear palsy, inherited frontotemporal dementia and parkinsonism linked to chromosome 17 (FTDP-7) and renal, breast, lung, prostate cancers as well as acute myelogenous leukemia (AML) may be symptomatic or disease modifying. In one embodiment, treatment of dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), and renal, breast, lung, prostate cancers as well as acute myelogenous leukemia (A L) refers to symptomatic treatment.

In the context of the present invention, treatment of withdrawal symptoms/relapse associated with drug addiction and L-Dopa induced dyskinesia refers to symptomatic treatment.

Accordingly, the present invention further provides a method for the prevention and/or treatment of neurological disorders such as but not limited to Parkinson's disease and Alzheimer's disease, said method comprising administering to a subject in need thereof a therapeutic effective amount of a compound or a composition as defined herein. The methods of the present invention can be utilized in a variety of settings, including, for example, in selecting the optimal treatment course for a patient, in predicting the likelihood of success when treating an individual patient with a particular treatment regimen, in assessing disease progression, in monitoring treatment efficacy, in determining prognosis for individual patients and in assessing predisposition of an individual to benefit from a particular therapy.

In the invention, particular preference is given to compounds of Formula I or any subgroup thereof that in the inhibition assay for LRRK2 described below inhibit kinase activity with an $IC_{50}$ value of less than 10 µM, preferably less than 1 µM, most preferably less than 100 nM.

Said inhibition may be effected in vitro and/or in vivo, and when effected in vivo, is preferably effected in a selective manner, as defined above.

The term "LRRK2 kinase-mediated condition" or "disease", as used herein, means any disease or other deleterious condition in which the LRKK2 kinase is known to play a role. The term "LRRK2 kinase-mediated condition" or "disease" also means those diseases or conditions that are alleviated by treatment with a LRRK2 kinase inhibitor. Accordingly, another embodiment of the present invention relates to treating or lessening the severity of one or more diseases in which the LRRK2 kinase is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369, 087 and No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinyl pyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

For local administration, the compounds may advantageously be used in the form of a spray, ointment or transdermal patch or another suitable form for topical, transdermal and/or intradermal administration.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of Formula or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used orally or parenterally.

The invention will now be illustrated by means of the following synthetic and biological examples, which do not limit the scope of the invention in any way.

EXAMPLES

A. Compound Synthesis and Physicochemical Properties

The compounds of this invention can be prepared by any of several standard synthetic processes commonly used by those skilled in the art of organic chemistry. The compounds are generally prepared from starting materials which are either commercially available or prepared by standard means obvious to those skilled in the art.

For some compounds that were purified by reversed phase high-performance liquid chromatography (HPLC) the used method is described below (indicated in the compound procedure with HPLC method A). When necessary, these methods can be slightly adjusted by a person skilled in the art to obtain a more optimal result for the separation.

HPLC Method A

The crude product was purified by reversed phase HPLC, using a Gilson semi-preparative HPLC system operated by Gilson UNIPOINT software.

The purification was carried out on a Phenomenex Luna column (100 mm long×21.2 mm i.d.; 5 µm particles) at room temperature, with a constant flow rate of 20.0 mL/min. A gradient elution was performed from 32% (25 mM NH4HCO3 aqueous solution)/68% (Acetonitrile-Methanol 1:1) to 4% (25 mM NH4HCO3 aqueous solution)/96% (Acetonitrile-Methanol 1:1) in 20 minutes. The UV detector was set to 226 nm, which corresponds to the wavelength of maximum absorbance observed for the compound.

General schemes:

As indicated herein before, the present invention in general provides compounds according to formula I, for use in the diagnosis, prevention and/or treatment of LRRK2-kinase associated diseases:

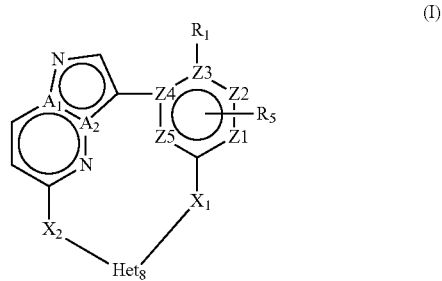

(I)

With reference to the general reaction schemes suitable for preparing said compounds, these compounds can be represented by formulas Ia or Ib respectively, for which the general reaction schemes can be found herein below.

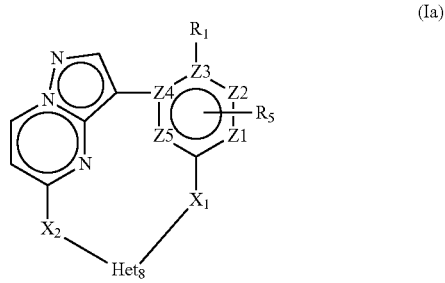

(Ia)

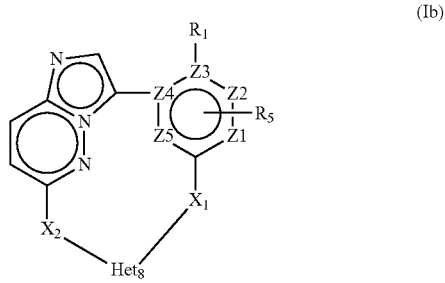

(Ib)

General Schemes:

In general the compounds of formula (I) can be prepared as shown in scheme 1 below wherein a pyrazolo[1,5-a]

pyrimidine or a imidazo[2,1-f]pyridazine of formula (II) is converted by reaction with a compound of formula (III) into a compound of formula (IV), which is then reacted with a (hetero-)aryl of formula (V) to form a compound of formula (VI). The compound of formula (VI) can be cyclized to form a compound of formula (I).

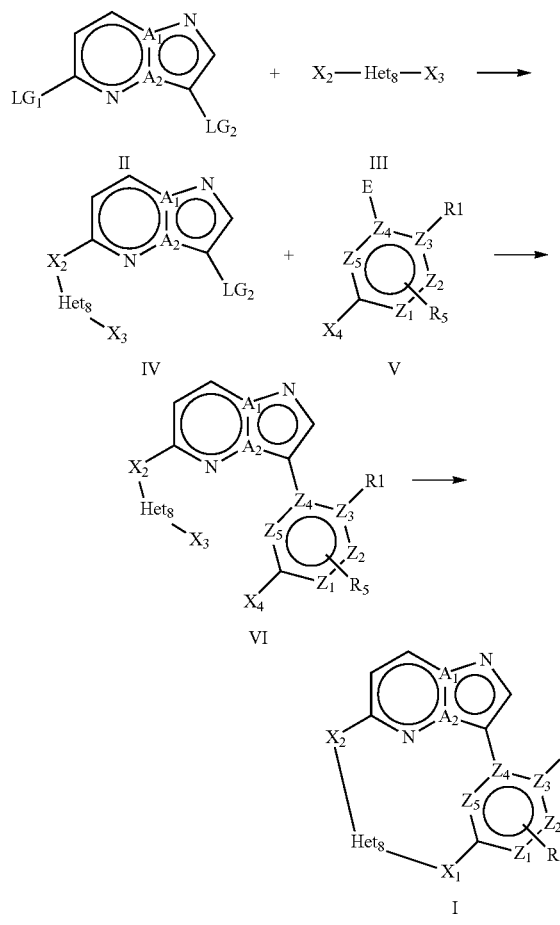

In the above scheme:
LG$_1$ and LG$_2$ each independently represent suitable leaving or functional groups;
X$_3$ and X$_4$ together with the functional moiety to which they are attached represent an unprotected or a protected functional group which upon reaction (after deprotection) produce together X$_1$ as defined in formula I;
E represents a suitable functional group that can be used to form a direct bond between the (hetero-)aryl group and the scaffold.

In the above reaction of the compound of formula (II) with the compound of formula (III) the leaving groups LG$_1$ and LG$_2$ are advantageously a halo group such as a chlorine or a bromine group. The reaction can be affected by a substitution for example by treating the compound of formula (II) with the compound of formula (III) in an organic solvent such as acetonitrile with an appropriate base such as for example triethylamine at an elevated temperature for example under reflux.

Compounds of formula (III) can be obtained through various selective reaction steps by standard means obvious to those skilled in the art.

The reaction of the compound (IV) with a (hetero-)aryl compound of formula (V) is advantageously effected through the coupling of a boronic acid E or boronic ester E derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example under reflux.

The cyclisation of the compound of formula (VI) can be effected for example under Mitsunobu conditions using for example diisopropyl azodicarboxylate and triphenylphosphine in a solvent mixture such as 2-methyl-1,4-dioxane and toluene at an elevated temperature such as 90° C.

The resulting compound of formula (I) can optionally be treated to introduce substituents such as an alkyl group.

In general the compounds of formula (I) can be prepared as shown in scheme 2 below wherein a pyrazolo[1,5-a]pyrimidine or a imidazo[2,1-f]pyridazine of formula (II) is converted by reaction with a compound of formula (VII) into a compound of formula (VIII), which is then transformed into a compound of formula (Iv) and reacted with a (hetero-)aryl of formula (V) to form a compound of formula (VI). The compound of formula (VI) can be cyclized to form a compound of formula (I).

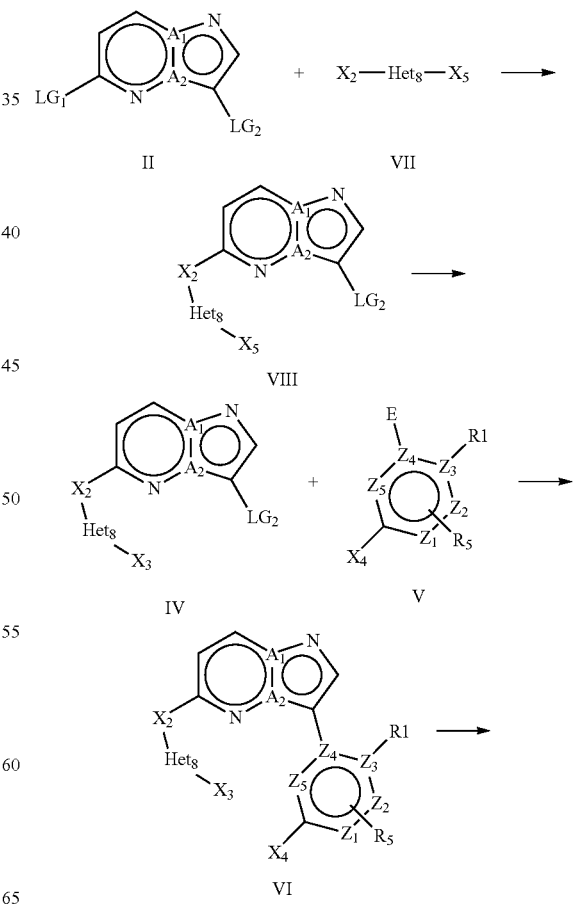

129
-continued

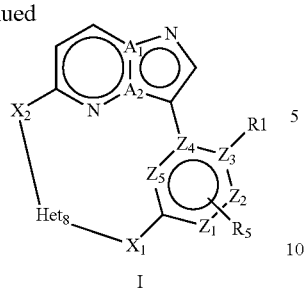

In the above scheme:
LG$_1$ and LG$_2$ each independently represent suitable leaving or functional groups;
X$_5$ is converted into a functional group X$_3$;
X$_3$ and X$_4$ together with the functional moiety to which they are attached represent an unprotected or a protected functional group which upon reaction (after deprotection) produce together X$_1$ as defined in formula I;
E represents a suitable functional group that can be used to form a direct bond between the (hetero-)aryl group and the scaffold.

In the above reaction of the compound of formula (II) with the compound of formula (VII) the leaving groups LG$_1$ and LG$_2$ are advantageously a halo group such as a chlorine or a bromine group. The reaction can be affected by a substitution for example by treating the compound of formula (II) with the compound of formula (VII) in an organic solvent such as acetonitrile with an appropriate base such as for example triethylamine at an elevated temperature for example under reflux.

Compounds of formula (VII) can be obtained through various selective reaction steps by standard means obvious to those skilled in the art.

Compounds of formula (VII) can be converted to compounds of formula (IV) by reaction with a suitable protected or unprotected linker group.

The reaction of the compound (IV) with a (hetero-)aryl compound of formula (V) is advantageously effected through the coupling of a boronic acid E or boronic ester E derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example under reflux.

The cyclisation of the compound of formula (VI) can be effected for example under Mitsunobu conditions using for example diisopropyl azodicarboxylate and triphenylphosphine in a solvent mixture such as 2-methyl-1,4-dioxane and toluene at an elevated temperature such as 90° C.

The resulting compound of formula (I) can optionally be treated to introduce substituents such as an alkyl group.

130

Example N1

Example N1 is prepared following general scheme 1.

Preparation of Intermediate 1

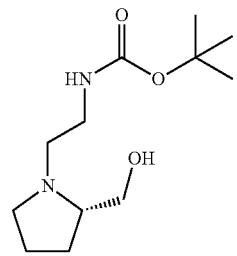 [SMILES: CC(C)(C)OC(=O)NCCN1CCC[C@H]1CO]

A mixture of 2-(tert-butoxycarbonylamino)ethyl methanesulfonate (1.20 g, 5.01 mmol), [(2S)-pyrrolidin-2-yl]methanol (0.99 g, 10.02 mmol), sodium carbonate (1.593 g, 15.03 mmol) and potassium iodide (1.081 g, 6.51 mmol) in N,N-dimethylformamide (32 ml) was stirred at 60° C. overnight. The solvent was removed under reduced pressure, dichloromethane was added and the mixture was filtered over Celite®. The solvent was removed under reduced pressure and the residue was purified by reversed phase column chromatography (HPLC method A).

Yield: 513 mg of intermediate 1 (42%)
LCMS method 2: MH$^+$=245, RT=1.165 min

Preparation of Intermediate 2

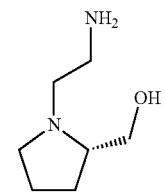

Intermediate 1 (513 mg, 2.10 mmol) was dissolved in 4N hydrochloric acid in 1,4-dioxane (6.3 ml). The mixture was stirred at room temperature overnight. The solvent was removed under reduced pressure, toluene was added twice and removed twice under reduced pressure. The product was obtained as the HCl salt and used without further purification in the next step.

LCMS method 1: MH$^+$=145, RT=0.128 min

Preparation of Intermediate 3

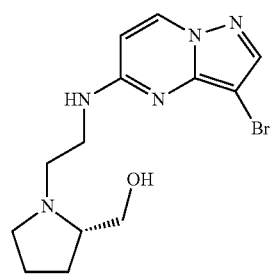 [SMILES: OC[C@@H]1CCCN1CCNc1ccn2ncc(Br)c2n1]

To a mixture of intermediate 2 (300 mg, 2.10 mmol) and triethylamine (1.162 ml, 8.36 mmol) in acetonitrile (6.27 ml)

was added 3-bromo-5-chloro-pyrazolo[1,5-a]pyrimidine (485 mg, 2.09 mmol). The reaction mixture was stirred at 80° C. overnight. The reaction mixture was cooled and the solvent was removed under reduced pressure. The residue was purified by flash column chromatography over silica gel using dichloromethane and a 7N ammonia solution in methanol as eluents (gradient elution from 2% to 10% of 7N ammonia solution in methanol). The product fractions were collected and the solvent was removed under reduced pressure.

LCMS method 2: MH$^+$=340, RT=1.548 min

Preparation of Intermediate 4

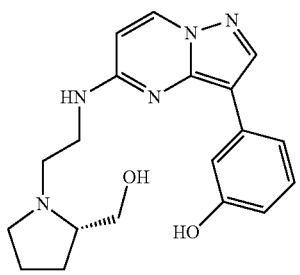 [SMILES: OC[C@@H]1CCCN1CCNc1ccn2ncc(-c3cccc(O)c3)c2n1]

Intermediate 3 (1.71 mmol), 3-hydroxyphenyl)boronic acid (350 mg, 2.56 mmol), 2-dicyclohexylphosphino-2',4',6'-triisopropylbiphenyl (Xphos) (33 mg, 0.07 mmol) and potassium phosphate tribasic (1.08 g, 3 eq.) were dissolved in a mixture of 1,4-dioxane and water (3:1, 10.3 ml) and the mixture was degassed by bubbling nitrogen gas through the mixture. Tetrakis(triphenylphosphine)palladium(0) (35 mg, 0.03 mmol) was added and the mixture was stirred under nitrogen gas at 80° C. for 5 hours. More 3-hydroxyphenyl)boronic acid (175 mg, 1.28 mmol), tetrakis(triphenylphosphine)palladium(0) (17 mg, 0.015 mmol), 2-dicyclohexylphosphino-2',4',6'-triisopropylbiphenyl (Xphos) (16 mg, 0.035 mmol) and potassium phosphate tribasic (540 mg, 1.5 eq.) were added and the mixture was stirred under nitrogen gas at 80° C. overnight. The reaction mixture was cooled and the solvent was removed under reduced pressure. The residue was purified by flash column chromatography over silica gel using dichloromethane and a 7N ammonia solution in methanol as eluents (gradient elution from 2% to 10% of 7N ammonia solution in methanol). The product fractions were collected and the solvent was removed under reduced pressure.

Yield: 239 mg of intermediate 4 (40%)
LCMS method 2: MH$^+$=354, RT=1.718 min

Preparation of Example N1

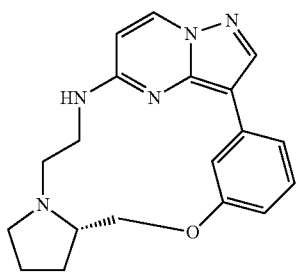 [SMILES: c1cc2cc(c1)-c1cnn3ccc(nc13)NCCN1CCC[C@H]1CO2]

A solution of intermediate 4 (239 mg, 0.68 mmol) in 2-methyltetrahydrofuran (20 ml/mmol) was degassed by bubbling nitrogen gas through the mixture. A solution of diisopropyl azodicarboxylate (400 mg, 2.04 mmol) in toluene (20 ml/mmol) was degassed by bubbling nitrogen gas through the mixture. Both solutions were added dropwise and simultaneously over a period of 2.5 hours at 90° C. to a degassed solution of triphenylphosphine (535 mg, 2.04 mmol) in toluene (75 ml/mmol). The mixture was stirred at 90° C. for 1 hour. The reaction mixture was cooled and the solvent was removed under reduced pressure. The residue was purified by flash column chromatography over silica gel using dichloromethane and a 7N ammonia solution in methanol as eluents (gradient elution from 2% to 10% of 7N ammonia solution in methanol). The product fractions were collected and the solvent was removed under reduced pressure.

The residue was purified by reversed phase column chromatography (HPLC method A).

Yield: 56 mg of example N1 (12%)
LCMS method 2: MH$^+$=336, RT=2.132 min

Example N1 (40 mg, 0.12 mmol) was dissolved in a mixture of dichloromethane and methanol (4:1, 0.5 ml) and 4N hydrochloric acid in 1,4-dioxane (10 µl) was added. The mixture was stirred at room temperature for 1 hour. The solvent was removed under reduced pressure, triturated with diisopropyl ether and dried under reduced pressure. The product was obtained as the HCl salt.

Yield: 6 mg of example N1 (15%)
LCMS method 2: MH$^+$=336, RT=2.127 min

Example N2

Example N2 is prepared following general scheme 1.

Preparation of Intermediate 5

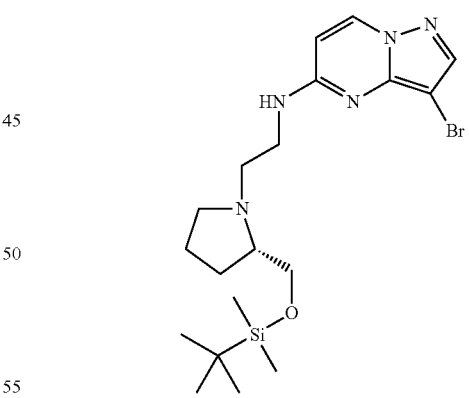

tert-Butyl-chlorodimethylsilane (0.90 g, 6.0 mmol) was added portionwise to a mixture of intermediate 3 (1.70 g, 5.0 mmol) and triethylamine (1.21 g, 12.0 mmol) in dichloromethane (15 ml). The reaction was stirred at room temperature for 24 hours. Water was added and the aqeuous layer was extracted with dichloromethane. The solvent was removed under reduced pressure and the product was used in the next step without further purification.

Yield: 2.24 g of intermediate 5 (99%)
LCMS method 2: MH$^+$=354, RT=2.625 min

Preparation of Intermediate 6

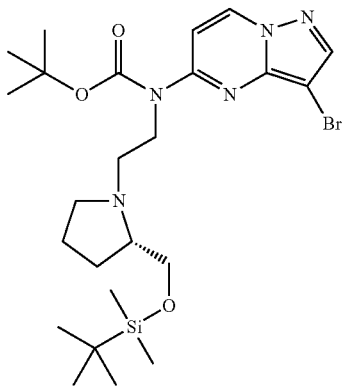 [SMILES: CC(C)(C)OC(=O)N(CCN1CCC[C@H]1CO[Si](C)(C)C(C)(C)C)c1ccn2ncc(Br)c2n1]

tert-Butoxycarbonyl anhydride (1.18 g, 5.42 mmol) was added to a mixture of Intermediate 5 (2.24 g, 4.93 mmol), 4-(dimethylamino)pyridine (31 mg, 0.25 mmol) in tetrahydrofuran (15 ml). The solution was stirred under reflux for 2 hours. The solvent was removed under reduced pressure. Water was added and the aqueous layer was extracted with ethyl acetate. The organic layer was dried, filtered and the solvent was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

Yield: 1.7 g of intermediate 6 (62%)

LCMS method 2: MH⁺=554, RT=3.094 min

Preparation of Intermediate 7

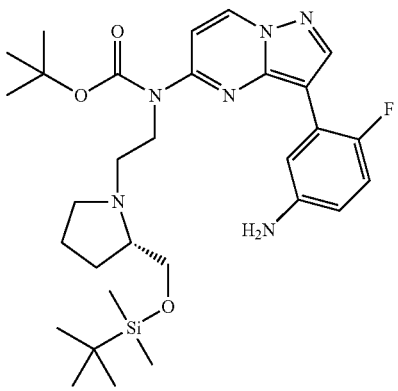 [SMILES: CC(C)(C)OC(=O)N(CCN1CCC[C@H]1CO[Si](C)(C)C(C)(C)C)c1ccn2ncc(-c3cc(N)ccc3F)c2n1]

A mixture of 1,4-dioxane and water (3:1, 8.1 ml) was degassed by bubbling nitrogen gas through the mixture. Intermediate 6 (1.50 g, 2.70 mmol), (5-amino-2-fluorophenyl)boronic acid (500 mg, 3.24 mmol), tetrakis(triphenylphosphine)palladium(0) (533 mg, 0.46 mmol), 2-dicyclohexylphosphino-2',4',6'-triisopropylbiphenyl (Xphos) (872 mg, 1.83 mmol) and potassium phosphate tribasic (1.7 g, 3 eq.) were added and the mixture was stirred under nitrogen gas at 85° C. overnight. More (5-amino-2-fluorophenyl)boronic acid (1.2 eq.), tetrakis(triphenylphosphine)palladium(0) (0.02 eq.), 2-dicyclohexylphosphino-2',4',6'-triisopropylbiphenyl (Xphos) (0.08 eq.) were added and the mixture was stirred under nitrogen gas at 85° C. overnight. The reaction mixture was cooled and diluted with ethyl acetate. The organic layer was washed with water, dried, filtered and the solvent was removed under reduced pressure. The residue was purified by flash column chromatography over silica gel using heptane and ethyl acetate as eluents (gradient elution from 0% to 60% ethyl acetate). The product fractions were collected and the solvent was removed under reduced pressure.

Yield: 1.30 g of intermediate 7 (82%)

Preparation of Intermediate 8

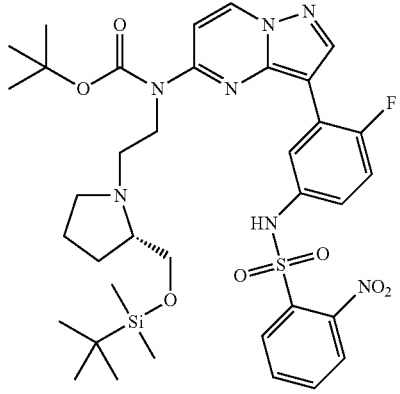 [SMILES: CC(C)(C)OC(=O)N(CCN1CCC[C@H]1CO[Si](C)(C)C(C)(C)C)c1ccn2ncc(-c3cc(NS(=O)(=O)c4ccccc4[N+](=O)[O-])ccc3F)c2n1]

2-Nitrobenzenesulfonyl chloride (0.59 g, 2.66 mmol) was added to a solution of intermediate 7 (1.30 g, 2.22 mmol), pyridine (236 µl, 2.66 mmol) and 4-(dimethylamino)pyridine (13 mg, 0.11 mmol) in dichloromethane (6.66 ml). The reaction mixture was stirred at room temperature overnight. Dichloromethane was added and the organic layer was washed with a 1N aqueous hydrochloric acid solution. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

Yield: 1.033 g of intermediate 8 (60%)

LCMS method 1: MH⁺=770, RT=1.176 min

Preparation of Intermediate 9

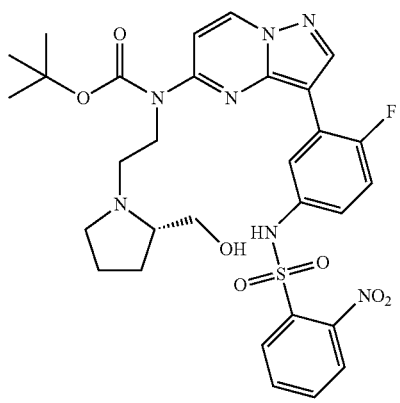 [SMILES: CC(C)(C)OC(=O)N(CCN1CCC[C@H]1CO)c1ccn2ncc(-c3cc(NS(=O)(=O)c4ccccc4[N+](=O)[O-])ccc3F)c2n1]

Intermediate 8 (800 mg, 1.04 mmol) was dissolved in acetic acid/water/tetrahydrofuran (3:1:1, 3.12 ml) and the mixture was stirred at room temperature overnight. The reaction mixture was concentrated under reduced pressure and toluene was added 3 times and concentrated 3 times under reduced pressure. The residue was purified by flash column chromatography over silica gel using heptane and ethyl acetate as eluents. The product fractions were collected and the solvent was removed under reduced pressure.

Yield: 580 mg of intermediate 9 (85%)
LCMS method 1: MH$^+$=656, RT=0.830 min

Preparation of Intermediate 10

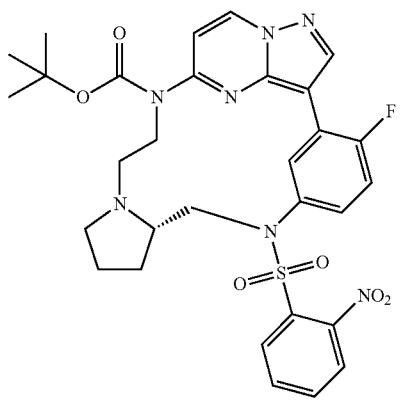 [SMILES: CC(C)(C)OC(=O)N1CCN2CCC[C@H]2CN(S(=O)(=O)c2ccccc2[N+](=O)[O-])c2ccc(F)c(c2)-c2cnn3ccc1nc23]

A solution of intermediate 9 (580 mg, 0.88 mmol) in 2-methyltetrahydrofuran (20 ml/mmol) was degassed by bubbling nitrogen gas through the mixture. A solution of diisopropyl azodicarboxylate (180 mg, 0.88 mmol) in toluene (20 ml/mmol) was degassed by bubbling nitrogen gas through the mixture. Both solution were added simultaneously and dropwise over a period of 3 hours at 90° C. to a degassed solution of triphenylphosphine (231 mg, 0.88 mmol) in toluene (75 ml/mmol). The mixture was stirred at 90° C. for 1 hour. The reaction mixture was cooled and the solvent was removed under reduced pressure. The residue was purified by flash column chromatography over silica gel using heptane and ethyl acetate as eluents. The product fractions were collected and the solvent was removed under reduced pressure.

Yield: 470 mg of intermediate 10 (84%)
LCMS method 1: MH$^+$=638, RT=0.957 min

Preparation of Intermediate 11

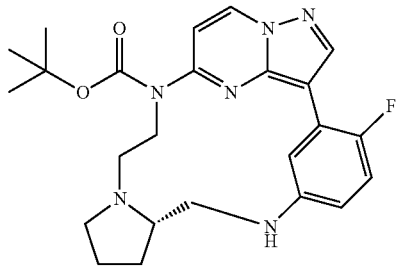 [SMILES: CC(C)(C)OC(=O)N1CCN2CCC[C@H]2CNc2ccc(F)c(c2)-c2cnn3ccc1nc23]

To a solution of intermediate 10 (400 mg, 0.63 mmol) in N,N-dimethylformamide (2.0 ml) were added cesium carbonate (411 mg, 1.26 mmol) and thiophenol (80 μl, 0.76 mmol). The reaction mixture was stirred at room temperature for 17 hours. More cesium carbonate (0.5 eq.) and thiophenol (0.1 eq.) were added and the reaction was stirred at room temperature. A 1N aqueous sodium hydroxide solution was added and the water layer was extracted with ethyl acetate. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

LCMS method 1: MH$^+$=453, RT=0.771 min

Preparation of Example N2

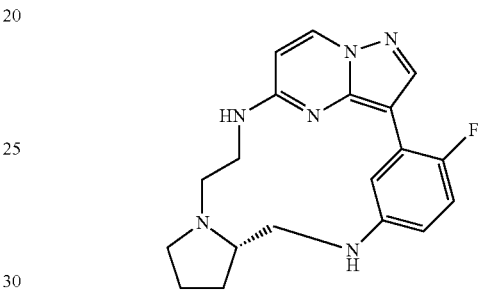

Intermediate 11 (358 mg, 0.79 mmol) was dissolved in 4N hydrochloric acid in 1,4-dioxane (3.16 ml). The mixture was stirred at room temperature overnight. The solvent was removed under reduced pressure. Diethylether was added, the compound was filtered and dried under reduced pressure. The compound was obtained as the hydrochloric acid salt.

Yield: 100 mg of example N2 (36%)
LCMS method 2: MH$^+$=353, RT=1.952 min

Example N3

Example N3 may be prepared following general scheme 1 and according to the procedures illustrated for the preparation of example N2. The product was obtained as the HCl salt.

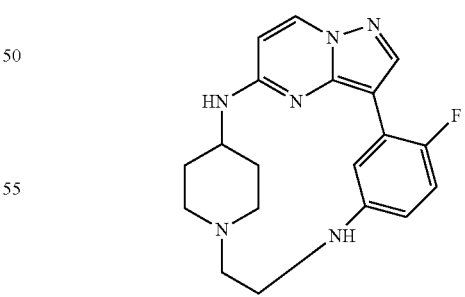

Example N4

Example N4 may be prepared following general scheme 1 and according to the procedures illustrated for the preparation of example N2. The product was obtained as the HCl salt.

137

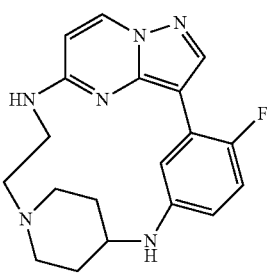 [SMILES: Fc1ccc2cc1-c1cnn3ccc(nc13)NCCN1CCC(CC1)N2]

Example N5

Example N5 may be prepared following general scheme 2.

Preparation of Intermediate 12

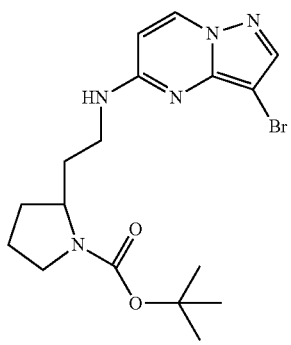 [SMILES: CC(C)(C)OC(=O)N1CCCC1CCNc1ccn2ncc(Br)c2n1]

A mixture of 3-bromo-5-chloro-pyrazolo[1,5-a]pyrimidine (1.0 g, 4.30 mmol), tert-butyl 2-(2-aminoethyl)pyrrolidine-1-carboxylate (1.01 g, 4.73 mmol) and triethylamine (0.878 ml, 5.16 mmol) in acetonitrile (12.9 ml) was stirred under reflux for 16 hours. The reaction mixture was cooled and ethyl acetate was added. The organic layer was washed with water, dried, filtered and the solvent was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

Yield: 1.654 g of intermediate 12 (94%)
LCMS method 1: MH$^+$=410, RT=1.000 min

Preparation of Intermediate 13

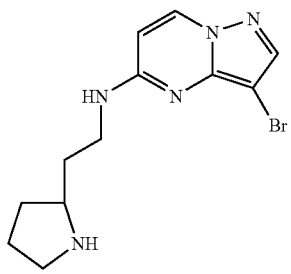 [SMILES: Brc1cnn2ccc(NCCC3CCCN3)nc12]

138

Intermediate 12 (1.654 g, 4.03 mmol) was dissolved in 4N hydrochloric acid in methanol (12.09 ml). The mixture was stirred at room temperature for 2 hours. The solvent was removed under reduced pressure. Toluene was added twice and removed twice under reduced pressure. The compound was obtained as the hydrochloric acid salt and used without further purification in the next step.

LCMS method 1: MH$^+$=347, RT=0.287 min

Preparation of Intermediate 14

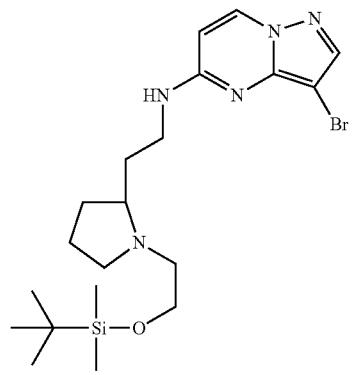 [SMILES: CC(C)(C)[Si](C)(C)OCCN1CCCC1CCNc1ccn2ncc(Br)c2n1]

2-bromoethoxy-tert-butyl-dimethylsilane (880 μl, 4.03 mmol) and cesiumcarbonate (3.939 g, 12.09 mmol) were added to a solution of Intermediate 13 (4.03 mmol) in N,N-dimethylformamide (12.09 ml). The reaction mixture was stirred at 60° C. for 6 hours. Water was added and the aqueous layer was extracted with ethyl acetate and a mixture dichloromethane/methanol (9:1). The organic layer was dried, filtered and the solvent was removed under reduced pressure. The residue was purified by flash column chromatography over silica gel using dichloromethane and methanol as eluents (gradient elution from 0% to 10% of methanol). The product fractions were collected and the solvent was removed under reduced pressure.

Yield: 1.227 g of intermediate 14 (65%)
LCMS method 1: MH$^+$=469, RT=0.779 min

Preparation of Intermediate 15

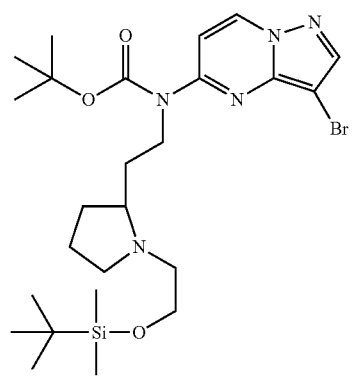 [SMILES: CC(C)(C)OC(=O)N(CCC1CCCN1CCO[Si](C)(C)C(C)(C)C)c1ccn2ncc(Br)c2n1]

tert-Butoxycarbonyl anhydride (0.90 ml, 3.93 mmol) was added to a mixture of Intermediate 14 (1.227 g, 2.62 mmol), 4-(dimethylamino)pyridine (16 mg, 0.13 mmol) in tetrahydrofuran (7.86 ml). The solution was stirred under reflux for 16 hours. tert-Butoxycarbonyl anhydride (0.90 ml, 3.93 mmol), 4-(dimethylamino)pyridine (16 mg, 0.13 mmol) and triethylamine (0.502 ml) were added and the mixture was stirred at 70° C. for 20 hours. The reaction mixture was cooled, ethyl acetate was added and the organic layer was extracted with water. The organic layer was dried, filtered and the solvent was removed under reduced pressure. The residue was purified by flash column chromatography over silica gel using dichloromethane and methanol as eluents (gradient elution from 0% to 7% of methanol). The product fractions were collected and the solvent was removed under reduced pressure.

Yield: 1.387 g of intermediate 15 (93%)

LCMS method 1: $MH^+$=569, RT=1.095 min

Preparation of Intermediate 16

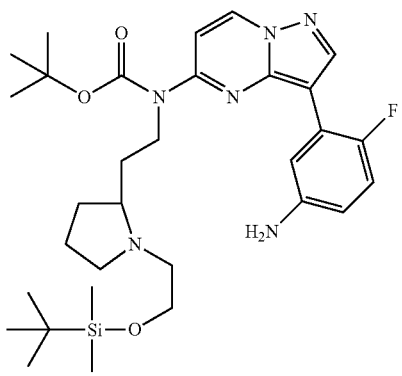 [SMILES: CC(C)(C)OC(=O)N(CCC1CCCN1CCO[Si](C)(C)C(C)(C)C)c1ccn2ncc(-c3cc(N)ccc3F)c2n1]

A mixture of 1,4-dioxane and water (3:1, 7.32 ml) was degassed by bubbling nitrogen gas through the mixture. Intermediate 15 (1.387 g, 2.44 mmol), (5-amino-2-fluorophenyl)boronic acid (690 mg, 2.93 mmol), tetrakis(triphenylphosphine)palladium(0) (58 mg, 0.05 mmol), 2-dicyclohexylphosphino-2',4',6'-triisopropylbiphenyl (Xphos) (48 mg, 0.10 mmol) and potassium phosphate tribasic (1.553 g, 3 eq.) were added and the mixture was stirred under nitrogen gas at 85° C. for 16 hours. The reaction mixture was cooled and diluted with ethyl acetate. The organic layer was washed with water, dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 0.99 g of intermediate 16 (68%)

LCMS method 1: $MH^+$=599, RT=1.053 min

Preparation of Intermediate 17

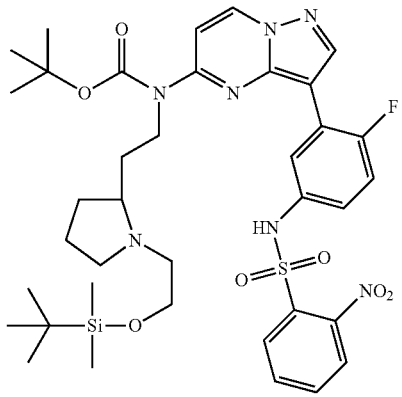 [SMILES: CC(C)(C)OC(=O)N(CCC1CCCN1CCO[Si](C)(C)C(C)(C)C)c1ccn2ncc(-c3cc(NS(=O)(=O)c4ccccc4[N+](=O)[O-])ccc3F)c2n1]

2-Nitrobenzenesulfonyl chloride (0.44 g, 2.00 mmol) was added to a solution of intermediate 17 (0.99 g, 1.67 mmol), pyridine (148 µl, 1.67 mmol) and 4-(dimethylamino)pyridine (10 mg, 0.08 mmol) in dichloromethane (5.0 ml). The reaction mixture was stirred at room temperature for 4 hours. More 2-nitrobenzenesulfonyl chloride (0.088 g, 0.4 mmol) was added and the mixture was stirred at room temperature for 1 hour. Dichloromethane was added and the organic layer was washed with a 1N aqueous hydrochloric acid solution. The organic layer was dried, filtered and the solvent was removed under reduced pressure. The residue was purified by flash column chromatography over silica gel using dichloromethane and methanol as eluents (gradient elution from 0% to 7% methanol). The product fractions were collected and the solvent was removed under reduced pressure.

Yield: 0.975 g of intermediate 17 (74%)

LCMS method 1: $MH^+$=784, RT=1.168 min

Preparation of Intermediate 18

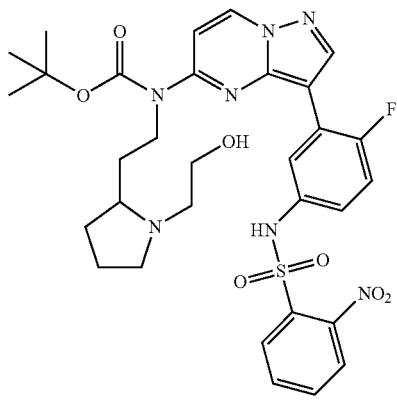 [SMILES: CC(C)(C)OC(=O)N(CCC1CCCN1CCO)c1ccn2ncc(-c3cc(NS(=O)(=O)c4ccccc4[N+](=O)[O-])ccc3F)c2n1]

Tetrabutylammonium fluoride (1.89 g, 1.89 mmol) was added to a solution of intermediate 17 (925 mg, 1.18 mmol) in tetrahydrofuran (3.54 ml). The reaction mixture was stirred at room temperature for 24 hours. The mixture was diluted with ethyl acetate and washed with water and a saturated aqueous sodium bicarbonate solution. The organic layer was dried, filtered and the solvent was removed under reduced pressure. Acetonitrile was added, the solid was filtered and dried under reduced pressure.

Yield: 680 mg of intermediate 18 (86%)
LCMS method 1: MH$^+$=670, RT=0.804 min

Preparation of Intermediate 19

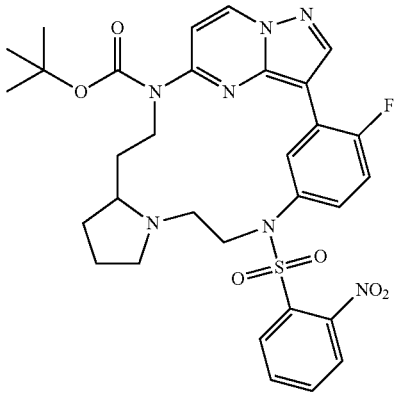 [SMILES: CC(C)(C)OC(=O)N1CCC2CCCN2CCN(S(=O)(=O)c2ccccc2[N+](=O)[O-])c2ccc(F)c(c2)-c2cnn3ccc1nc23]

A solution of intermediate 18 (580 mg, 0.87 mmol) in 2-methyltetrahydrofuran (20 ml/mmol) and in dry N,N-dimethylformamide (2 ml) and a solution of diisopropyl azodicarboxylate (520 mg, 2.61 mmol) in toluene (20 ml/mmol) were added simultaneously and dropwise over a period of 2 hours at 90° C. to a solution of triphenylphosphine (685 mg, 2.61 mmol) in toluene (75 ml/mmol). The mixture was stirred at 90° C. for 30 minutes. The reaction mixture was cooled and the solvent was removed under reduced pressure. The residue was purified by flash column chromatography over silica gel using dichloromethane and methanol as eluents (gradient elution from 0% to 3% methanol). The product fractions were collected and the solvent was removed under reduced pressure.

Yield: 547 mg of intermediate 19 (96%)
LCMS method 1: MH$^+$=652, RT=0.929 min

Preparation of Intermediate 20

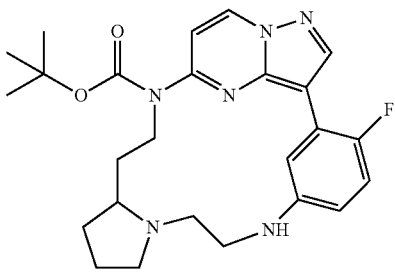 [SMILES: CC(C)(C)OC(=O)N1CCC2CCCN2CCNc2ccc(F)c(c2)-c2cnn3ccc1nc23]

To a solution of intermediate 19 (546 mg, 0.84 mmol) in N,N-dimethylformamide (2.52 ml) were added cesium carbonate (547 mg, 1.68 mmol) and thiophenol (100 μl, 1.01 mmol). The reaction mixture was stirred at room temperature for 3 hours. Ethyl acetate was added and the organic layer was washed with a 1N aqueous sodium hydroxide solution. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 206 mg of intermediate 20 (53%)
LCMS method 1: MH$^+$=467, RT=2.367 min

Preparation of Example N5

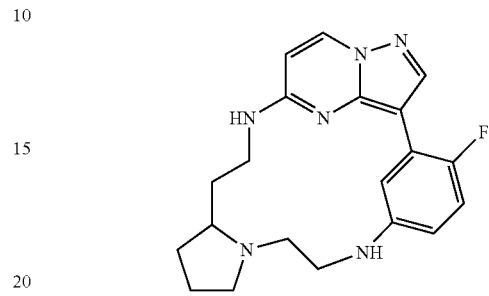

Intermediate 20 (206 mg, 0.44 mmol) was dissolved in 4N hydrochloric acid in methanol (1.32 ml). The mixture was stirred at room temperature overnight and at 45° C. for 6 hours. Diethylether was added, the compound was filtered and dried under reduced pressure at 60° C. for 16 hours. The product was obtained as the HCl salt.

LCMS method 2: MH$^+$=367, RT=1.880 min

Example N6

Example N6 may be prepared following general scheme 1 and according to the procedures illustrated for the preparation of example N2. The product was obtained as the HCl salt.

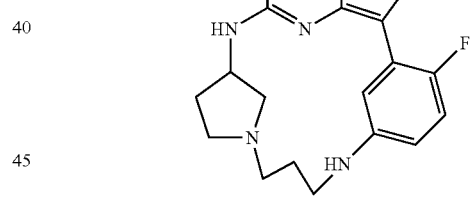

Example N7

Example N7 may be prepared following general scheme 1.

Preparation of Intermediate 21

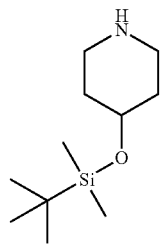

tert-Butyl-chlorodimethylsilane (4.47 g, 29.66 mmol) was added to a mixture of piperidin-4-ol (2.00 g, 19.77 mmol) and imidazole (2.692 g, 39.54 mmol) in dichloromethane (59.31 ml). The reaction was stirred at room temperature for 72 hours. The solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

LCMS method 1: MH$^+$=216, RT=0.516 min

Preparation of Intermediate 22

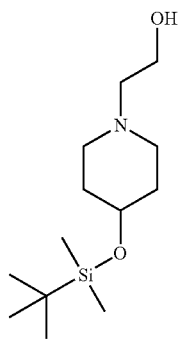 [SMILES: CC(C)(C)[Si](C)(C)OC1CCN(CCO)CC1]

A mixture of intermediate 21 (19.77 mmol), 2-bromoethanol (2.81 ml, 39.54 mmol) and potassium carbonate (21.86 g, 158.16 mmol) in acetonitrile (59.31 ml) is refluxed for 20 hours. Water was added and the aqueous layer was extracted with ethyl acetate and a mixture of dichloromethane and methanol (9:1). The organic layer was dried, filtered and the solvent was removed under reduce pressure. The residue was purified by flash column chromatography over silica gel using dichloromethane and methanol as eluents (gradient elution from 0% to 10% methanol). The product fractions were collected and the solvent was removed under reduced pressure.

Yield: 3.06 g of intermediate 22 (60%)
LCMS method 1: MH$^+$=260, RT=0.601 min

Preparation of Intermediate 23

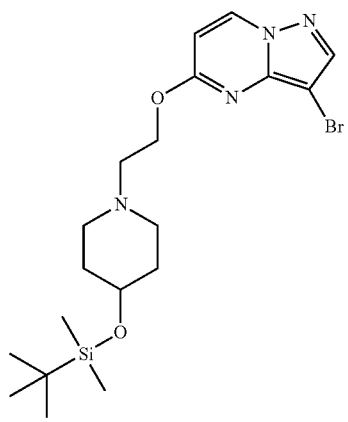 [SMILES: CC(C)(C)[Si](C)(C)OC1CCN(CCOc2ccn3ncc(Br)c3n2)CC1]

Sodium hydride (60% in mineral oil, 155 mg, 6.45 mmol) was added at 0° C. to a solution of 3-bromo-5-chloropyrazolo[1,5-a]pyrimidine (1.50 g, 6.45 mmol) and intermediate 22 (2.01 g, 7.74 mmol) in dry N,N-dimethylformamide (19.35 ml). The reaction mixture was stirred at room temperature for 1 hour.

A saturated aqueous ammonium chloride solution was added and the aqueous layer was extracted with ethyl acetate and a mixture of dichloromethane and methanol (9:1). The solvent was removed under reduced pressure. The residue was purified by flash column chromatography over silica gel using heptane and ethyl acetate as eluents (gradient elution from 0% to 7% of ethyl acetate). The product fractions were collected and the solvent was removed under reduced pressure.

Yield: 1.688 g of intermediate 23 (57%)
LCMS method 1: MH$^+$=456, RT=0.880 min

Preparation of Intermediate 24

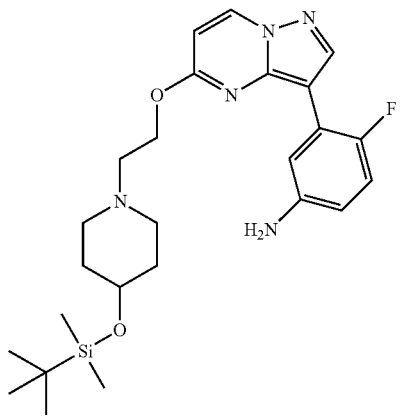 [SMILES: CC(C)(C)[Si](C)(C)OC1CCN(CCOc2ccn3ncc(-c4cc(N)ccc4F)c3n2)CC1]

A mixture of 1,4-dioxane and water (3:1, 21.0 ml) was degassed by bubbling nitrogen gas through the mixture. Intermediate 23 (1.588 g, 3.49 mmol), (5-amino-2-fluorophenyl)boronic acid (0.99 g, 4.19 mmol), tetrakis(triphenylphosphine)palladium(0) (81 mg, 0.07 mmol), 2-dicyclohexylphosphino-2',4',6'-triisopropylbiphenyl (Xphos) (67 mg, 0.14 mmol) and potassium phosphate tribasic (2.222 g, 3 eq.) were added and the mixture was stirred under nitrogen gas at 85° C. for 16 hours. The reaction mixture was cooled and diluted with ethyl acetate. The organic layer was washed with water, dried, filtered and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 1.40 g of intermediate 24 (83%)
LCMS method 1: MH$^+$=486, RT=0.853 min

Preparation of Intermediate 25

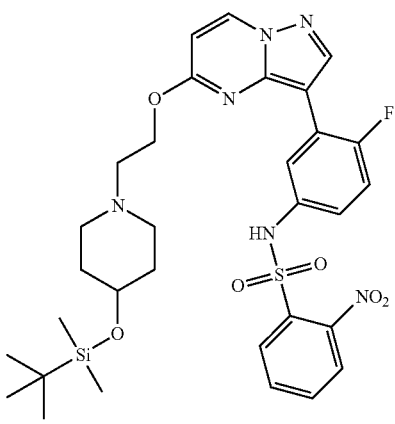 [SMILES: CC(C)(C)[Si](C)(C)OC1CCN(CCOc2ccn3ncc(-c4cc(NS(=O)(=O)c5ccccc5[N+](=O)[O-])ccc4F)c3n2)CC1]

2-Nitrobenzenesulfonyl chloride (0.77 g, 3.46 mmol) was added portionwise to a solution of intermediate 24 (1.40 g, 2.88 mmol), pyridine (256 µl, 2.88 mmol) and 4-(dimethylamino)pyridine (17 mg, 0.14 mmol) in dichloromethane (8.64 ml). The reaction mixture was stirred at room temperature for 3 hours. Dichloromethane was added and the organic layer was washed with a 1N aqueous hydrochloric acid solution. The organic layer was dried, filtered and the solvent was removed under reduced pressure. The residue was purified by flash column chromatography over silica gel using dichloromethane and methanol as eluents (gradient elution from 0% to 8% methanol). The product fractions were collected and the solvent was removed under reduced pressure.

Yield: 1.486 g of intermediate 25 (77%)
LCMS method 1: MH$^+$=671, RT=0.936 min

Preparation of Intermediate 26

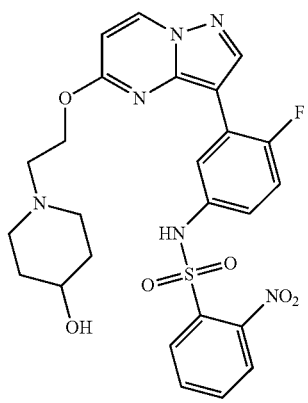 [SMILES: O=[N+]([O-])c1ccccc1S(=O)(=O)Nc1ccc(F)c(-c2cnn3ccc(OCCN4CCC(O)CC4)nc23)c1]

Tetrabutylammonium fluoride (4.44 g, 4.44 mmol) was added to a solution of intermediate 25 (1.486 g, 2.22 mmol) in tetrahydrofuran (6.66 ml). The reaction mixture was stirred at room temperature for 20 hours. More tetrabutylammonium fluoride (1 eq.) was added and the mixture was stirred at room temperature for 24 hours and at 60° C. for 4 hours. The mixture was diluted with ethyl acetate and washed with water and a saturated aqueous sodium bicarbonate solution. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

Yield: 800 mg of intermediate 26 (65%)
LCMS method 1: MH$^+$=557, RT=0.559 min

Preparation of Intermediate 27

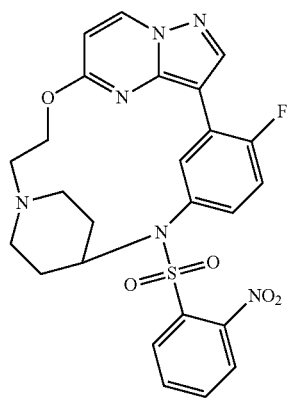 [SMILES: O=[N+]([O-])c1ccccc1S(=O)(=O)N1c2ccc(F)c(c2)-c2cnn3ccc(nc23)OCCN2CCC1CC2]

A solution of intermediate 26 (650 mg, 1.17 mmol) in 2-methyltetrahydrofuran (20 ml/mmol) and a solution of diisopropyl azodicarboxylate (1.16 g, 5.85 mmol) in toluene (20 ml/mmol) were added simultaneously and dropwise over a period of 3 hours at 90° C. to a solution of triphenylphosphine (1.534 g, 5.85 mmol) in toluene (75 ml/mmol). The mixture was stirred at 90° C. for 30 minutes. The reaction mixture was cooled and the solvent was removed under reduced pressure. The residue was purified by flash column chromatography over silica gel using dichloromethane and methanol as eluents (gradient elution from 0% to 7% methanol). The product fractions were collected and the solvent was removed under reduced pressure.

Yield: 239 mg of intermediate 27 (38%)
LCMS method 1: MH$^+$=539, RT=0.662 min

Preparation of Example N7

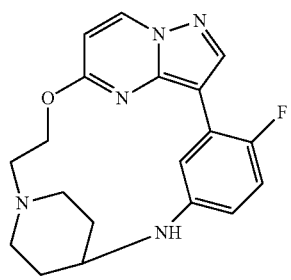 [SMILES: Fc1ccc2cc1-c1cnn3ccc(nc13)OCCN1CCC(CC1)N2]

To a solution of intermediate 27 (200 mg, 0.37 mmol) in N,N-dimethylformamide (1.11 ml) were added cesium carbonate (241 mg, 0.74 mmol) and thiophenol (40 µl, 0.44 mmol). The reaction mixture was stirred at room temperature for 2 hours. The solvent was removed under reduced pressure. The residue was purified by reversed phase column chromatography (HPLC method A). The product fractions were collected and the solvent was removed under reduced pressure.

Yield: 65 mg of example N7 (50%)
LCMS method 2: MH+=354, RT=1.873 min

Example N8

Example N8 may be prepared following general scheme 1.

Preparation of Intermediate 28

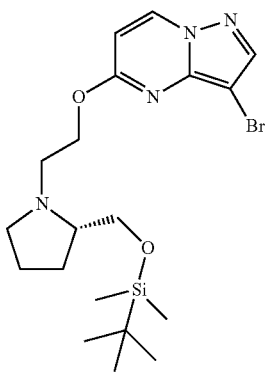 [SMILES: CC(C)(C)[Si](C)(C)OC[C@@H]1CCCN1CCOc1ccn2ncc(Br)c2n1]

tert-Butyl-chlorodimethylsilane (1.59 g, 10.55 mmol) was added to a mixture of intermediate 3 (2.99 g, 8.79 mmol) and triethylamine (3.05 ml, 21.97 mmol) in dichloromethane (26.37 ml). The reaction was stirred at room temperature for 5 hours. More triethylamine (0.30 ml, 2.197 mmol) and tert-butyl-chlorodimethylsilane (0.159 g, 1.055 mmol) were added and the reaction mixture was stirred at room temperature overnight. The reaction mixture was diluted with dichloromethane. The organic layer was washed with water and brine, dried, filtered and the solvent was removed under reduced pressure. The residue was purified by flash column chromatography over silica gel using dichloromethane and 7N ammonia in methanol as eluents (gradient elution from 0% to 10%). The product fractions were collected and the solvent was removed under reduced pressure.

Yield: 3.14 g of intermediate 28 (79%)
LCMS method 1: MH+=456, RT=0.676 min

Preparation of Intermediate 29

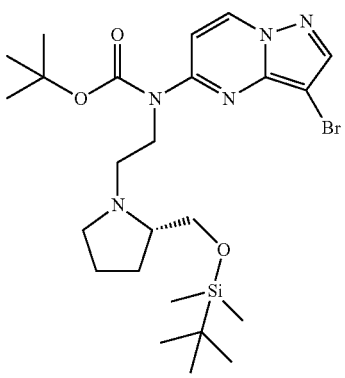 [SMILES: CC(C)(C)OC(=O)N(CCN1CCC[C@H]1CO[Si](C)(C)C(C)(C)C)c1ccn2ncc(Br)c2n1]

tert-Butoxycarbonyl anhydride (1.81 g, 8.29 mmol) was added to a mixture of intermediate 28 (3.14 g, 6.91 mmol), trimethylamine (1.248 ml, 8.98 mmol) and 4-(dimethylamino)pyridine (43 mg, 0.35 mmol) in tetrahydrofuran (20.73 ml). The solution was stirred at 80° C. for 2.5 hours. More tert-butoxycarbonyl anhydride (362 mg, 1.658 mmol), 4-(dimethylamino)pyridine (9 mg, 0.07 mmol) and triethylamine (0.250 ml, 1.796 mmol) were added and the mixture was stirred at 80° C. for 2 hours. The reaction mixture was cooled and the solvent was removed under reduced pressure. Dichloromethane was added and the organic layer was extracted with water and brine. The organic layer was dried, filtered and the solvent was removed under reduced pressure. The residue was purified by flash column chromatography over silica gel using dichloromethane and methanol as eluents (gradient elution from 0% to 10% of methanol). The product fractions were collected and the solvent was removed under reduced pressure.

Yield: 3.47 g of intermediate 29 (91%)
LCMS method 1: MH+=556, RT=0.855 min

Preparation of Intermediate 30

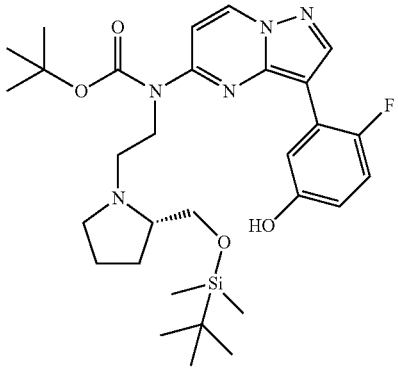 [SMILES: CC(C)(C)OC(=O)N(CCN1CCC[C@H]1CO[Si](C)(C)C(C)(C)C)c1ccn2ncc(-c3cc(O)ccc3F)c2n1]

Intermediate 29 (1.40 g, 2.52 mmol), 4-fluoro-3-(4,4,5,5-tetramethyl-1,3,2-dioxaborolan-2-yl)phenol (720 mg, 3.02 mmol), 2-dicyclohexylphosphino-2',4',6'-triisopropylbiphenyl (Xphos) (119 mg, 0.25 mmol) and potassium phosphate tribasic (1.60 g, 3 eq.) were dissolved in a mixture of 1,4-dioxane and water (3:1, 7.56 ml) and the mixture was degassed by bubbling nitrogen gas through the mixture. Tetrakis(triphenylphosphine)palladium(0) (116 mg, 0.10 mmol) was added and the mixture was stirred under nitrogen gas at 80° C. overnight. More 4-fluoro-3-(4,4,5,5-tetramethyl-1,3,2-dioxaborolan-2-yl)phenol (216 mg, 0.906 mmol), 2-dicyclohexylphosphino-2',4',6'-triisopropylbiphenyl (Xphos) (36 mg, 0.075 mmol) potassium phosphate tribasic (480 mg, 0.9 eq.) and tetrakis(triphenylphosphine)palladium(0) (35 mg, 0.03 mmol) were added and the mixture was stirred under nitrogen gas at 80° C. for 6 hours. The reaction mixture was cooled and the solvent was removed under reduced pressure. Ethyl acetate and water were added and the aqueous layer was extracted twice with ethyl acetate. The combined organic layers were dried, filtered and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure.

Yield: 1.23 g of intermediate 30 (83%)
LCMS method 1: MH+=586, RT=0.983 min

Preparation of Intermediate 31

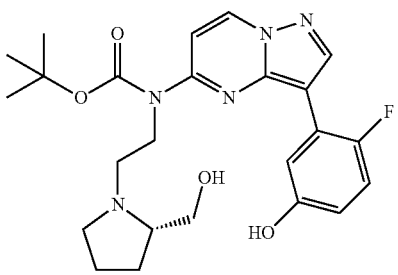 [SMILES: CC(C)(C)OC(=O)N(CCN1CCC[C@H]1CO)c1ccn2ncc(-c3cc(O)ccc3F)c2n1]

Tetrabutylammonium fluoride (1M solution in tetrahydrofuran, 0.66 g, 2.52 mmol) was added to a solution of intermediate 31 (1.23 g, 2.10 mmol) in tetrahydrofuran (6.30 ml). The reaction mixture was stirred at room temperature overnight. More tetrabutylammonium fluoride (1M solution in tetrahydrofuran, 66 mg, 0.252 mmol) was added and mixture was stirred at room temperature for 2 hours. The solvent was removed under reduced pressure and dichloromethane was added. The organic layer was washed with water and a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 710 mg of intermediate 31 (72%)

LCMS method 1: MH$^+$=472, RT=0.640 min

Preparation of Intermediate 32

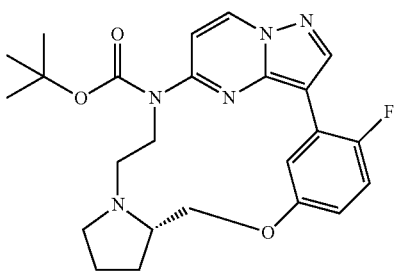 [SMILES: CC(C)(C)OC(=O)N1CCN2CCC[C@H]2COc2ccc(F)c(c2)-c2cnn3ccc1nc23]

A solution of intermediate 31 (680 mg, 1.44 mmol) in 2-methyltetrahydrofuran (20 ml/mmol) was degassed by bubbling nitrogen gas through the mixture. A solution of diisopropyl azodicarboxylate (860 mg, 4.32 mmol) in toluene (20 ml/mmol) was degassed by bubbling nitrogen gas through the mixture. Both solutions were added simultaneously and dropwise over a period of 45 minutes at 90° C. to a degassed solution of triphenylphosphine (1.133 g, 4.32 mmol) in toluene (75 ml/mmol). The mixture was stirred at 90° C. for 1 hour. The reaction mixture was cooled and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 346 mg of intermediate 32 (53%)

LCMS method 1: MH$^+$=454, RT=2.660 min

Preparation of Example N8

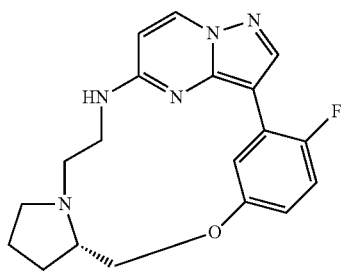 [SMILES: Fc1ccc2cc1-c1cnn3ccc(nc13)NCCN1CCC[C@H]1CO2]

A mixture of intermediate 31 (346 mg, 0.76 mmol) and 4N hydrochloric acid in 1,4-dioxane (2.28 ml) was stirred at room temperature for 4 hours, at 50° C. for 2 hours and overnight at room temperature. Diethyl ether and methanol (1 ml) were added and the mixture was stirred at room temperature for 30 minutes. The solid was filtered, washed with diethyl ether and a small amount of methanol and dried under vacuum at 60° C. The product was obtained as the HCl salt.

Yield: 225 mg of example N8 (84%)

LCMS method 2: MH$^+$=354, RT=2.098 min

Example N9

Example N9 may be prepared following general scheme 2.

Preparation of Intermediate 33

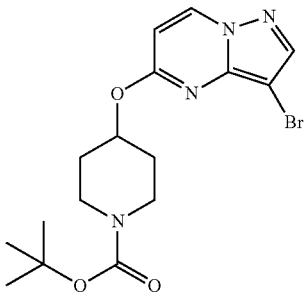 [SMILES: CC(C)(C)OC(=O)N1CCC(Oc2ccn3ncc(Br)c3n2)CC1]

A mixture of 3-bromo-5-chloro-pyrazolo[1,5-a]pyrimidine (2.00 g, 8.60 mmol) and tert-butyl 4-hydroxypiperidine-1-carboxylate (1.99 g, 9.89 mmol) in dry tetrahydrofuran (25.80 ml) was stirred at room temperature for 1 hour. Sodium hydride (60% in mineral oil, 310 mg, 12.90 mmol) was added and the reaction mixture was stirred at room temperature for 1 hour. More sodium hydride (60% in mineral oil, 30%) was added and the reaction mixture was stirred at room temperature for 1 hour. The reaction mixture was cooled to 0° C. and a saturated aqueous ammonium chloride solution was added and the aqueous layer was extracted with ethyl acetate. The solvent was removed under reduced pressure. The residue was purified by flash column chromatography over silica gel using heptane and ethyl acetate as eluents (gradient elution from 0% to 30% of ethyl acetate). The product fractions were collected and the solvent was removed under reduced pressure.

Yield: 826 mg of intermediate 33 (24%)
LCMS method 1: MH⁺=398, RT=1.125 min

Preparation of Intermediate 34

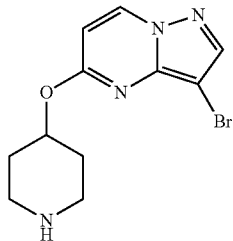 [SMILES: Brc1cnn2ccc(OC3CCNCC3)nc12]

Intermediate 33 (826 mg, 2.08 mmol) was dissolved in 4N hydrochloric acid in methanol (6.24 ml). The mixture was stirred at room temperature for 4 hours. Toluene was added twice and removed twice under reduced pressure. The compound was obtained as the hydrochloric acid salt and was used without further purification in the next step.

Yield: 678 mg of intermediate 34 (98%)
LCMS method 2: MH⁺=298, RT=0.306 min

Preparation of Intermediate 35

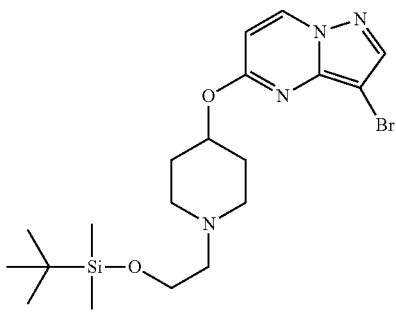 [SMILES: CC(C)(C)[Si](C)(C)OCCN1CCC(Oc2ccn3ncc(Br)c3n2)CC1]

Sodium triacetoxyborohydride (1.339 g, 6.32 mmol) was added portionwise to a solution of intermediate 34 (1.054 g, 3.16 mmol), 2-[tert-butyl(dimethyl)silyl]oxyacetaldehyde (90%, 830 mg, 4.74 mmol) and triethylamine (1.318 ml, 9.48 mmol) in a mixture of 1,2-dichloroethane (9 ml) and methanol (4 ml). The reaction mixture was stirred at room temperature for 2 hours. A saturated aqueous sodium bicarbonate solution was added and the aqueous layer was extracted with dichloromethane. The organic layer was dried, filtered and the solvent was removed under reduced pressure. The residue was purified by flash column chromatography over silica gel using dichloromethane and methanol as eluents (gradient elution from 0% to 3% methanol). The product fractions were collected and the solvent was removed under reduced pressure.

Yield: 1.233 g of intermediate 35 (86%)
LCMS method 1: MH⁺=456, RT=0.725 min

Preparation of Intermediate 36

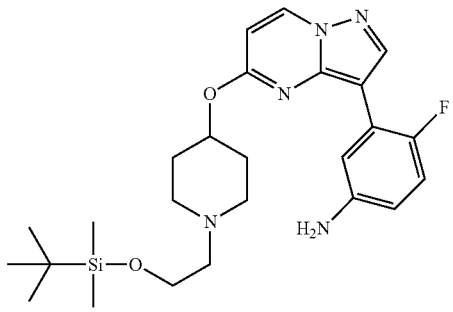 [SMILES: CC(C)(C)[Si](C)(C)OCCN1CCC(Oc2ccn3ncc(-c4cc(N)ccc4F)c3n2)CC1]

A mixture of 1,4-dioxane and water (3:1, 12.0 ml) was degassed by bubbling nitrogen gas through the mixture. Intermediate 35 (818 mg, 1.80 mmol), (5-amino-2-fluorophenyl)boronic acid (0.42 g, 2.70 mmol), tetrakis(triphenylphosphine)palladium(0) (46 mg, 0.04 mmol), 2-dicyclohexylphosphino-2',4',6'-triisopropylbiphenyl (Xphos) (33 mg, 0.07 mmol) and potassium phosphate tribasic (1.146 g, 3 eq.) were added and the mixture was stirred under nitrogen gas at 85° C. for 16 hours. The reaction mixture was cooled and diluted with ethyl acetate. The organic layer was washed with water, dried, filtered and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 731 mg of intermediate 36 (84%)
LCMS method 1: MH⁺=486, RT=0.877 min

Preparation of Intermediate 37

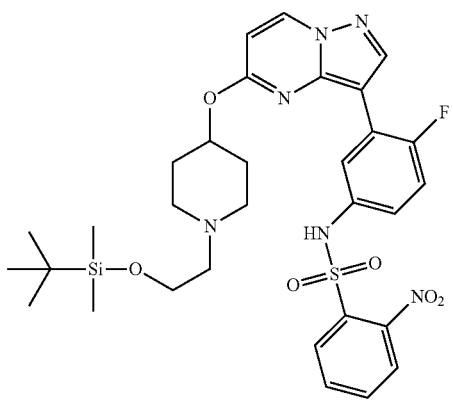 [SMILES: CC(C)(C)[Si](C)(C)OCCN1CCC(Oc2ccn3ncc(-c4cc(NS(=O)(=O)c5ccccc5[N+](=O)[O-])ccc4F)c3n2)CC1]

2-Nitrobenzenesulfonyl chloride (0.40 g, 1.81 mmol) was added portionwise to a solution of intermediate 36 (731 mg, 1.51 mmol), pyridine (134 µl, 1.51 mmol) and 4-(dimethylamino)pyridine (10 mg, 0.08 mmol) in dichloromethane (4.53 ml). The reaction mixture was stirred at room temperature for 3 hours. Dichloromethane was added and the organic layer was washed with a 1N aqueous hydrochloric acid solution. The organic layer was dried, filtered and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 746 mg of intermediate 37 (74%)
LCMS method 1: MH$^+$=671, RT=1.039 min

Preparation of Intermediate 38

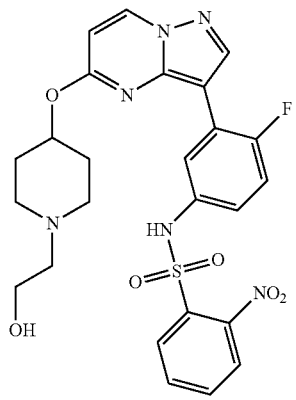 [SMILES: O=[N+]([O-])c1ccccc1S(=O)(=O)Nc1ccc(F)c(-c2cnn3ccc(OC4CCN(CCO)CC4)nc23)c1]

Tetrabutylammonium fluoride (1.33 g, 1.33 mmol) was added to a solution of intermediate 37 (746 mg, 1.11 mmol) in tetrahydrofuran (3.33 ml). The reaction mixture was stirred at room temperature for 48 hours. The mixture was diluted with ethyl acetate and washed with water and a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 362 mg of intermediate 38 (59%)
LCMS method 1: MH$^+$=557, RT=0.648 min

Preparation of Intermediate 39

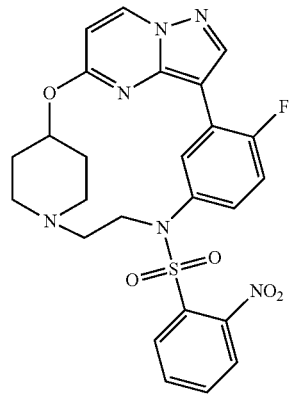 [SMILES: O=[N+]([O-])c1ccccc1S(=O)(=O)N1CCN2CCC(CC2)Oc2ccn3ncc(c3n2)-c2cc1ccc2F]

A solution of intermediate 38 (287 mg, 0.52 mmol) in 2-methyltetrahydrofuran (20 ml/mmol) and a solution of diisopropyl azodicarboxylate (0.52 g, 2.60 mmol) in toluene (20 ml/mmol) were added simultaneously and dropwise over a period of 2 hours at 90° C. to a solution of triphenylphosphine (682 mg, 2.60 mmol) in toluene (75 ml/mmol). The mixture was stirred at 90° C. for 30 minutes. The reaction mixture was cooled and the solvent was removed under reduced pressure. The residue was purified by flash column chromatography over silica gel using dichloromethane and ethyl acetate as eluents (gradient elution from 0% to 50% ethyl acetate). The product fractions were collected and the solvent was removed under reduced pressure.

Yield: 141 mg of intermediate 39 (50%)
LCMS method 1: MH$^+$=539, RT=2.337 min

Preparation of Example N9

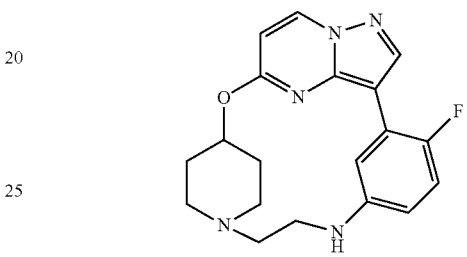

To a solution of intermediate 39 (141 mg, 0.26 mmol) in N,N-dimethylformamide (0.78 ml) were added cesium carbonate (169 mg, 0.52 mmol) and thiophenol (30 µl, 0.31 mmol). The reaction mixture was stirred at room temperature for 5 hours. The solvent was removed under reduced pressure. The residue was purified by reversed phase column chromatography (HPLC method A). The product fractions were collected and the solvent was removed under reduced pressure. The product was dried under vacuum at 60° C. for 16 hours.

Yield: 18 mg of example N9 (20%)
LCMS method 2: MH$^+$=354, RT=1.977 min

Example N10

Example N10 may be prepared following general scheme 1 and according to the procedures illustrated for the preparation of example N2. The product was obtained as the HCl salt.

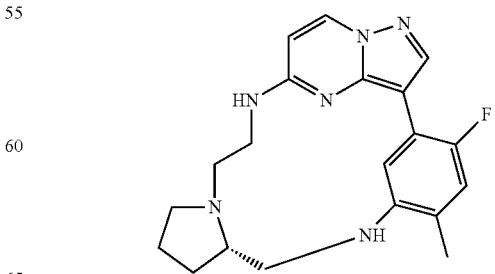

Example N11

Example N11 may be prepared following general scheme 1 and starting from example N8.

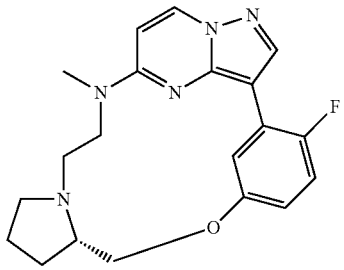 [SMILES: CN1CCN2CCC[C@H]2COc2ccc(F)c(c2)-c2cnn3ccc1nc23]

A mixture of example N8 (133 mg, 0.38 mmol) and sodium hydride (60% in mineral oil, 100 mg, 4.18 mmol) in anhydrous N,N-dimethylformamide (1.14 ml) was stirred under nitrogen atmosphere for 1 hour. Iodomethane (27 µl, 0.44 mmol) was added and the reaction mixture was stirred at room temperature for 2 hours. Water was added and the aqueous layer was extracted with dichloromethane. The organic layer was dried, filtered and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 105 mg of example N11 (75%)
LCMS method 2: MH$^+$=368, RT=2.107 min

Example N11 (105 mg, 0.29 mmol) was dissolved in dichloromethane (2 ml). 4N hydrochloric acid in 1,4-dioxane (0.87 ml) was added and the reaction mixture was stirred at room temperature for 5 hours. Diethyl ether and methanol (1 ml) were added and the mixture was stirred at room temperature for 30 minutes. The solid was filtered, washed with diethyl ether and a small amount of methanol. The compound was dried under vacuum at 60° C. The product was obtained as the HCl salt.

Yield: 87 mg of example N11 (82%)
LCMS method 2: MH$^+$=368, RT=2.114 min

Example N12

Example N12 may be prepared following general scheme 1 and according to the procedures illustrated for the preparation of example N8. The product was obtained as the HCl salt.

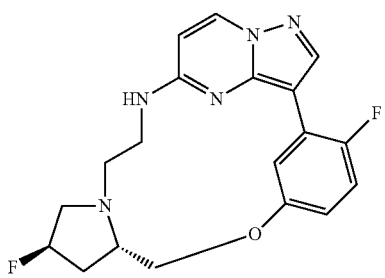 [SMILES: Fc1ccc2cc1-c1cnn3ccc(nc13)NCCN1C[C@H](F)C[C@H]1CO2]

Example N13

Example N13 may be prepared following general scheme 2.

Preparation of Intermediate 40

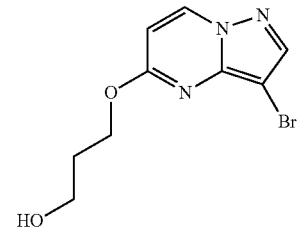 [SMILES: OCCCOc1ccn2ncc(Br)c2n1]

Sodium hydride (60% in mineral oil, 170 mg, 7.10 mmol) was added at 0° C. to a solution of propane-1,3-diol (2.337 ml, 32.25 mmol) in anhydrous tetrahydrofuran (19.35 ml). The reaction mixture was stirred at room temperature for 30 minutes. The mixture was cooled to 0° C. and 3-bromo-5-chloro-pyrazolo[1,5-a]pyrimidine (1.50 g, 6.45 mmol) was added in one portion. The reaction mixture was stirred at room temperature for 10 minutes. Dry N,N-dimethylformamide (2 ml) was added and the reaction mixture was stirred at room temperature for 2 hours.

The reaction mixture was poured into a 50% aqueous ammoniumchloride solution. The aqueous layer was extracted with dichloromethane. The combined organic layers were washed with brine, dried, filtered and the solvent was removed under reduced pressure. The residue was suspended in ethyl acetate (5 ml), the slurry was heated at 60° C. for 10 minutes and then cooled to room temperature. The solid was filtered, washed with ethyl acetate and dried under reduced pressure.

Yield: 1.25 g of intermediate 40 (71%)
LCMS method 1: MH$^+$=273, RT=0.539 min

Preparation of Intermediate 41

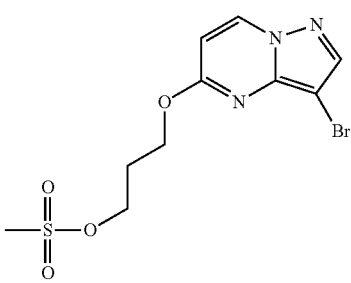 [SMILES: CS(=O)(=O)OCCCOc1ccn2ncc(Br)c2n1]

Intermediate 40 (4.04 g, 14.85 mmol) and triethylamine (3.097 ml, 22.28 mmol) were dissolved in anhydrous dichloromethane (45 ml). The reaction mixture was cooled to 0° C. under nitrogen atmosphere and a slurry of methylsulfonyl methanesulfonate (2.85 g, 16.34 mmol) in anhydrous dichloromethane (20 ml) was added dropwise. The reaction mixture was stirred for at 0° C. for 15 minutes and at room temperature for 3 hours. The reaction mixture was diluted with dichloromethane and the organic layer was washed with brine. The organic layer was dried, filtered and the solvent was removed under reduced pressure. The compound was used without further purification used in the next step.

LCMS method 2: MH$^+$=351, RT=0.701 min

Preparation of Intermediate 42

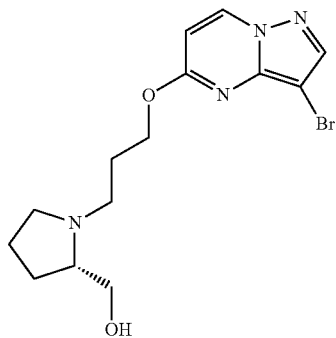 [SMILES: OC[C@@H]1CCCN1CCCOc1ccn2ncc(Br)c2n1]

Intermediate 41 (7.40 mmol), (S)-(+)-2-pyrrolidinemethanol (750 mg, 7.40 mmol), sodium carbonate (2.353 g, 22.2 mmol) and potassium iodide (1.597 g, 9.62 mmol) were suspended in N,N-dimethylformamide (6 ml/mmol). The reaction mixture was stirred at 60° C. for 4 hours. More (S)-(+)-2-pyrrolidinemethanol (10%), sodium carbonate (10%) and potassium iodide (10%) were added and the reaction mixture was stirred at 60° C. for 2 hours. Water was added and the aqueous layer was extracted with a mixture of dichloromethane and methanol (9:1). The combined organic layers were dried, filtered and the solvent was removed under reduced pressure. The residue was purified by flash column chromatography over silica gel using 7N ammonia solution and methanol as eluents (gradient elution from 0% to 5% ammonia solution). The product fractions were collected and the solvent was removed under reduced pressure.

Yield: 1.53 g of intermediate 42 (58%)
LCMS method 2: MH$^+$=356, RT=1.601 min

Preparation of Intermediate 43

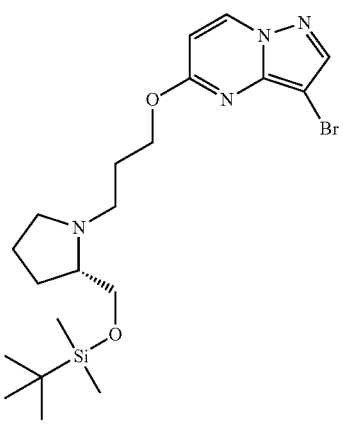 [SMILES: CC(C)(C)[Si](C)(C)OC[C@@H]1CCCN1CCCOc1ccn2ncc(Br)c2n1]

tert-Butyl-chlorodimethylsilane (0.78 g, 5.17 mmol) was added to a mixture of intermediate 42 (1.53 g, 4.31 mmol) and triethylamine (1.09 g, 10.77 mmol) in dichloromethane (12.93 ml). The reaction was stirred at room temperature for 4 hours. More tert-butyl-chlorodimethylsilane (20%) and triethylamine (20%) were added and the mixture was stirred at room temperature for 1.5 hours. The reaction mixture was diluted with dichloromethane and the organic layer was washed with water and brine. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 1.81 g of intermediate 43 (89%)
LCMS method 1: MH$^+$=470, RT=0.707 min

Preparation of Intermediate 44

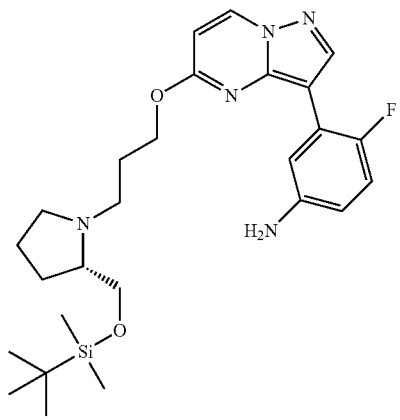 [SMILES: CC(C)(C)[Si](C)(C)OC[C@@H]1CCCN1CCCOc1ccn2ncc(-c3cc(N)ccc3F)c2n1]

A mixture of 1,4-dioxane and water (3:1, 11.25 ml) was degassed by bubbling nitrogen gas through the mixture. Intermediate 43 (1.76 g, 3.75 mmol), (5-amino-2-fluorophenyl)boronic acid (0.70 g, 4.50 mmol), tetrakis(triphenylphosphine)palladium(0) (174 mg, 0.15 mmol), 2-dicyclohexylphosphino-2',4',6'-triisopropylbiphenyl (Xphos) (181 mg, 0.38 mmol) and potassium phosphate tribasic (2.38 g, 3 eq.) were added and the mixture was stirred under nitrogen gas at 80° C. overnight. More (5-amino-2-fluoro-phenyl)boronic acid (30%), 2-dicyclohexylphosphino-2',4',6'-triisopropylbiphenyl (Xphos) (30%), potassium phosphate tribasic (30%) and tetrakis(triphenylphosphine)palladium(0) (30%) were added and the reaction mixture was stirred under nitrogen gas at 80° C. for 4 hours. The reaction mixture was cooled and the solvent was removed under reduced pressure. The residue was diluted with dichloromethane and washed with water. The aqueous layer was extracted with dichloromethane. The combined organic layers were dried, filtered and the solvent was removed under reduced pressure. The residue was purified by flash column chromatography over silica gel using dichloromethane and methanol as eluents (gradient elution from 0% to 8% methanol). The product fractions were collected and the solvent was removed under reduced pressure.

Yield: 1.36 g of intermediate 44 (73%)
LCMS method 1: MH$^+$=500, RT=0.889 min

Preparation of Intermediate 45

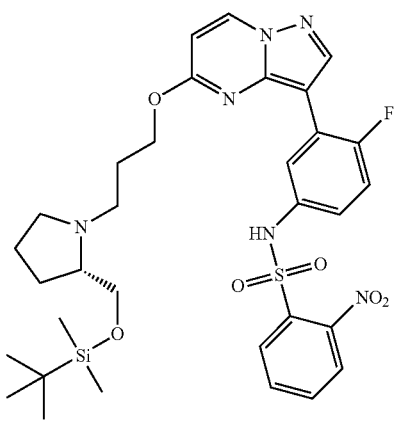 [SMILES: CC(C)(C)[Si](C)(C)OC[C@@H]1CCCN1CCCOc1ccn2ncc(-c3cc(NS(=O)(=O)c4ccccc4[N+](=O)[O-])ccc3F)c2n1]

2-Nitrobenzenesulfonyl chloride (0.66 g, 2.99 mmol) was added to a solution of intermediate 44 (1.36 g, 2.72 mmol) and pyridine (286 µl, 3.54 mmol) in dichloromethane (8.16 ml). The reaction mixture was stirred at room temperature overnight. Dichloromethane was added and the organic layer was washed with a 1N aqueous hydrochloric acid solution. The aqueous layer was extracted with dichloromethane. The combined organic layers were dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 1.65 g of intermediate 45 (89%)
LCMS method 1: MH$^+$=685, RT=1.020 min

Preparation of Intermediate 46

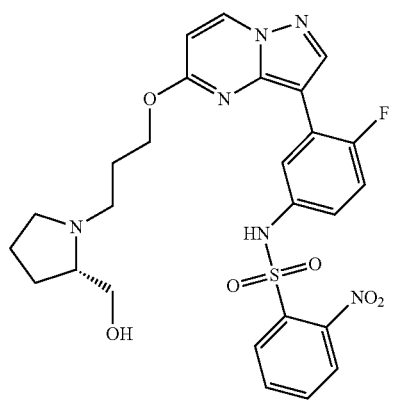 [SMILES: O=[N+]([O-])c1ccccc1S(=O)(=O)Nc1ccc(F)c(-c2cnn3ccc(OCCCN4CCC[C@H]4CO)nc23)c1]

Tetrabutylammonium fluoride (0.76 g, 2.89 mmol) was added to a solution of intermediate 45 (1.65 g, 2.41 mmol) in tetrahydrofuran (7.23 ml). The reaction mixture was stirred at room temperature for 3 hours. More tetrabutylammonium fluoride (30%) was added and the reaction mixture was stirred at 80° C. for 3 hours. The mixture was cooled and the solvent was removed under reduced pressure. The residue was dissolved in dichloromethane and washed with water and a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 955 mg of intermediate 46 (69%)
LCMS method 1: MH$^+$=571, RT=0.646 min

Preparation of Intermediate 47

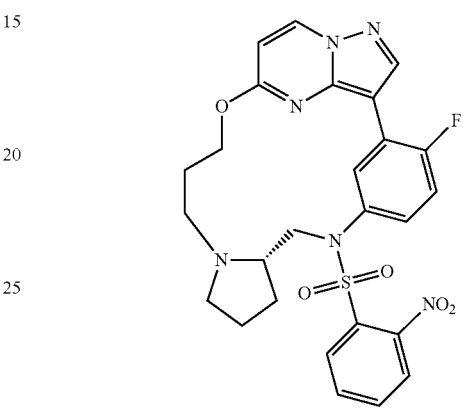

A solution of intermediate 46 (915 mg, 1.60 mmol) in 2-methyltetrahydrofuran (20 ml/mmol) was degassed by bubbling nitrogen gas through the mixture. A solution of diisopropyl azodicarboxylate (950 mg, 4.80 mmol) in toluene (20 ml/mmol) was degassed by bubbling nitrogen gas through the mixture. Both solutions were added simultaneously and dropwise over a period of 3 hours at 90° C. to a degassed solution of triphenylphosphine (1.259 g, 4.80 mmol) in toluene (75 ml/mmol). The mixture was stirred at 90° C. for 1 hour. The reaction mixture was cooled and the solvent was removed under reduced pressure. The residue was purified by flash column chromatography over silica gel using heptane and ethyl acetate as eluents (gradient elution from 20% to 80% ethyl acetate) and dichloromethane/ethyl acetate (1:1) was used to collect the product fractions. The solvent was removed under reduced pressure.

LCMS method 1: MH$^+$=553, RT=0.712 min

Preparation of Example N13

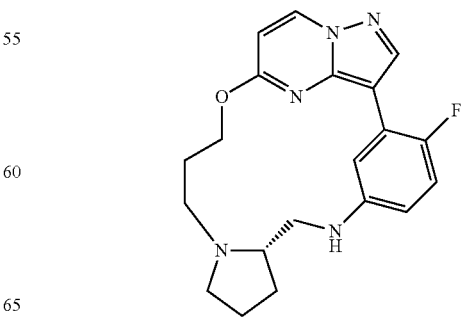

To a solution of intermediate 42 (1.60 mmol) in N,N-dimethylformamide (4.80 ml) were added cesium carbonate (1.043 g, 3.20 mmol) and thiophenol (200 µl, 1.92 mmol). The reaction mixture was stirred at room temperature overnight. A 1N aqueous sodium hydroxide solution was added and the aqueous layer was extracted with dichloromethane. The combined organic layers were dried, filtered and the solvent was removed under reduced pressure. The residue was purified by flash column chromatography over silica gel using dichloromethane and methanol as eluents (gradient elution from 0% to 8% methanol). The product fractions were collected and the solvent was removed under reduced pressure.

Yield: 358 mg of example N13 (61%)

LCMS method 2: MH$^+$=368, RT=2.064 min

Example N13 (358 mg, 0.97 mmol) was dissolved in a mixture of dichloromethane/methanol (4:1, 6.25 ml). 4N hydrochloric acid in 1,4-dioxane (50 µl) was added and the reaction mixture was stirred at room temperature for 30 minutes. Diethyl ether was added and the mixture was stirred at room temperature for 30 minutes. The solid was filtered and the compound was dried under vacuum at 60° C. for 16 hours. The product was obtained as the HCl salt.

Yield: 314 mg of example N13 (88%)

LCMS method 2: MH$^+$=368, RT=1.987 min

Example N14

Example N14 may be prepared following general scheme 1 and according to the procedures illustrated for the preparation of example N8. The product was obtained as the HCl salt.

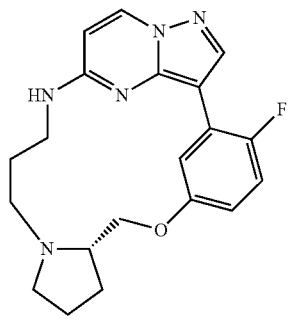 [SMILES: Fc1ccc2cc1-c1cnn3ccc(nc13)NCCCN1CCC[C@H]1CO2]

Example N15

Example N15 may be prepared following general scheme 1.

3-bromo-N-[1-[2-[tert-butyl(dimethyl)silyl]oxyethyl]-4-piperidyl]pyrazolo[1,5-a]pyrimidin-5-amine can be prepared according to the methods described to obtain intermediate 5.

Preparation of Intermediate 48

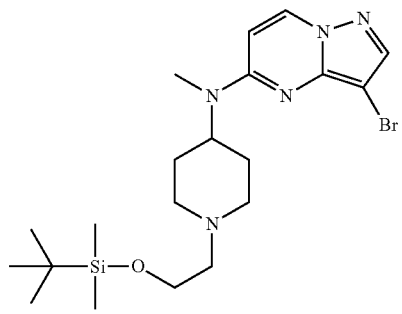 [SMILES: CN(c1ccn2ncc(Br)c2n1)C1CCN(CCO[Si](C)(C)C(C)(C)C)CC1]

A mixture of intermediate 3-bromo-N-[1-[2-[tert-butyl(dimethyl)silyl]oxyethyl]-4-piperidyl]pyrazolo[1,5-a]pyrimidin-5-amine (1.5 g, 3.30 mmol) and sodium hydride (60% in mineral oil, 790 mg, 33 mmol) in anhydrous N,N-dimethylformamide (9.9 ml) was stirred under nitrogen atmosphere for 1 hour. Iodomethane (237 µl, 3.80 mmol) was added and the reaction mixture was stirred at room temperature for 2 hours. Water was added and the aqueous layer was extracted with dichloromethane. The organic layer was dried, filtered and the solvent was removed under reduced pressure. The residue was purified by flash column chromatography over silica gel using 7N ammonia solution in methanol and dichloromethane as eluents (gradient elution from 0% to 5% ammonia in methanol). The product fractions were collected and the solvent was removed under reduced pressure.

Yield: 1.00 g of intermediate 48 (65%)

LCMS method 2: MH$^+$=469, RT=0.706 min

Preparation of Intermediate 49

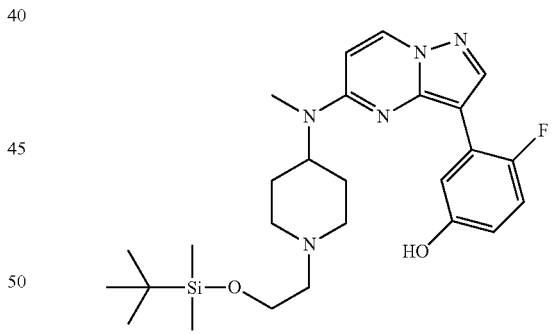

A mixture of 1,4-dioxane and water (3:1, 6.39 ml) was degassed by bubbling nitrogen gas through the mixture. Intermediate 48 (1.00 g, 2.13 mmol), 4-fluoro-3-(4,4,5,5-tetramethyl-1,3,2-dioxaborolan-2-yl)phenol (0.61 g, 2.56 mmol), tetrakis(triphenylphosphine)palladium(0) (104 mg, 0.09 mmol), 2-dicyclohexylphosphino-2',4',6'-triisopropylbiphenyl (Xphos) (100 mg, 0.21 mmol) and potassium phosphate tribasic (1.36 g, 3 eq.) were added and the mixture was stirred under nitrogen gas at 80° C. overnight. The reaction mixture was cooled and the solvent was removed under reduced pressure. The residue was diluted with dichloromethane and washed with water. The aqueous layer was extracted with dichloromethane. The combined organic layers were dried, filtered and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 786 mg of intermediate 49 (74%)
LCMS method 1: MH$^+$=500, RT=0.866 min

Preparation of Intermediate 50

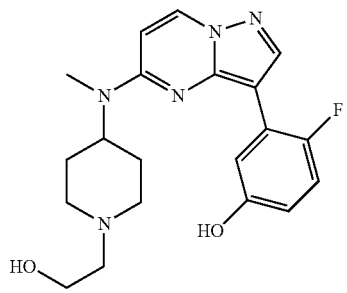 [SMILES: CN(c1ccn2ncc(-c3cc(O)ccc3F)c2n1)C1CCN(CCO)CC1]

Tetrabutylammonium fluoride (0.49 g, 1.88 mmol) was added to a solution of intermediate 49 (786 mg, 1.57 mmol) in tetrahydrofuran (4.71 ml). The reaction mixture was stirred at room temperature overnight. More tetrabutylammonium fluoride (10%) was added and the reaction mixture was stirred at room temperature for 2 hours. The solvent was removed under reduced pressure. The residue was dissolved in dichloromethane and washed with water and a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 8% methanol). The product fractions were collected and the solvent was removed under reduced pressure.

Yield: 450 mg of intermediate 50 (74%)
LCMS method 1: MH$^+$=386, RT=0.445 min

Preparation of Intermediate 51

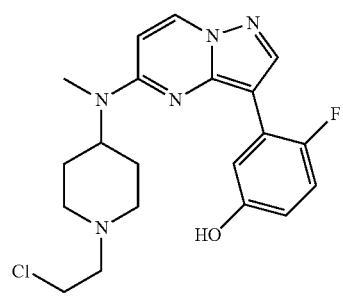 [SMILES: CN(c1ccn2ncc(-c3cc(O)ccc3F)c2n1)C1CCN(CCCl)CC1]

Pyridine (230 µl, 2.85 mmol) was added to a solution of intermediate 50 (365 mg, 0.95 mmol) in dry dichloromethane (10 ml/mmol). The mixture was cooled to 0° C. and thionyl chloride (210 µl, 2.85 mmol). The reaction mixture was stirred at room temperature for 1 hour and under reflux for 2.5 hours. The mixture was diluted with dichloromethane and washed with water and a saturated aqueous sodium bicarbonate solution. The organic layer was dried, filtered and the solvent was removed under reduced pressure. The compound was used in the next step with further purification.

LCMS method 1: MH$^+$=404, RT=0.549 min

Preparation of Example N15

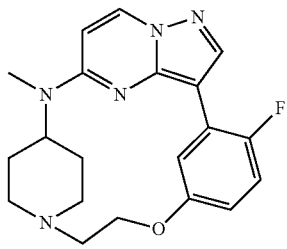 [SMILES: CN1c2ccn3ncc(c3n2)-c2cc(ccc2F)OCCN2CCC1CC2]

Intermediate 51 (0.95 mmol) was dissolved in N,N-dimethylformamide (32 ml) and added dropwise at 90° C. over a period of 2 hours to a suspension of cesiumcarbonate (1.55 g, 4.75 mmol) in N,N-dimethylformamide (63 ml). The reaction mixture was stirred at 90° C. for 1 hour. The mixture was cooled and water was added. The aqueous layer was extracted with dichloromethane. The combined organic layers were washed with water and brine, dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure. The product was further purified by reversed phase column chromatography (HPLC method A). The product fractions were collected and the solvent was removed under reduced pressure.

Yield: 96 mg of example N15 (27%)
LCMS method 1: MH$^+$=368, RT=2.073 min

Example N16

Example N16 may be prepared following general scheme 1 and according to the procedures illustrated for the preparation of example N2.

Preparation of Intermediate 52

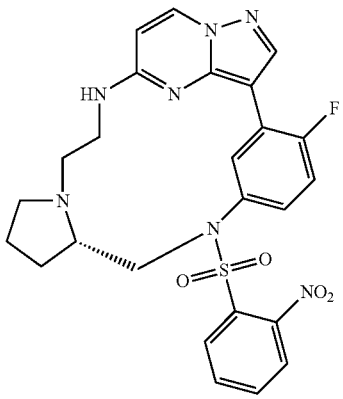 [SMILES: O=[N+]([O-])c1ccccc1S(=O)(=O)N1C[C@@H]2CCCN2CCNc2ccn3ncc(c3n2)-c2cc1ccc2F]

A mixture of intermediate 10 (0.92 mmol) and 4N hydrochloric acid in 1,4-dioxane (2.76 ml) was stirred at room temperature for 2 hours and at 50° C. for 2 hours. Ethyl acetate and brine were added. The two layers were separated and the organic layer was washed with water. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 243 mg of intermediate 52 (49%)

LCMS method 1: MH$^+$=538, RT=1.174 min

Preparation of Intermediate 53

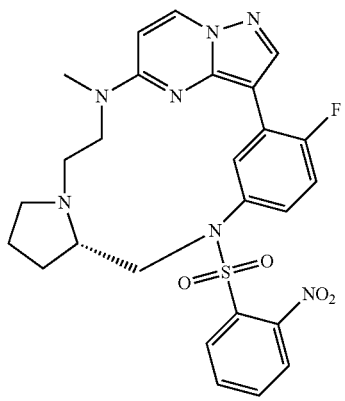 [SMILES: CN1CCN2CCC[C@H]2CN(S(=O)(=O)c2ccccc2[N+](=O)[O-])c2ccc(F)c(c2)-c2cnn3ccc1nc23]

Intermediate 52 (223 mg, 0.41 mmol) was dissolved in anhydrous N,N-dimethylformamide (2 ml). Sodium hydride (60% in mineral oil, 30 mg, 0.82 mmol) was added and the reaction mixture was stirred at room temperature for 1 hour. Iodomethane (29 µl, 0.47 mmol) was added and the reaction mixture was stirred at room temperature for 2 hours. Ethyl acetate and water were added. The two layers were separated and the organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 106 mg of intermediate 53 (47%)

LCMS method 1: MH$^+$=552, RT=1.204 min

Preparation of Example N16

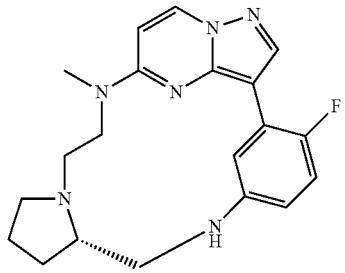 [SMILES: CN1CCN2CCC[C@H]2CNc2ccc(F)c(c2)-c2cnn3ccc1nc23]

A mixture of intermediate 53 (106 mg, 0.19 mmol) and cesium carbonate (124 g, 0.38 mmol) in N,N-dimethylformamide (2.0 ml) was stirred for 2 minutes. Thiophenol (20 µl, 0.23 mmol) was added and the reaction mixture was stirred at room temperature overnight. Ethyl acetate and water were added. The two layers were separated and the organic layer was dried, filtered and the solvent was removed under reduced pressure. The residue was purified by flash column chromatography over silica gel using dichloromethane and ethyl acetate as eluents (gradient elution from 0% to 30% ethyl acetate). The product fractions were collected and the solvent was removed under reduced pressure.

Yield: 29 mg of example N16 (42%)

LCMS method 2: MH$^+$=367, RT=2.047 min

Example N17

Example N17 may be prepared following general scheme 1 and according to the procedures illustrated for the preparation of example N8. The product was obtained as the HCl salt.

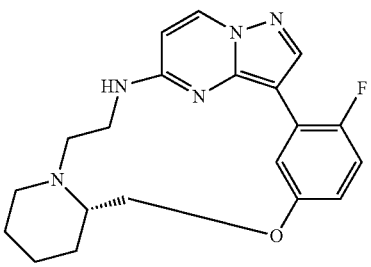 [SMILES: Fc1ccc2cc1-c1cnn3ccc(nc13)NCCN1CCCC[C@H]1CO2]

Example N18

Example N18 is obtained as a side-product during the Mitsunobu reaction in the preparation of example N17. The product was obtained as the HCl salt.

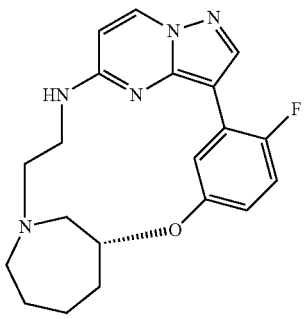 [SMILES: Fc1ccc2cc1-c1cnn3ccc(nc13)NCCN1CCCC[C@H](C1)O2]

Example N19

Example N19 may be prepared following general scheme 1 and starting from example N17 according to the procedures of the last two steps described in the preparation of example N11. The product was obtained as the HCl salt.

167

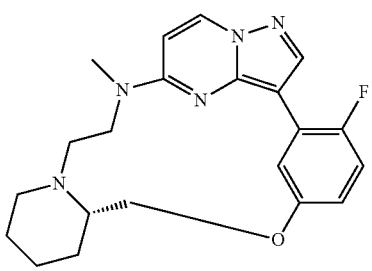 [SMILES: CN1CCN2CCCC[C@H]2COc2ccc(F)c(c2)-c2cnn3ccc1nc23]

Example N20

Example N20 may be prepared following general scheme 1.

Preparation of Intermediate 54

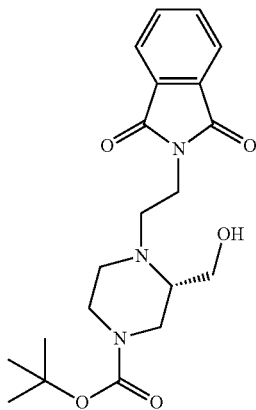 [SMILES: CC(C)(C)OC(=O)N1CCN(CCN2C(=O)c3ccccc3C2=O)[C@H](CO)C1]

tert-Butyl (3S)-3-(hydroxymethyl)piperazine-1-carboxylate (2.0 g, 9.25 mmol), 2-(1,3-dioxoisoindolin-2-yl)ethyl methanesulfonate (3.74 g, 13.88 mmol), sodium carbonate (2.941 g, 27.75 mmol) and potassium iodide (1.997 g, 12.03 mmol) was stirred at 70° C. overnight. The reaction mixture was cooled and the solvent was removed under reduced pressure. Dichloromethane was added to the residue and the mixture was filtered over a path of Celite®. The solvent of the filtrate was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 2.8 g of intermediate 54 (78%)
LCMS method 1: MH$^+$=390, RT=1.314 min

Preparation of Intermediate 55

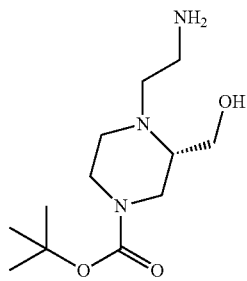 [SMILES: CC(C)(C)OC(=O)N1CCN(CCN)[C@H](CO)C1]

168

A mixture of intermediate 54 (3.50 g, 8.99 mmol) and hydrazine (64%, 860 mg, 13.48 mmol) in ethanol (45 ml) was heated at 60° C. overnight. The reaction mixture was cooled and the suspension was filtered to remove the white solid. The solvent of the filtrate was removed under reduced pressure and the residue was dissolved in ethyl acetate. The organic layer washed with an aqueous 1M sodium hydroxide solution and brine. The organic layer was dried, filtered and the solvent was removed under reduced pressure. The product was used without further purification in the next step.

Preparation of Intermediate 56

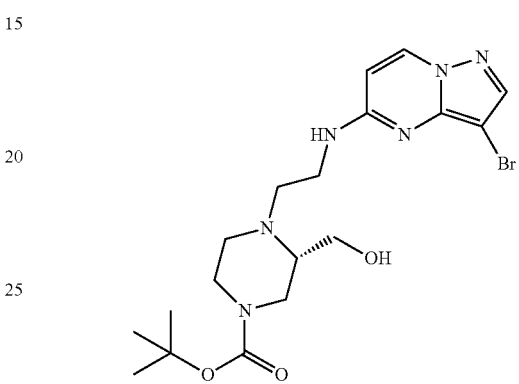

To a mixture of intermediate 55 (2.34 g, 9.03 mmol) and triethylamine (5.076 ml, 36.12 mmol) in acetonitrile (27.09 ml) was added 3-bromo-5-chloro-pyrazolo[1,5-a]pyrimidine (2.10 g, 9.03 mmol). The reaction mixture was stirred at 80° C. for 2 hours. The reaction mixture was cooled and the solvent was removed under reduced pressure. The residue was purified by flash column chromatography over silica gel using dichloromethane and methanol as eluents. The product fractions were collected and the solvent was removed under reduced pressure.

Yield: 2.077 g of intermediate 56 (51%)
LCMS method 1: MH$^+$=456, RT=1.005 min

Preparation of Intermediate 57

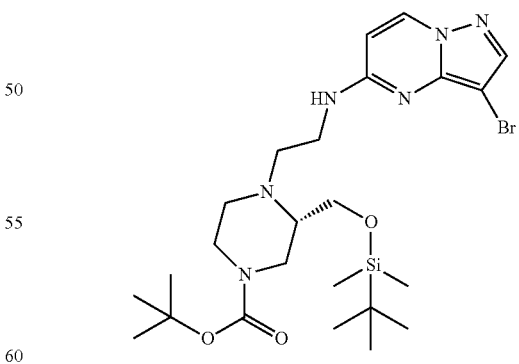

A mixture of intermediate 56 (2.077 g, 4.56 mmol), tert-butylchlorodimethylsilane (760 mg, 5.02 mmol) and triethylamine (824 µl, 5.93 mmol) in dichloromethane (15 ml) was stirred at room temperature for 18 hours. More tert-butyl-chlorodimethylsilane (0.6 eq.) and triethylamine (2 eq.) were added and the mixture was stirred at room for 4 hours. More tert-butyl-chlorodimethylsilane (0.1 eq.) was added and the mixture was stirred at room for 1 hour. The solvent was removed under reduced pressure. The compound was used without further purification in the next step.

LCMS method 1: MH$^+$=570, RT=1.537 min

Preparation of Intermediate 58

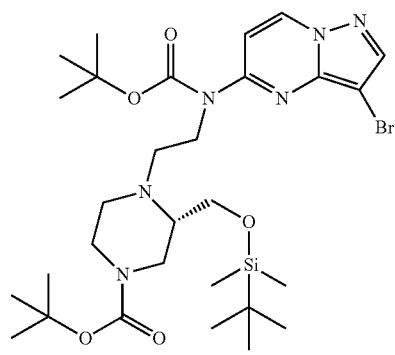 [SMILES: CC(C)(C)OC(=O)N1CCN(CCN(C(=O)OC(C)(C)C)c2ccn3ncc(Br)c3n2)[C@H](CO[Si](C)(C)C(C)(C)C)C1]

A mixture of intermediate 57 (4.56 mmol), tert-butoxycarbonyl anhydride (1.26 ml, 5.47 mmol), trimethylamine (1.901 ml, 13.68 mmol) and 4-(dimethylamino)pyridine (56 mg, 0.46 mmol) in tetrahydrofuran (30 ml) was stirred at 65° C. for 4 hours. More tert-butoxycarbonyl anhydride (1.2 eq.) and 4-(dimethylamino)pyridine (0.1 eq.) were added. The reaction mixture was cooled, ethyl acetate was added and the organic layer was extracted with water. The organic layer was dried, filtered and the solvent was removed under reduce pressure. The residue was purified by flash column chromatography over silica gel using heptane and ethyl acetate as eluents. The product fractions were collected and the solvent was removed under reduced pressure.

Yield: 2.636 g of intermediate 58 (86%)
LCMS method 1: MH$^+$=670, RT=1.778 min

Preparation of Intermediate 59

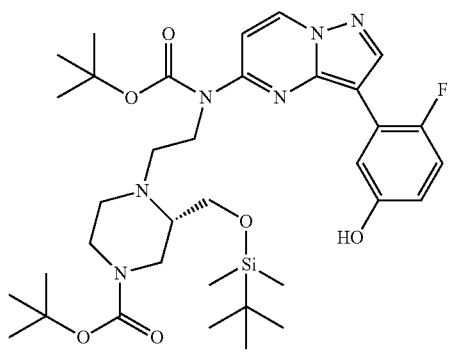 [SMILES: CC(C)(C)OC(=O)N1CCN(CCN(C(=O)OC(C)(C)C)c2ccn3ncc(-c4cc(O)ccc4F)c3n2)[C@H](CO[Si](C)(C)C(C)(C)C)C1]

A mixture of 1,4-dioxane and water (3:1, 24 ml) was degassed by bubbling nitrogen gas through the mixture. Intermediate 58 (2.636 g, 3.94 mmol), 4-fluoro-3-(4,4,5,5-tetramethyl-1,3,2-dioxaborolan-2-yl)phenol (1.13 g, 4.73 mmol), tetrakis(triphenylphosphine)palladium(0) (93 mg, 0.08 mmol), 2-dicyclohexylphosphino-2',4',6'-triisopropyl-biphenyl (Xphos) (153 mg, 0.32 mmol) and potassium phosphate tribasic (3 eq.) were added and the mixture was stirred under nitrogen gas at 85° C. overnight. The reaction mixture was cooled. Ethyl acetate and water were added and the two layers were separated. The organic layer was dried, filtered and the solvent was removed under reduced pressure. The residue was purified by flash column chromatography over silica gel using dichloromethane and ethyl acetate as eluents (gradient elution from 0% to 30% of ethyl acetate). The product fractions were collected and the solvent was removed under reduced pressure.

Yield: 2.232 g of intermediate 59 (81%)
LCMS method 2: MH$^+$=701, RT=3.794 min

Preparation of Intermediate 60

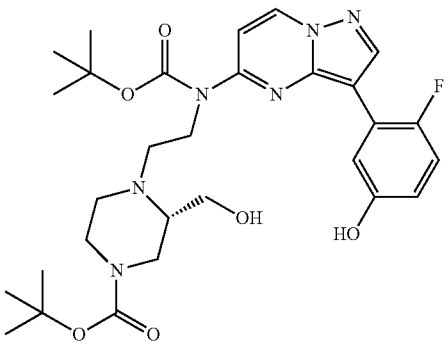 [SMILES: CC(C)(C)OC(=O)N1CCN(CCN(C(=O)OC(C)(C)C)c2ccn3ncc(-c4cc(O)ccc4F)c3n2)[C@H](CO)C1]

Tetrabutylammonium fluoride (1M solution in tetrahydrofuran, 4.77 ml, 4.77 mmol) was added to a solution of intermediate 59 (2.232 g, 3.18 mmol) in tetrahydrofuran (20 ml). The reaction mixture was stirred at room temperature for 2 hours. The mixture was diluted with ethyl acetate and washed with a saturated aqueous sodium bicarbonate solution and brine. The organic layer was dried, filtered and the solvent was removed under reduced pressure. The residue was purified by flash column chromatography over silica gel using dichloromethane and methanol as eluents (gradient elution from 0% to 10% of methanol). The product fractions were collected and the solvent was removed under reduced pressure.

Yield: 1.774 g of intermediate 60 (95%)
LCMS method 1: MH$^+$=587, RT=1.430 min

Preparation of Intermediate 61

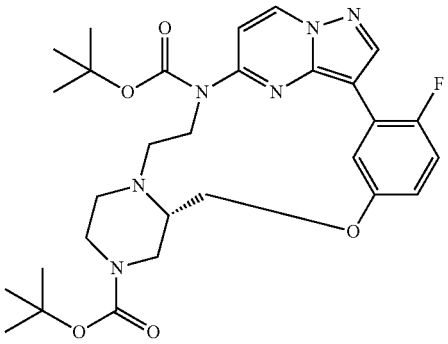 [SMILES: CC(C)(C)OC(=O)N1CCN2CCN(C(=O)OC(C)(C)C)c3ccn4ncc(c4n3)-c3cc(ccc3F)OC[C@@H]2C1]

A solution of intermediate 60 (100 mg, 0.17 mmol) in 2-methyltetrahydrofuran (20 ml/mmol) was degassed by bubbling nitrogen gas through the mixture. A solution of diisopropyl azodicarboxylate (170 mg, 0.85 mmol) in toluene (20 ml/mmol) was degassed by bubbling nitrogen gas through the mixture. Both solutions were added simultaneously and dropwise over a period of 4 hours at 110° C. to a degassed solution of triphenylphosphine (223 mg, 0.85 mmol) in toluene (75 ml/mmol). The mixture was stirred at 110° C. for 1 hour. The reaction mixture was cooled and the solvent was removed under reduced pressure. The residue was purified by flash column chromatography over silica gel using heptane and ethyl acetate as eluents. The product fractions were collected and the solvent was removed under reduced pressure.

Yield: 27 mg of intermediate 61 (28%)
LCMS method 2: MH$^+$=569, RT=5.191 min

Preparation of Example N20

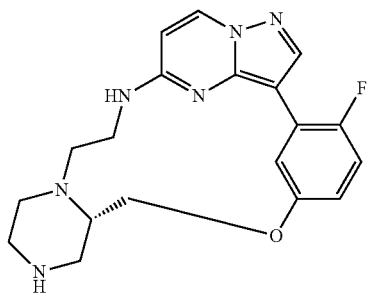 [SMILES: Fc1ccc2cc1-c1cnn3ccc(nc13)NCCN1CCNC[C@H]1CO2]

A mixture of intermediate 31 (610 mg, 1.07 mmol) and 4N hydrochloric acid in 1,4-dioxane (10 ml) was stirred at room temperature for 2 hours. Diethyl was added, the solid was filtered and dried under vacuum. The product was obtained as the HCl salt.

LCMS method 2: MH$^+$=369, RT=1.987 min

Example N21

Example N21 may be prepared following general scheme 1 and according to the procedures illustrated for the preparation of example N7. The product was obtained as the HCl salt.

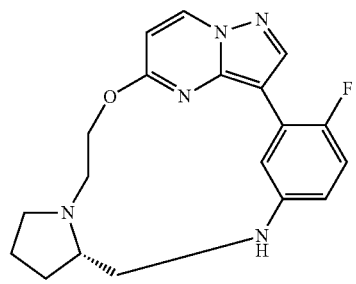 [SMILES: Fc1ccc2cc1-c1cnn3ccc(nc13)OCCN1CCC[C@H]1CN2]

Example N22

Example N22 may be prepared following general scheme 1 and according to the procedures illustrated for the preparation of example N8. The product was obtained as the HCl salt.

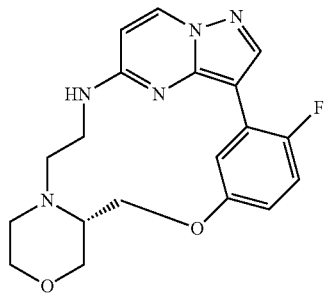 [SMILES: Fc1ccc2cc1-c1cnn3ccc(nc13)NCCN1CCOC[C@H]1CO2]

Example N23

Example N23 may be prepared following general scheme 1 and starting from example N20.

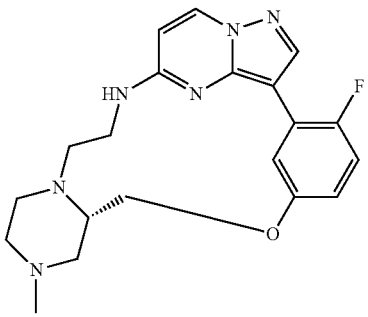 [SMILES: CN1CCN2CCNc3ccn4ncc(c4n3)-c3cc(ccc3F)OC[C@@H]2C1]

A mixture of example N20 (230 mg, 0.57 mmol), formaldehyde (37%, 50 mg, 1.14 mmol) and triethylamine (238 μl, 1.71 mmol) in a mixture of dichloromethane and methanol (4:1, 5 ml) was stirred at room temperature for 1 hour. Sodium triacetoxyborohydride (242 mg, 1.14 mmol) was added. The reaction mixture was stirred at room temperature for 3 hours. Dichloromethane was added and the organic layer was extracted with a saturated aqueous sodium bicarbonate solution. The organic layer was dried, filtered and the solvent was removed under reduced pressure. The residue was purified by flash column chromatography over silica gel using heptane and ethyl acetate as eluents. The product fractions were collected and the solvent was removed under reduced pressure.

Yield: 139 mg of example N23 (64%)
LCMS method 2: MH$^+$=383, RT=2.061 min

Example N24

Example N24 may be prepared following general scheme 1 and starting from example N23.

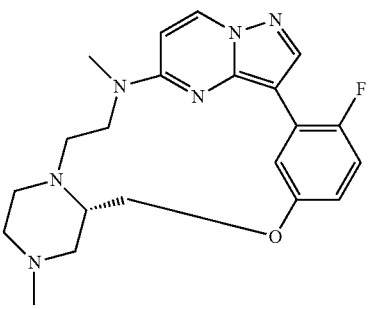 [SMILES: CN1CCN2CCN(C)c3ccn4ncc(c4n3)-c3cc(ccc3F)OC[C@@H]2C1]

Example N23 (63 mg, 0.16 mmol) was dissolved in anhydrous N,N-dimethylformamide (1 ml). Sodium hydride (60% in mineral oil, 40 mg, 1.60 mmol) was added and the reaction mixture was stirred at room temperature for 1 hour. Iodomethane (11 µl, 0.18 mmol) was added and the reaction mixture was stirred at room temperature for 2 hours. Ethyl acetate and an aqueous saturated ammonium chloride solution were added. The two layers were separated and the organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 44 mg of example N24 (69%)

LCMS method 2: MH$^+$=397, RT=2.127 min

Example N25

Example N25 may be prepared following general scheme 1 and starting from example N22 using the procedure applied for the preparation of N11. The product was obtained as the HCl salt.

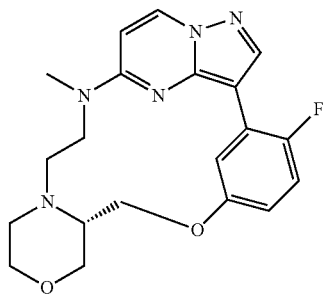 [SMILES: CN1CCN2CCOC[C@H]2COc2ccc(F)c(c2)-c2cnn3ccc1nc23]

Example N26

Example N26 may be prepared following general scheme 1 and starting from example N8.

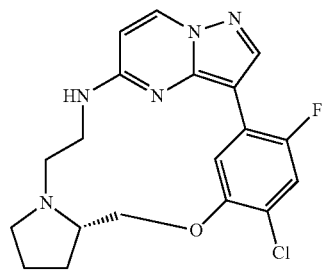 [SMILES: Fc1cc(Cl)c2cc1-c1cnn3ccc(nc13)NCCN1CCC[C@H]1CO2]

1-Chloropyrrolidine-2,5-dione (50 mg, 0.34 mmol) was added in one portion to a stirred suspension of example N8 (100 mg, 0.28 mmol) in chloroform (3 ml). The reaction mixture was stirred for at room temperature for 5 hours. The reaction mixture was diluted with a mixture of dichloromethane and methanol 95:5 and washed with an aqueous saturated sodium bicarbonate solution. The aqueous layer was extracted with dichloromethane. The combined organic layers were dried, filtered and the solvent was removed under reduced pressure. The residue was purified by flash column chromatography over silica gel using heptane and ethyl acetate as eluents (gradient elution from 0% to 20% ethyl acetate) followed by using dichloromethane and methanol as eluents (gradient elution from 0% to 6% methanol). The product fractions were collected and the solvent was removed under reduced pressure. The residue was further purified by reversed phase column chromatography (HPLC method A). The product fractions were collected and the solvent was removed under reduced pressure.

The residue was dissolved in dichloromethane and 4N hydrochloric acid in methanol was added The mixture was concentrated, ethanol was added and the solvent was removed under reduced pressure. The product was obtained as the HCl salt.

Yield: 27 mg of example N26 (25%)

LCMS method 2: MH$^+$=388, RT=2.250 min

Example N27

Example N27 may be prepared following general scheme 1 and according to the procedures illustrated for the preparation of example N8.

Preparation of Intermediate 62

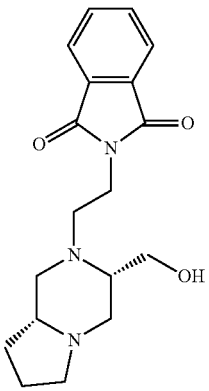 [SMILES: O=C1c2ccccc2C(=O)N1CCN1C[C@H]2CCCN2C[C@H]1CO]

A mixture of [(3S,8aR)-1,2,3,4,6,7,8,8a-octahydropyrrolo[1,2-a]pyrazin-3-yl]methanol (1.9 g, 12.16 mmol) and 2-(1,3-dioxoisoindolin-2-yl)acetaldehyde (2.76 g, 14.59 mmol) in dichloromethane (36.48 ml) was stirred at room temperature for 1.5 hours. Sodium triacetoxyborohydride (5.154 g, 24.32 mmol) was added. The reaction mixture was stirred at room temperature for 16 hours. Dichloromethane was added, the mixture was stirred and 5 ml of a saturated aqueous sodium bicarbonate solution was added dropwise, followed by 5 ml of water. The two layers were separated and aqueous layer was extracted with dichloromethane. The combined organic layers were dried, filtered and the solvent was removed under reduced pressure. The residue was purified by flash column chromatography over silica gel using dichloromethane and a 7N ammonia solution in methanol as eluents (gradient elution from 0% to 5% 7N ammonia solution in methanol). The product fractions were collected and the solvent was removed under reduced pressure.

Yield: 3.52 g of intermediate 62 (88%)

LCMS method 2: MH$^+$=330, RT=1.547 min

Preparation of Intermediate 63

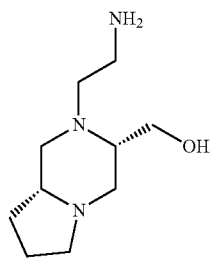 [SMILES: NCCN1C[C@H]2CCCN2C[C@H]1CO]

A mixture of intermediate 62 (2.90 g, 8.80 mmol) and hydrazine (50/60% in water, 850 μl, 26.40 mmol) in ethanol (51 ml) was stirred at room temperature for 16 hours. The solvent was removed under reduced pressure and the residue was co-evaporated with toluene. The residue was suspended in a mixture of ethyl acetate and methanol (95/5), filtered and the solid was washed with ethyl acetate. The solvent of the filtrate was removed under reduced pressure. The product was used without further purification in the next step.

The subsequent steps to obtain example N27 are based on the procedures used for the preparation of N8.

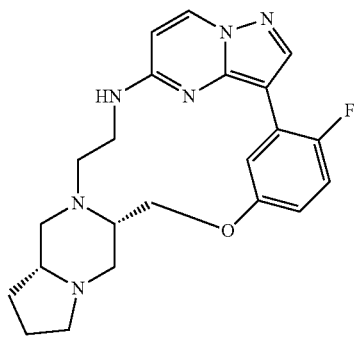 [SMILES: Fc1ccc2cc1-c1cnn3ccc(nc13)NCCN1C[C@H]3CCCN3C[C@H]1CO2]

Example N28

Example N28 is obtained as a side-product during the Mitsunobu reaction in the preparation of example N20. The product was obtained as the HCl salt.

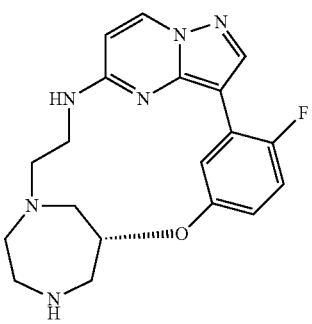 [SMILES: Fc1ccc2cc1-c1cnn3ccc(nc13)NCCN1CCNC[C@H](C1)O2]

Example N29

Example N29 may be prepared following general scheme 1, starting from example N27 and according to the procedures illustrated for the preparation of example N11.

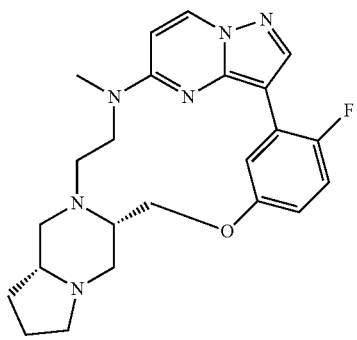 [SMILES: CN1CCN2C[C@H]3CCCN3C[C@H]2COc2ccc(F)c(c2)-c2cnn3ccc1nc23]

Example N30

Example N30 may be prepared following general scheme 1 and according to the procedures illustrated for the preparation of example N8.

Preparation of Intermediate 64

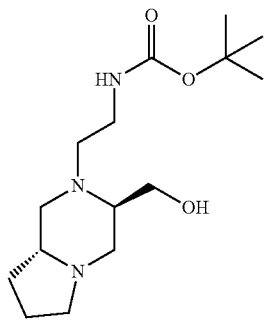 [SMILES: CC(C)(C)OC(=O)NCCN1C[C@H]2CCCN2C[C@@H]1CO]

[(3R,8aR)-1,2,3,4,6,7,8,8a-octahydropyrrolo[1,2-a]pyrazin-3-yl]methanol (300 mg, 1.92 mmol) and tert-butyl N-(2-oxoethyl)carbamate (366 mg, 2.30 mmol) in dichloromethane (5.76 ml) was stirred at room temperature for 1.5 hours. Sodium triacetoxyborohydride (814 mg, 3.84 mmol) was added. The reaction mixture was stirred at room temperature for 1 hour. More sodium triacetoxyborohydride (814 mg, 3.84 mmol) was added and the reaction mixture was stirred at room temperature for 15 hours. A saturated aqueous sodium bicarbonate solution was added till pH 7 and the aqueous layer was extracted with a mixture of dichloromethane and methanol (9:1). The solvent of both layers was removed under reduced pressure. The residues were combined and purified by flash column chromatography over silica gel using dichloromethane and methanol as eluents (gradient elution from 0% to 20% methanol). The product fractions were collected and the solvent was removed under reduced pressure.

Yield: 409 mg of intermediate 64 (71%)

LCMS method 1: MH$^+$=300, RT=0.304 min

Preparation of Intermediate 65

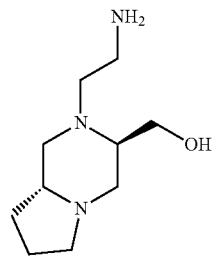 [SMILES: NCCN1C[C@H]2CCCN2C[C@@H]1CO]

Intermediate 64 (409 mg, 1.37 mmol) was stirred in a 4N hydrochloric acid solution in 1,4-dioxane at room temperature for 2 hours. The solvent was removed under reduced pressure. The product was used without further purification in the next step.

The following steps to obtain example N30 are based on the procedures used for the preparation of N8. The product was obtained as the HCl salt.

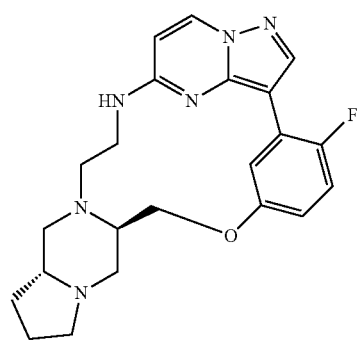 [SMILES: Fc1ccc2cc1-c1cnn3ccc(nc13)NCCN1C[C@H]3CCCN3C[C@@H]1CO2]

Example N31

Example N31 may be prepared following general scheme 1 and according to the procedures illustrated for the preparation of example N18 and N11.

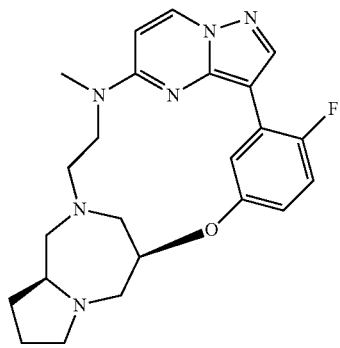 [SMILES: CN1CCN2C[C@H](CN3CCC[C@H]3C2)Oc2ccc(F)c(c2)-c2cnn3ccc1nc23]

Example N32

Example N32 may be prepared following general scheme 1 and starting from example N20.

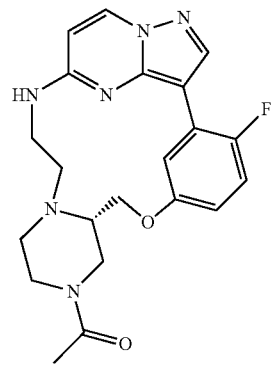 [SMILES: CC(=O)N1CCN2CCNc3ccn4ncc(c4n3)-c3cc(ccc3F)OC[C@@H]2C1]

N,N,N',N'-Tetramethyl-O-(1H-benzotriazol-1-yl)uronium hexafluorophosphate (167 mg, 0.44 mmol) was added to a mixture of example N20 (80 mg, 0.20 mmol), acetic acid (10 µl, 0.22 mmol) and N,N-diisopropylethylamine (245 µl, 1.40 mmol) in dimethylformamide (0.60 ml). The reaction mixture was stirred at room temperature for 2 hours. The solvent was removed under reduced pressure and the residue was purified by reversed phase column chromatography (HPLC method A). The product fractions were collected and the solvent was removed under reduced pressure.

Yield: 17 mg of example N32 (21%)

LCMS method 2: MH$^+$=411, RT=2.345 min

Example N33

Example N33 may be prepared following general scheme 1 and according to the procedures illustrated for the preparation of example N8. The product was obtained as the HCl salt.

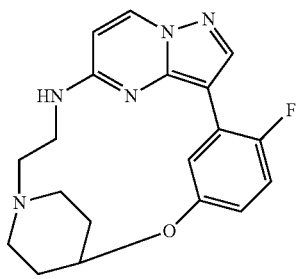

Example N34

Example N34 may be prepared following general scheme 1, starting from example N33 and according to the procedures illustrated for the preparation of example N11. The product was obtained as the HCl salt.

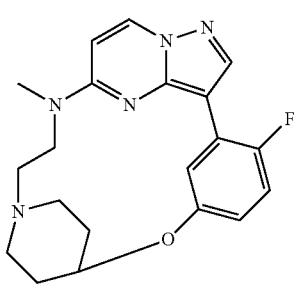 [SMILES: CN1CCN2CCC(CC2)Oc2ccc(F)c(c2)-c2cnn3ccc1nc23]

Example N35

Example N35 may be prepared following general scheme 1 and according to the procedures illustrated for the preparation of example N20. The product was obtained as the HCl salt.

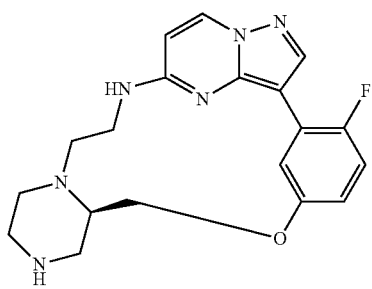 [SMILES: Fc1ccc2cc1-c1cnn3ccc(nc13)NCCN1CCNC[C@@H]1CO2]

Example N36

Example N36 may be prepared following general scheme 1, starting from example N35 and according to the procedures illustrated for the preparation of example N23.

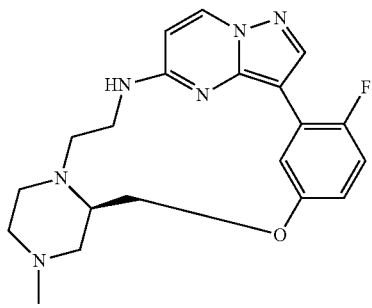 [SMILES: CN1CCN2CCNc3ccn4ncc(c4n3)-c3cc(ccc3F)OC[C@H]2C1]

Example N37

Example N37 may be prepared following general scheme 2.

Preparation of Intermediate 66

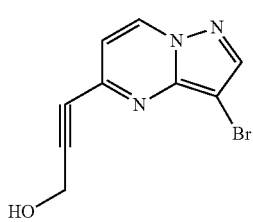 [SMILES: OCC#Cc1ccn2ncc(Br)c2n1]

3-Bromo-5-chloro-pyrazolo[1,5-a]pyrimidine (4.0 g, 17.21 mmol) was dissolved in tetrahydrofuran (51.63 ml), diisopropylamine (14.47 ml, 103.26 mmol) was added and the mixture was purged with nitrogen. Bis(triphenylphosphine)palladium(II) dichloride (1.207 g, 1.72 mmol) and copper(I) iodide (328 mg, 2.15 mmol) were added under nitrogen atmosphere followed by prop-2-yn-1-ol (1.206 ml, 20.65 mmol). The reaction mixture was stirred at room temperature for 20 hours. The mixture was concentrated under reduced pressure. The solid was filtered off and the filtrate was adsorbed onto silica gel and purified by flash chromatography over silica gel, using heptane and ethyl acetate as eluents (gradient elution from 0% to 100% of ethyl acetate) and then using dichloromethane and methanol as eluents (gradient elution from 0.2% to 10% of methanol). The product fractions were collected and the solvent was removed under reduced pressure.

LCMS method 1: MH$^+$=253, RT=0.424 min

Preparation of Intermediate 67

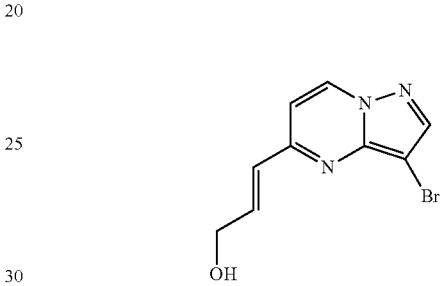

Intermediate 66 (5.81 g, 23.05 mmol) was suspended in a mixture of dichloromethane and methanol (1:1, 310 ml). Diphenyl sulphide (39 mg, 0.23 mmol) was added and the mixture was purged with nitrogen. Wet Pd/C (20% in weight of intermediate 66) was added and the mixture was stirred under hydrogen atmosphere at room temperature for 14 hours. More wet Pd/C (20% in weight of intermediate 66) was added and the mixture was stirred under hydrogen atmosphere for 20 hours. The catalyst was removed by filtration over Celite® and was washed with a mixture of dichloromethane and methanol (4:1). The solvent of the filtrate was removed under reduced pressure and the residue was purified by flash chromatography over silica gel, using dichloromethane and methanol as eluents (gradient elution from 0% to 5% of methanol. The product fractions were collected and the solvent was removed under reduced pressure.

Yield: 3.393 g of intermediate 67 (58%)

LCMS method 2: MH$^+$=255, RT=2.082 min

Preparation of Intermediate 68

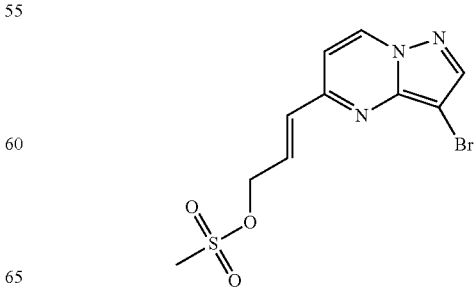

A solution of methylsulfonyl methanesulfonate (3.139 g, 18.02 mmol) in dichloromethane (12 ml) was added dropwise to a stirred solution of intermediate 67 (3.052 g, 12.01 mmol) and N,N-diisopropylethylamine (5.311 ml, 31.23 mmol) in dichloromethane (24 ml) at 0° C. The reaction mixture was stirred at 0° C. for 1 hour. The reaction mixture was diluted with dichloromethane and the organic layer was washed with water. The organic layer was dried, filtered and the solvent was removed under reduced pressure. The compound was used without further purification in the next step.

LCMS method 2: MH$^+$=333, RT=2.806 min

Preparation of Intermediate 69

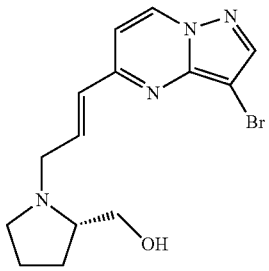 [SMILES: OC[C@@H]1CCCN1C/C=C/c1ccn2ncc(Br)c2n1]

Intermediate 68 (12.01 mmol), (S)-(+)-2-pyrrolidinemethanol (1.823 g, 18.02 mmol), sodium carbonate (3.819 g, 36.03 mmol) and potassium iodide (1.591 g, 15.61 mmol) were suspended in N,N-dimethylformamide (36 ml). The reaction mixture was stirred at 60° C. overnight. The reaction mixture was cooled and the solvent was removed under reduced pressure. Ethyl acetate was added and the organic layer was washed with water. The aqueous layer was extracted with a mixture of dichloromethane/methanol (9:1). The combined organic layers were dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 1.125 g of intermediate 69 (28%)
LCMS method 2: MH$^+$=338, RT=1.480 min

Preparation of Intermediate 70

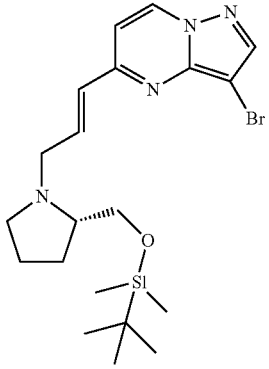

tert-Butyl-chlorodimethylsilane (755 mg, 5.01 mmol) was added to a mixture of intermediate 69 (1.125 g, 3.34 mmol) and triethylamine (1.161 ml, 8.35 mmol) in dichloromethane (10 ml). The reaction was stirred at room temperature overnight. Dichloromethane was added and the organic layer was washed with water. The organic layer was dried, filtered and the solvent was removed under reduced pressure. The residue was purified by flash column chromatography over silica gel using dichloromethane and methanol as eluents (gradient elution from 0% to 5% methanol). The product fractions were collected and the solvent was removed under reduced pressure.

Yield: 775 mg of intermediate 70 (51%)
LCMS method 2: MH$^+$=452, RT=2.819 min

Preparation of Intermediate 71

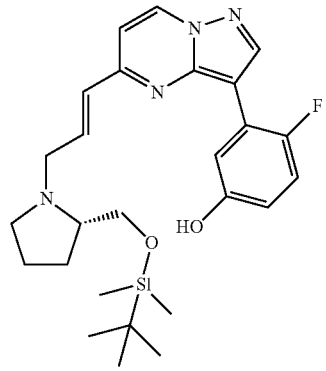

A mixture of 1,4-dioxane and water (3:1, 10 ml) was degassed by bubbling nitrogen gas through the mixture. Intermediate 70 (775 mg, 1.72 mmol), 4-fluoro-3-(4,4,5,5-tetramethyl-1,3,2-dioxaborolan-2-yl)phenol (490 mg, 2.06 mmol), tetrakis(triphenylphosphine)palladium(0) (35 mg, 0.03 mmol), 2-dicyclohexylphosphino-2',4',6'-triisopropylbiphenyl (Xphos) (33 mg, 0.07 mmol) and potassium phosphate tribasic (3 eq.) were added and the mixture was stirred under nitrogen gas at 85° C. for 16 hours. The reaction mixture was cooled. Ethyl acetate was added and the organic layer was washed with water. The organic layer was dried, filtered and the solvent was removed under reduced pressure. The residue was purified by flash column chromatography over silica gel using dichloromethane and methanol as eluents (gradient elution from 0% to 5% of methanol). The product fractions were collected and the solvent was removed under reduced pressure.

LCMS method 2: MH$^+$=483, RT=1.836 min

Preparation of Intermediate 72

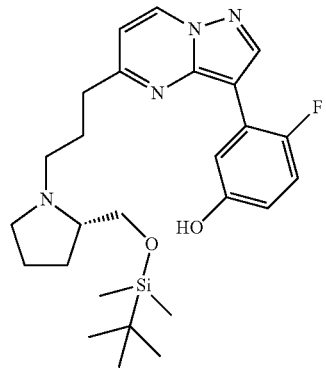 [SMILES: CC(C)(C)[Si](C)(C)OC[C@@H]1CCCN1CCCc1ccn2ncc(-c3cc(O)ccc3F)c2n1]

Intermediate 71 (851 mg, 1.76 mmol) was suspended in ethanol (5.28 ml) and the mixture was purged with nitrogen. Wet Pd/C (10%, 85 mg, 1.76) was added and the mixture was stirred under hydrogen atmosphere at room temperature for 15 hours. The catalyst was removed by filtration over Celite® and was washed with a mixture of dichloromethane and methanol (4:1). The solvent of the filtrate was removed under reduced pressure and the residue was purified by flash chromatography over silica gel, using dichloromethane and methanol as eluents (gradient elution from 0% to 8% of methanol). The product fractions were collected and the solvent was removed under reduced pressure.

Yield: 402 mg of intermediate 72 (47%)
LCMS method 2: MH$^+$=485, RT=2.811 min

Preparation of Intermediate 73

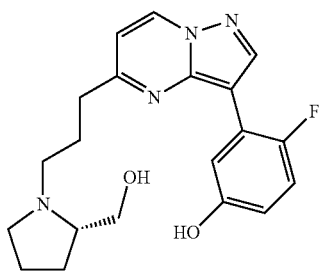 [SMILES: OC[C@@H]1CCCN1CCCc1ccn2ncc(-c3cc(O)ccc3F)c2n1]

Tetrabutylammonium fluoride (1M solution in tetrahydrofuran, 1.0 ml, 1.0 mmol) was added to a solution of intermediate 72 (402 mg, 0.83 mmol) in tetrahydrofuran (2.49 ml). The reaction mixture was stirred at room temperature for 16 hours. The mixture was diluted with ethyl acetate and washed with water and a saturated aqueous sodium bicarbonate solution. The organic layer was dried, filtered and the solvent was removed under reduced pressure. Acetonitrile was added, the solid was filtered and dried under reduced pressure.

Yield: 232 mg of intermediate 73 (85%)
LCMS method 2: MH$^+$=371, RT=1.814 min

Preparation of Example N37

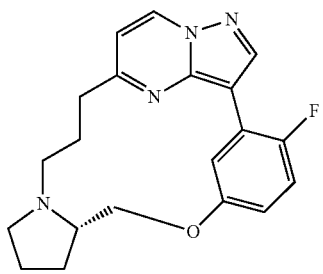 [SMILES: Fc1ccc2cc1-c1cnn3ccc(nc13)CCCN1CCC[C@H]1CO2]

A solution of intermediate 73 (182 mg, 0.49 mmol) in 2-methyltetrahydrofuran (20 ml/mmol) was degassed by bubbling nitrogen gas through the mixture. A solution of diisopropyl azodicarboxylate (291 mg, 1.47 mmol) in toluene (20 ml/mmol) was degassed by bubbling nitrogen gas through the mixture. Both solutions were added simultaneously and dropwise over a period of 3 hours at 90° C. to a degassed solution of triphenylphosphine (386 mg, 1.47 mmol) in toluene (75 ml/mmol). The mixture was stirred at 90° C. for 30 minutes. The reaction mixture was cooled and the solvent was removed under reduced pressure. The residue was purified by flash column chromatography over silica gel using heptane and ethyl acetate as eluents (gradient elution from 0% to 50% of ethyl acetate) followed by dichloromethane and methanol as eluents (gradient elution from 0% to 10% of methanol). The product fractions were collected and the solvent was removed under reduced pressure. The residue was purified by reversed phase column chromatography (HPLC method A). The product fractions were collected and the solvent was removed under reduced pressure.

Yield: 328 mg of example N37 (19%)
LCMS method 2: MH$^+$=353, RT=2.061 min

Example N38

Example N38 may be prepared following general scheme 1 and according to the procedures illustrated for the preparation of example N30. The product was obtained as the HCl salt.

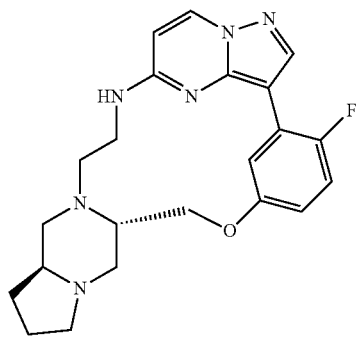 [SMILES: Fc1ccc2cc1-c1cnn3ccc(nc13)NCCN1C[C@@H]3CCCN3C[C@H]1CO2]

Example N39

Example N39 may be prepared following general scheme 1 and according to the procedures illustrated for the preparation of examples N27 and N8.

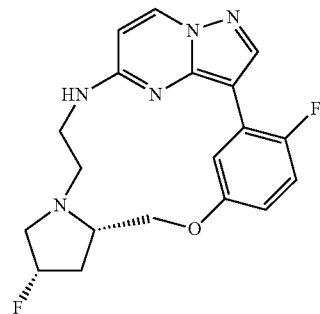 [SMILES: Fc1ccc2cc1-c1cnn3ccc(nc13)NCCN1C[C@@H](F)C[C@H]1CO2]

Example N40

Example N40 may be prepared following general scheme 1 and according to the procedures illustrated for the preparation of example N8 using a tert-butyl diphenylsilyl protecting group instead of a tert-butyl dimethylsilyl protecting group. The product was obtained as the HCl salt.

185

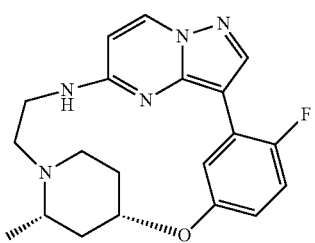 [SMILES: C[C@H]1C[C@@H]2CCN1CCNc1ccn3ncc(c3n1)-c1cc(ccc1F)O2]

Example N41

Example N41 may be prepared following general scheme 1 and according to the procedures illustrated for the preparation of example N8 using a tert-butyl diphenylsilyl protecting group instead of a tert-butyl dimethylsilyl protecting group.

Preparation of Intermediate 74

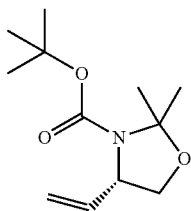 [SMILES: C=C[C@H]1COC(C)(C)N1C(=O)OC(C)(C)C]

A solution of 1N hexamethyldisilazane sodium salt in anhydrous tetrahydrofuran (25.52 ml, 25.52 mmol) was added dropwise over a period of 15 minutes to a suspension of methyltriphenylphosphonium iodide (10.316 g, 15.52 mmol) in anhydrous tetrahydrofuran (75 ml) at −20 to −25° C. and the mixture was stirred at 20 to −25° C. for 15 minutes. A solution of (R)-(+)-3-boc-2,2-dimethyloxazolidine-4-carboxaldehyde (4.50 g, 19.63 mmol) in anhydrous tetrahydrofuran (75 ml) was added dropwise over a period of 15 minutes and the mixture was stirred at 0° C. for 5 hours and at room temperature for 16 hours. The reaction mixture was cooled to 5° C. and an aqueous saturated ammonium chloride solution was added and the mixture was stirred for 10 minutes. The product was extracted with a mixture of heptane and ethyl acetate (1:1). The combined organic layers were washed with brine, dried, filtered and the solvent was removed under reduced pressure. The residue was purified by flash column chromatography over silica gel using heptane and ethyl acetate as eluents (gradient elution from 0% to 15% of ethyl acetate). The product fractions were collected and the solvent was removed under reduced pressure.

Yield: 3.80 g of intermediate 74 (85%)

Preparation of Intermediate 75

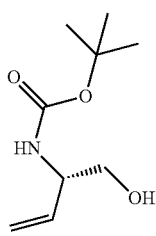

p-Toluene sulfonic acid monohydrate (1.084 g, 5.70 mmol) was added to a stirred solution of intermediate 74 (3.60 g, 15.84 mmol) in methanol (158 ml). The reaction mixture was stirred at room temperature for 16 hours. To the reaction mixture was added sodium bicarbonate (1 ml). The volume was reduced to 10 ml under reduced pressure. The residue was dissolved in ethyl acetate and water. The aqueous layer was extracted with ethyl acetate. The combined organic layers were washed with brine, dried, filtered and the solvent was removed under reduced pressure. The product was used without further purification in the next step.

Preparation of Intermediate 76

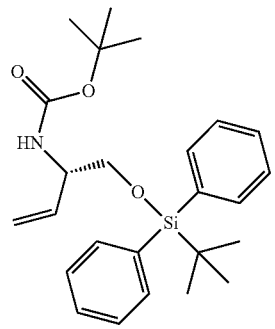 [SMILES: C=C[C@@H](CO[Si](c1ccccc1)(c1ccccc1)C(C)(C)C)NC(=O)OC(C)(C)C]

Imidazole (1.402 g, 20.59 mmol), 4-(dimethylamino)pyridine (387 mg, 3.17 mmol) and tert-butyl(chloro)diphenylsilane (4.56 g, 17.42 mmol) were added to a stirred solution of intermediate 75 (15.84 mmol) in dichloromethane (31 ml). The reaction mixture was stirred at room temperature for 72 hours. The solids were filtered off and washed with dichloromethane. The filtrate was washed with water and brine, dried, filtered and the solvent was removed under reduced pressure. The residue was purified by flash column chromatography over silica gel using heptane and ethyl acetate as eluents (gradient elution from 0% to 10% of ethyl acetate). The product fractions were collected and the solvent was removed under reduced pressure. Yield: 6.20 g of intermediate 76 (92%)

Preparation of Intermediate 77

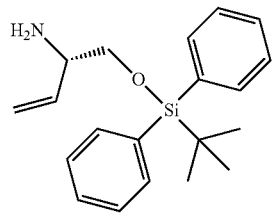 [SMILES: C=C[C@H](N)CO[Si](c1ccccc1)(c1ccccc1)C(C)(C)C]

A solution of intermediate 76 (6.20 g, 14.57 mmol) in dichloromethane (10 ml) was added to a stirred mixture of trifluoroacetic acid and dichloromethane (1:1, 130 ml). The reaction mixture was stirred at room temperature for 2 hours. The solvent was removed under reduced pressure. The residue was dissolved in dichloromethane. An aqueous saturated sodium bicarbonate solution was added portionwise. The mixture was stirred at room temperature for 30 minutes. The two layers were separated and the organic layer was washed with an aqueous saturated sodium bicarbonate solution. The organic layer was dried, filtered and the solvent was removed under reduced pressure. The product was used without further purification in the next step.

Yield: 4.32 g of intermediate 77 (91%)

LCMS method 2: MH$^+$=326, RT=2.785 min

Preparation of Intermediate 78

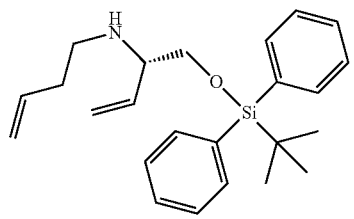 [SMILES: C=CCCN[C@@H](C=C)CO[Si](c1ccccc1)(c1ccccc1)C(C)(C)C]

A mixture of intermediate 77 (4.10 g, 12.59 mmol) and potassium carbonate (1.74 g, 12.59 mmol) in acetonitrile (37.77 ml) was stirred at room temperature for 30 minutes. 4-Bromo-1-butene (1.164 ml, 12.59 mmol) was added and the reaction mixture was stirred at 90° C. for 16 hours. The mixture was cooled to room temperature. The solids were filtered off and washed with ethyl acetate. The solvent of the filtrate was removed under reduced pressure. The residue was dissolved in ethyl acetate and was washed with an aqueous saturated sodium bicarbonate solution and brine. The organic layer was dried, filtered and the solvent was removed under reduced pressure. The product was used without further purification in the next step. LCMS method 2: MH$^+$=380, RT=3.072 min Preparation of Intermediate 79

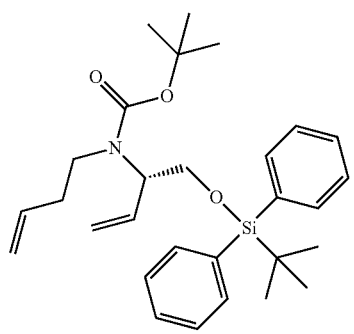 [SMILES: C=CCCN(C(=O)OC(C)(C)C)[C@@H](C=C)CO[Si](c1ccccc1)(c1ccccc1)C(C)(C)C]

A solution of tert-butoxycarbonyl anhydride (2.75 g, 12.59 mmol) in tetrahydrofuran (7 ml) was added dropwise to a stirred solution of intermediate 78 (12.59 mmol) and triethylamine (2.624 ml, 18.88 mmol) in tetrahydrofuran (30 ml). The solution was stirred at room temperature for 16 hours. The solvent was removed under reduced pressure and a mixture of ethyl acetate and heptane (8:2) was added. The organic layer was washed with an aqueous saturated sodium bicarbonate solution and brine. The organic layer was dried, filtered and the solvent was removed under reduced pressure. The residue was purified by flash column chromatography over silica gel using heptane and ethyl acetate as eluents (gradient elution from 0% to 7% of ethyl acetate). The product fractions were collected and the solvent was removed under reduced pressure.

Yield: 3.75 g of intermediate 79 (62%)

LCMS method 2: MH$^+$=380 (MH$^+$-Boc), RT=4.238 min

Preparation of Intermediate 80

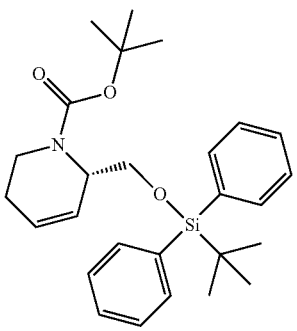 [SMILES: CC(C)(C)OC(=O)N1CCC=C[C@H]1CO[Si](c1ccccc1)(c1ccccc1)C(C)(C)C]

Dichloromethane was refluxed under nitrogen atmosphere for 2 hours. A solution of Grubb's catalyst (second generation, 310 mg, 0.37 mmol) in dichloromethane (10 ml) was added to a solution of intermediate 79 (3.52 g, 7.34 mmol) in dichloromethane (279 ml) under nitrogen atmosphere. The reaction mixture was stirred under nitrogen atmosphere at 30° C. for 16 hours.

More Grubb's catalyst (second generation, 0.03 eq.) was added and the mixture was stirred under nitrogen atmosphere at 30° C. for 16 hours. The solvent was removed under reduced pressure. The residue was purified by flash column chromatography over silica gel using heptane and ethyl acetate as eluents (gradient elution from 0% to 5% of ethyl acetate). The product fractions were collected and the solvent was removed under reduced pressure.

Yield: 1.90 g of intermediate 80 (57%)

Preparation of Intermediate 81

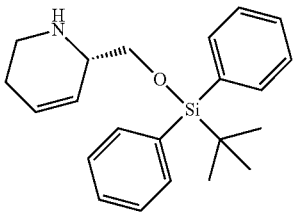 [SMILES: CC(C)(C)[Si](OC[C@@H]1C=CCCN1)(c1ccccc1)c1ccccc1]

A solution of intermediate 80 (1.90 g, 4.21 mmol) in dichloromethane (10 ml) was added to a stirred mixture of trifluoroacetic acid and dichloromethane (1:3, 47 ml). The reaction mixture was stirred at room temperature for 2 hours. The mixture was diluted with dichloromethane and washed with water, an aqueous 1N sodium hydroxide solution and brine. The organic layer was dried, filtered and the solvent was removed under reduced pressure. The product was used without further purification in the next step.

LCMS method 2: MH$^+$=352, RT=2.917 min

Preparation of Intermediate 82

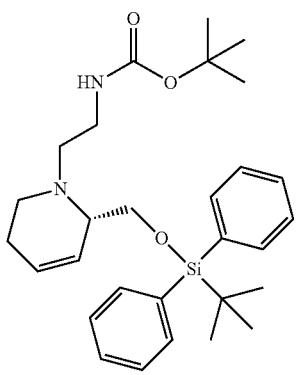 [SMILES: CC(C)(C)OC(=O)NCCN1CCC=C[C@H]1CO[Si](c1ccccc1)(c1ccccc1)C(C)(C)C]

A mixture of 2-(tert-butoxycarbonylamino)ethyl methanesulfonate (1.20 g, 5.01 mmol), intermediate 81 (1.50 g, 4.26 mmol), sodium carbonate (1.593 g, 15.03 mmol) and potassium iodide (1.081 g, 6.51 mmol) in N,N-dimethylformamide (25 ml) was stirred at 60° C. overnight. The reaction mixture was poured into water and extracted with ethyl acetate. The combined organic layers were dried, filtered and the solvent was removed under reduced pressure. The solvent was removed under reduced pressure and the residue was purified by flash column chromatography over silica gel using heptane and ethyl acetate as eluents (gradient elution from 0% to 40% of ethyl acetate). The product fractions were collected and the solvent was removed under reduced pressure.

Yield: 1.16 g of intermediate 82 (47%)

LCMS method 2: MH$^+$=495, RT=3.374 min

Preparation of Intermediate 83

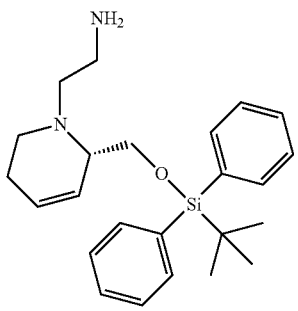 [SMILES: CC(C)(C)[Si](OC[C@@H]1C=CCCN1CCN)(c1ccccc1)c1ccccc1]

Intermediate 82 (1.16 g, 2.34 mmol) was stirred in mixture of trifluoroacetic acid and dichloromethane (1:3, 10 ml). The reaction mixture was stirred at room temperature for 2 hours. An aqueous 1N sodium hydroxide solution was added to the reaction mixture until pH 11. The product was extracted with dichloromethane. The combined organic layers were dried, filtered and the solvent was removed under reduced pressure. The product was used without further purification in the next step.

LCMS method 2: MH$^+$=395

Preparation of Example N41

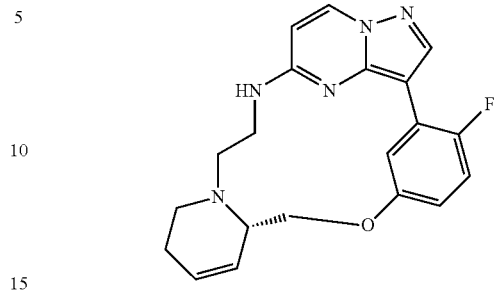

The subsequent steps to obtain example N41 are based on the procedures used for the preparation of N8 and using intermediate 83. The product was obtained as the HCl salt.

Example N42

Example N42 may be prepared following general scheme 1, starting from example N38 and according to the procedures illustrated for the preparation of example N11.

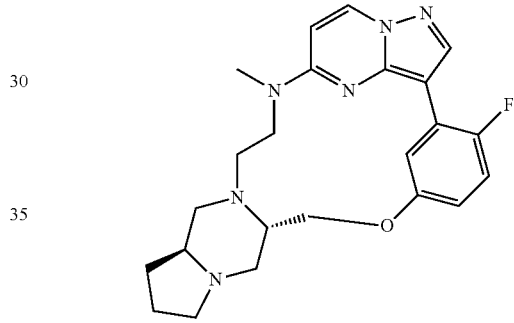

Example N43

Example N43 is obtained as a side-product during the Mitsunobu reaction in the preparation of example N38.

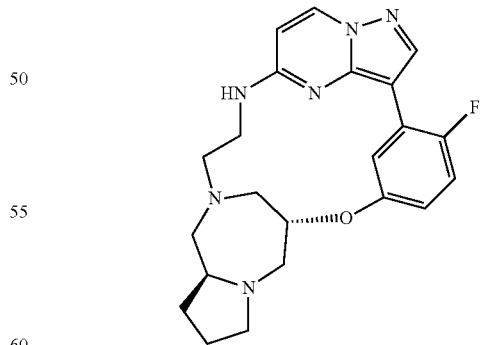

Example N44

Example N44 may be prepared following general scheme 1, starting from example N43 and according to the procedures illustrated for the preparation of example N11.

191

Example N45

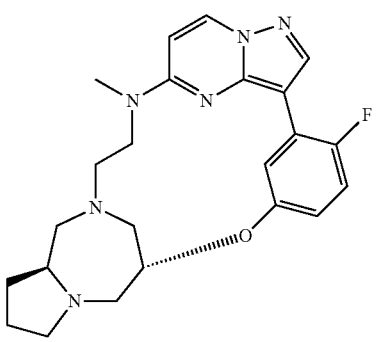 [SMILES: CN1CCN2C[C@@H](CN3CCC[C@H]3C2)Oc2ccc(F)c(c2)-c2cnn3ccc1nc23]

Example N45 may be prepared following general scheme 1 and according to the procedures illustrated for the preparation of example N20 using a tert-butyl diphenylsilyl protecting group instead of a tert-butyl dimethylsilyl protecting group.

Preparation of Intermediate 84

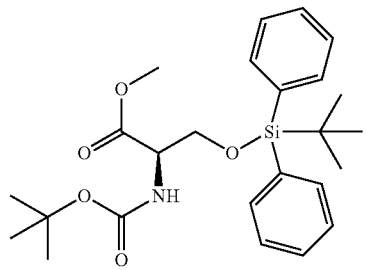 [SMILES: COC(=O)[C@@H](CO[Si](c1ccccc1)(c1ccccc1)C(C)(C)C)NC(=O)OC(C)(C)C]

A mixture of methyl (2R)-2-(tert-butoxycarbonylamino)-3-hydroxy-propanoate (9.90 g, 45.16 mmol), 4-(dimethylamino)pyridine (55 mg, 4.52 mmol) and imidazole (4.612 g, 67.74 mmol) in dichloromethane (135.48 ml) was cooled to 0° C. under nitrogen atmosphere. tert-Butyl(chloro)diphenylsilane (12.919 ml, 49.68 mmol) was added dropwise over a period of 15 minutes. The reaction mixture was stirred at 30° C. for 16 hours. The reaction mixture was diluted with dichloromethane and was washed with an aqueous 1N hydrochloric acid solution and an aqueous saturated sodium bicarbonate solution. The solvent of the organic layer was removed under reduced pressure. The residue was purified by flash column chromatography over silica gel using heptane and ethyl acetate as eluents (gradient elution from 0% to 15% of ethyl acetate). The product fractions were collected and the solvent was removed under reduced pressure. Toluene was added and removed under reduced pressure.

LCMS method 2: MH$^+$=358 (MH$^+$–Boc), RT=2.269 min

192

Preparation of Intermediate 85

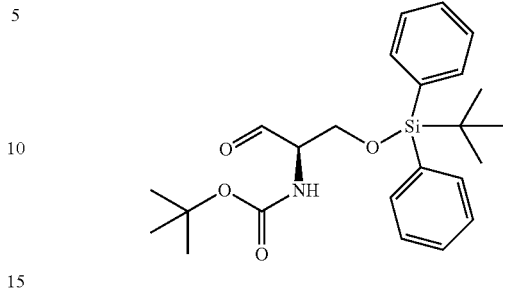

A stirred solution of intermediate 84 (21.0 g, 45.89 mmol) in anhydrous diethylether (137.67 ml) was cooled to –78° C. under nitrogen atmosphere. Diisobutylaluminum hydride solution (DIBAL) (1M in tetrahydrofuran, 55.07 mmol) was added over a period of 30 minutes. The reaction mixture was stirred at –78° C. for 1 hour. The reaction was quenched by slow addition of methanol (5.5 ml). The mixture was stirred at –78° C. for 15 minutes. The cold solution was poured into an aqueous saturated Rochelle salt solution (2 ml:1 mmol DIBAL) and stirred at room temperature for 3.5 hours. The layers were separated and the product was extracted with ethyl acetate. The combined organic layers were washed with brine, dried, filtered and the solvent was removed under reduced pressure. The product was used without further purification in the next step.

Preparation of Intermediate 86

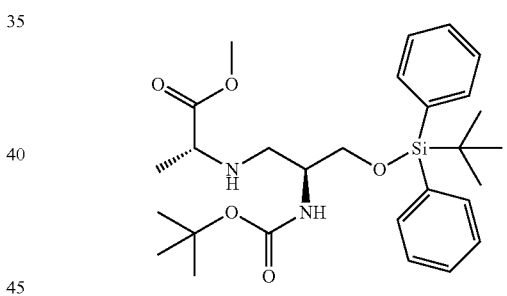

Methyl (2R)-2-aminopropanoate hydrochloride (4.80 g, 34.42 mmol) was added to a stirred mixture of intermediate 85 (45.89 mmol) and N,N-diisopropylethylamine (12.024 ml, 68.84 mmol) in dichloromethane (137.67 ml). The mixture was stirred at room temperature for 16 hours. Sodium triacetoxyborohydride (14.591 g, 68.84 mmol) was added portionwise. The reaction mixture was stirred at room temperature for 5 hours. The reaction mixture was diluted with dichloromethane and an aqueous 1N hydrochloric acid solution (75 ml) was added slowly. The mixture was stirred at room temperature for 10 minutes. The two layers were separated and the organic layer was washed with an aqueous saturated sodium bicarbonate solution. The organic layer was dried, filtered and the solvent was removed under reduced pressure. The residue was purified by flash column chromatography over silica gel using heptane and ethyl acetate as eluents (gradient elution from 5% to 50% ethyl acetate). The product fractions were collected and the solvent was removed under reduced pressure.

Yield: 16.30 g of intermediate 86 (69%)

LCMS method 2: MH$^+$=515

Preparation of Intermediate 87

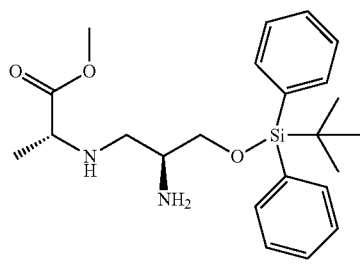 [SMILES: COC(=O)[C@@H](C)NC[C@H](N)CO[Si](c1ccccc1)(c1ccccc1)C(C)(C)C]

Intermediate 86 (2.60 g, 5.05 ml) was dissolved in dichloromethane (15.15 ml) and cooled to 0° C. under nitrogen atmosphere. Trifluoroacetic acid (4 ml) was added portionwise. The reaction mixture was stirred at room temperature for 3 hours. The reaction was slowly poured into an aqueous saturated sodium bicarbonate solution and stirred at room temperature for 30 minutes. The aqueous layer was extracted with dichloromethane. The combined organic layers were dried, filtered and the solvent was removed under reduced pressure. The product was used without further purification in the next step.

LCMS method 2: MH$^+$=415

Preparation of Intermediate 88

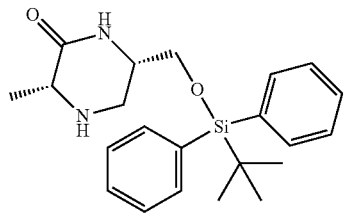 [SMILES: C[C@H]1NC[C@@H](CO[Si](c2ccccc2)(c2ccccc2)C(C)(C)C)NC1=O]

Triethylamine (2.10 ml, 15.15 mmol) was added to a stirred solution of intermediate 87 (5.05 mmol) in dichloromethane (15.15 ml). The reaction mixture was stirred at 40° C. for 16 hours. The reaction mixture was used directly in the next step.

Preparation of Intermediate 89

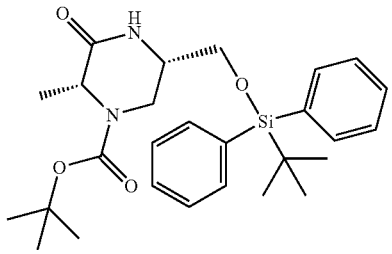 [SMILES: C[C@@H]1C(=O)N[C@H](CO[Si](c2ccccc2)(c2ccccc2)C(C)(C)C)CN1C(=O)OC(C)(C)C]

A solution of tert-butoxycarbonyl anhydride (1.32 g, 6.06 mmol) in dichloromethane (15 ml) was added potion wise to a stirred solution of intermediate 88 (5.05 mmol, crude from previous step). The reaction mixture was stirred at room temperature for 16 hours. The reaction was diluted with dichloromethane and was washed with an aqueous 1N hydrochloric acid solution and an aqueous saturated sodium bicarbonate solution. The organic layer dried, filtered and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure.

Yield: 1.95 g of intermediate 89 (80%)
LCMS method 2: RT=4.923 min

Preparation of Intermediate 90

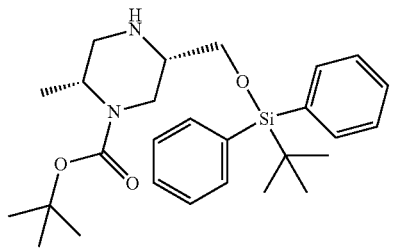 [SMILES: C[C@@H]1CN[C@H](CO[Si](c2ccccc2)(c2ccccc2)C(C)(C)C)CN1C(=O)OC(C)(C)C]

Intermediate 89 (5.35 g, 11.08 mmol) was dissolved in anhydrous tetrahydrofuran (33.24 ml) and cooled to 0° C. under nitrogen atmosphere. Borane dimethysulfide (2N solution in tetrahydrofuran, 5.89 ml, 77.56 mmol) was added portionwise. The reaction mixture was stirred under nitrogen atmosphere at 0° C. for 30 minutes and at room temperature for 16 hours. The reaction mixture was cooled to 0° C. and methanol (40 ml) was added dropwise. The mixture was stirred at room temperature for 1 hour. The solvent was removed under reduced pressure and the residue was co-evaporated twice with methanol. The product was used without further purification in the next step.

LCMS method 2: MH$^+$=469

Preparation of Intermediate 91

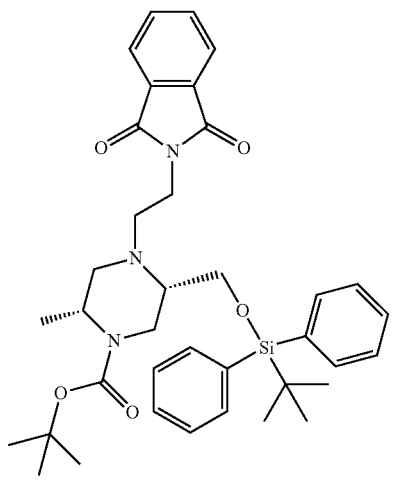 [SMILES: C[C@@H]1CN(CCN2C(=O)c3ccccc3C2=O)[C@H](CO[Si](c2ccccc2)(c2ccccc2)C(C)(C)C)CN1C(=O)OC(C)(C)C]

A mixture of intermediate 90 (6.150 g, 13.12 mmol) and 2-(1,3-dioxoisoindolin-2-yl)acetaldehyde (4.96 g, 26.24 mmol) in dichloromethane (39.36 ml) was stirred under nitrogen atmosphere at room temperature for 16 hours. Sodium triacetoxyborohydride (4.171 g, 19.68 mmol) was added portionwise. The reaction mixture was stirred at room temperature for 1 hour. The reaction mixture was quenched by the addition of an aqueous saturated sodium bicarbonate solution. The water layer was extracted with dichloromethane. The combined organic layers were washed with brine, dried, filtered and the solvent was removed under reduced pressure. The residue was purified by flash column chromatography over silica gel using heptane and ethyl acetate as eluents (gradient elution from 0% to 40% of ethyl acetate). The product fractions were collected and the solvent was removed under reduced pressure.

Yield: 6.80 g of intermediate 91 (81%)

LCMS method 2: MH$^+$=642, RT=3.377 min

Preparation of Intermediate 92

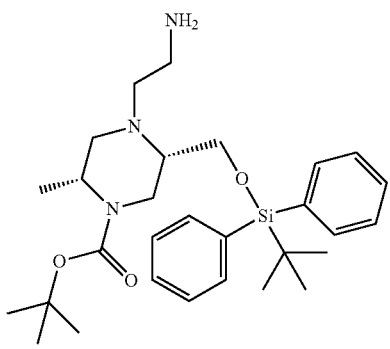 [SMILES: C[C@@H]1CN(CCN)[C@H](CO[Si](c2ccccc2)(c2ccccc2)C(C)(C)C)CN1C(=O)OC(C)(C)C]

A mixture of intermediate 92 (6.70 g, 10.44 mmol) and hydrazine (50/60% aqueous solution, 0.50 ml, 15.66 mmol) in ethanol (53 ml) was stirred at 70° C. for 4 hours. The reaction mixture was cooled and the suspension was filtered to remove the solid. The solid was washed with ethyl acetate. The solvent of the filtrate was removed under reduced pressure and the residue was re-dissolved in ethyl acetate. The organic layer washed with an aqueous 1M sodium hydroxide solution. The organic layer was dried, filtered and the solvent was removed under reduced pressure. The product was used without further purification in the next step.

LCMS method 2: MH$^+$=512

Preparation of Example N45

The following steps to obtain example N45 are based on the procedures used for the preparation of N20 and using intermediate 92.

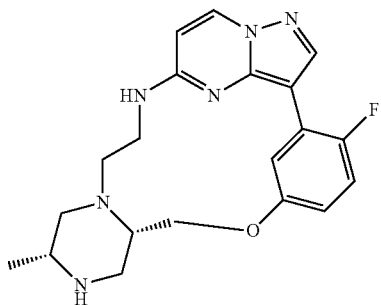 [SMILES: C[C@@H]1CN2CCNc3ccn4ncc(c4n3)-c3cc(ccc3F)OC[C@@H]2CN1]

Example N46

Example N46 may be prepared following general scheme 1, starting from example N45 and according to the procedures illustrated for the preparation of example N23.

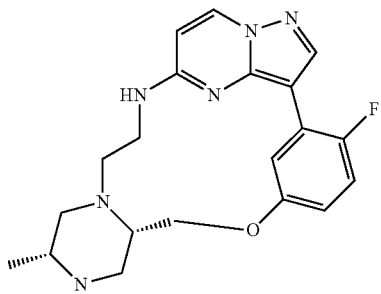

Example N47

Example N47 may be prepared following general scheme 1, starting from example N45.

Preparation of Example N47

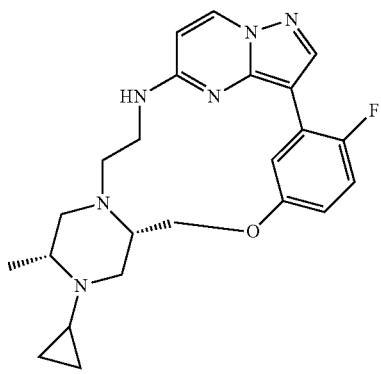 [SMILES: C[C@@H]1CN2CCNc3ccn4ncc(c4n3)-c3cc(ccc3F)OC[C@@H]2CN1C1CC1]

Example N45 (120 mg, 0.31 mmol) and cyclopropylboronic acid (50 mg, 0.62 mmol) were dissolved in 1,2-dichloroethane (2 ml). Copper(II) acetate (113 mg, 0.62 mmol), 2,2'-bipyridyl (97 mg, 0.62 mmol) and sodium carbonate (2.0 eq., 131 mg) were added. The reaction was stirred at the open air at 70° C. for 16 hours. The reaction mixture was quenched by the addition of an aqueous saturated ammonium chloride solution and was stirred at room temperature for 30 minutes. The mixture was diluted with dichloromethane. The two layers were separated and the organic layer was washed with an aqueous saturated ammonium chloride solution and brine. The organic layer was dried, filtered and the solvent was removed under reduced pressure. The residue was purified by flash column chromatography over silica gel using dichloromethane and a 7N ammonia solution and methanol as eluents (gradient elution from 0% to 3% methanol). The product fractions were collected and the solvent was removed under reduced pressure.

Yield: 90 mg of example N47 (69%)
LCMS method 2: MH$^+$=423, RT=2.369 min

Example N48

Example N48 may be prepared following general scheme 1, starting from example N45 and according to the procedures illustrated for the preparation of example N23.

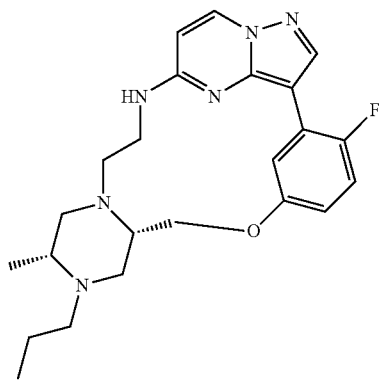 [SMILES: CCCN1C[C@H]2COc3ccc(F)c(c3)-c3cnn4ccc(nc34)NCCN2C[C@H]1C]

Example N49

Example N49 may be prepared following general scheme 1, starting from example N45 and according to the procedures illustrated for the preparation of example N23.

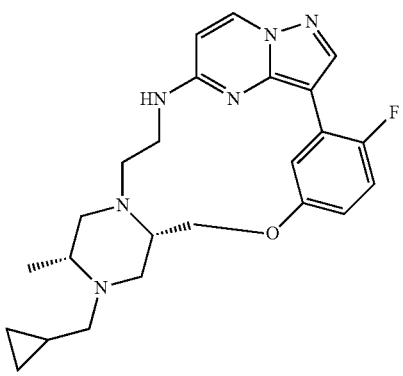 [SMILES: C[C@@H]1CN2CCNc3ccn4ncc(c4n3)-c3cc(ccc3F)OC[C@@H]2CN1CC1CC1]

Example N50

Example N50 may be prepared following general scheme 1, starting from example N45 and according to the procedures illustrated for the preparation of example N23.

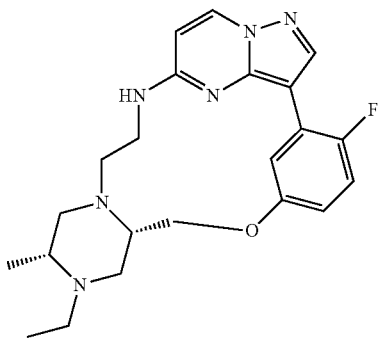 [SMILES: CCN1C[C@H]2COc3ccc(F)c(c3)-c3cnn4ccc(nc34)NCCN2C[C@H]1C]

Example N51

Example N51 may be prepared following general scheme 1 and according to the procedures illustrated for the preparation of example N28. The product was obtained as the HCl salt.

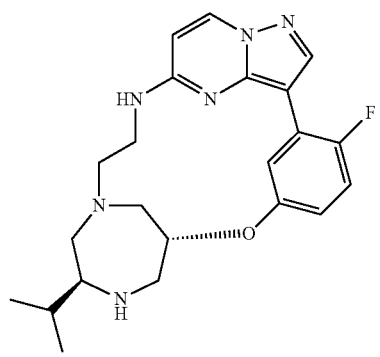 [SMILES: CC(C)[C@H]1CN2CCNc3ccn4ncc(c4n3)-c3cc(ccc3F)O[C@H](CN1)C2]

Example N52

Example N52 may be prepared following general scheme 1.

Preparation of Intermediate 93

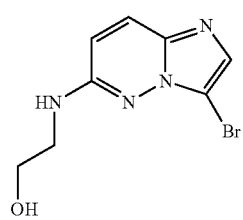 [SMILES: OCCNc1ccc2ncc(Br)n2n1]

3-bromo-6-chloro-imidazo[1,2-b]pyridazine (8.90 g, 38.28 mmol) and 2-aminoethanol (23.15 ml, 382.80 mmol) were suspended in n-butanol (114.84 ml) in a pressure tube and heated at 150° C. for 20 hours. The reaction mixture was cooled and the volume was reduced under reduced pressure. The mixture was triturated with ethyl acetate. The solids were filtered off and dried for 1 hour under reduced pressure at 70° C.

Yield: 7.50 g of intermediate 93 (76%)
LCMS method 2: MH$^+$=258, RT=1.223 min

Preparation of Intermediate 94

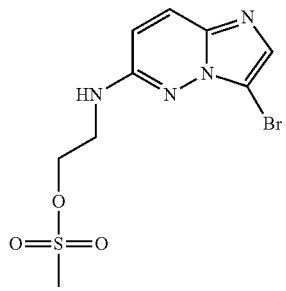 [SMILES: CS(=O)(=O)OCCNc1ccc2ncc(Br)n2n1]

Intermediate 93 (5.0 g, 19.45 mmol) and triethylamine (4.055 ml, 29.17 mmol) were dissolved in N,N-dimethylformamide (150 ml). The reaction mixture was cooled to 0° C. under nitrogen atmosphere and a solution of methylsulfonyl methanesulfonate (4.41 g, 25.29 mmol) in dichloromethane (20 ml) was added dropwise. The reaction mixture was stirred at room temperature for 2 hours. The reaction mixture was poured slowly into water (600 ml). The solids were filtered off and toluene was added and removed under reduced pressure. The solids were dried under vacuum. The compound was used without further purification in the next step.

Yield: 6.29 g of intermediate 94 (96%)

LCMS method 2: $MH^+=336$, RT=1.767 min

Preparation of Intermediate 95

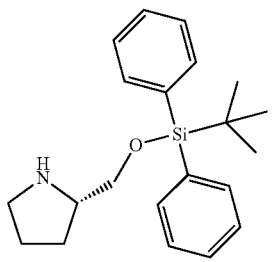 [SMILES: CC(C)(C)[Si](OC[C@@H]1CCCN1)(c1ccccc1)c1ccccc1]

[(2S)-pyrrolidin-2-yl]methanol (2.50 g, 24.72 mmol) and imidazole (2.52 g, 37.08 mmol) were dissolved in dichloromethane (74.16 ml) and cooled to 0° C. under nitrogen atmosphere. tert-butyl(chloro)diphenylsilane (7.118 g, 27.19 mmol) was added and the reaction mixture was stirred at room temperature for 16 hours. The reaction mixture was diluted with dichloromethane and washed with an aqueous 1N hydrochloric acid solution and an aqueous saturated sodium bicarbonate solution. The organic layer was dried, filtered and the solvent was removed under reduced pressure. The residue was purified by flash column chromatography over silica gel using dichloromethane and a 7N ammonia solution in methanol as eluents (gradient elution from 0% to 6% of methanol). The product fractions were collected and the solvent was removed under reduced pressure.

Yield: 8.00 g of intermediate 95 (95%)

LCMS method 2: $MH^+=340$

Preparation of Intermediate 96

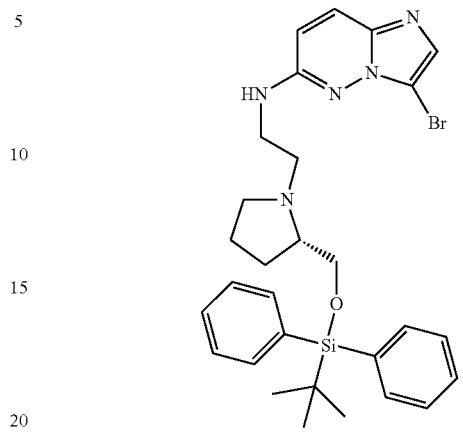

A mixture of intermediate 94 (3.10 g, 9.25 mmol), intermediate 95 (1.20 g, 11.10 mmol), sodium carbonate (2.941 g, 27.75 mmol) and potassium iodide (1.997 g, 12.03 mmol) in dimethyl sulfoxide (27.75 ml) was stirred at 60° C. for 16 hours. The reaction mixture was poured into water (350 ml) and extracted with ethyl acetate. The combined organic layers were washed with brine, dried, filtered and the solvent was removed under reduced pressure. The residue was purified by flash column chromatography over silica gel using dichloromethane and methanol as eluents (gradient elution from 0% to 5% of methanol). The product fractions were collected and the solvent was removed under reduced pressure. The residue was purified by a second flash column chromatography over silica gel using heptane and ethyl acetate as eluents (gradient elution from 0% to 80% of ethyl acetate) and using dichloromethane and methanol as eluents (gradient elution from 0% to 4% of methanol). The product fractions were collected and the solvent was removed under reduced pressure.

Yield: 2.00 g of intermediate 96 (37%)

LCMS method 2: $MH^+=579$, RT=3.081 min

Preparation of Intermediate 97

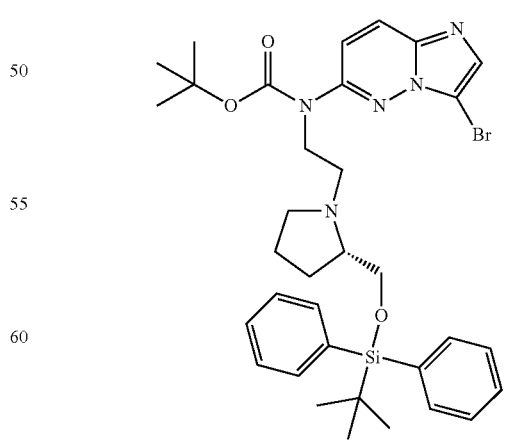

4-(Dimethyl amino)pyridine (0.20 g, 1.64 mmol) was added to a stirred solution of intermediate 96 (1.90 g, 3.28 mmol) and di-tert-butyl dicarbonate (1.07 g, 4.92 mmol) in tetrahydrofuran (15 ml). The reaction mixture was stirred at 65° C. for 4 hours. The reaction mixture was cooled and the solvent was removed under reduced pressure. The residue was purified by flash column chromatography over silica gel using dichloromethane and methanol as eluents (gradient elution from 0% to 4% of methanol). The product fractions were collected and the solvent was removed under reduced pressure.

Yield: 2.15 g of intermediate 97 (97%)
LCMS method 2: MH$^+$=679, RT=3.623 min

Preparation of Intermediate 98

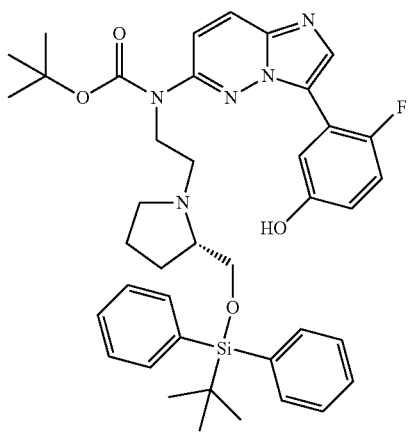 [SMILES: CC(C)(C)OC(=O)N(CCN1CCC[C@H]1CO[Si](c1ccccc1)(c1ccccc1)C(C)(C)C)c1ccc2ncc(-c3cc(O)ccc3F)n2n1]

Intermediate 57 (2.15 g, 78.20 mmol), 4-fluoro-3-(4,4,5,5-tetramethyl-1,3,2-dioxaborolan-2-yl)phenol (1.06 g, 4.44 mmol) and potassium phosphate tribasic (3 eq.) were dissolved in a mixture of 1,4-dioxane and water (3:1, 9.51 ml). The reaction mixture was degassed by bubbling nitrogen gas through the mixture. 2-Dicyclohexylphosphino-2',4',6'-triisopropylbiphenyl (Xphos) (153 mg, 0.32 mmol) and tetrakis(triphenylphosphine)palladium(0) (186 mg, 0.16 mmol) were added and the mixture was stirred under nitrogen gas at 85° C. for 16 hours. The reaction mixture was cooled. Dichloromethane was added and the organic layer was washed with water and brine. The organic layer was dried, filtered and the solvent was removed under reduced pressure. The residue was purified by flash column chromatography over silica gel using dichloromethane and methanol as eluents (96,5:3,5). The product fractions were collected and the solvent was removed under reduced pressure.

Yield: 1.76 g of intermediate 98 (78%)
LCMS method 2: MH$^+$=710, RT=3.520 min

Preparation of Intermediate 99

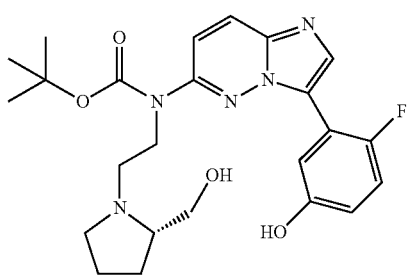 [SMILES: CC(C)(C)OC(=O)N(CCN1CCC[C@H]1CO)c1ccc2ncc(-c3cc(O)ccc3F)n2n1]

A solution of intermediate 98 (1.71 g, 2.41 mmol) in tetrahydrofuran (7.23 ml) was cooled to 0° C. under nitrogen atmosphere. Tetrabutylammonium fluoride (1M solution in tetrahydrofuran, 3.61 mmol) was added. The reaction mixture was stirred at room temperature for 20 hours. The solvent was removed under reduced pressure and the residue was diluted with ethyl acetate and washed with an aqueous saturated sodium bicarbonate solution. The organic layer was dried, filtered and the solvent was removed under reduced pressure. The residue was purified by flash column chromatography over silica gel using dichloromethane and methanol as eluents. The product fractions were collected and the solvent was removed under reduced pressure.

Yield: 840 mg of intermediate 99 (74%)
LCMS method 2: MH$^+$=472, RT=2.068 min

Preparation of Intermediate 100

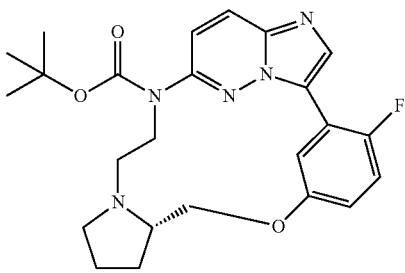 [SMILES: CC(C)(C)OC(=O)N1CCN2CCC[C@H]2COc2ccc(F)c(c2)-c2cnc3ccc1nn23]

A solution of intermediate 99 (440 mg, 0.93 mmol) in 2-methyltetrahydrofuran (20 ml/mmol) was degassed by bubbling nitrogen gas through the mixture. A solution of diisopropyl azodicarboxylate (550 mg, 2.79 mmol) in anhydrous toluene (20 ml/mmol) was degassed by bubbling nitrogen gas through the mixture. Both solutions were added simultaneously and dropwise over a period of 2 hours at 90° C. to a degassed solution of triphenylphosphine (732 mg, 2.79 mmol) in anhydrous toluene (75 ml/mmol). The reaction mixture was cooled and the solvent was removed under reduced pressure. The residue was purified by flash column chromatography over silica gel using dichloromethane and methanol as eluents (gradient elution from 0% to 4% of methanol). The product fractions were collected and the solvent was removed under reduced pressure.

Yield: 590 mg of intermediate 100 (70%)
LCMS method 2: MH$^+$=453, RT=2.293 min

Preparation of Example N52

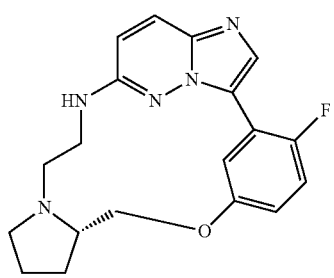 [SMILES: Fc1ccc2cc1-c1cnc3ccc(nn13)NCCN1CCC[C@H]1CO2]

Intermediate 100 (590 mg, 0.65 mmol) was dissolved in a 4N hydrochloric acid solution in methanol (4 ml). The reaction mixture was stirred at 50° C. for 16 hours. The reaction was cooled, slowly poured into an aqueous saturated sodium bicarbonate solution and stirred at room temperature for 30 minutes. The aqueous layer was extracted with dichloromethane. The combined organic layers were dried, filtered and the solvent was removed under reduced pressure. The residue was purified by flash column chromatography over silica gel using dichloromethane and a 7N ammonia solution and methanol as eluents (gradient elution from 0% to 4% methanol). The product fractions were collected and the solvent was removed under reduced pressure. The residue was further purified by reversed phase column chromatography (HPLC method A). The product fractions were collected and the solvent was removed under reduced pressure.

Yield: 29 mg of example N52 (6%)

LCMS method 2: MH$^+$=353, RT=1.398 min

Example N53

Example N53 may be prepared following general scheme 1 and according to the procedures illustrated for the preparation of example N45. The product was obtained as the HCl salt.

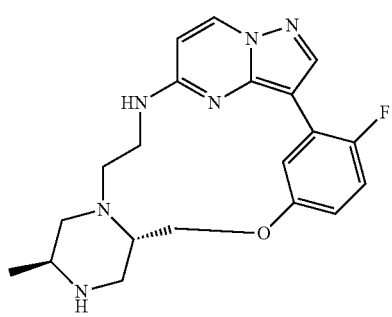 [SMILES: C[C@H]1CN2CCNc3ccn4ncc(c4n3)-c3cc(ccc3F)OC[C@@H]2CN1]

Example N54

Example N54 is obtained as a side-product during the Mitsunobu reaction in the preparation of example N53. The product was obtained as the HCl salt.

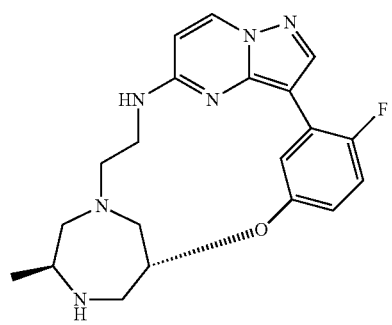 [SMILES: C[C@H]1CN2CCNc3ccn4ncc(c4n3)-c3cc(ccc3F)O[C@H](CN1)C2]

Example N55

Example N55 may be prepared following general scheme 1 and according to the procedures illustrated for the preparation of example N45. The product was obtained as the HCl salt.

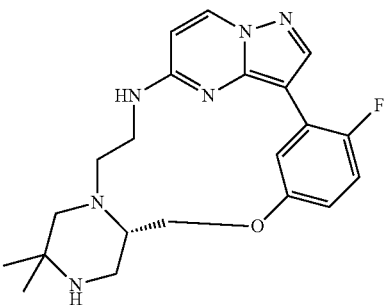 [SMILES: CC1(C)CN2CCNc3ccn4ncc(c4n3)-c3cc(ccc3F)OC[C@@H]2CN1]

Example N56

Example N56 may be prepared following general scheme 1 and according to the procedures illustrated for the preparation of example N11.

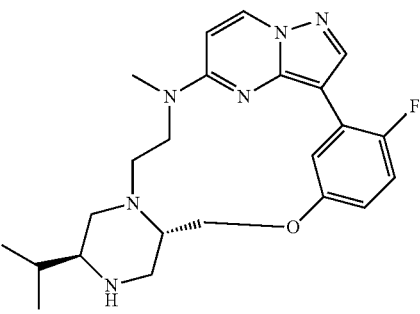 [SMILES: CC(C)[C@H]1CN2CCN(C)c3ccn4ncc(c4n3)-c3cc(ccc3F)OC[C@@H]2CN1]

Example N57

Example N57 may be prepared following general scheme 2.

Preparation of Intermediate 101

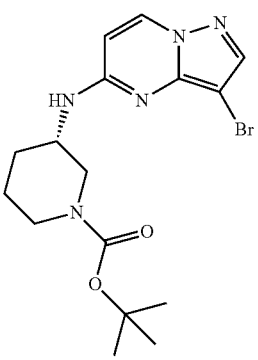 [SMILES: CC(C)(C)OC(=O)N1CCC[C@H](Nc2ccn3ncc(Br)c3n2)C1]

A mixture of tert-butyl (3S)-3-aminopiperidine-1-carboxylate (2.00 g, 9.99 mmol), 3-bromo-5-chloro-pyrazolo[1,5-a]pyrimidine (3.48 g, 14.98 mmol) and N,N-diisopropylethylamine (2.616 ml, 14.98 mmol) in acetonitrile (30 ml) was stirred at 90° C. for 24 hours. More 3-bromo-5-chloro-pyrazolo[1,5-a]pyrimidine (0.5 eq.) was added and the mixture was stirred at 90° C. for 22 hours. The reaction mixture was cooled and the solvent was removed under reduced pressure. Ethyl acetate was added an the organic layer was washed with water. The organic layer was dried, filtered and the solvent was removed under reduced pressure. The residue was purified by flash column chromatography over silica gel using dichloromethane and methanol as eluents (gradient elution from 0% to 8% of methanol). The product fractions were collected and the solvent was removed under reduced pressure.

LCMS method 2: MH$^+$=397, RT=4.609 min

Preparation of Intermediate 102

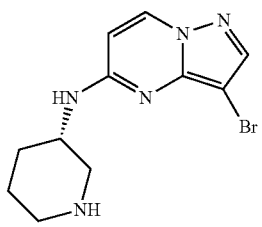 [SMILES: Brc1cnn2ccc(N[C@H]3CCCNC3)nc12]

Intermediate 101 (4.08 g, 10.30 mmol) was stirred in a 4N hydrochloric acid solution in methanol (30 ml) at room temperature for 4 hours. Methanol and toluene were added and nitrogen gas was bubbled through the mixture. The solvent was removed under reduced pressure. Toluene was added twice and removed twice under reduced pressure. The product was used without further purification in the next step.

LCMS method 2: MH$^+$=297, RT=1.418 min

Preparation of Intermediate 103

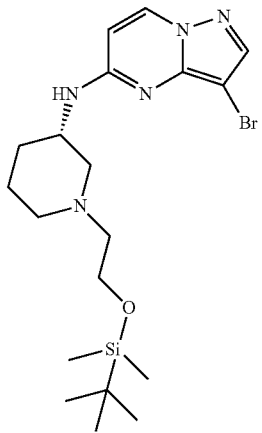 [SMILES: CC(C)(C)[Si](C)(C)OCCN1CCC[C@H](Nc2ccn3ncc(Br)c3n2)C1]

2-bromoethoxy-tert-butyl-dimethyl-silane (1.245 ml, 5.83 mmol) was added to a suspension of intermediate 102 (4.86 mmol), triethylamine (2.027 ml, 14.58 mmol) and potassium iodide (807 mg, 4.86 mmol) in N,N-dimethylacetamide (6.7 ml). The reaction mixture was stirred at 80° C. for 16 hours. The reaction mixture was cooled, ethyl acetate was added and the organic layer was washed with water. The organic layer was dried, filtered and the solvent was removed under reduced pressure. The residue was purified by flash column chromatography over silica gel using dichloromethane and methanol as eluents (gradient elution from 0% to 8% of methanol). The product fractions were collected and the solvent was removed under reduced pressure.

LCMS method 2: MH$^+$=455, RT=2.377 min

Preparation of Intermediate 104

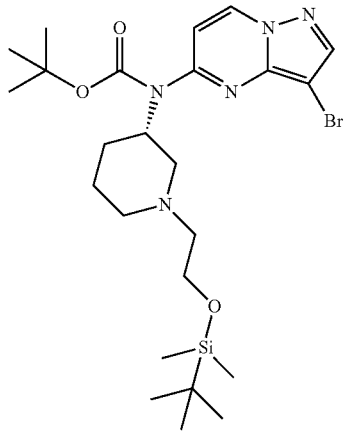 [SMILES: CC(C)(C)OC(=O)N(c1ccn2ncc(Br)c2n1)[C@H]1CCCN(CCO[Si](C)(C)C(C)(C)C)C1]

Di-tert-butyl dicarbonate (1.111 g, 5.09 mmol) was added to a mixture of intermediate 103 (1.925 g, 4.24 mmol), triethylamine (0.884 ml, 6.36 mmol) and 4-(dimethyl amino)pyridine (0.259 g, 2.12 mmol) in tetrahydrofuran (12.72 ml). The reaction mixture was stirred at 70° C. for 2 hours. More di-tert-butyl dicarbonate (1.2 eq.) and triethylamine (0.4 eq.) were added and mixture was stirred at 70° C. for 16 hours. More di-tert-butyl dicarbonate (3 eq.) and 4-(dimethyl amino)pyridine (0.3 eq.) were added and mixture was stirred again at 70° C. for 20 hours. The crude reaction mixture was purified and the reaction was reinitiated using di-tert-butyl dicarbonate (2 eq.) and 4-(dimethyl amino) pyridine (0.8 eq.). The reaction mixture was stirred at 70° C. for 16 hours. The reaction mixture was cooled and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure.

Yield: 1.249 g of intermediate 104 (53%)
LCMS method 2: MH$^+$=555, RT=3.285 min Preparation of Intermediate 105

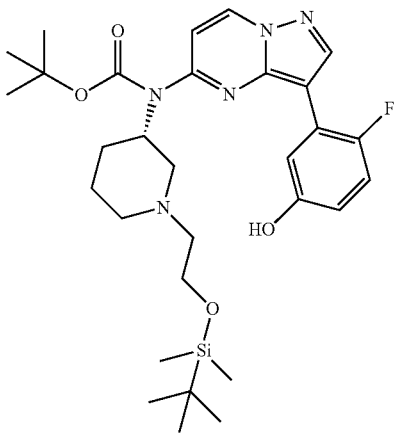 [SMILES: CC(C)(C)OC(=O)N(c1ccn2ncc(-c3cc(O)ccc3F)c2n1)[C@H]1CCCN(CCO[Si](C)(C)C(C)(C)C)C1]

A mixture of 1,4-dioxane and water (3:1, 12.0 ml) was degassed by bubbling nitrogen gas through the mixture. Intermediate 104 (1.149 g, 2.07 mmol), 4-fluoro-3-(4,4,5,5-tetramethyl-1,3,2-dioxaborolan-2-yl)phenol (0.59 g, 2.48 mmol), tetrakis(triphenylphosphine)palladium(0) (46 mg, 0.04 mmol), 2-dicyclohexylphosphino-2',4',6'-triisopropyl-biphenyl (Xphos) (38 mg, 0.08 mmol) and potassium phosphate tribasic (1.318 g, 3 eq.) were added and the mixture was stirred under nitrogen gas at 85° C. for 14 hours. The reaction mixture was cooled and ethyl acetate was added. The organic layer washed with water, dried, filtered and the solvent was removed under reduced pressure. The residue was purified by flash column chromatography over silica gel using heptane and ethyl acetate as eluents (gradient elution from 0% to 80% ethyl acetate). The product fractions were collected and the solvent was removed under reduced pressure.

LCMS method 2: MH$^+$=586, RT=3.335 min

Preparation of Intermediate 106

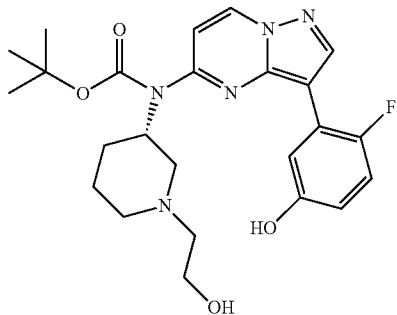 [SMILES: CC(C)(C)OC(=O)N(c1ccn2ncc(-c3cc(O)ccc3F)c2n1)[C@H]1CCCN(CCO)C1]

Tetrabutylammonium fluoride (1M solution in tetrahydrofuran, 2.48 ml, 2.48 mmol) was added to a solution of intermediate 105 (2.07 mmol) in tetrahydrofuran (6.21 ml). The reaction mixture was stirred at room temperature for 17 hours. The mixture was diluted with ethyl acetate and washed with water and a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 8% of methanol). The product fractions were collected and the solvent was removed under reduced pressure.

Yield: 844 mg of intermediate 106 (86%)
LCMS method 2: MH$^+$=472, RT=2.351 min

Preparation of Intermediate 107

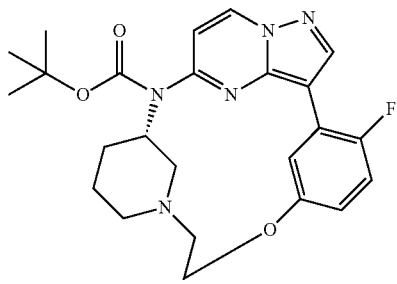 [SMILES: CC(C)(C)OC(=O)N1c2ccn3ncc(c3n2)-c2cc(ccc2F)OCCN2CCC[C@H]1C2]

A solution of intermediate 106 (744 mg, 1.58 mmol) in 2-methyltetrahydrofuran (20 ml/mmol) was degassed by bubbling nitrogen gas through the mixture. A solution of diisopropyl azodicarboxylate (1.566 ml, 7.90 mmol) in anhydrous toluene (20 ml/mmol) was degassed by bubbling nitrogen gas through the mixture. Both solutions were added simultaneously and dropwise over a period of 2 hours at 110° C. to a degassed solution of triphenylphosphine (2.072 g, 7.90 mmol) in anhydrous toluene (75 ml/mmol). The reaction mixture was stirred at 110° C. for 30 minutes. The mixture was cooled and the solvent was removed under reduced pressure. The residue was purified by flash column chromatography over silica gel using dichloromethane and ethyl acetate as eluents (gradient elution from 0% to 50% of ethyl acetate). The product fractions were collected and the solvent was removed under reduced pressure. The residue was triturated with acetonitrile, the solid was removed and dried under reduced pressure.

Yield: 678 mg of intermediate 107 (95%)
LCMS method 2: MH$^+$=454, RT=2.365 min

Preparation of Example N57

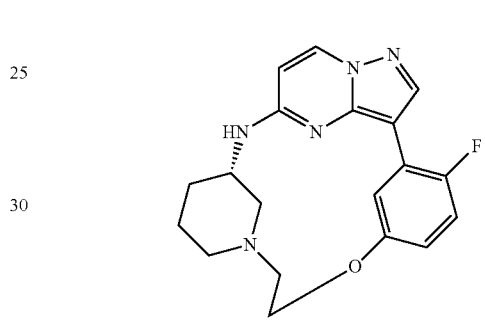

Intermediate 107 (678 mg, 1.49 mmol) was stirred in a 4N hydrochloric acid solution in methanol (4.47 ml) at room temperature for 4 hours and at 50° C. for 2 hours. The reaction mixture was stirred at room temperature for another 14 hours. Diethyl ether was added and nitrogen gas was bubbled through the mixture until the diethyl ether was evaporated. Diethyl ether and a few drops of methanol were added and the solid was filtered and dried under reduced pressure. The product was obtained as the HCl salt.

Yield: 219 mg of example N57 (38%)
LCMS method 2: MH$^+$=354, RT=2.056 min

Example N58

Example N58 is obtained as a side-product during the Mitsunobu reaction in the preparation of example N55. The product was obtained as the HCl salt.

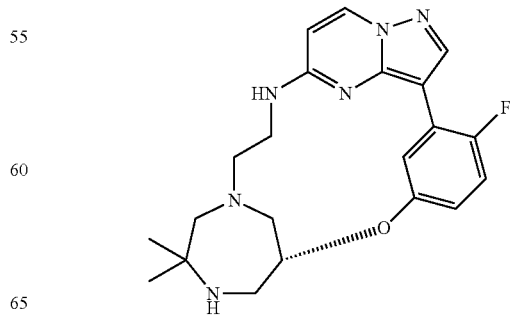

Example N59

Example N59 is obtained as a side-product during the Mitsunobu reaction in the preparation of example N52. The product was obtained as the HCl salt.

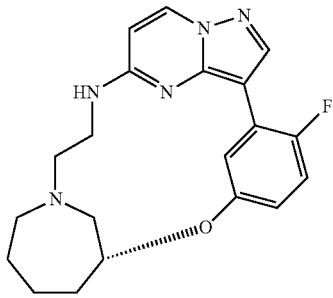 [SMILES: Fc1ccc2cc1-c1cnn3ccc(nc13)NCCN1CCCC[C@H](C1)O2]

Example N60

Example N60 may be prepared following general scheme 2 and according to the procedures illustrated for the preparation of example N57. The product was obtained as the HCl salt.

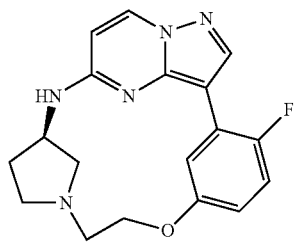 [SMILES: Fc1ccc2cc1-c1cnn3ccc(nc13)N[C@@H]1CCN(CCO2)C1]

Example N61

Example N61 may be prepared following general scheme 2, starting from example N60 and according to the procedures illustrated for the preparation of example N11. The product was obtained as the HCl salt.

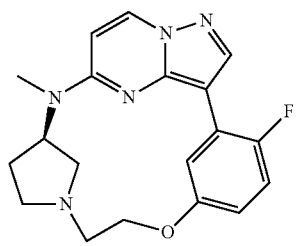 [SMILES: CN1c2ccn3ncc(c3n2)-c2cc(ccc2F)OCCN2CC[C@@H]1C2]

Example N62

Example N62 may be prepared following general scheme 1, starting from example N55 and according to the procedures illustrated for the preparation of example N47.

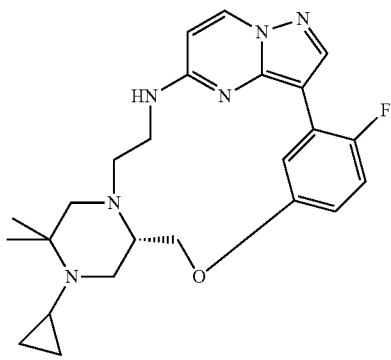 [SMILES: CC1(C)CN2CCNc3ccn4ncc(c4n3)-c3cc(ccc3F)OC[C@@H]2CN1C1CC1]

Example N63

Example N63 is obtained as a side-product during the Suzuki reaction in the preparation of example N62.

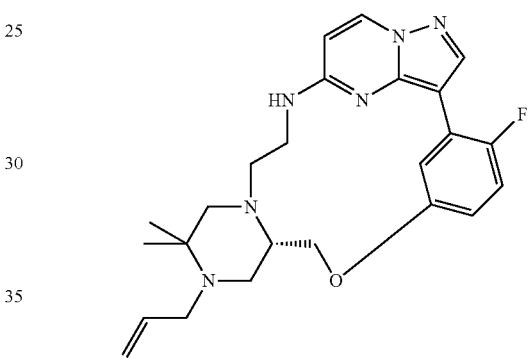

TABLE 1

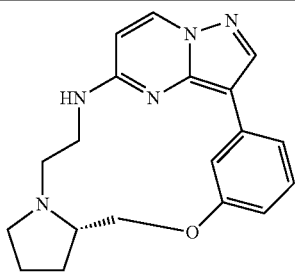

Compound N1, Example N1

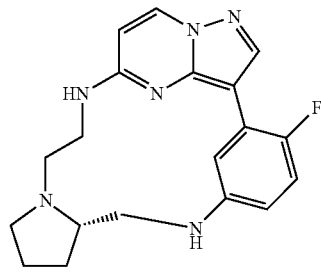 [SMILES: Fc1ccc2cc1-c1cnn3ccc(nc13)NCCN1CCC[C@H]1CN2]

Compound N2, Example N2

TABLE 1-continued
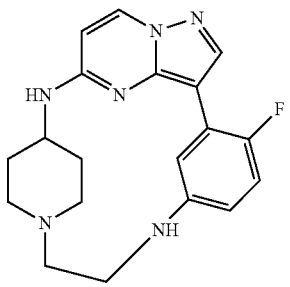 [SMILES: Fc1ccc2cc1-c1cnn3ccc(nc13)NC1CCN(CCN2)CC1]
Compound N3, Example N3
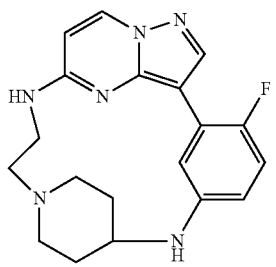 [SMILES: Fc1ccc2cc1-c1cnn3ccc(nc13)NCCN1CCC(CC1)N2]
Compound N4, Example N4
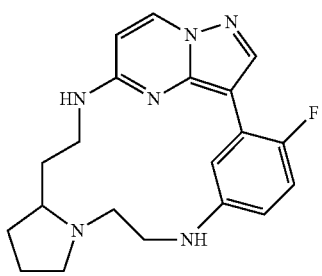 [SMILES: Fc1ccc2cc1-c1cnn3ccc(nc13)NCCC1CCCN1CCN2]
Compound N5, Example N5
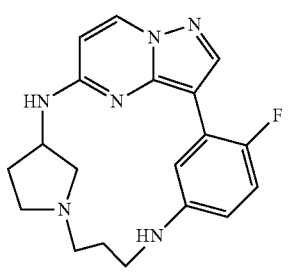 [SMILES: Fc1ccc2cc1-c1cnn3ccc(nc13)NC1CCN(CCCN2)C1]
Compound N6, Example N6
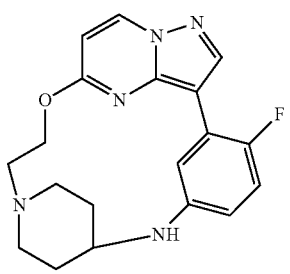 [SMILES: Fc1ccc2cc1-c1cnn3ccc(nc13)OCCN1CCC(CC1)N2]
Compound N7, Example N7
TABLE 1-continued
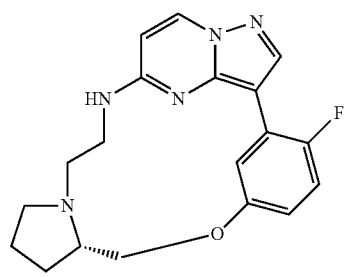 [SMILES: Fc1ccc2cc1-c1cnn3ccc(nc13)NCCN1CCC[C@H]1CO2]
Compound N8, Example N8
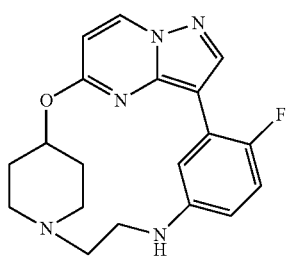 [SMILES: Fc1ccc2cc1-c1cnn3ccc(nc13)OC1CCN(CCN2)CC1]
Compound N9, Example N9
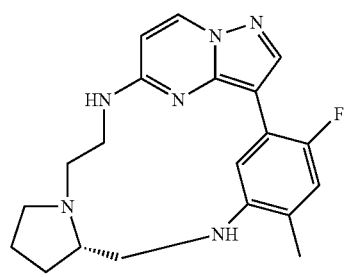 [SMILES: Cc1cc(F)c2cc1NC[C@@H]1CCCN1CCNc1ccn3ncc-2c3n1]
Compound N10, Example N10
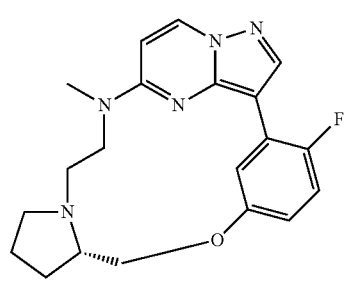 [SMILES: CN1CCN2CCC[C@H]2COc2ccc(F)c(c2)-c2cnn3ccc1nc23]
Compound N11, Example N11
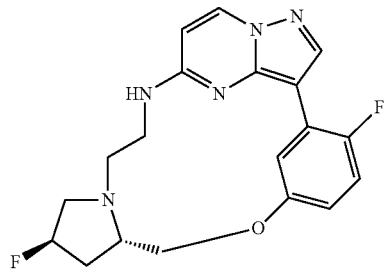 [SMILES: Fc1ccc2cc1-c1cnn3ccc(nc13)NCCN1C[C@H](F)C[C@H]1CO2]
Compound N12, Example N12

TABLE 1-continued
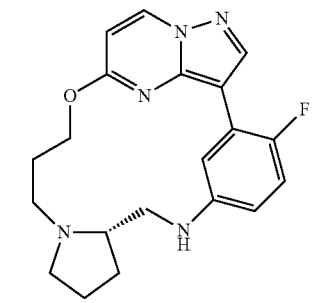 [SMILES: Fc1ccc2cc1-c1cnn3ccc(nc13)OCCCN1CCC[C@H]1CN2]
Compound N13, Example N13
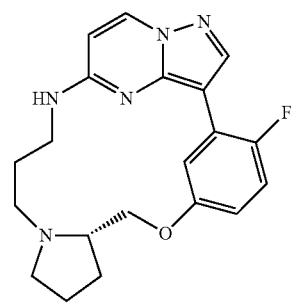 [SMILES: Fc1ccc2cc1-c1cnn3ccc(nc13)NCCCN1CCC[C@H]1CO2]
Compound N14, Example N14
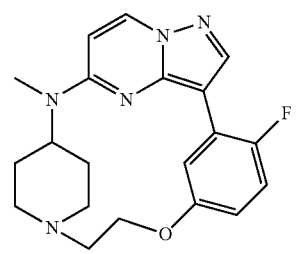 [SMILES: CN1c2ccn3ncc(c3n2)-c2cc(ccc2F)OCCN2CCC1CC2]
Compound N15, Example N15
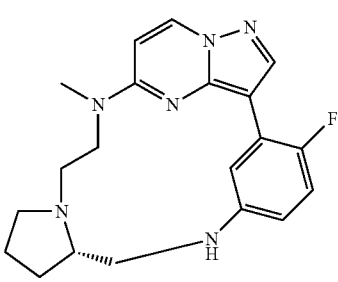 [SMILES: CN1CCN2CCC[C@H]2CNc2ccc(F)c(c2)-c2cnn3ccc1nc23]
Compound N16, Example N16
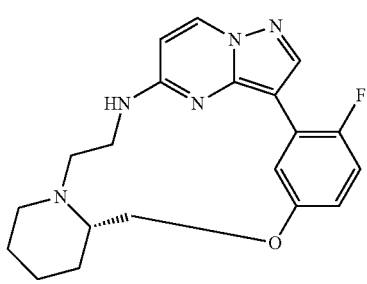 [SMILES: Fc1ccc2cc1-c1cnn3ccc(nc13)NCCN1CCCC[C@H]1CO2]
Compound N17, Example N17
TABLE 1-continued
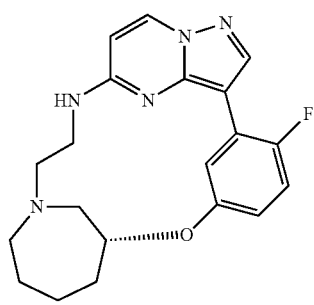 [SMILES: Fc1ccc2cc1-c1cnn3ccc(nc13)NCCN1CCCC[C@H](C1)O2]
Compound N18, Example N18
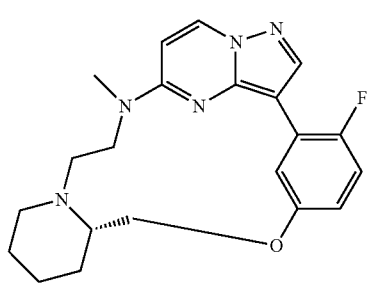 [SMILES: CN1CCN2CCCC[C@H]2COc2ccc(F)c(c2)-c2cnn3ccc1nc23]
Compound N19, Example N19
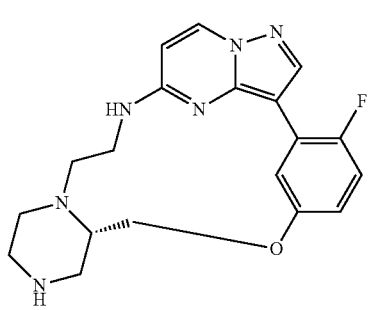 [SMILES: Fc1ccc2cc1-c1cnn3ccc(nc13)NCCN1CCNC[C@H]1CO2]
Compound N20, Example N20
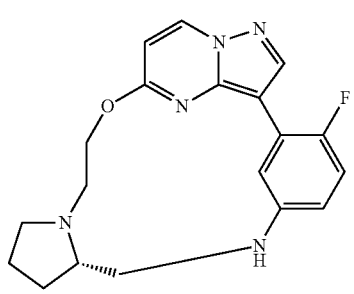 [SMILES: Fc1ccc2cc1-c1cnn3ccc(nc13)OCCN1CCC[C@H]1CN2]
Compound N21, Example N21

TABLE 1-continued
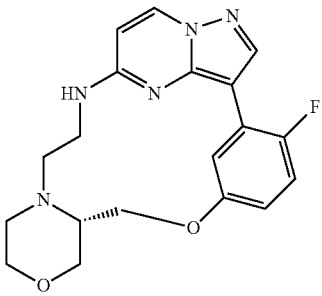 [SMILES: Fc1ccc2cc1-c1cnn3ccc(nc13)NCCN1CCOC[C@H]1CO2]
Compound N22, Example N22
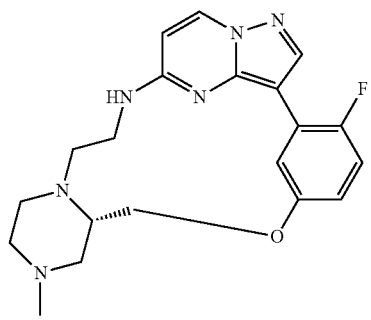 [SMILES: CN1CCN2CCNc3ccn4ncc(c4n3)-c3cc(ccc3F)OC[C@@H]2C1]
Compound N23, Example N23
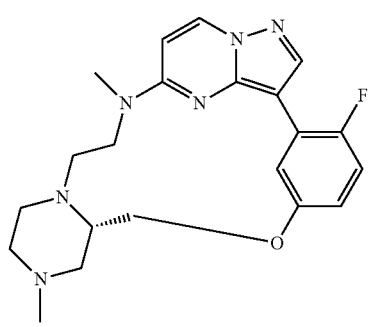 [SMILES: CN1CCN2CCN(C)c3ccn4ncc(c4n3)-c3cc(ccc3F)OC[C@@H]2C1]
Compound N24, Example N24
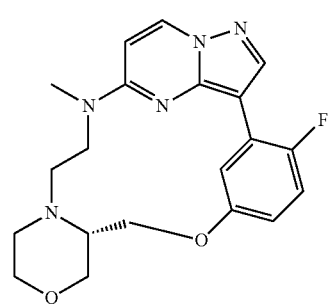 [SMILES: CN1CCN2CCOC[C@H]2COc2ccc(F)c(c2)-c2cnn3ccc1nc23]
Compound N25, Example N25
TABLE 1-continued
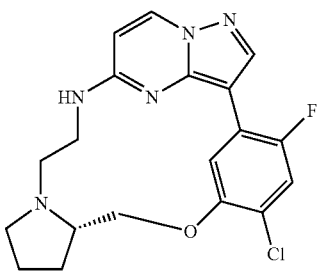 [SMILES: Fc1cc(Cl)c2cc1-c1cnn3ccc(nc13)NCCN1CCC[C@H]1CO2]
Compound N26, Example N26
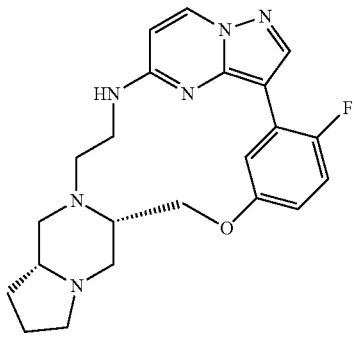 [SMILES: Fc1ccc2cc1-c1cnn3ccc(nc13)NCCN1C[C@H]3CCCN3C[C@H]1CO2]
Compound N27, Example N27
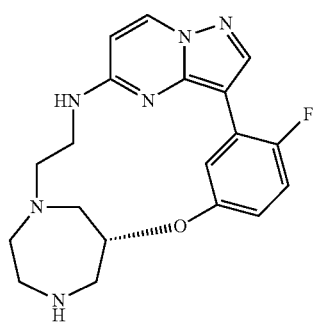 [SMILES: Fc1ccc2cc1-c1cnn3ccc(nc13)NCCN1CCNC[C@H](C1)O2]
Compound N28, Example N28
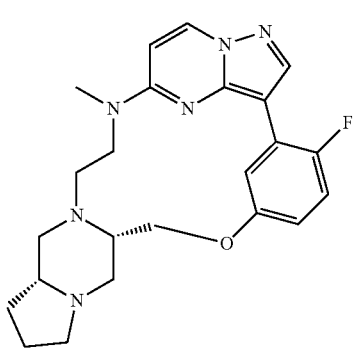 [SMILES: CN1CCN2C[C@H]3CCCN3C[C@H]2COc2ccc(F)c(c2)-c2cnn3ccc1nc23]
Compound N29, Example N29

TABLE 1-continued
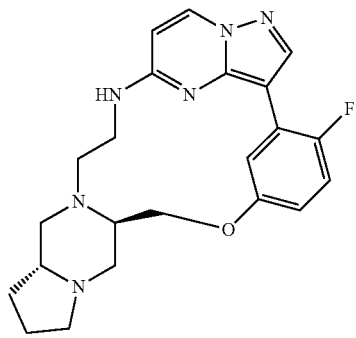 [SMILES: Fc1ccc2cc1-c1cnn3ccc(nc13)NCCN1C[C@H]3CCCN3C[C@@H]1CO2]
Compound N30, Example N30
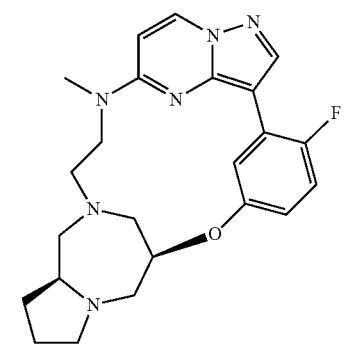 [SMILES: CN1CCN2C[C@H](CN3CCC[C@H]3C2)Oc2ccc(F)c(c2)-c2cnn3ccc1nc23]
Compound N31, Example N31
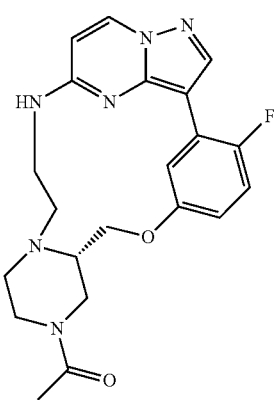 [SMILES: CC(=O)N1CCN2CCNc3ccn4ncc(c4n3)-c3cc(ccc3F)OC[C@@H]2C1]
Compound N32, Example N32
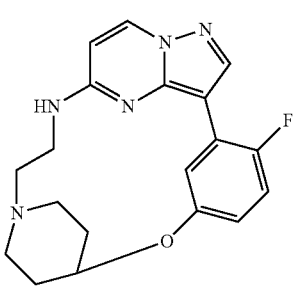 [SMILES: Fc1ccc2cc1-c1cnn3ccc(nc13)NCCN1CCC(CC1)O2]
Compound N33, Example N33
TABLE 1-continued
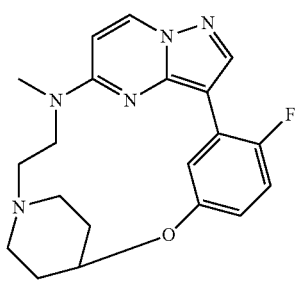 [SMILES: CN1CCN2CCC(CC2)Oc2ccc(F)c(c2)-c2cnn3ccc1nc23]
Compound N34, Example N34
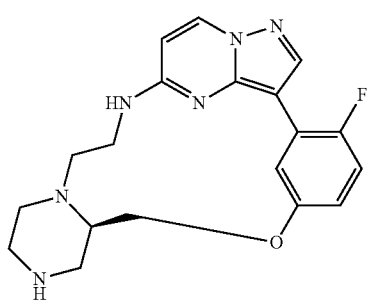 [SMILES: Fc1ccc2cc1-c1cnn3ccc(nc13)NCCN1CCNC[C@@H]1CO2]
Compound N35, Example N35
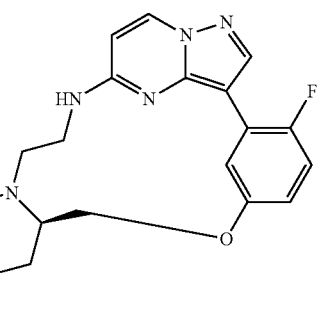
Compound N36, Example N36
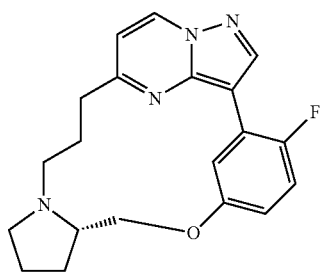 [SMILES: Fc1ccc2cc1-c1cnn3ccc(nc13)CCCN1CCC[C@H]1CO2]
Compound N37, Example N37

TABLE 1-continued
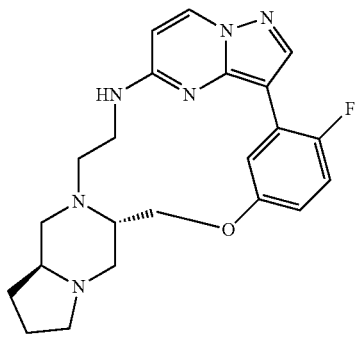 [SMILES: Fc1ccc2cc1-c1cnn3ccc(nc13)NCCN1C[C@@H]3CCCN3C[C@H]1CO2]
Compound N38, Example N38
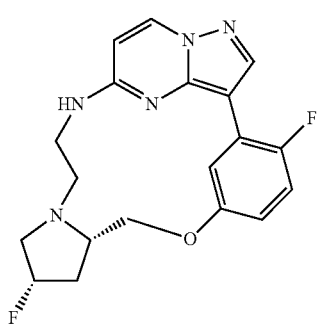 [SMILES: Fc1ccc2cc1-c1cnn3ccc(nc13)NCCN1C[C@@H](F)C[C@H]1CO2]
Compound N39, Example N39
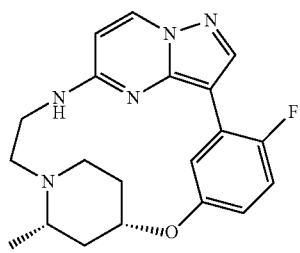 [SMILES: C[C@H]1C[C@@H]2CCN1CCNc1ccn3ncc(c3n1)-c1cc(ccc1F)O2]
Compound N40, Example N40
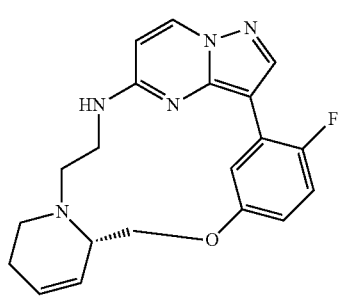 [SMILES: Fc1ccc2cc1-c1cnn3ccc(nc13)NCCN1CCC=C[C@H]1CO2]
Compound N41, Example N41
TABLE 1-continued
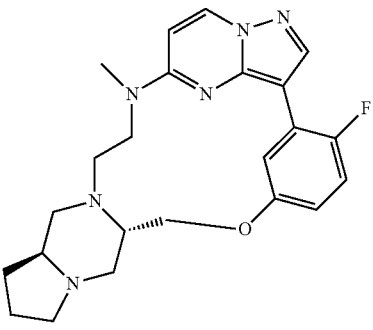 [SMILES: CN1CCN2C[C@@H]3CCCN3C[C@H]2COc2ccc(F)c(c2)-c2cnn3ccc1nc23]
Compound N42, Example N42
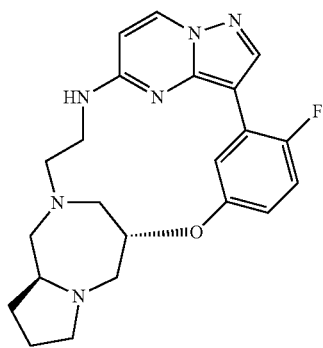 [SMILES: Fc1ccc2cc1-c1cnn3ccc(nc13)NCCN1C[C@@H](CN3CCC[C@H]3C1)O2]
Compound N43, Example N43
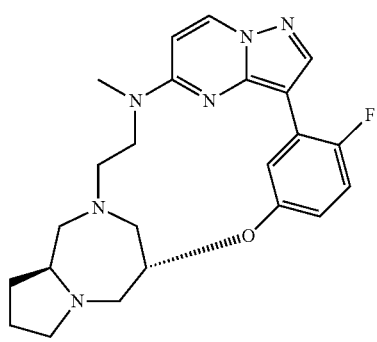 [SMILES: CN1CCN2C[C@@H](CN3CCC[C@H]3C2)Oc2ccc(F)c(c2)-c2cnn3ccc1nc23]
Compound N44, Example N44
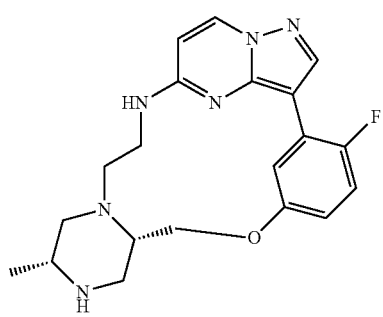 [SMILES: C[C@@H]1CN2CCNc3ccn4ncc(c4n3)-c3cc(ccc3F)OC[C@@H]2CN1]
Compound N45, Example N45

TABLE 1-continued
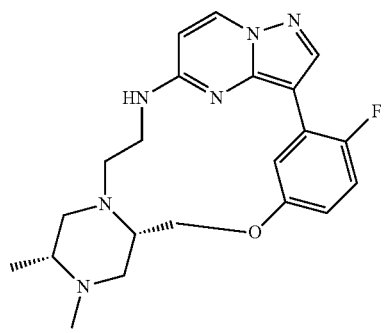 [SMILES: C[C@@H]1CN2CCNc3ccn4ncc(c4n3)-c3cc(ccc3F)OC[C@@H]2CN1C]
Compound N46, Example N46
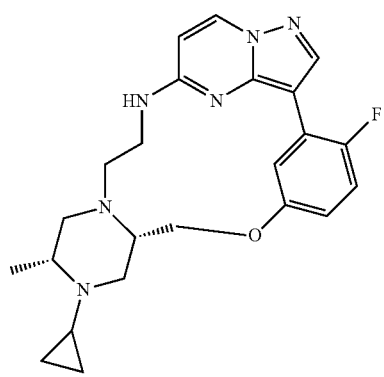 [SMILES: C[C@@H]1CN2CCNc3ccn4ncc(c4n3)-c3cc(ccc3F)OC[C@@H]2CN1C1CC1]
Compound N47, Example N47
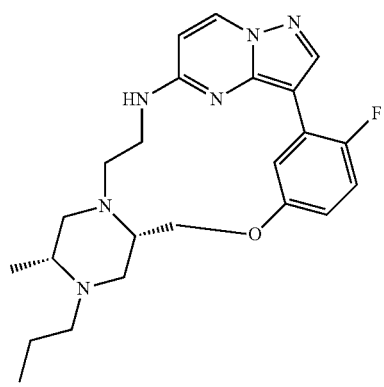 [SMILES: CCCN1C[C@H]2COc3ccc(F)c(c3)-c3cnn4ccc(nc34)NCCN2C[C@H]1C]
Compound N48, Example N48
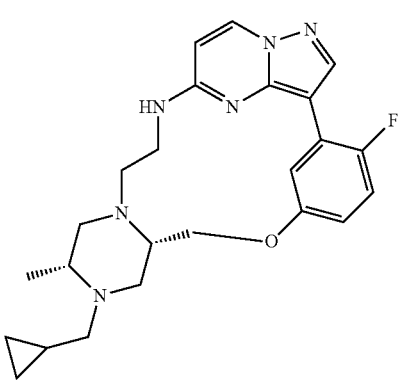 [SMILES: C[C@@H]1CN2CCNc3ccn4ncc(c4n3)-c3cc(ccc3F)OC[C@@H]2CN1CC1CC1]
Compound N49, Example N49
TABLE 1-continued
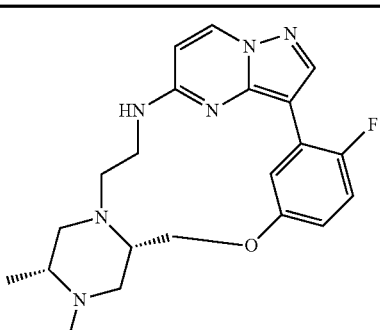
Compound N50, Example N50
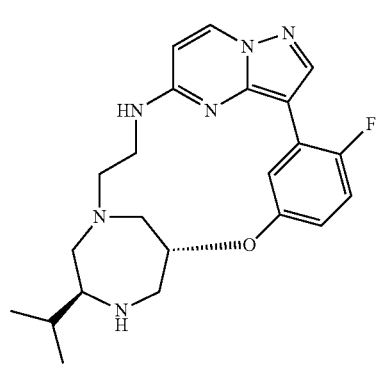 [SMILES: CC(C)[C@H]1CN2CCNc3ccn4ncc(c4n3)-c3cc(ccc3F)O[C@H](CN1)C2]
Compound N51, Example N51
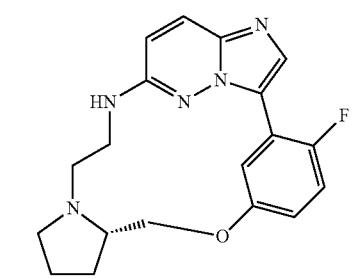 [SMILES: Fc1ccc2cc1-c1cnc3ccc(nn13)NCCN1CCC[C@H]1CO2]
Compound N52, Example N52
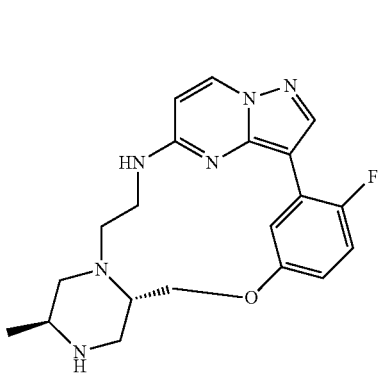 [SMILES: C[C@H]1CN2CCNc3ccn4ncc(c4n3)-c3cc(ccc3F)OC[C@@H]2CN1]
Compound N53, Example N53

TABLE 1-continued
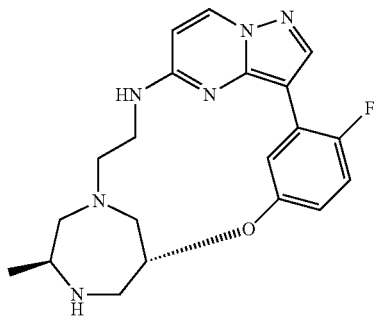 [SMILES: C[C@H]1CN2CCNc3ccn4ncc(c4n3)-c3cc(ccc3F)O[C@H](CN1)C2]
Compound N54, Example N54
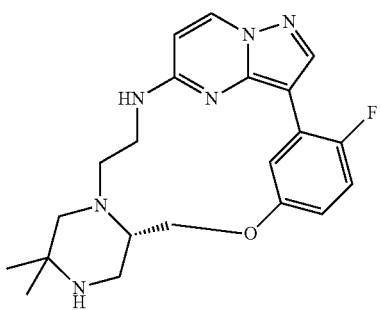 [SMILES: CC1(C)CN2CCNc3ccn4ncc(c4n3)-c3cc(ccc3F)OC[C@@H]2CN1]
Compound N55, Example N55
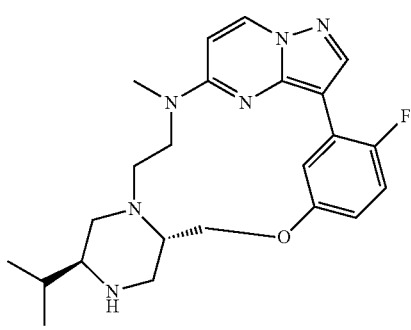 [SMILES: CC(C)[C@H]1CN2CCN(C)c3ccn4ncc(c4n3)-c3cc(ccc3F)OC[C@@H]2CN1]
Compound N56, Example N56
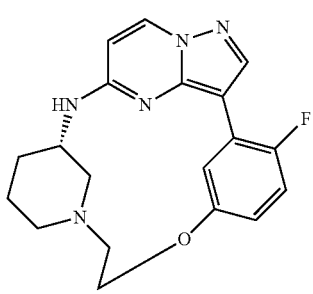 [SMILES: Fc1ccc2cc1-c1cnn3ccc(nc13)N[C@H]1CCCN(CCO2)C1]
Compound N57, Example N57
TABLE 1-continued
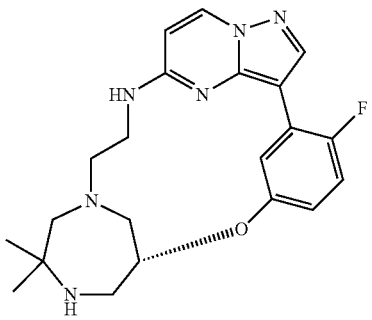 [SMILES: CC1(C)CN2CCNc3ccn4ncc(c4n3)-c3cc(ccc3F)O[C@H](CN1)C2]
Compound N58, Example N58
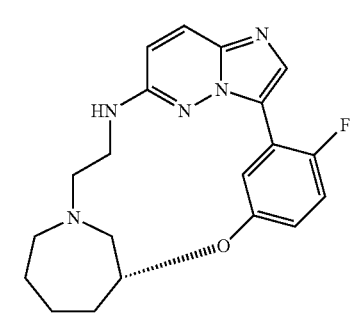 [SMILES: Fc1ccc2cc1-c1cnc3ccc(nn13)NCCN1CCCC[C@H](C1)O2]
Compound N59, Example N59
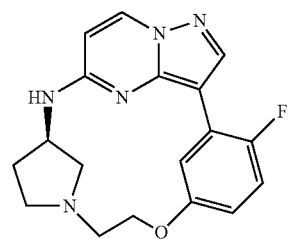 [SMILES: Fc1ccc2cc1-c1cnn3ccc(nc13)N[C@@H]1CCN(CCO2)C1]
Compound N60, Example N60
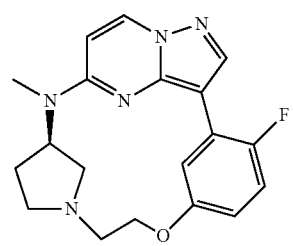 [SMILES: CN1c2ccn3ncc(c3n2)-c2cc(ccc2F)OCCN2CC[C@@H]1C2]
Compound N61, Example N61

TABLE 1-continued

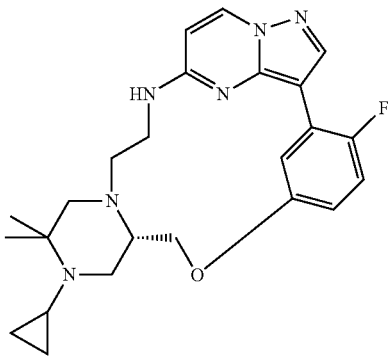 [SMILES: CC1(C)CN2CCNc3ccn4ncc(c4n3)-c3cc(ccc3F)OC[C@@H]2CN1C1CC1]

Compound N62, Example N62

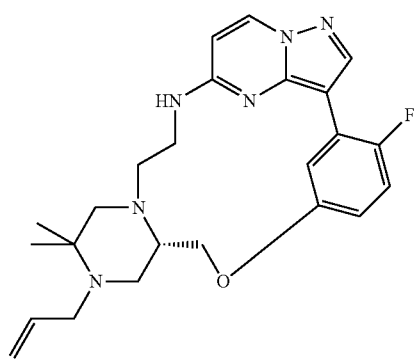 [SMILES: C=CCN1C[C@H]2COc3ccc(F)c(c3)-c3cnn4ccc(nc34)NCCN2CC1(C)C]

Compound N63, Example N63

Compound Identification
Melting Points

For the melting point determination of the compounds of the present invention, the following method was used.

Melting Point Method

For a number of compounds, melting points (m.p.) were determined in open capillary tubes on a Mettler FP62 apparatus. Melting points were measured with a temperature ranging from 50° C. to 300° C., using a gradient of 10° C./minute. The melting point value was read from a digital display and was not corrected.

TABLE 2

Melting points

| COMPOUND NUMBER | MELTING POINT (° C.) |
|---|---|
| N1 | 272.3 |
| N2 | >300 |
| N3 | ND* |
| N4 | 245 |
| N5 | 271.9 |
| N6 | 283.4 |
| N7 | 258.8 |
| N8 | >300 |
| N9 | 294.5 |
| N10 | >300 |
| N11 | >300 |
| N12 | ND* |
| N13 | >300 |
| N14 | >300 |
| N15 | ND* |
| N16 | 211.5 |
| N17 | >300 |
| N18 | 275.1 |
| N19 | 288.5 |
| N20 | 282.5 |
| N21 | 295.3 |
| N22 | >300 |
| N23 | 183.2 |
| N24 | 208.3 |
| N25 | 288.6 |
| N26 | >300 |
| N27 | 199.9 |
| N36 | 189.8 |
| N37 | 168.1 |
| N38 | >300 |
| N39 | ND* |
| N40 | ND* |
| N41 | ND* |
| N42 | ND* |
| N43 | 178.1 |
| N44 | ND* |
| N45 | 188.1 |
| N46 | 164.7 |
| N47 | 154.6 |
| N48 | 139.6 |
| N49 | 153.0 |
| N50 | 112.9 |
| N51 | 256.8 |
| N52 | 286.9 |
| N53 | 276.8 |
| N54 | 283.5 |
| N55 | 281 |
| N56 | 223.3 |
| N57 | >300 |
| N58 | N/A |
| N59 | 260.3 |
| N60 | >300 |
| N61 | 298.7 |
| N62 | 226.5 |
| N63 | 266.1 |

*Not determined

LCMS

For LCMS-characterization of the compounds of the present invention, the following method was used.

General Procedure LCMS

All analyses were performed using an Agilent 6110 series LC/MSD quadrupole coupled to an Agilent 1290 series liquid chromatography (LC) system consisting of a binary pump with degasser, auto sampler, thermostated column compartment and diode array detector. The mass spectrometer (MS) was operated with an atmospheric pressure electro-spray ionization (API-ES) source in positive ion mode. The capillary voltage was set to 3000 V, the fragmentor voltage to 70 V and the quadrupole temperature was maintained at 100° C. The drying gas flow and temperature values were 12.0 L/min and 350° C. respectively. Nitrogen was used as the nebulizer gas, at a pressure of 35 psig. Data acquisition was performed with Agilent Chemstation software.

LCMS Method 1

In addition to the general procedure LCMS1: Analyses were carried out on a Phenomenex Kinetex C18 column (50 mm long×2.1 mm i.d.; 1.7 µm particles) at 60° C., with a flow rate of 1.5 mL/min. A gradient elution was performed from 90% (water+0.1% formic acid)/10% Acetonitrile to 10% (water+0.1% formic acid)/90% acetonitrile in 1.50 minutes, then the final mobile phase composition was held for an additional 0.40 min. The standard injection volume was 2 µL. Acquisition ranges were set to 254 nm for the UV-PDA detector and 80-800 m/z for the MS detector.

LCMS Method 2

In addition to the general procedure LCMS1: Analyses were carried out on a YMC pack ODS-AQ C18 column (50 mm long×4.6 mm i.d.; 3 μm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

TABLE 3

LCMS data

| COMPOUND NUMBER | MASS (MH)+ PEAK | RETENTION TIME (min) | LCMS METHOD |
|---|---|---|---|
| N1 | 336.2 | 2.127 | 2 |
| N2 | 353.0 | 1.952 | 2 |
| N3 | 353.1 | 1.957 | 2 |
| N4 | 353.1 | 1.095 | 2 |
| N5 | 367.0 | 1.880 | 2 |
| N6 | 353.2 | 1.527 | 2 |
| N7 | 354.2 | 1.873 | 2 |
| N8 | 354.1 | 2.098 | 2 |
| N9 | 354.1 | 1.977 | 2 |
| N10 | 367.2 | 2.127 | 2 |
| N11 | 368.1 | 2.114 | 2 |
| N12 | 372.2 | 2.140 | 2 |
| N13 | 368.2 | 1.987 | 2 |
| N14 | 368.2 | 2.040 | 2 |
| N15 | 368.2 | 2.073 | 2 |
| N16 | 367.2 | 2.047 | 2 |
| N17 | 368.2 | 2.147 | 2 |
| N18 | 368.2 | 2.220 | 2 |
| N19 | 382.2 | 2.193 | 2 |
| N20 | 369.2 | 1.987 | 2 |
| N21 | 354.2 | 1.96 | 2 |
| N22 | 370.2 | 2.113 | 2 |
| N23 | 383.0 | 2.061 | 2 |
| N24 | 397.1 | 2.127 | 2 |
| N25 | 384.1 | 2.532 | 2 |
| N26 | 388.1 | 2.250 | 2 |
| N27 | 409.2 | 2.147 | 2 |
| N28 | 369.0 | 1.996 | 2 |
| N29 | 423.2 | 2.307 | 2 |
| N30 | 409.2 | 2.080 | 2 |
| N31 | 423.2 | 2.267 | 2 |
| N32 | 411.2 | 2.345 | 2 |
| N33 | 354.1 | 1.922 | 2 |
| N34 | 368.2 | 2.0870 | 2 |
| N35 | 369.1 | 1.885 | 2 |
| N36 | 383.2 | 2.033 | 2 |
| N37 | 353.1 | 2.061 | 2 |
| N38 | 409.2 | 2.080 | 2 |
| N39 | 372.2 | 2.0270 | 2 |
| N40 | 368.2 | 2.0610 | 2 |
| N41 | 366.1 | 2.1220 | 2 |
| N42 | 423.1 | 2.201 | 2 |
| N43 | 409.1 | 2.176 | 2 |
| N44 | 423.1 | 2.272 | 2 |
| N45 | 383.1 | 2.092 | 2 |
| N46 | 397 | 2.150 | 2 |
| N47 | 423.0 | 2.369 | 2 |
| N48 | 424.9 | 2.241 | 2 |
| N49 | 437.0 | 2.355 | 2 |
| N50 | 411.0 | 1.979 | 2 |
| N51 | 410.5 | 2.31 | 2 |
| N52 | 353.40 | 1.398 | 2 |
| N53 | 382.44 | 2.004 | 2 |
| N54 | 382.44 | 2.073 | 2 |
| N55 | 396.47 | 2.181 | 2 |
| N56 | 424.53 | 2.282 | 2 |
| N57 | 353.40 | 2.056 | 2 |
| N58 | 396.47 | 2.191 | 2 |
| N59 | 367.43 | 1.433 | 2 |
| N60 | 339.38 | 1.924 | 2 |

TABLE 3-continued

LCMS data

| COMPOUND NUMBER | MASS (MH)+ PEAK | RETENTION TIME (min) | LCMS METHOD |
|---|---|---|---|
| N61 | 353.40 | 1.977 | 2 |
| N62 | 436.54 | 2.422 | 2 |
| N63 | 436.54 | 2.418 | 2 |

Kinase Activity Assay

The inhibition of LRRK2 kinase was assessed using LRRK2 recombinant protein in an in vitro peptide-based kinase assay.

Protocol

A radiometric protein kinase assay ($^{33}$PanQinase® Activity Assay) is used for measuring the kinase activity. All assays are performed in 96-well FlashPlates™ from Perkin Elmer in a 50 μl reaction volume. The reaction cocktail is pipetted in 4 steps in the following order:

10 μl of non-radioactive ATP solution (in H2O)
25 μl of assay buffer/[γ-$^{33}$P]-ATP mixture
5 μl of test sample in 10% DMSO
10 μl of enzyme/substrate mixture The assay for LRRK2 contains 70 mM HEPES-NaOH pH 7.5, 3 mM MgCl$_2$, 3 mM MnCl$_2$, 3 μM Na-orthovanadate, 1.2 mM DTT, 50 μg/ml PEG20000, ATP (0.3 μM), [γ-$^{33}$P]-ATP (approx. 4×1005 cpm per well), protein kinase LRRK2 (7.3 nM) and substrate (GSK3(14-27), 1.0 μg/50 μl).

The kinase is obtained from Invitrogen Corporation.

The reaction cocktails were incubated at 30° C. for 60 minutes. The reaction was stopped with 50 μl of 2% (v/v) H$_3$PO$_4$, plates were aspirated and washed two times with 200 μl 0.9% (w/v) NaCl. Incorporation of $^{33}$Pi (counting of "cpm") was determined with a microplate scintillation counter.

Compounds

The compounds are dissolved to 10 mM in DMSO. Where needed, solutions are sonicated in a bath sonicator.

Table 2 provides the pIC$_{50}$ values of the compounds according to the invention, obtained using the above mentioned kinase assay.

TABLE 4

| Compound No | IC$_{50}$ for LRRK2 |
|---|---|
| N1 | +++ |
| N2 | +++ |
| N3 | +++ |
| N4 | +++ |
| N5 | +++ |
| N6 | +++ |
| N7 | +++ |
| N8 | +++ |
| N9 | ++ |
| N10 | +++ |
| N11 | +++ |
| N12 | +++ |
| N13 | ++ |
| N14 | +++ |
| N15 | +++ |
| N16 | +++ |
| N17 | +++ |
| N18 | +++ |
| N19 | +++ |
| N20 | +++ |
| N21 | +++ |
| N22 | +++ |
| N23 | +++ |
| N24 | +++ |

TABLE 4-continued

| Compound No | IC$_{50}$ for LRRK2 |
| --- | --- |
| N25 | +++ |
| N26 | +++ |
| N27 | +++ |
| N28 | +++ |
| N29 | +++ |
| N30 | +++ |
| N31 | +++ |
| N32 | +++ |
| N33 | +++ |
| N34 | +++ |
| N35 | +++ |
| N36 | +++ |
| N37 | +++ |
| N38 | +++ |
| N39 | ++ |
| N40 | +++ |
| N41 | +++ |
| N42 | +++ |
| N43 | +++ |
| N44 | +++ |
| N45 | +++ |
| N46 | +++ |
| N47 | +++ |
| N48 | +++ |
| N49 | +++ |
| N50 | +++ |
| N51 | +++ |
| N52 | +++ |
| N53 | +++ |
| N54 | +++ |
| N55 | +++ |
| N56 | ++ |
| N57 | +++ |
| N58 | +++ |
| N59 | +++ |
| N60 | +++ |
| N61 | +++ |
| N62 | +++ |
| N63 | +++ |

++ indicates an IC50 of between 100 nM and 1 μM, and +++ indicates an IC50 < 100 nM

The invention claimed is:

1. A compound of Formula I or a stereoisomer, tautomer, racemic, salt, hydrate, N-oxide form, or solvate thereof,

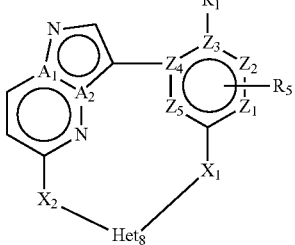

I

Wherein:
$R_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;

$R_5$ is attached to $Z_1$ or $Z_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;

$R_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;

$R_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;

$R_4$ and $R_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$, $R_{35}$ and $R_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;

$R_{27}$ and $R_{28}$ are each independently selected from —H, —C$_{1-6}$alkyl, —C$_{3-6}$cycloalkyl and -Het$_2$:

$R_{37}$ and $R_{38}$ are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;

$X_1$ is selected from —C$_{1-6}$alkyl-, —O—C$_{1-6}$alkyl-, —S—C$_{1-6}$alkyl-, —C$_{1-6}$alkyl-, —NR$_3$-C$_{1-6}$alkyl-, —NR$_3$—C$_{1-6}$alkyl-, —NR$_3$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{33}$R$_{34}$;

$X_2$ is selected from —C$_{1-6}$alkyl-, —O—C$_{1-6}$alkyl-, —S—C$_{1-6}$alkyl-, —C$_{1-6}$alkyl-NR$_2$—C$_{1-6}$alkyl-, —NR$_2$—C$_{1-6}$alkyl-, —NR$_2$—, and —O—; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;
  wherein when R$_1$ is —H, then at least one heteroatom of Het$_8$ is attached to X$_2$;
Z$_1$, Z$_2$, Z$_3$, Z$_4$ and Z$_5$ are each independently selected from C and N; and
A$_1$ and A$_2$ are each independently selected from C and N.

2. A compound as defined in claim 1, wherein:
R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;
R$_5$ is attached to Z$_1$ or Z$_5$ and is selected from —H, -halo, —OH, —C$_{1-6}$alkyl, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;
R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;
R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;
R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —O—C$_{3-6}$cycloalkyl, —Ar$_4$ and -Het$_4$;
R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$ R$_{34}$, R$_{35}$ and R$_{36}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_6$ and -Het$_6$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_6$, —Ar$_6$ and —NR$_{37}$R$_{38}$;
R$_{27}$ and R$_{28}$, are each independently selected from —H, —C$_{1-6}$alkyl, —C$_{3-6}$cycloalkyl and -Het$_2$;
R$_{37}$ and R$_{38}$, are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_7$ and -Het$_7$;
X$_1$ is selected from —C$_{1-6}$alkyl-, —O—C$_{1-6}$alkyl-, —S—C$_{1-6}$alkyl-, —C$_{1-6}$alkyl-NR$_3$—C$_{1-6}$alkyl-, —NR$_3$—C$_{1-6}$alkyl-, —NR$_3$— and —O—;
X$_2$ is selected from —C$_{1-6}$alkyl-, —O—C$_{1-6}$alkyl-, —S—C$_{1-6}$alkyl-, —C$_{1-6}$alkyl-NR$_2$—C$_{1-6}$alkyl-, —NR$_2$—C$_{1-6}$ alkyl-, —NR$_2$—, and —O—;
Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;
Het$_1$, Het$_2$, Het$_4$, Het$_5$, Het$_6$, and Het$_7$ are each independently a 3- to 10-membered heterocycle having from 1 to 3 heteroatoms selected from O, N and S; each of said Het$_1$, Het$_2$, Het$_4$, Het$_5$, Het$_6$, and Het$_7$ is optionally and independently substituted with from 1 to 3 substituents selected from -halo, —OH, —C$_{1-6}$alkyl, —O—C$_{1-6}$alkyl, —S—C$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;
Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —C$_{1-6}$alkyl, —C$_{1-6}$alkylene, —C$_{1-6}$alkyl-C$_{3-6}$cycloalkyl, —C$_{3-6}$cycloalkyl, —O—C$_{1-6}$alkyl, —S—C$_{1-6}$alkyl, =O, —(C=O)—C$_{1-6}$alkyl, —C$_{1-6}$alkyl-O—C$_{1-6}$alkyl and —NR$_{21}$R$_{22}$; wherein each of said —C$_{1-6}$alkyl is optionally and independently substituted with from 1 to 3 -halo;
  wherein when R$_1$ is —H then at least one heteroatom of Het$_8$ is attached to X$_2$
Z$_1$, Z$_2$, Z$_3$, Z$_4$ and Z$_5$ are each independently selected from C and N; and
A$_1$ and A$_2$ are each independently selected from C and N.

3. A compound as defined in claim 1, wherein:
R$_1$ is selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —O—C$_{3-6}$cycloalkyl, —Ar$_1$ and -Het$_1$; wherein each of said —C$_{1-6}$alkyl is optionally and independently substituted with from 1 to 3 substituents selected from -halo, —OR$_{35}$, —NR$_{11}$R$_{12}$, —O—C$_{1-6}$alkyl, and —S—C$_{1-6}$alkyl;
R$_5$ is attached to Z$_1$ or Z$_5$ and is selected from —H, -halo, —OH, —C$_{1-6}$alkyl, —O—C$_{1-6}$alkyl, —S—C$_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —C$_{3-6}$cycloalkyl, —O—C$_{3-6}$cycloalkyl, —Ar$_5$ and -Het$_5$; wherein each of said —C$_{1-6}$alkyl is optionally and independently substituted with from 1 to 3 substituents selected from -halo, —OR$_{36}$, —NR$_{23}$R$_{24}$, —O—C$_{1-6}$alkyl, and —S—C$_{1-6}$alkyl;
R$_2$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{27}$, and —NR$_{13}$R$_{14}$;
R$_3$ is selected from —H, -halo, —OH, —C$_{1-6}$alkyl, and —C$_{3-6}$cycloalkyl; wherein each of said —C$_{1-6}$alkyl is optionally and independently substituted with from 1 to 3 substituents selected from -halo, —OR$_{28}$, and —NR$_{15}$R$_{16}$;
R$_4$ and R$_8$ are each independently selected from -halo, —OH, —C$_{1-6}$alkyl, —O—C$_{1-6}$alkyl, —S—C$_{1-6}$alkyl, —NR$_{17}$R$_{18}$, —O—C$_{3-6}$cycloalkyl, —C$_{3-6}$cycloalkyl, —Ar$_4$ and -Het$_4$;

233

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$, $R_{34}$ $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_2$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a bivalent 3- to 10-membered heterocycle having from 1 to 3 heteroatoms selected from O, N and S; wherein at least one of said heteroatoms is attached to $X_1$ or $X_2$;
wherein when $R_1$ is —H then at least one heteroatom of $Het_8$ is attached to $X_2$; and
wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and $A_1$ and $A_2$ are each independently selected from C and N.

4. A compound of Formula Ia or a stereoisomer, tautomer, racemic, salt, hydrate, N-oxide form, or solvate thereof,

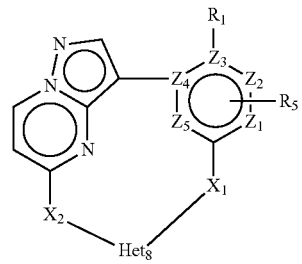

Ia

Wherein:

$R_1$ is selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —O—$C_{3-6}$cycloalkyl, —$Ar_1$ and -$Het_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)—$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_4$ and $R_8$ are each independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —O—$C_{3-6}$cycloalkyl, —$Ar_4$ and -$Het_4$;

$R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{31}$, $R_{32}$, $R_{33}$ $R_{34}$, $R_{35}$ and $R_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —NR—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-NR$_3$—$C_{1-6}$alkyl-, —NR$_2$—$C_{1-6}$alkyl-, —NR$_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —NR$_{31}$R$_{32}$;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —NR$_{21}$R$_{22}$; wherein each of said —$C_{1-6}$alkyl is optionally and independently substituted with from 1 to 3 -halo;
  wherein when R$_1$ is —H then at least one heteroatom of Het$_8$ is attached to X$_2$; and $Z_1$, $Z_2$, $Z_3$, $Z_4$ and $Z_5$ are each independently selected from C and N.

5. A compound as defined in claim 4, wherein:
R$_1$ is selected from —H, -halo, —OH, —$C_{1-6}$alkyl, —O—$C_{1-6}$alkyl, —S—$C_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —$C_{3-6}$cycloalkyl, —O—$C_{3-6}$cycloalkyl, —Ar$_1$ and -Het$_1$; wherein each of said —$C_{1-6}$alkyl is optionally and independently substituted with from 1 to 3 substituents selected from -halo, —OR$_{35}$, —NR$_{11}$R$_{12}$, —O—$C_{1-6}$alkyl, and —S—$C_{1-6}$alkyl;

R$_5$ is attached to Z$_1$ or Z$_5$ and is selected from —H, -halo, —OH, —$C_{1-6}$alkyl, —O—$C_{1-6}$alkyl, —S—$C_{1-6}$alkyl, —NR$_6$R$_7$, —(C=O)—R$_8$, —(C=S)—R$_8$, —SO$_2$—R$_8$, —CN, —NR$_6$—SO$_2$—R$_8$, —$C_{3-6}$cycloalkyl, —O—$C_{3-6}$cycloalkyl, —Ar$_5$ and -Het$_5$; wherein each of said —$C_{1-6}$alkyl is optionally and independently substituted with from 1 to 3 substituents selected from -halo, —OR$_{36}$, —NR$_{23}$R$_{24}$, —O—$C_{1-6}$alkyl, and —S—$C_{1-6}$alkyl;

R$_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —OR$_{27}$, and —NR$_{13}$R$_{14}$;

R$_3$ is selected from —H, -halo, —OH, —$C_{1-6}$alkyl, —$C_{3-6}$cycloalkyl; wherein each of said —$C_{1-6}$alkyl is optionally and independently substituted with from 1 to 3 substituents selected from -halo, —OR$_{28}$, and —NR$_{15}$R$_{16}$;

R$_4$ and R$_8$ are each independently selected from -halo, —OH, —$C_{1-6}$alkyl, —O—$C_{1-6}$alkyl, —S—$C_{1-6}$alkyl, —NR$_{17}$R$_{18}$, —$C_{3-6}$cycloalkyl, —O—$C_{3-6}$cycloalkyl, —Ar$_4$ and -Het$_4$;

R$_6$, R$_7$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{31}$, R$_{32}$, R$_{33}$, R$_{34}$, R$_{35}$ and R$_{36}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —Ar$_6$ and -Het$_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -Het$_6$, —Ar$_6$ and —NR$_{37}$R$_{38}$;

R$_{27}$ and R$_{28}$, are each independently selected from —H, —$C_{1-6}$alkyl, —$C_{3-6}$cycloalkyl and -Het$_2$:

R$_{37}$ and R$_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —Ar$_7$ and -Het$_7$;

X$_1$ is selected from —$C_{1-6}$alkyl-, —O—$C_{1-6}$alkyl-, —S—$C_{1-6}$alkyl-, —$C_{1-6}$alkyl-NR$_3$—$C_{1-6}$alkyl-, —NR$_3$—$C_{1-6}$alkyl-, —NR$_3$— and —O—;

X$_2$ is selected from —$C_{1-6}$alkyl-, —O—$C_{1-6}$alkyl-, —S—$C_{1-6}$alkyl-, —$C_{1-6}$alkyl-NR$_2$—$C_{1-6}$alkyl-, —NR$_2$—$C_{1-6}$ alkyl-, —NR$_2$—, and —O—;

Ar$_1$, Ar$_4$, Ar$_5$, Ar$_6$, and Ar$_7$ are each independently a 5- to 10-membered aromatic cycle optionally comprising 1 to 3 heteroatoms selected from O, N and S; each of said Ar$_1$, Ar$_4$, Ar$_5$, Ar$_6$, and Ar$_7$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3 -halo;

Het$_1$, Het$_2$, Het$_4$, Het$_5$, Het$_6$, and Het$_7$ are each independently a 3- to 10-membered heterocycle having from 1 to 3 heteroatoms selected from O, N and S; wherein each of said Het$_1$, Het$_2$, Het$_4$, Het$_5$, Het$_6$, and Het$_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Het$_8$ is a 3- to 10-membered heterocycle having from 1 to 3 heteroatoms selected from O, N and S;
  wherein said Het$_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —NR$_{21}$R$_{22}$; wherein each of said —$C_{1-6}$alkyl is optionally and independently substituted with from 1 to 3 -halo;
  wherein when R$_1$ is —H then at least one heteroatom of Het$_8$ is attached to X$_2$; and $Z_1$, $Z_2$, $Z_3$, $Z_4$ and $Z_5$ are each independently selected from C and N.

6. A compound as defined in claim 4 wherein:
R$_1$ is selected from —H, -halo, —OH, —$C_{1-6}$alkyl, —O—$C_{1-6}$alkyl, —S—$C_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —$C_{3-6}$cycloalkyl, —O—$C_{3-6}$cycloalkyl, —Ar$_1$ and -Het$_1$; wherein each of said —$C_{1-6}$alkyl is optionally and independently substituted with from 1 to 3 substituents selected from -halo, —$OR_{35}$, —$NR_{11}R_{12}$, —O—$C_{1-6}$alkyl, and —S—$C_{1-6}$alkyl;

$R_5$ is attached to $Z_1$ or $Z_5$ and is selected from —H, -halo, —OH, —$C_{1-6}$alkyl, —O—$C_{1-6}$alkyl, —S—$C_{1-6}$alkyl, —$NR_6R_7$, —(C=O)—$R_8$, —(C=S)-$R_8$, —$SO_2$—$R_8$, —CN, —$NR_6$—$SO_2$—$R_8$, —$C_{3-6}$cycloalkyl, —O—$C_{3-6}$cycloalkyl, —$Ar_5$ and -$Het_5$; wherein each of said —$C_{1-6}$alkyl is optionally and independently substituted with from 1 to 3 substituents selected from -halo, —$OR_{36}$, —$NR_{23}R_{24}$, —O—$C_{1-6}$alkyl, and —S—$C_{1-6}$alkyl;

$R_2$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{27}$, and —$NR_{13}R_{14}$;

$R_3$ is selected from —H, -halo, —OH, —$C_{1-6}$alkyl, and —$C_{3-6}$cycloalkyl; wherein each of said —$C_{1-6}$alkyl is optionally and independently substituted with from 1 to 3 substituents selected from -halo, —$OR_{28}$, and —$NR_{15}R_{16}$;

$R_6$, $R_7$, $R_9$, $R_{10}$, $R_{11}$, $R_{12}$, $R_{13}$, $R_{14}$, $R_{15}$, $R_{16}$, $R_{19}$, $R_{20}$, $R_{21}$, $R_{22}$, $R_{31}$, $R_{32}$, $R_{33}$ and $R_{34}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_6$ and -$Het_6$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_6$, —$Ar_6$ and —$NR_{37}R_{38}$;

$R_{27}$ and $R_{28}$, are each independently selected from —H, —$C_{1-6}$alkyl, —$C_{3-6}$cycloalkyl and -$Het_2$:

$R_{37}$ and $R_{38}$, are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_7$ and -$Het_7$;

$X_1$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_3$—$C_{1-6}$alkyl-, —$NR_3$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{33}R_{34}$;

$X_2$ is selected from —$C_{1-6}$alkyl-, —O—$C_{1-6}$alkyl-, —S—$C_{1-6}$alkyl-, —$C_{1-6}$alkyl-$NR_3$—$C_{1-6}$alkyl-, —$NR_2$—$C_{1-6}$alkyl-, —$NR_2$—, and —O—; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{31}R_{32}$;

$Ar_1$, $Ar_4$, $Ar_5$, $Ar_6$, and $Ar_7$ are each independently a 5- to 10-membered aromatic cycle optionally comprising 1 to 3 heteroatoms selected from O, N and S; each of said $Ar_1$, $Ar_4$, $Ar_5$, $Ar_6$, and $Ar_7$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_4$, $Het_5$, $Het_6$, and $Het_7$ are each independently a 3- to 10-membered heterocycle having from 1 to 3 heteroatoms selected from O, N and S; wherein each of said $Het_1$, $Het_2$, $Het_4$, $Het_5$, $Het_6$, and $Het_7$ is optionally and independently substituted with from 1 to 3 substituents selected from -halo, —OH, —$C_{1-6}$alkyl, —O—$C_{1-6}$alkyl, —S—$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Het_8$ is a 3- to 10-membered heterocycle having from 1 to 3 heteroatoms selected from O, N and S; wherein at least one of said heteroatoms is attached to $X_1$ or $X_2$;

wherein when $R_1$ is —H, then at least one heteroatom of $Het_8$ is attached to $X_2$; and wherein said $Het_8$ is optionally and independently substituted with from 1 to 3 substituents selected from -halo, —OH, —$C_{1-6}$alkyl, —$C_{1-6}$alkylene, —$C_{1-6}$alkyl-$C_{3-6}$cycloalkyl, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl-O—$C_{1-6}$alkyl and —$NR_{21}R_{22}$; wherein each of said —$C_{1-6}$alkyl is optionally and independently substituted with from 1 to 3 -halo; and $Z_1$, $Z_2$, $Z_3$, $Z_4$ and $Z_5$ are each independently selected from C and N.

7. A compound of Formula I or a stereoisomer, tautomer, racemic, salt, hydrate, N-oxide form, or solvate thereof as defined in claim 1, wherein each of said $Z_1$, $Z_2$, $Z_3$, $Z_4$ and $Z_5$ is C.

8. A compound as defined in claim 1 wherein:

$A_1$ and $A_2$ are each independently selected from C and N;

$R_1$ is selected from —H and -halo;

$R_5$ is selected from —H, -halo and —$C_{1-6}$alkyl;

$R_2$ is selected from —H and —$C_{1-6}$alkyl;

$R_3$ is selected from —H and —$C_{1-6}$alkyl;

$X_1$ is selected from —O—$C_{1-6}$alkyl-, —$NR_3$—$C_{1-6}$alkyl-, —$NR_3$—, and —O—;

$X_2$ is selected from —$C_{1-6}$alkyl-, —O—$C_{1-6}$alkyl-, —$NR_2$—$C_{1-6}$alkyl-, —$NR_2$—, and —O—;

$Het_8$ is a 3- to 10-membered heterocycle; wherein said $Het_8$ is optionally substituted with 1 to 3 substituents selected from -halo, —OH, —$C_{1-6}$alkyl, —$C_{1-6}$alkylene, —$C_{3-6}$cycloalkyl, —$C_{1-6}$alkyl-$C_{3-6}$cycloalkyl, —(C=O)—$C_{1-6}$alkyl, and —(C=O)—$C_{3-6}$cycloalkyl; and $Z_1$, $Z_2$, $Z_3$, $Z_4$ and $Z_5$ are each C.

9. A compound as defined in claim 8 wherein:

$A_1$ and $A_2$ are each independently selected from C and N;

$R_1$ is selected from —H and -halo;

$R_5$ is selected from —H, -halo and —$C_{1-6}$alkyl;

$R_2$ is selected from —H and —$C_{1-6}$alkyl;

$R_3$ is selected from —H and —$C_{1-6}$alkyl;

$X_1$ is selected from —O—$C_{1-6}$alkyl-, —$NR_3$—$C_{1-6}$alkyl-, —$NR_3$—, and —O—;

$X_2$ is selected from —O—$C_{1-6}$alkyl-, —$NR_2$—$C_{1-6}$alkyl-, —$NR_2$—, and —O—;

$Het_8$ is a 3- to 10-membered heterocycle; wherein said $Het_8$ is optionally substituted with 1 to 3 substituents selected from -halo, —OH, —$C_{1-6}$alkyl, —$C_{1-6}$alkylene, —$C_{3-6}$cycloalkyl, and —$C_{1-6}$alkyl$C_{3-6}$cycloalkyl; and $Z_1$, $Z_2$, $Z_3$, $Z_4$ and $Z_5$ are each C.

10. A compound as defined in claim 8 wherein $A_1$ is N and $A_2$ is C.

11. A compound of Formula Ia or a stereoisomer, tautomer, racemic, salt, hydrate, N-oxide form, or solvate thereof,

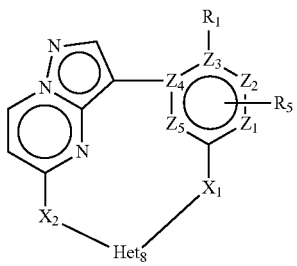

Ia

Wherein:
$R_1$ is selected from —H and -halo;
$R_5$ is attached to $Z_1$ and is selected from —H and —$C_{1-6}$alkyl;
$R_2$ is selected from —H and —$C_{1-6}$alkyl;
$R_3$ is selected from —H and —$C_{1-6}$alkyl;
$X_1$ is selected from —O—$C_{1-6}$alkyl-, —$NR_3$—$C_{1-6}$alkyl-, —$NR_3$—, and —O—;
$X_2$ is selected from —O—$C_{1-6}$alkyl-, —$NR_2$—$C_{1-6}$alkyl-, —$NR_2$—, and —O—;
$Het_8$ is a 3- to 10-membered N-containing heterocycle; wherein said $Het_8$ is optionally substituted with 1 to 3 substituents selected from -halo, —OH, —$C_{1-6}$alkyl, —$C_{1-6}$alkylene, —$C_{3-6}$cycloalkyl, —O—$C_{1-6}$alkyl, —S—$C_{1-6}$alkyl, =O, —(C=O)—$C_{1-6}$alkyl, —$C_{1-6}$alkyl—O—$C_{1-6}$alkyl and —$NR_{21}R_{22}$; and
$Z_1$, $Z_2$, $Z_3$, $Z_4$ and $Z_5$ are each C.

12. A compound selected from:

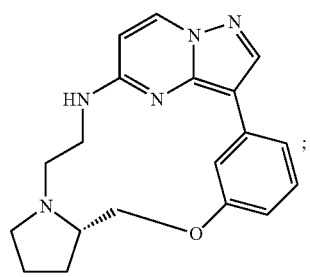

Compound N1

Example N1

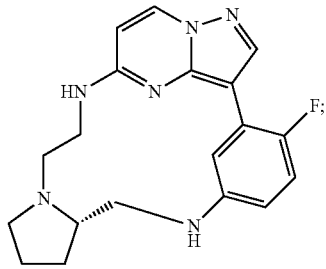

Compound N2

Example N2

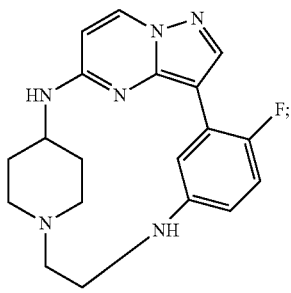

Compound N3

Example N3

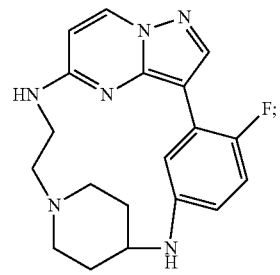

Compound N4

Example N4

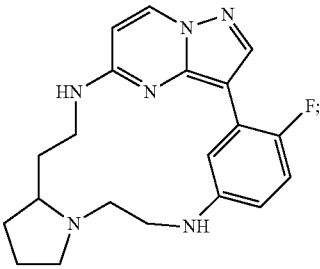

Compound N5

Example N5

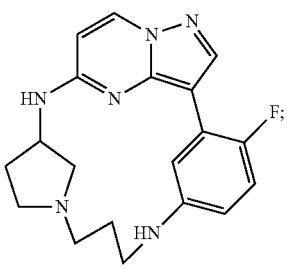

Compound N6

Example N6

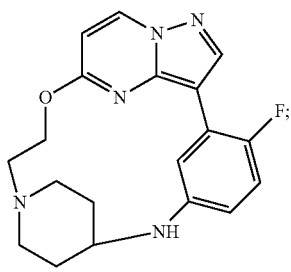

Compound N7

Example N7

Compound N8
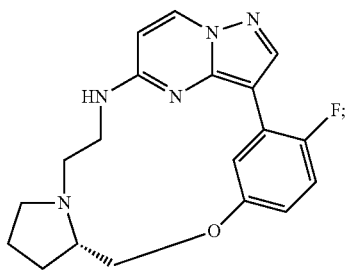
Example N8
Compound N9
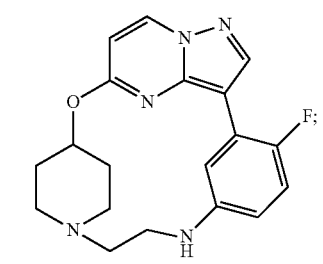
Example N9
Compound N10
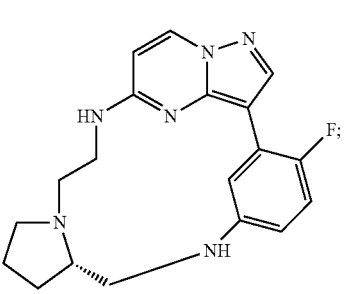
Example N10
Compound N11
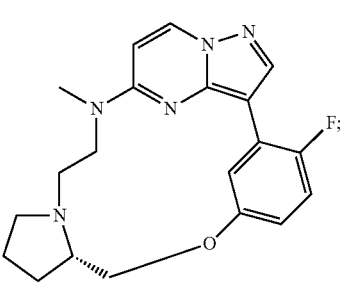
Example N11
Compound N12
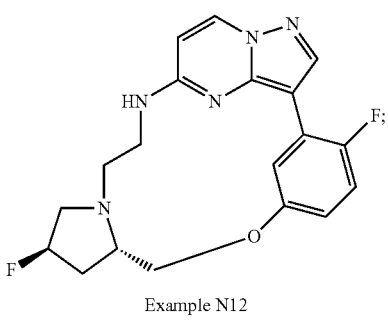
Example N12
Compound N13
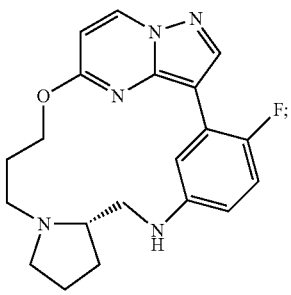
Example N13
Compound N14
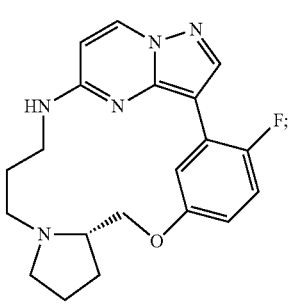
Example N14
Compound N15
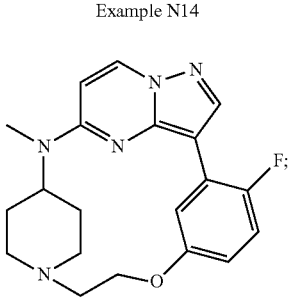
Example N15
Compound N16
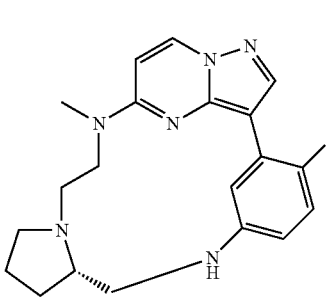
Example N16
Compound N17
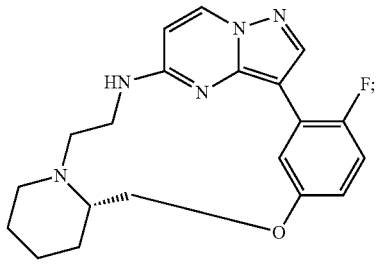
Example N17

Compound N18
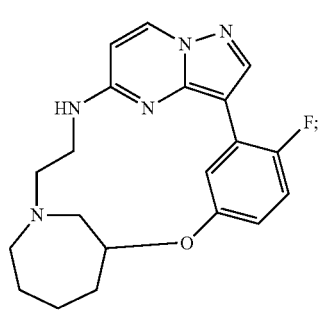
Example N18
Compound N19
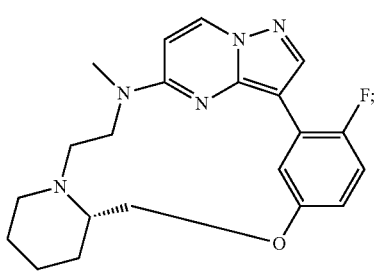
Example N19
Compound N20
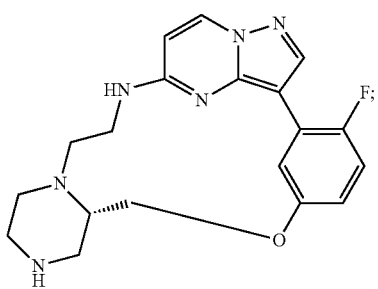
Example N20
Compound N21
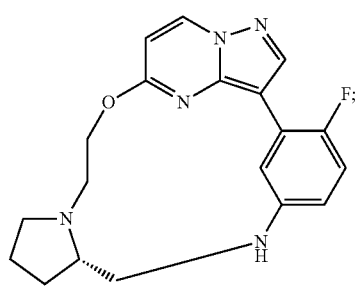
Example N21
Compound N22
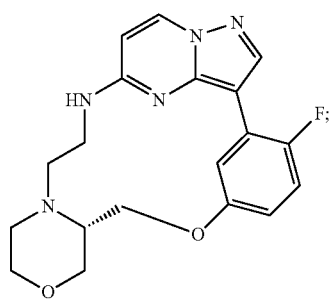
Example N22
Compound N23
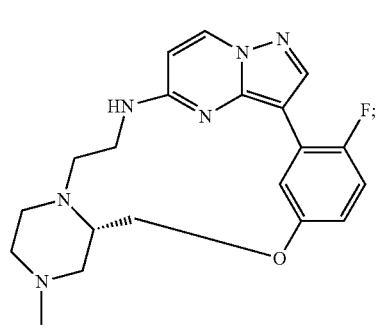
Example N23
Compound N24
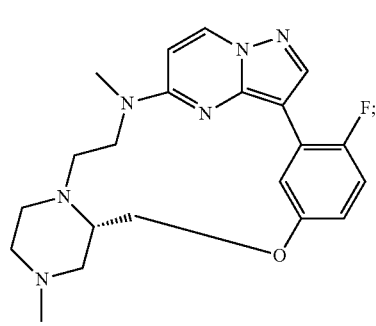
Example N24
Compound N25
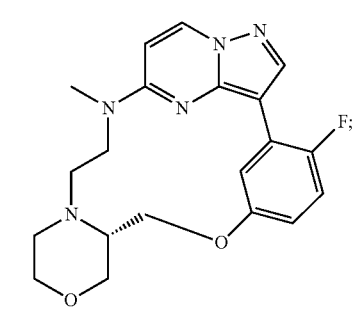
Example N25
Compound N26
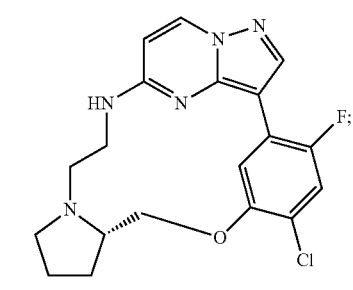
Example N26

Compound N27
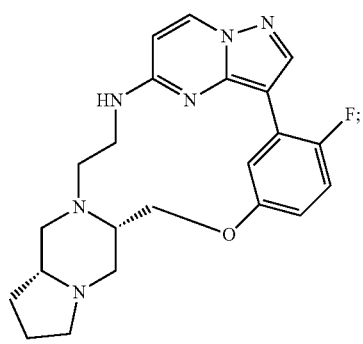
Example N27
Compound N28
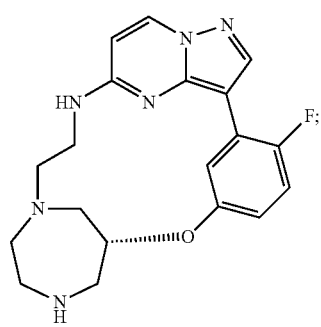
Example N28
Compound N29
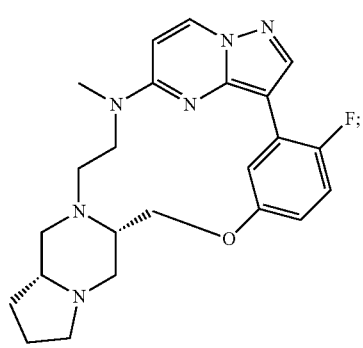
Example N29
Compound N30
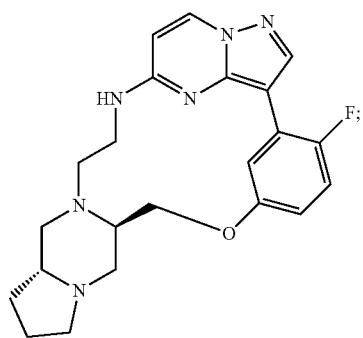
Example N30
Compound N31
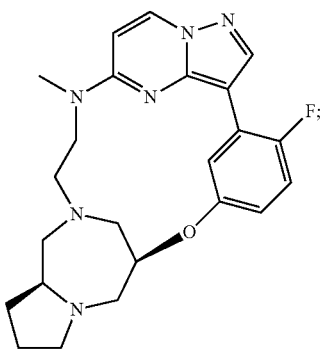
Example N31
Compound N32
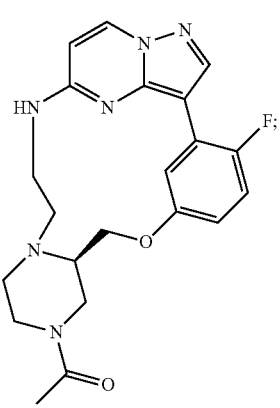
Example N32
Compound N33
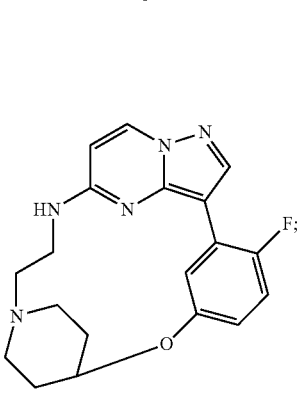
Example N33
Compound N34
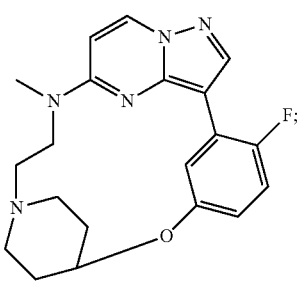
Example N34

247
-continued
Compound N35
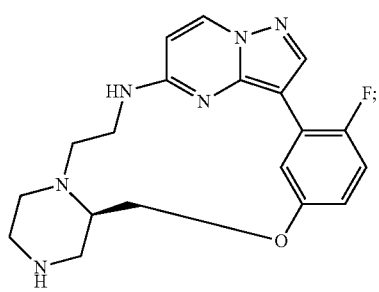
Example N35
Compound N36
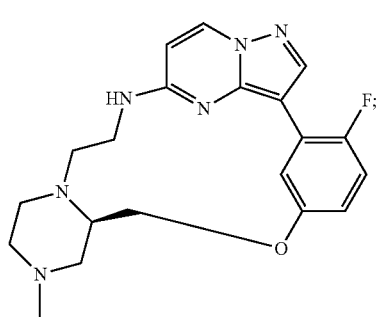
Example N36
Compound N37
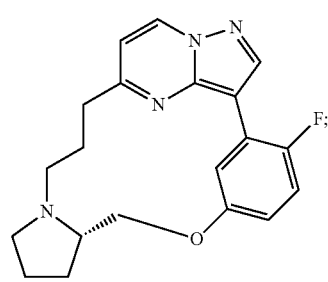
Example N37
Compound N38
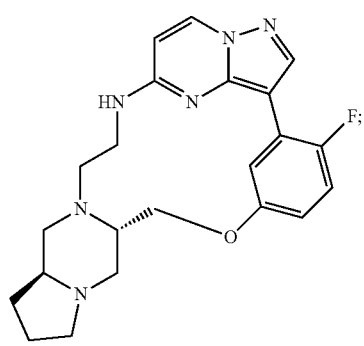
Example N38
248
-continued
Compound N39
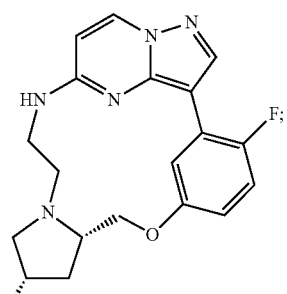
Example N39
Compound N40
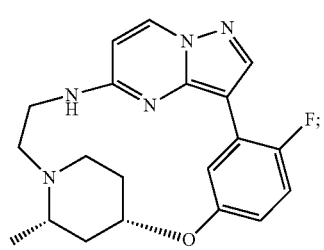
Example N40
Compound N41
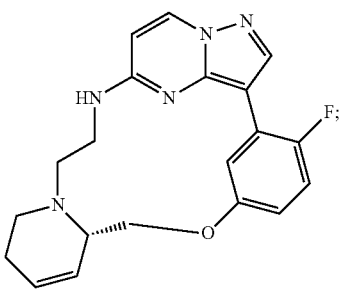
Example N41
Compound N42
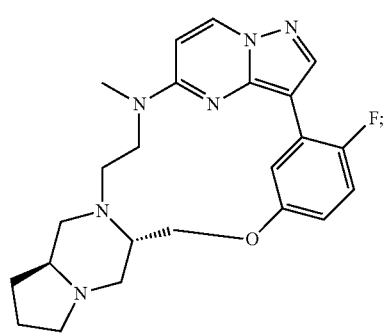
Example N42

Compound N43
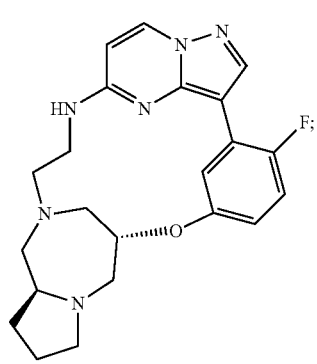
Example N43
Compound N44
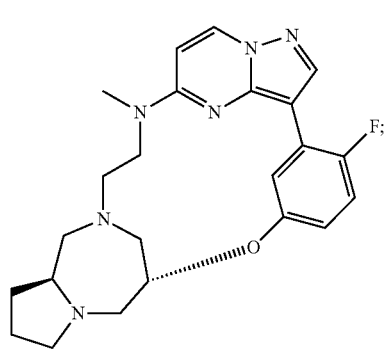
Example N44
Compound N45
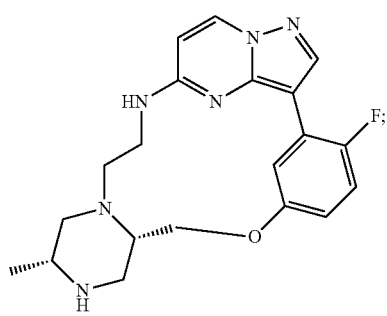
Example N45
Compound N46
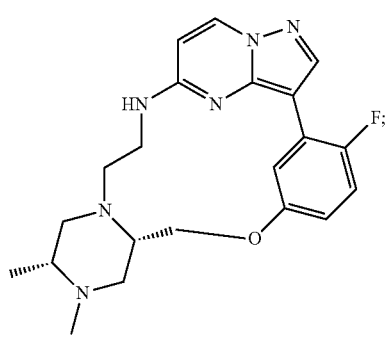
Example N46
Compound N47
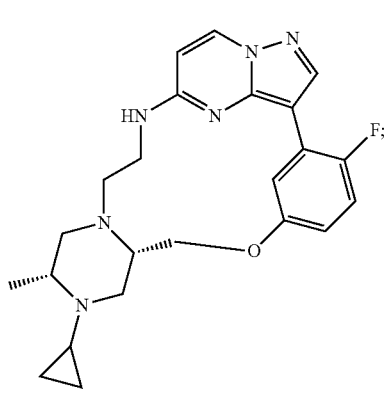
Example N47
Compound N48
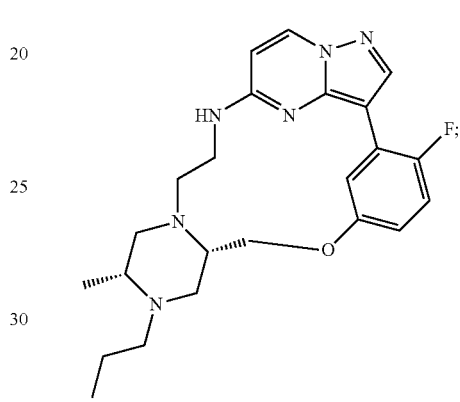
Example N48
Compound N49
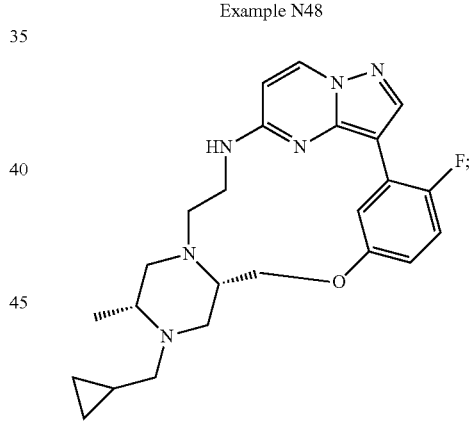
Example N49
Compound N50
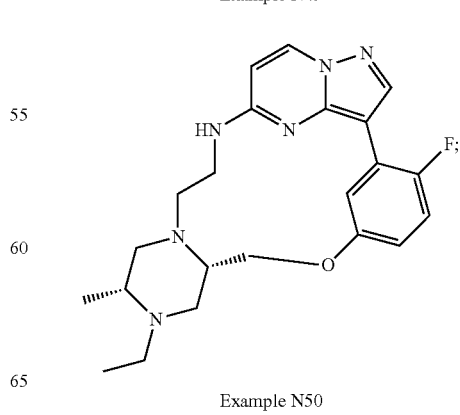
Example N50

Compound N51
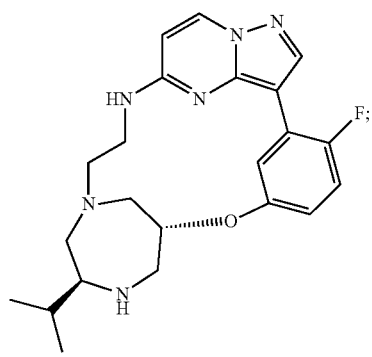
Example N51
Compound N52
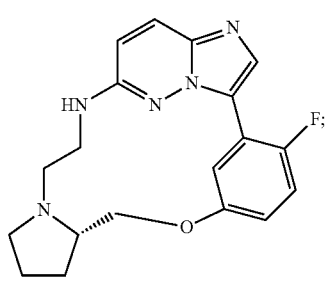
Example N52
Compound N53
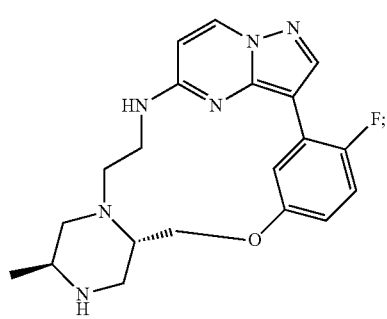
Example N53
Compound N54
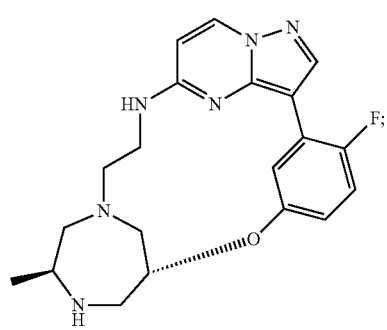
Example N54
Compound N55
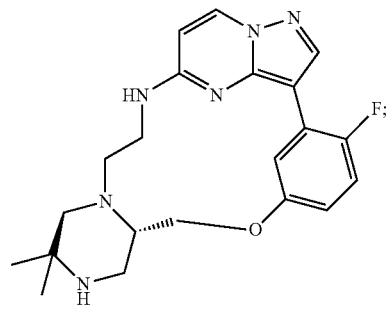
Example N55
Compound N56
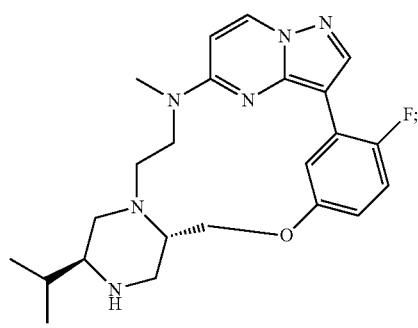
Example N56
Compound N57
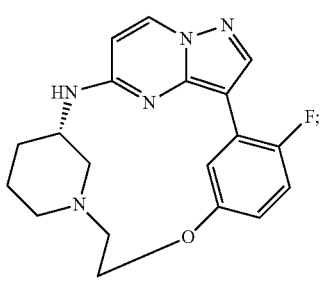
Example N57
Compound N58
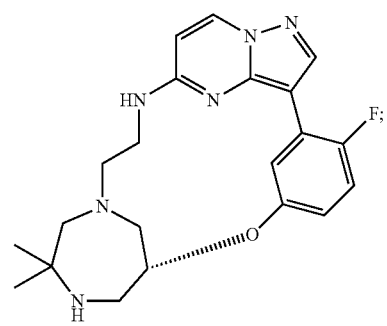
Example N58

Compound N59
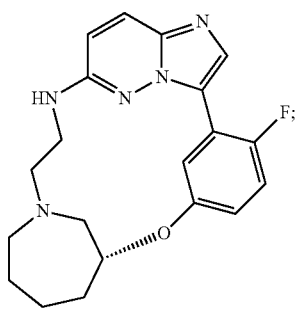
Example N59
Compound N60
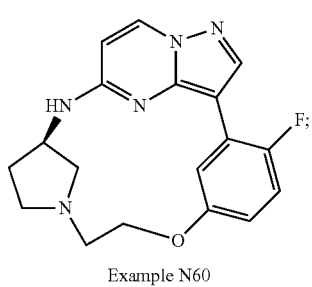
Example N60
Compound N61
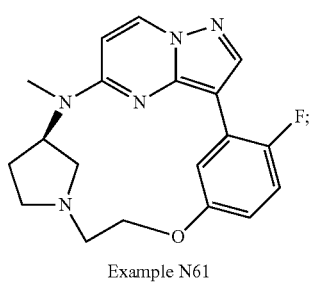
Example N61
Compound N62
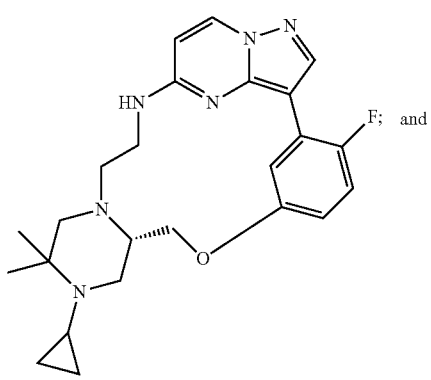
Example N62
Compound N63
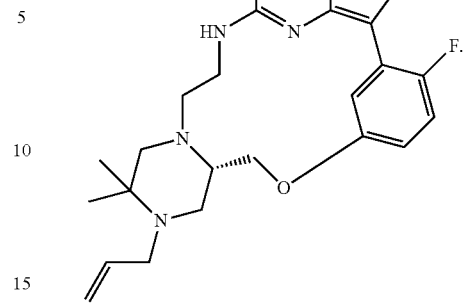
Example N63
13. A compound as defined in claim 11 which is selected from:
Compound N46
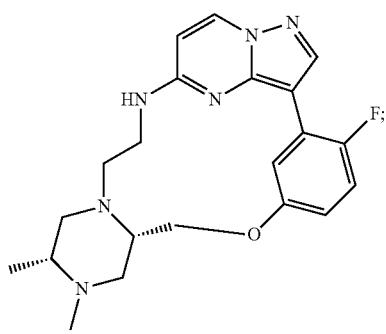
Example N46
Compound N49
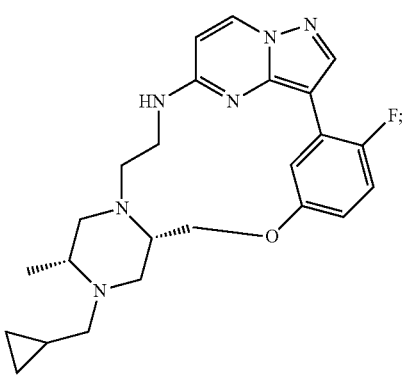
Example N49
Compound N47
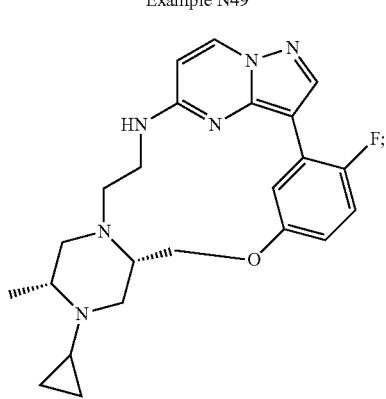
Example N47

Compound N27
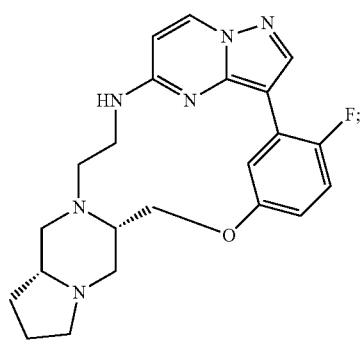
Example N27
Compound N48
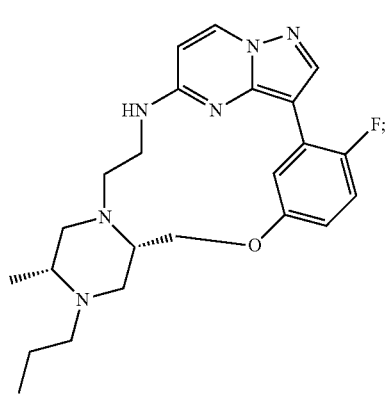
Example N48
Compound N43
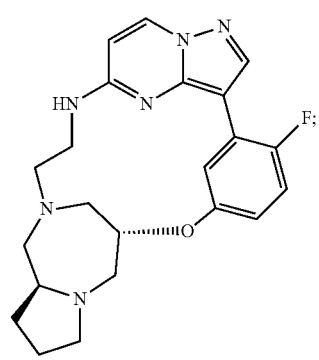
Example N43
Compound N50
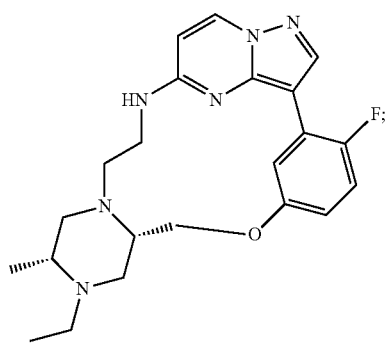
Example N50
Compound N44
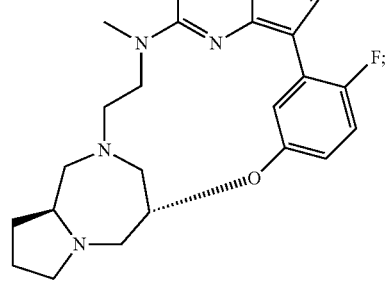
Example N44
Compound N45
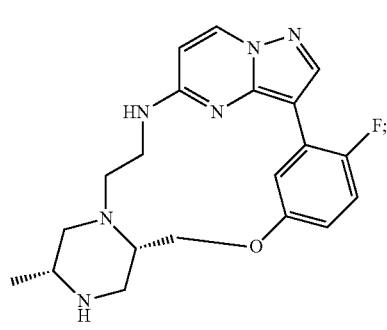
Example N45
Compound N59
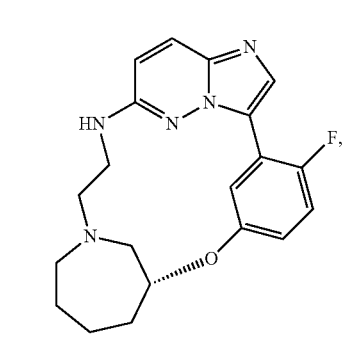
Example N59
Compound N60
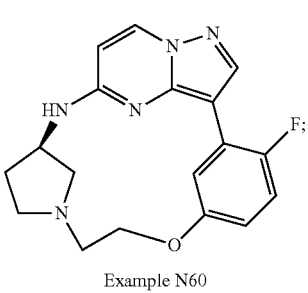
Example N60

Compound N62
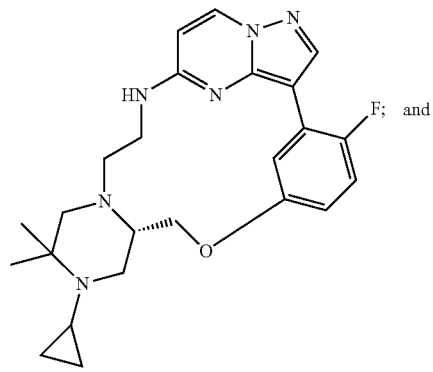
Example N62
Compound N63
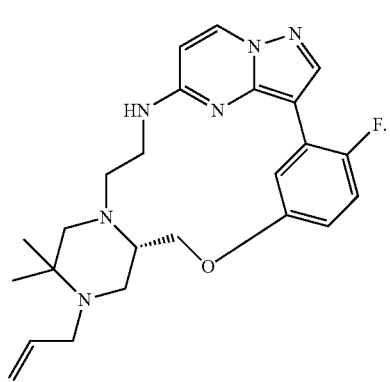
Example N63
14. A compound as defined in claim 13 which is selected from:
Compound N27
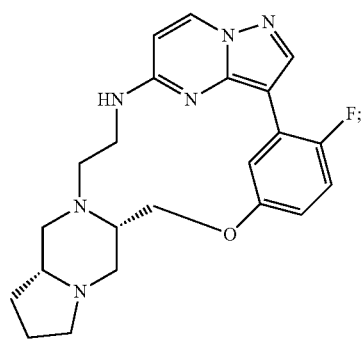
Example N27
Compound N43
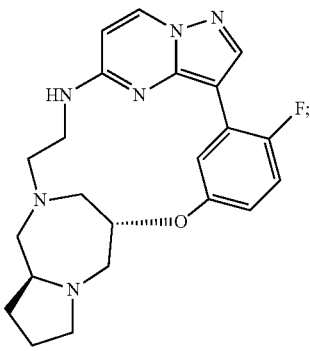
Example N43
Compound N44
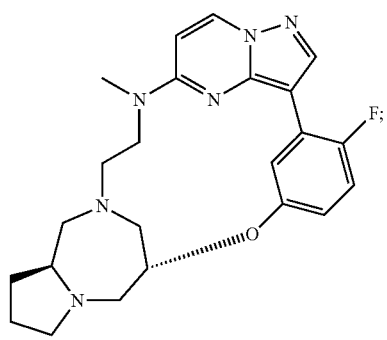
Example N44
Compound N45
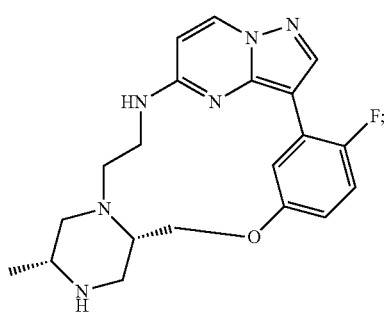
Example N45
Compound N59
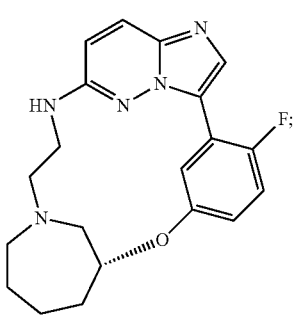
Example N59

-continued

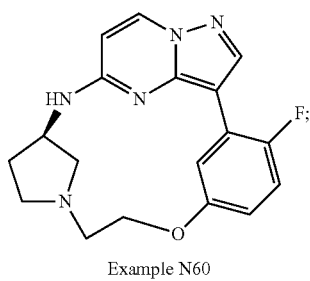

Compound N60

Example N60

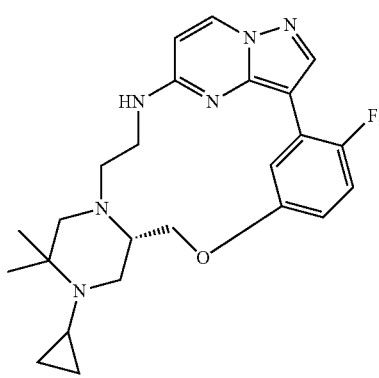

Compound N62

Example N62

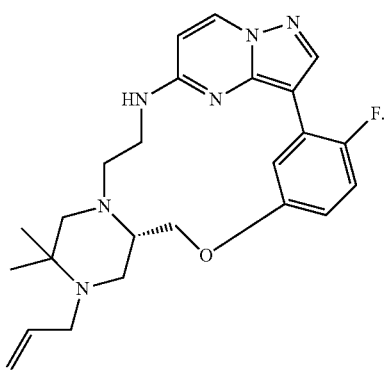

Compound N63

Example N63

15. A compound as defined in claim 12 which is selected from:

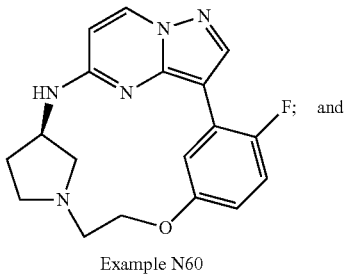

Compound N60; and

Example N60

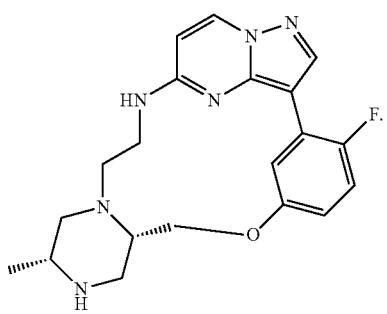

Compound N45

Example N45

16. A compound according to claim 1; wherein $R_5$ is linked to the aryl or heteroaryl moiety at position $Z_1$ in accordance with the numbering as provided in Formula I.

17. A compound according to claim 1; wherein said compound is the S-enantiomer.

18. A compound according to claim 1; wherein said compound is the R-enantiomer.

19. A pharmaceutical composition comprising a compound according to claim 1 and at least one pharmaceutically acceptable carrier, diluent, or excipient.

20. A method for the treatment of a leucine-rich repeat kinase 2 (LRRK2)-kinase associated disease; said method comprising administering to a subject in need thereof an effective amount of a compound according to claim 1, wherein the LRRK2-kinase associated disease is a neurological disorder chosen from Parkinson's disease and Alzheimer's disease.

21. A method for inhibiting the activity of a leucine-rich repeat kinase 2 (LRRK2), the method comprising administering to a subject in need thereof an effective amount of a compound according to claim 1.

22. A compound of Formula Ia or a stereoisomer, tautomer, racemic, salt, hydrate, N-oxide form, or solvate thereof as defined in claim 6, wherein each of said $Z_1$, $Z_2$, $Z_3$, $Z_4$ and $Z_5$ is C.

* * * * *